United States Patent
Brooks et al.

(10) Patent No.: US 6,417,212 B1
(45) Date of Patent: Jul. 9, 2002

(54) MODULATORS OF PEROXISOME PROLIFERATOR ACTIVATED RECEPTORS

(75) Inventors: Dawn A. Brooks, Indianapolis; Christopher J. Rito, Martinsville, both of IN (US); Anthony J. Shuker, Atlanta, GA (US); Samuel J. Dominianni, Indianapolis, IN (US); Alan M. Warshawsky, Carmel, IN (US); Lynn S. Gossett, Indianapolis, IN (US); Donald P. Matthews, Indianapolis, IN (US); David A. Hay, Indianapolis, IN (US); Robert J. Ardecky, Encinitas, CA (US); Pierre-Yves Michellys; John S. Tyhonas, both of San Diego, CA (US)

(73) Assignees: Eli Lilly & Company, Indianapolis, IN (US); Ligand Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/644,457

(22) Filed: Aug. 23, 2000

Related U.S. Application Data

(60) Provisional application No. 60/151,162, filed on Aug. 27, 1999.

(51) Int. Cl.[7] ............ C07D 263/36; A61K 31/42; A61P 25/00
(52) U.S. Cl. .................... 514/374; 548/235
(58) Field of Search ............ 514/374; 548/235

(56) References Cited

U.S. PATENT DOCUMENTS

| 5,089,514 A | 2/1992 | Hulin ............ 514/374 |
| 5,306,726 A | 4/1994 | Hulin ............ 514/375 |
| 5,902,726 A | 5/1999 | Kliewer et al. ........ 435/7.1 |
| 5,994,554 A | 11/1999 | Kliewer et al. ........ 548/183 |

FOREIGN PATENT DOCUMENTS

| EP | 0930299 A1 | 7/1999 |
| GB | 2 335 597 A | 9/1999 |
| JP | 325250 | 12/1996 |
| JP | 325264 | 12/1996 |
| WO | WO 93/21166 | * 10/1993 |
| WO | WO 94/01420 | 1/1994 |
| WO | WO 94/13650 | 6/1994 |
| WO | WO 95/17394 | 6/1995 |
| WO | WO 96/04260 | 2/1996 |
| WO | WO 96/23884 | 8/1996 |
| WO | WO 96/29405 | 9/1996 |
| WO | WO 96/33724 | * 10/1996 |
| WO | WO 96/40128 | * 12/1996 |
| WO | WO 97/10819 | * 3/1997 |
| WO | WO 97/25042 | * 7/1997 |
| WO | WO 97/28115 | * 8/1997 |
| WO | WO 97/31907 | * 9/1997 |
| WO | WO 97/47612 | * 12/1997 |
| WO | WO 98/05331 | * 2/1998 |
| WO | WO 98/29120 | * 7/1998 |
| WO | WO 98/39006 | * 9/1998 |
| WO | WO 98/43081 | * 10/1998 |

(List continued on next page.)

OTHER PUBLICATIONS

Kersten, S., "Roles of PPARs in health and disease," *Nature.*, 405:421–424 (2000).

Bright, S.W., "Competitive Particle Concentration Fluorescence Immunoassays for Measuring Anti–diabetic Drug Levels in Mouse Plasma", *Journal of Immunological Methods*, 207: 23–31 (1997).

Shinkai, H., "Isoxazolidine–3, 5–dione and Noncyclic 1,3–Dicarbonyl compounds as Hypoglycemic Agents", *J. Med. Chem.*, 41: 1927–1933 (1998).

*Primary Examiner*—Floyd D. Higel
*Assistant Examiner*—Andrea D. Small
(74) *Attorney, Agent, or Firm*—Hamilton, Brook, Smith & Reynolds, P.C.

(57) ABSTRACT

The present invention is directed to compounds represented by Structural Formula I and pharmaceutically acceptable salts, solvates and hydrates thereof, and methods of making, methods of using and pharmaceutical compositions having compounds represented by Structural Formula I and pharmaceutically acceptable salts, solvates and hydrates thereof:

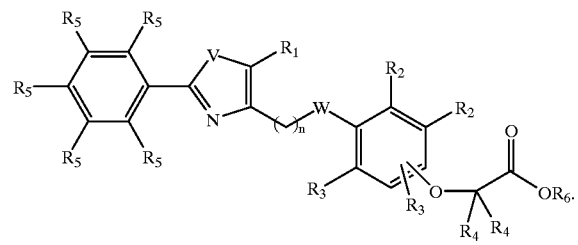

In Structural Formula I, n is 2, 3, or 4; V is O or S; W is O, S, or $SO_2$; $R_1$ is H, a C1–C4 alkyl, phenyl or trifluoromethyl; $R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl; $R_3$ are each, independently, H, a C1–C6 alkyl, an aryl-C1–C6 alkyl, a cycloalkyl-C1–C4 alkyl, an aryl, or a cycloalkyl; $R_4$ are each, independently, H, a C1–C4 alkyl, an aryl, or benzyl; $R_5$ are each, independently, H, a substituted or unsubstituted aryl or a heteroaryl, provided that at least one $R_5$ is a substituted or unsubstituted aryl or a substituted or unsubstituted heteroaryl; and $R_6$ is H, a C1–C4 alkyl, or an aminoalkyl.

55 Claims, 7 Drawing Sheets

U.S. PATENT DOCUMENTS

| | | | |
|---|---|---|---|
| WO | WO 98/54220 | * | 12/1998 |
| WO | WO 98/57631 | * | 12/1998 |
| WO | WO 99/05161 | * | 2/1999 |
| WO | WO 99/19313 | * | 4/1999 |
| WO | WO 99/20275 | * | 4/1999 |
| WO | WO 99/29317 | * | 6/1999 |
| WO | WO 99/32465 | * | 7/1999 |
| WO | WO 99/38850 | * | 8/1999 |
| WO | WO 99/46232 | * | 9/1999 |
| WO | WO 99/51740 | * | 10/1999 |
| WO | WO 99/58510 | * | 11/1999 |
| WO | WO 99/63983 | * | 12/1999 |
| WO | WO 00/04889 | * | 2/2000 |
| WO | WO 00/04890 | * | 2/2000 |
| WO | WO 00/08002 | * | 2/2000 |

* cited by examiner

MODULATORS OF PEROXISOME PROLIFERATOR ACTIVATED RECEPTORS

RELATED APPLICATION

This application claims the benefit of U.S. Provisional Application No. 60/151,162, filed Aug. 27, 1999, the entire teachings of which are incorporated herein by reference.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, PPARβ or NUC1, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol. The PPARγ receptor subtypes are reportedly involved in activating the program of adipocyte differentiation and are not involved in stimulating peroxisome proliferation in the liver.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non insulin dependent diabetes mellitus" (NIDDM) is the form of diabetes which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL is known as Syndrome X.

Current treatment for diabetes mellitus generally first involves treatment with diet and exercise. However, compliance can be poor and as the disease progresses treatment with hypoglycemics, typically sulfonylureas, is often necessary. Sulfonylureas stimulate the β cells of the liver to secrete more insulin. However, the response of the β cells eventually fails and treatment with insulin injection is necessary. In addition, both sulfonylurea treatment and insulin injection have the life threatening side effect of hypoglycemic coma. Therefore, patients using these treatments must carefully control dosage.

Thiazolidinediones are a class of compounds which have been shown to increase the sensitivity of insulin sensitive cells. Increasing insulin sensitivity rather than the amount of insulin in the blood reduces the likelihood of hypoglycemic coma. Thiazolidinediones have been shown to increase insulin sensitivity by binding to PPARγ receptors. However, side effects associated with treatment with thiazolidinediones include weight gain, and, for troglitazone, liver toxicity.

PPARα and PPARγ receptors have been implicated in diabetes mellitus, cardiovascular disease, obesity, and gastrointestinal disease, such as, inflammatory bowel disease. There exists a need for new pharmaceutical agents which modulate these receptors to prevent, treat and/or alleviate these diseases or conditions while ameliorating side effects of current treatments.

SUMMARY OF THE INVENTION

The present invention is directed to compounds represented by Structural Formula I and pharmaceutically acceptable salts, solvates and hydrates thereof:

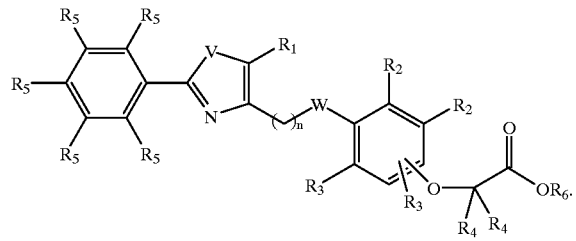

In Structural Formula I, n is 2, 3, or 4. V is O or S. W is O, S, or $SO_2$. $R_1$ is H, a C1–C4 alkyl, phenyl or trifluoromethyl. $R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl. $R_3$ are each, independently, H, a C1–C6 alkyl, an aryl-C1–C6 alkyl, a cycloalkyl-C1–C4 alkyl, an aryl, or a cycloalkyl. $R_4$ are each, independently, H, a C1–C4 alkyl, an aryl, or benzyl. $R_5$ are each, independently, H, a substituted or unsubstituted aryl or a heteroaryl, provided that at least one $R_5$ is a substituted or unsubstituted aryl or a substituted or unsubstituted heteroaryl. $R_6$ is H, a C1–C4 alkyl, or an aminoalkyl.

In one embodiment, the present invention relates to a method of modulating a peroxisome proliferator activated receptor by contacting the receptor with at least one compound represented by Structural Formula I, and pharmaceutically acceptable salts, solvates and hydrates thereof In another embodiment, the present invention also relates to pharmaceutical compositions which include a pharmaceutically acceptable carrier and at least one compound represented by Structural Formula I, and pharmaceutically acceptable salts, solvates and hydrates thereof.

In yet another embodiment, the present invention relates to a method of making a compound represented by Structural Formula I.

The compounds of the present invention and pharmaceutically acceptable salts, solvates and hydrates thereof are believed to be effective in treating Syndrome X, Type II diabetes, hyperglycemia, hyperlipidemia, obesity, coagaulopathy, hypertension, atherosclerosis, and other disorders related to Syndrome X and cardiovascular diseases because they lower one or more of the following in mammals: glucose, insulin, triglycerides, fatty acids and/or cholesterol. In addition, the compounds exhibit fewer side effects than compounds currently used to treat these conditions.

DETAILED DESCRIPTION OF THE INVENTION

Figure 1A:
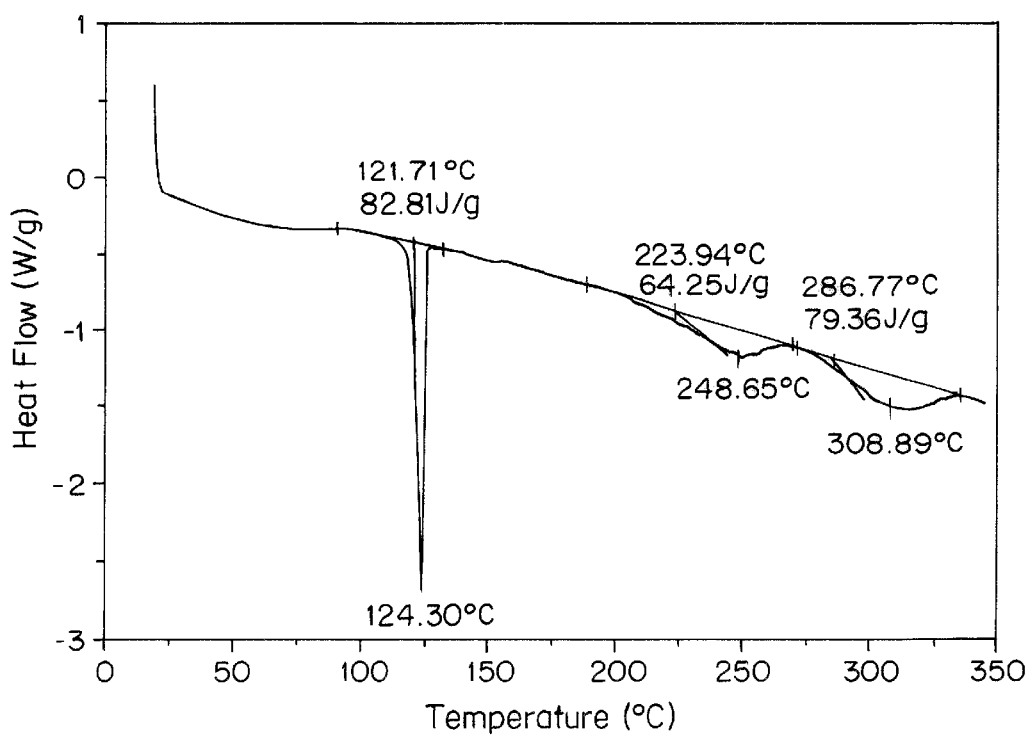
FIGS. 1A through 1M are differential scanning calorimetry analyses of several polymorphs of 2-methyl-2-{4-[2-(5-methyl-2-biphenyl-4-yl-oxazol-4-yl)ethoxy]phenoxy}propionic acid and its salts.
Figure 1B:
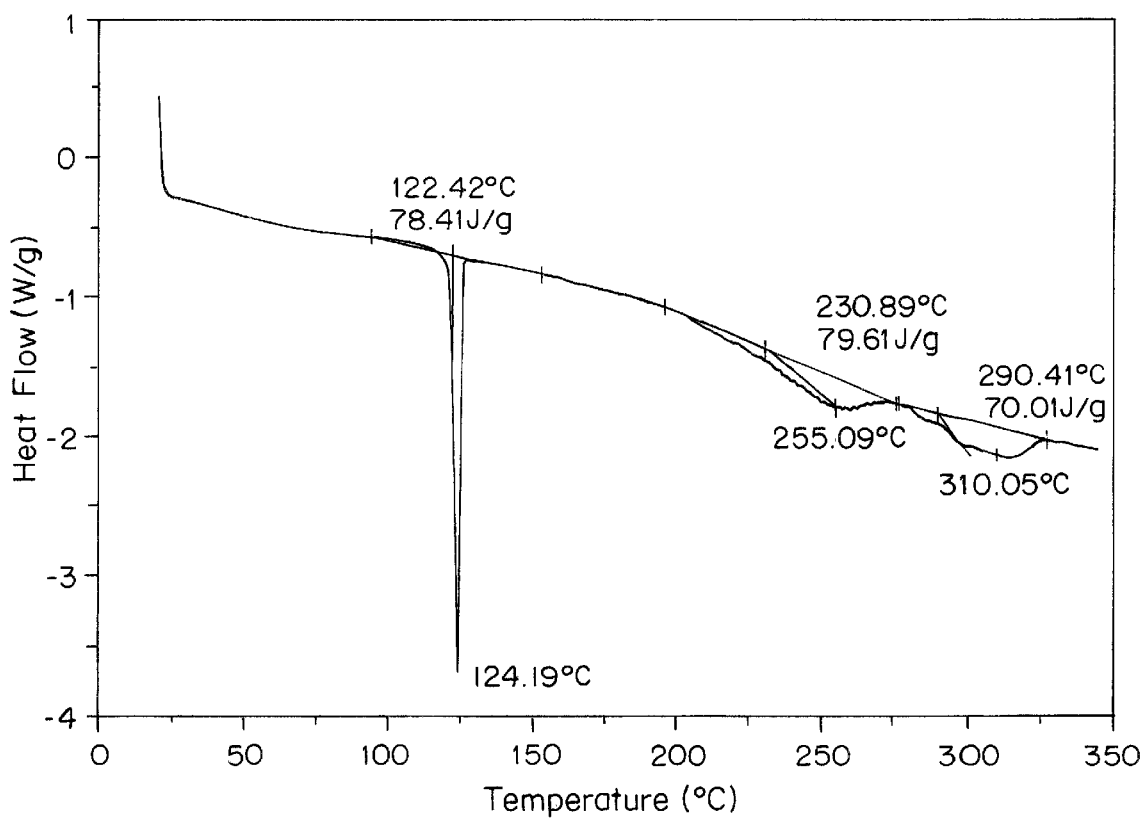
Figure 1C:
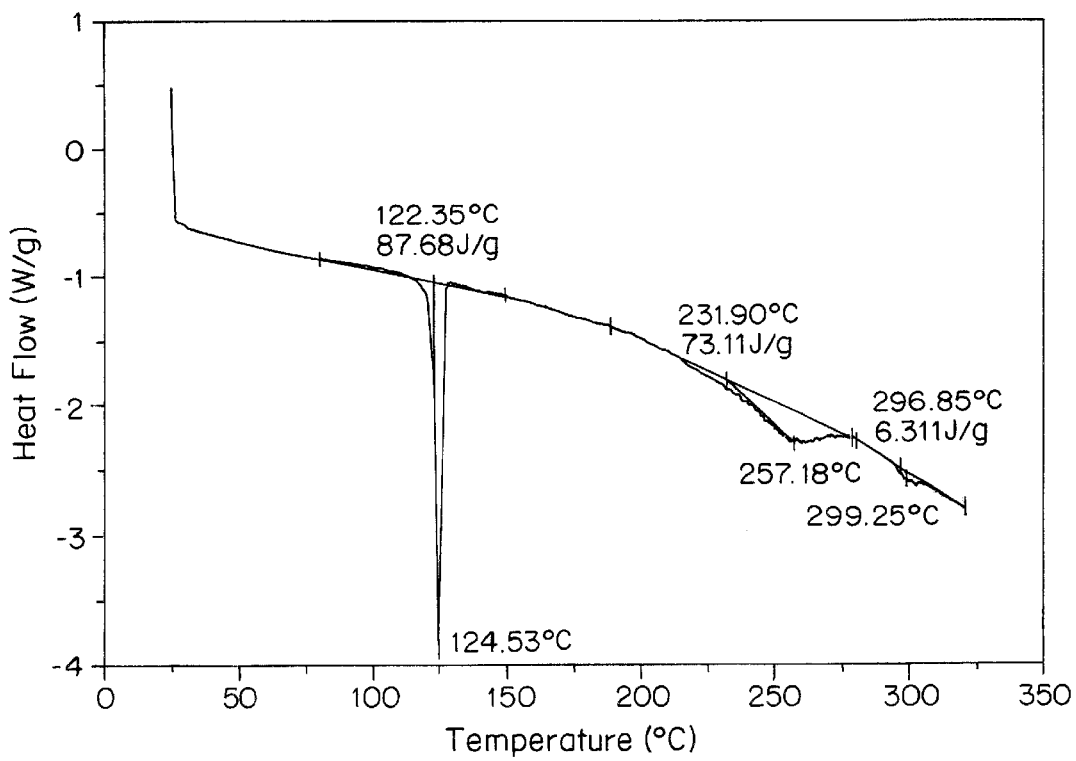
Figure 1D:
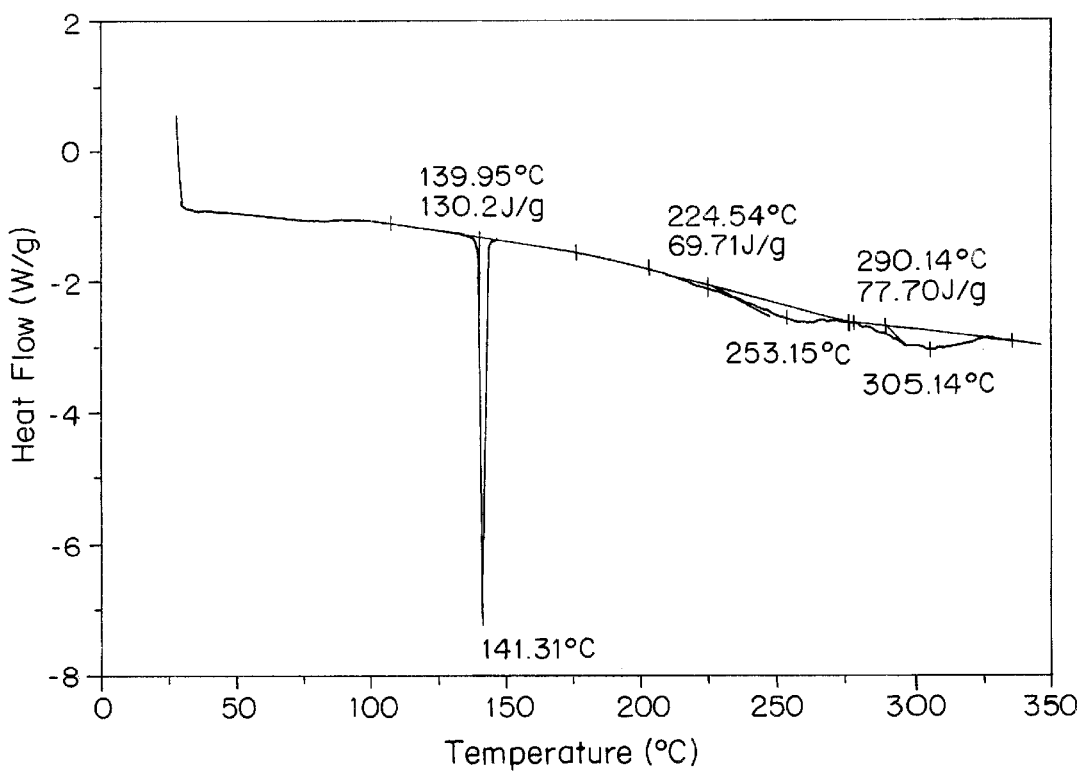
Figure 1E:
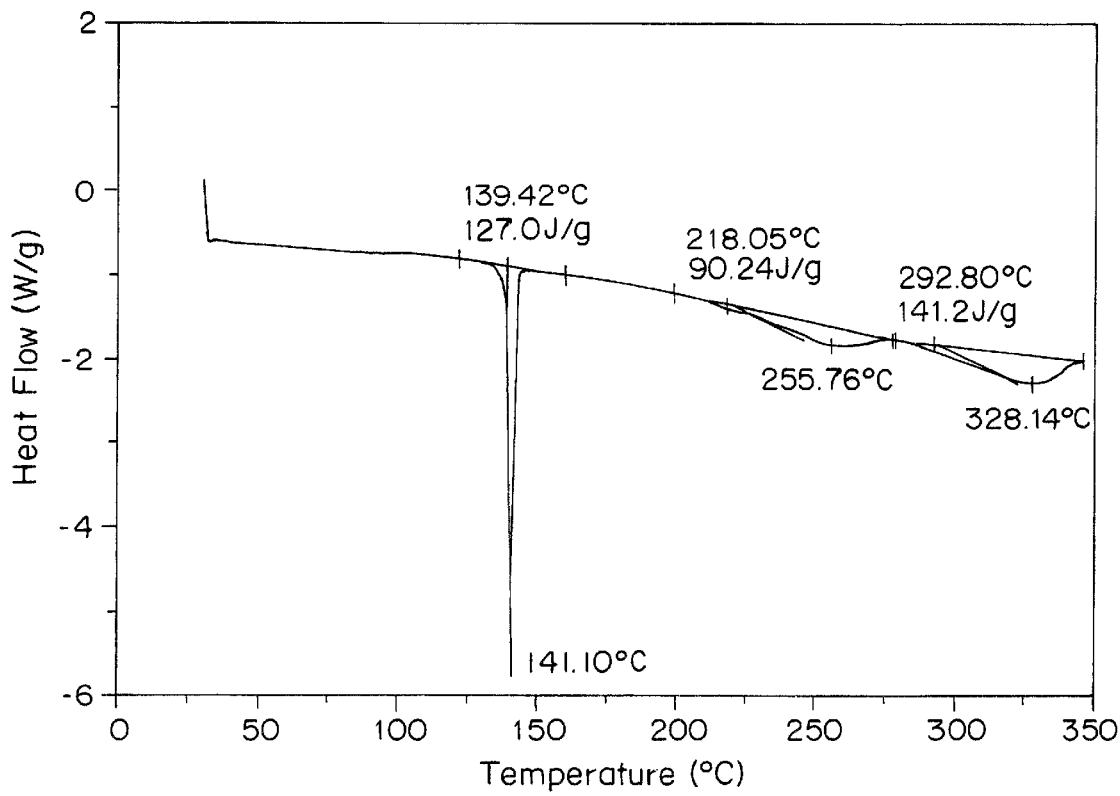
Figure 1F:
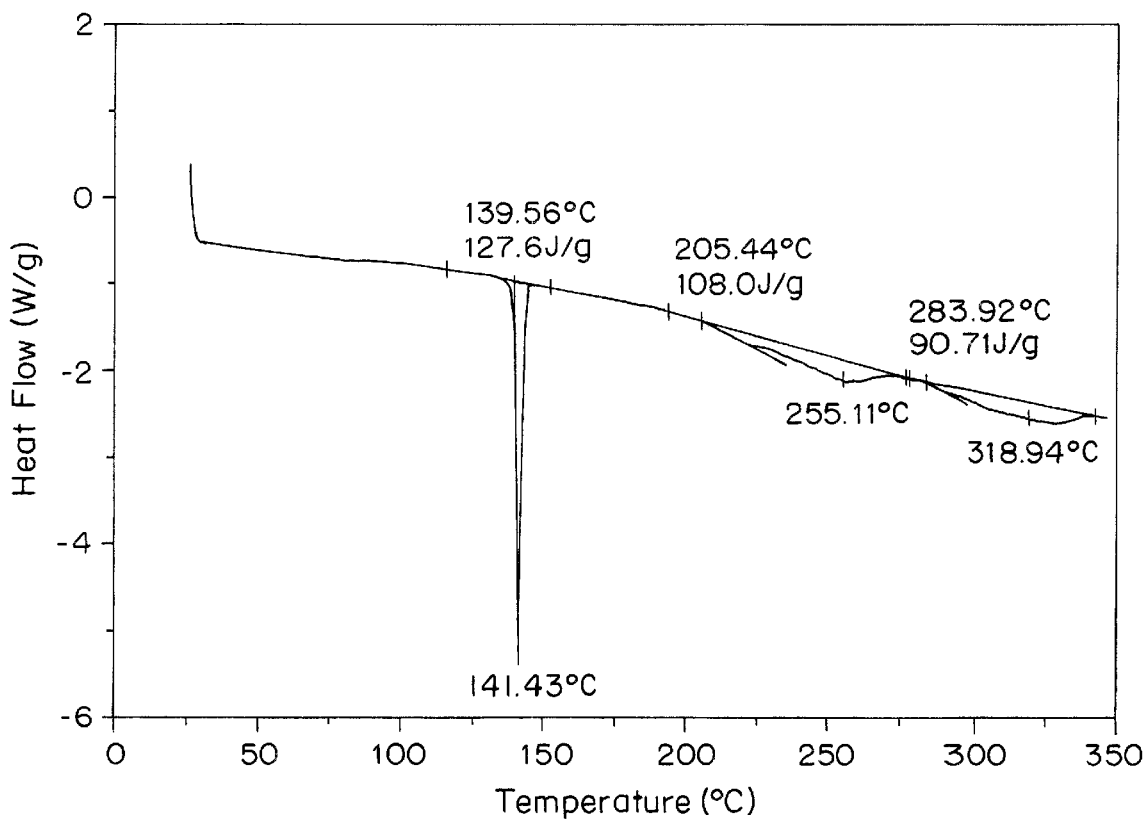
Figure 1G:
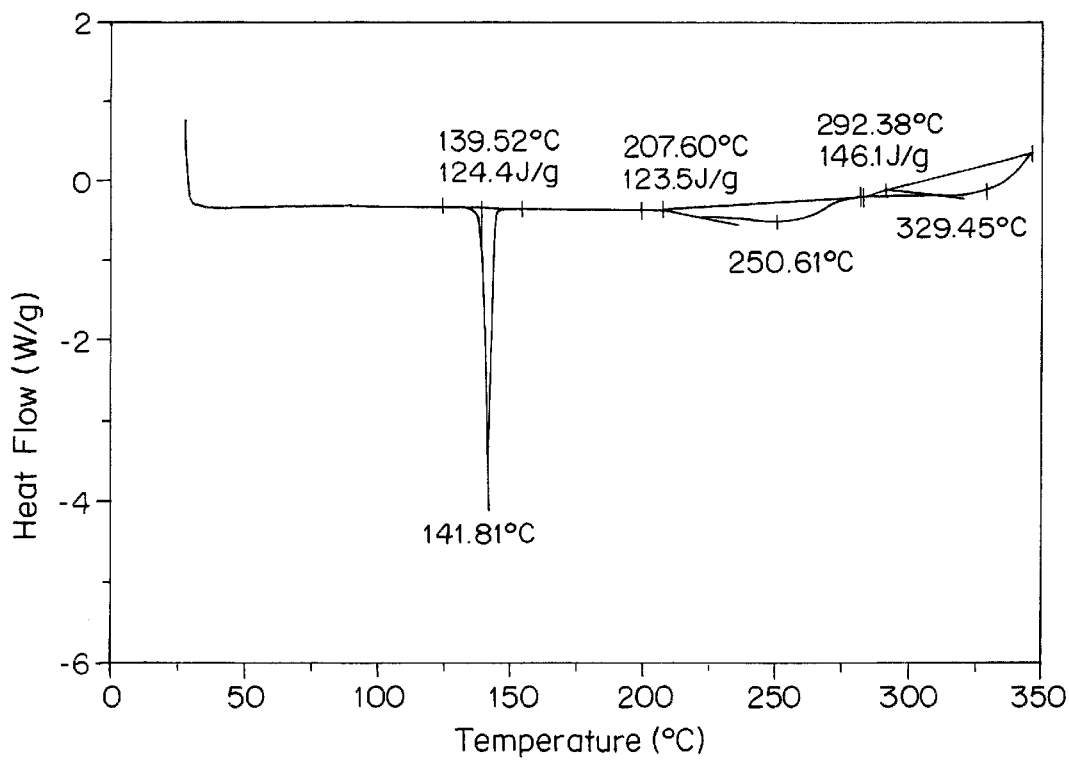
Figure 1H:
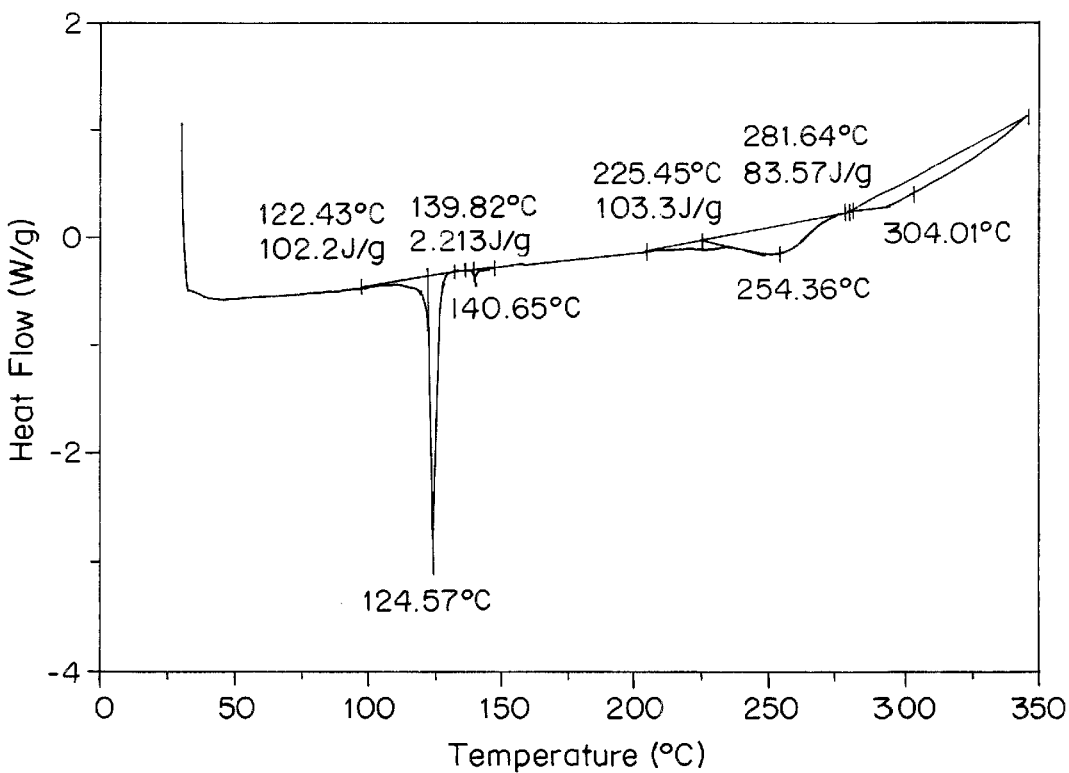
Figure 1I:
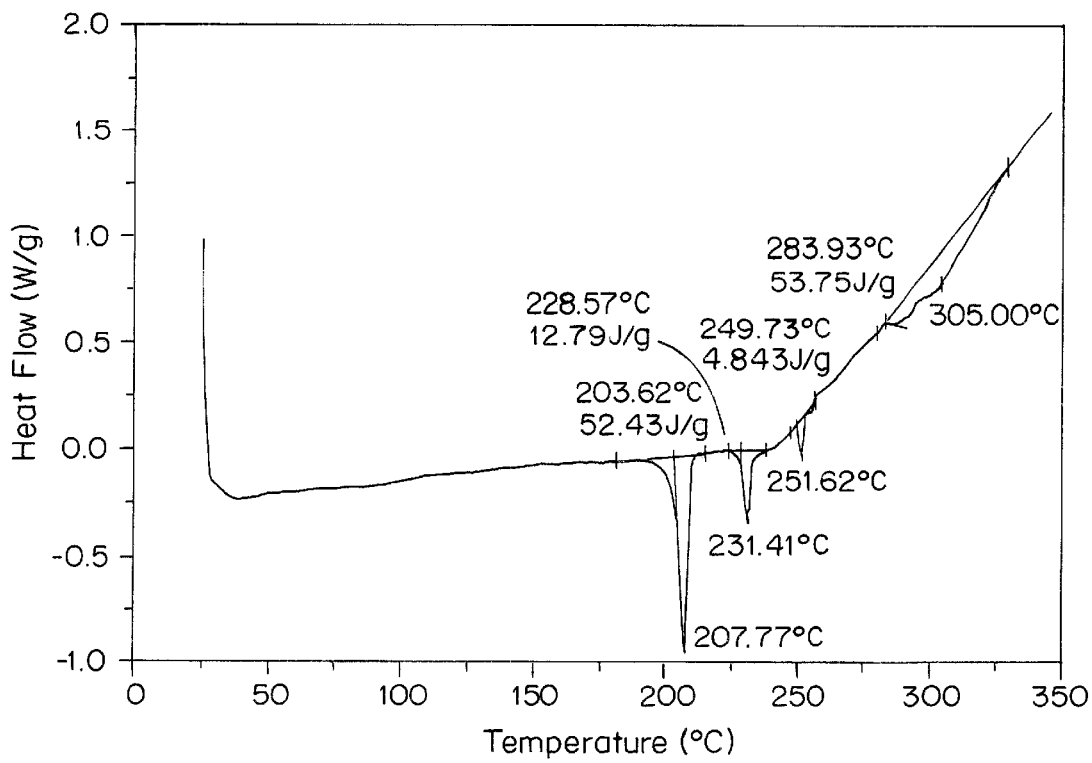
Figure 1J:
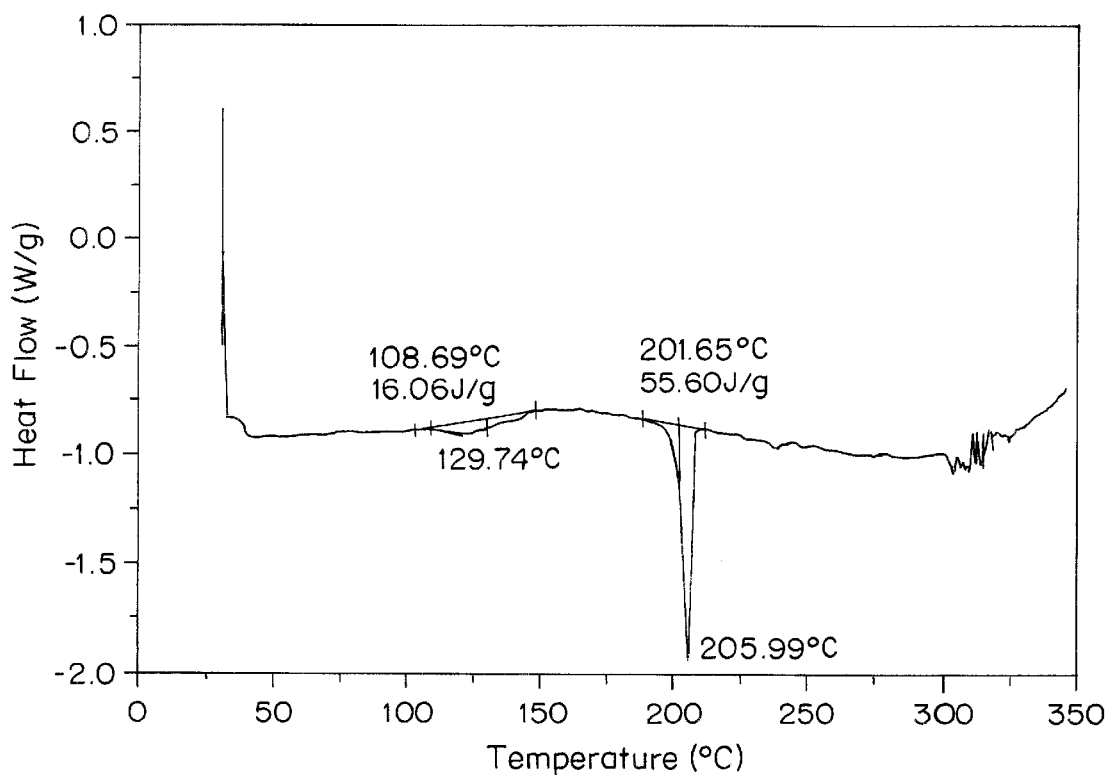
Figure 1K:
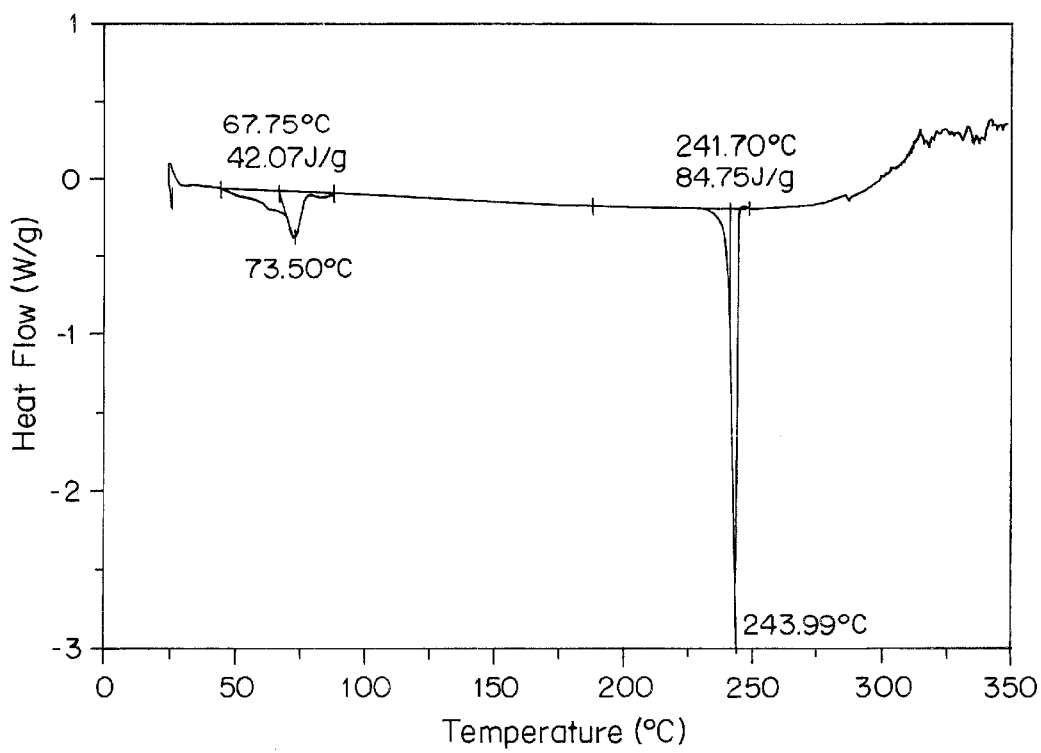
Figure 1L:
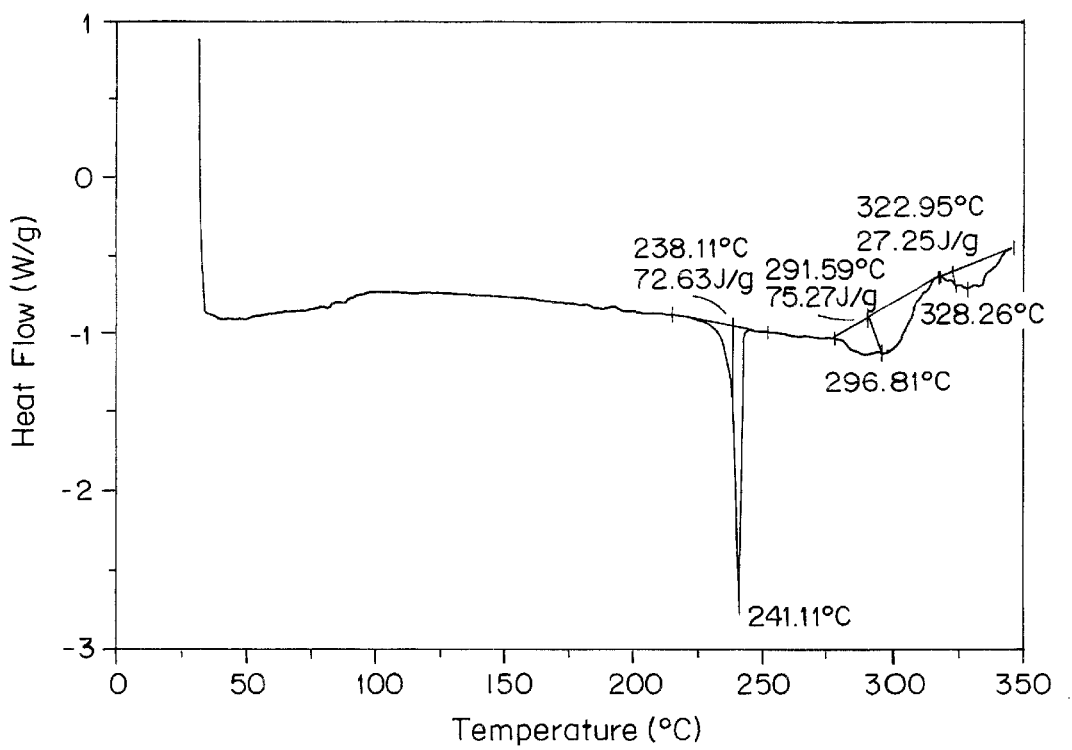
Figure 1M:
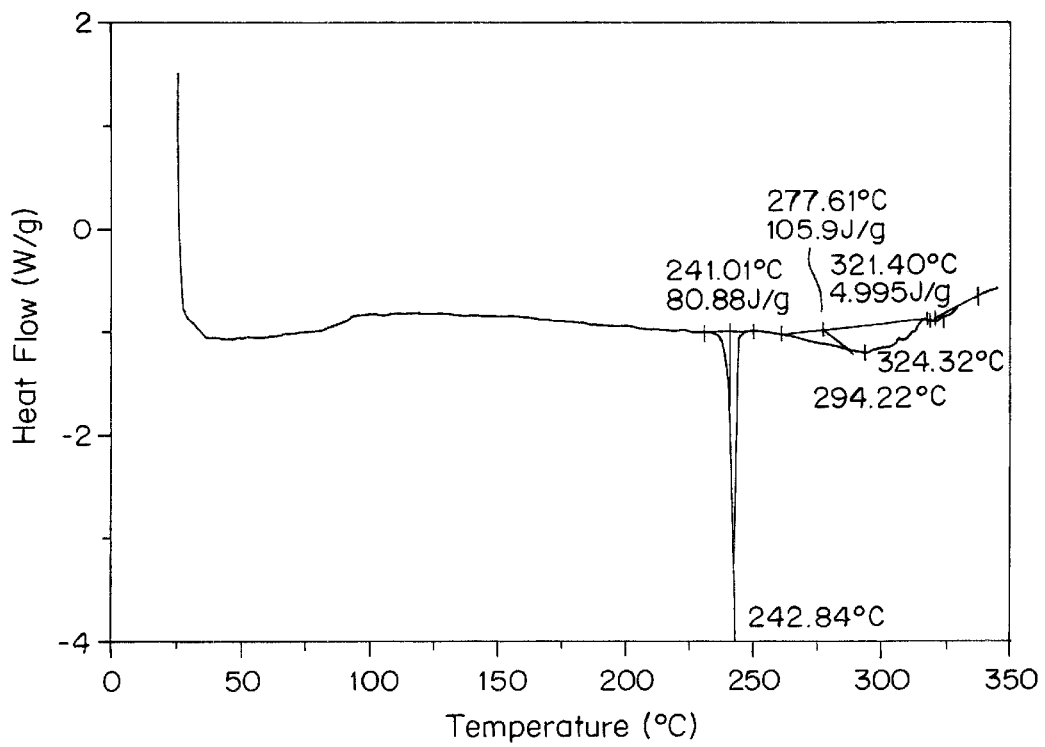

As used herein, alkyl groups include straight chained or branched $C_1$–$C_6$ hydrocarbons, which are completely saturated.

Cycloalkyl groups, as used herein, include $C_3$–$C_8$ hydrocarbons, which are completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl).

Heteroaryl groups, as used herein, are aromatic ring systems having at least one heteroatom such as nitrogen, sulfur or oxygen. Heteroaryl groups include thienyl (also referred to herein as "thiophenyl"), pyridyl, pyrrolyl, benzofuranyl, isoxazolyl, and pyrimidinyl.

An aryl-C1–C6-alkyl group, as used herein, is an aryl substituent that is linked to a compound by an alkyl group having from one to six carbon atoms.

A heteroaryl-C1–C6-alkyl group, as used herein, is a heteroaryl substituent that is linked to a compound by an alkyl group having from one to six carbon atoms.

A cycloalkyl-C1–C4-alkyl group, as used herein, is a cycloalkyl substituent that is linked to a compound by an alkyl group having from one to four carbon atoms.

An aminoalkyl group is an alkyl group having from one to six carbon atoms which is substituted with at least one amine represented by —$NR_{15}R_{16}$, in which $R_{15}$ and $R_{16}$ are each, independently, a C1–C6 alkyl or $R_{15}$ and $R_{16}$ taken together with the nitrogen to which they are attached form a five or six membered heterocycloalkyl.

A heterocycloalkyl is a non-aromatic ring which contains one or more oxygen, nitrogen or sulfur (e.g., morpholine, piperidine, piperazine, pyrrolidine, and thiomorpholine). Preferred heterocycloalkyl groups are morpholine and piperidine.

Substituents for an aryl or a heteroaryl group include halo; —COOH; C1–C6 alkoxy; nitro; cyano; CHO; hydroxyl; C1–C6 alkyl; C1–C6 alkyl substituted with a carboxylic acid group; —$C(O)NR_{10}R_{11}$, in which $R_{10}$ and $R_{11}$ are each, independently, H or a C1–C4 alkyl; and a C1–C6 alkyl substituted with one or more halo.

In a preferred embodiment, the compounds of the present invention, separately or with their respective pharmaceutical compositions, have an oxazole ring as the five membered ring, W is an oxygen and n is 2. This group of compounds can be represented by Structural Formula II:

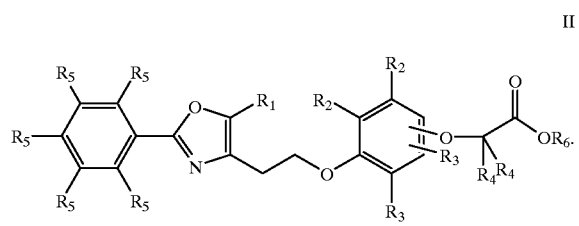

II

In Structural Formula II, $R_1$, $R_2$, $R_3$, $R_4$, $R_5$ and $R_6$ are as defined for Structural Formula I. Examples of compounds having Structural Formula II include, for instance, the compounds described in Examples 1–44, 47–58 and 60–62.

In a more preferred embodiment, the compounds of the present invention, and their respective pharmaceutical compositions, the oxazole ring is substituted with a biphenyl group, and the group represented by the formula —O—$CR_4R_4$—$C(O)OR_6$ is in the para position, as represented by Structural Formula III.

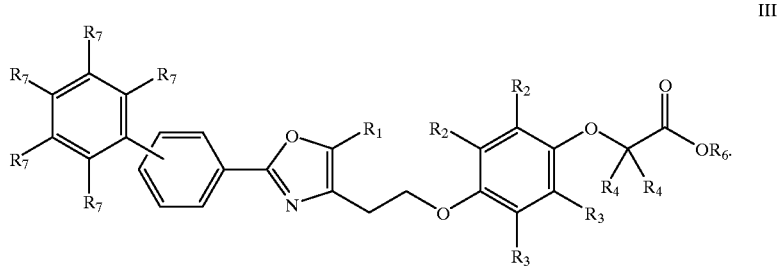

III

In Structural Formula III, $R_1$, $R_2$, $R_3$, $R_4$, and $R_6$ are as defined for Structural Formula I, and each $R_7$ is, independently, H, halo, a C1–C6 alkyl, trifluoromethyl, a C1–C6 alkoxy, C(O)OH, C(O)NHC(CH$_3$)$_3$, (CH$_2$)$_2$C(O)OH, or CHO.

In an even more preferred embodiment of the compounds of the present invention, each $R_2$ of the compounds, and their respective pharmaceutical compositions, is H. These compounds are represented by Structural Formula IV.

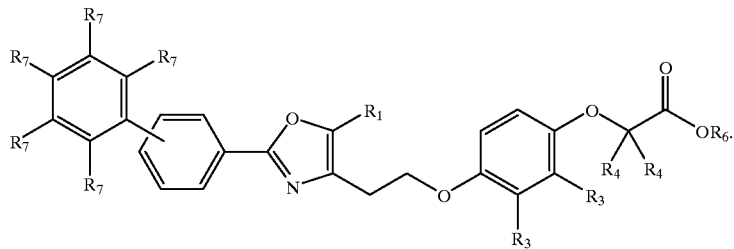

IV

In Structural Formula IV, $R_1$, $R_3$, $R_4$, and $R_6$ are as defined for Structural Formula I, and each $R_7$ is as defined for Structural Formula III. Compounds of the present invention having structural Formula IV, include, but are not limited to, the compounds described in Examples 1–3, 5–7, 9–16, 21–26, 28–36, 38–44, 47, 52–55 and 60–62.

In yet another preferred embodiment of the compounds of the present invention, each $R_2$ taken together with the phenyl to which they are bound form a naphthyl or 1,2,3,4-tetrahydronaphthyl. These compounds are represented by Structural Formula V.

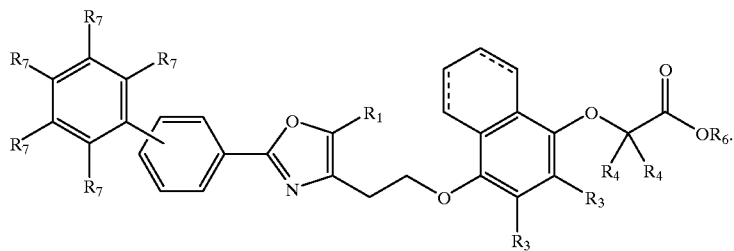

V

In Structural Formula V, $R_1$, $R_3$, $R_4$, and $R_6$ are as defined for Structural Formula I, and each $R_7$ is as defined for Structural Formula III. The dashed lines in Structural Formula V indicate that a double bond is optionally present.

In another embodiment, the compounds of the present invention have an oxazole ring which is substituted with a thienylphenyl as represented by Structural Formula VI.

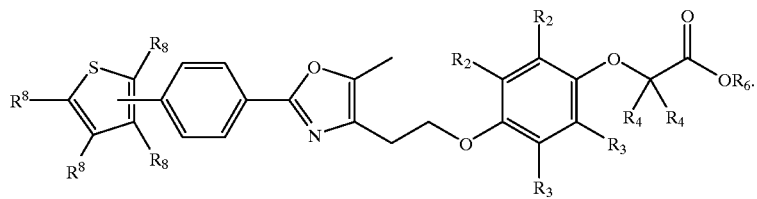

VI

In Structural Formula VI, $R_1$, $R_2$, $R_3$, $R_4$, and $R_6$ are as defined for Structural Formula I, and each $R_8$ is, independently, H, halo, a C1–C6 alkyl, trifluoromethyl, or a C1–C6 alkoxy.

In a further embodiment, the five membered ring is a thiazole ring, in the compounds of the present invention, and their respective pharmaceutical compositions. This group of compounds can be represented by Structural Formula VII.

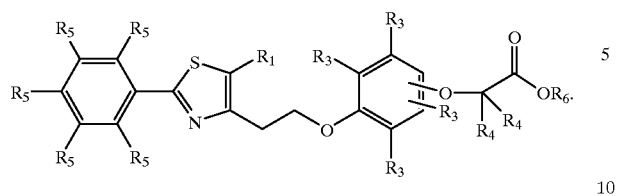

VII

In Structural Formula VII, $R_1$, $R_3$, $R_4$, $R_5$ and $R_6$ are as defined for Structural Formula I.

W is preferably O in compounds of the present invention and at least one $R_5$ is phenyl.

n is preferably 2.

V is preferably O in compounds of the present invention.

$R_1$ is preferably methyl for the compounds of the present invention.

$R_2$ and $R_3$ in Structural Formulas I, II, and III are preferably, independently, selected from the following group: H, methyl, propyl, n-butyl, phenyl, benzyl, methylcyclohexyl, and 2-phenylethyl.

Preferably, each $R_4$ is selected from the following group: methyl, ethyl, and benzyl in compounds of the present invention. More preferably, each $R_4$ is methyl.

In one embodiment, the phenyl substituent of the five membered ring of Structural Formulas I, II, and VII together with its $R_5$ substituents or the biphenyl group of Structural Formula III, together with its $R_7$ substituents, can be selected from the following group:

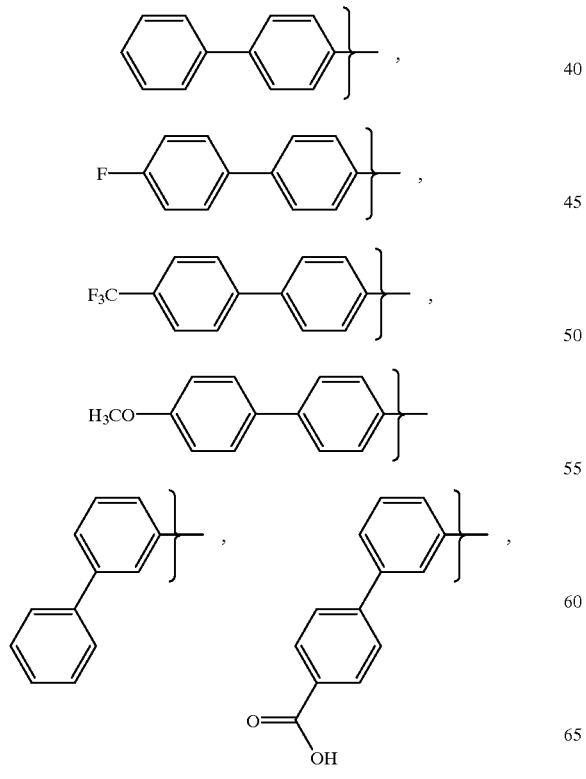

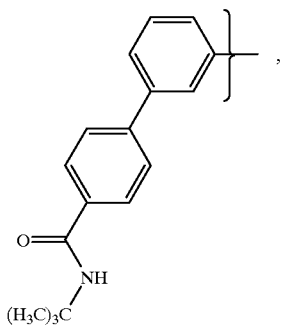

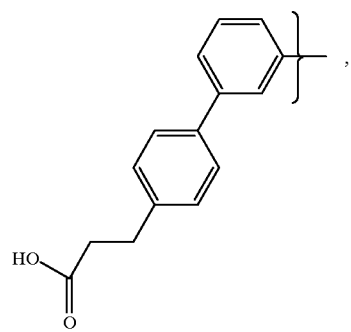

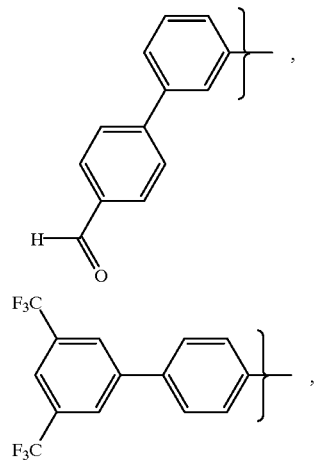

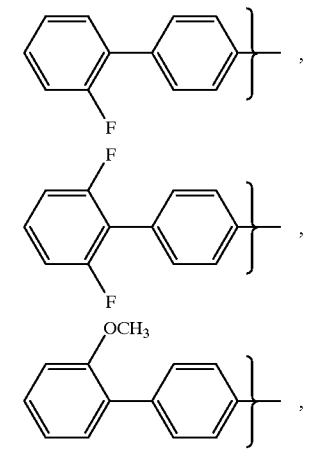

-continued

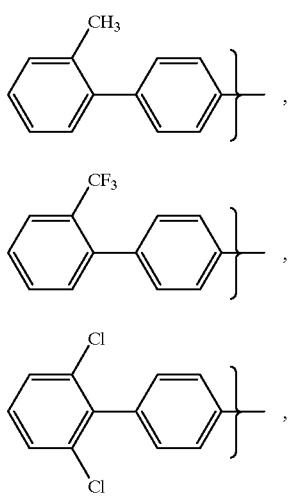

In another embodiment, the phenyl substituent of the five membered ring of Structural Formulas I, II, and VII together with its $R_5$ substituents can be selected from the following group:

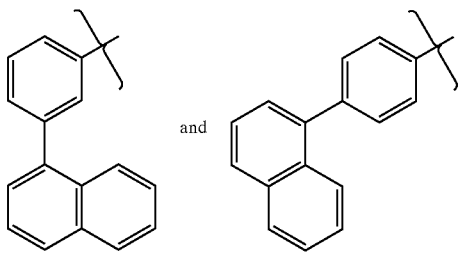

In yet another embodiment, the phenyl substituent of the five membered ring of Structural Formulas I, II, and VII together with its $R_5$ substituents can be selected from the following group:

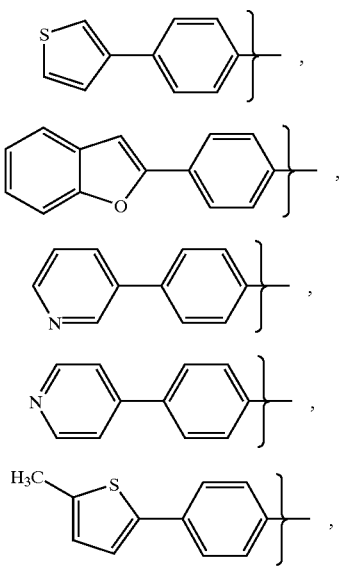

-continued

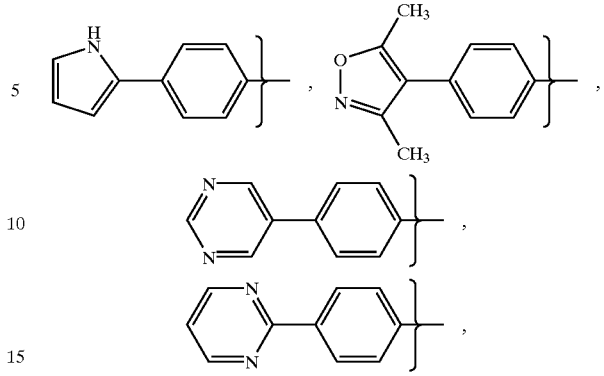

Compounds of the present invention include, but are not limited to, the following group of compounds:

2-(4-{2-[2-(4'-fluorobiphenyl-4-yl)-5-methyloxazol-4-yl]ethoxy}phenoxy)-2-methylpropionic acid;

2-(4-{2-[2-(4'-formylbiphenyl-3-yl)-5-methyloxazol-4-yl]ethoxy}phenoxy)-2-methylpropionic acid;

3'-(4-{2-[3-(1-carboxy-1-methylethoxy)phenoxy]ethyl}-5-methyloxazol-2-yl)-biphenyl-4-carboxylic acid;

2-[4-(2-{2-[4'-(2-carboxyethyl)biphenyl-3-yl]-5-methyloxazol-4-yl}ethoxy)phenoxy]-2-methylpropionic acid;

2-(4-{2-[2-(3',5'-bis-trifluoromethylbiphenyl-4-yl)-5-methyloxazol-4-yl]ethoxy}-phenoxy)-2-methyl propionic acid;

2-(4-{2-[2-(2'-methoxy-biphenyl-4-yl)-5-methyloxazol-4-yl]-ethoxy}-phenoxy)-2-methylpropionic acid;

2-methyl-2-(4-{2-[5-methyl-2-(2'-methyl-biphenyl-4-yl)-oxazol-4-yl]-ethoxy}-phenoxy)propionic acid;

2-methyl-2-(4-{2-[5-methyl-2-(2'-trifluoromethyl-biphenyl-4-yl)-oxazol-4-yl]-ethoxy}-phenoxy)propionic acid;

2-(4-{2-[2-(2'-fluorobiphenyl-4-yl)-5-methyloxazol-4-yl]-ethoxy}-phenoxy)-2-methylpropionic acid;

2-(4-{2-[2-(2',6'-difluorobiphenyl-4-yl)-5-methyloxazol-4-yl]-ethoxy}-phenoxy)-2-methylpropionic acid;

2-(4-{2-[2-(2',6'-dichloro-biphenyl-4-yl)-5-methyloxazol-4-yl]-ethoxy}-phenoxy)-2-methylpropionic acid;

2-(4-{2-[2-(4'-tert-butylcarbamoylbiphenyl-3-yl)-5-methyloxazol-4-yl]ethoxy}phenoxy)-2-methyl propionic acid;

2-[4-(2-{2-[4-(3,5-dimethyl-isoxazol-4-yl)-phenyl]-5-methyloxazol-4-yl}-ethoxy)-phenoxy]-2-methylpropionic acid;

2-methyl-2-[4-(2-{5-methyl-2-[4-(1H-pyrrol-2-yl)-phenyl]-oxazol-4-yl}-ethoxy)-phenoxy]propionic acid;

2-methyl-2-(4-{2-[5-methyl-2-(4-pyrimidin-2-yl-phenyl)-oxazol-4-yl]-ethoxy}-phenoxy)-propionic acid;

2-methyl-2-(4-{2-[5-methyl-2-(4-pyrimidin-5-yl-phenyl)-oxazol-4-yl]-ethoxy}-phenoxy)-propionic acid;

2-{3-[2-(2-biphenyl-4-yl-5-methyloxazol-4-yl)ethoxy]phenoxy}-2-methylpropionic acid;

2-{3-[2-(2-biphenyl-3-yl-5-methyloxazol-4-yl)ethoxy]phenoxy}-2-methylpropionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4-yl)-ethoxy]-2-cyclohexylmethyl-phenoxy}-2-methyl-propionic acid;

2-(4-{2-[2-(4-thiophen-2-yl-phenyl)-5-methyloxazol-4-yl]ethoxy}phenoxy)-2-methylpropionic acid;

2-{4-[2-(2-biphenyl-4-yl-5-methyloxazol-4-yl)ethoxy]-2-phenethylphenoxy}-2-methylpropionic acid;

2-{4-[2-(2-biphenyl-3-yl-5-methyloxazol-4-yl)ethoxy]-2-phenethylphenoxy}-2-methylpropionic acid;

2-{4-[2-(2-biphenyl-3-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-phenethylphenoxy}-2-methylpropionic acid;

2-{4-[2-(2-biphenyl-4-yl-5-methyloxazol-4-yl)ethoxy]-3-cyclohexylmethylphenoxy}-2-methylpropionic acid;

2-{2-benzyl-4-[2-(2-biphenyl-3-yl-5-methyloxazol-4-yl)ethoxy]-phenoxy}-2-methyl-propionic acid;

2-{2-benzyl-4-[2-(2-biphenyl-4-yl-5-methyloxazol-4-yl)ethoxy]-phenoxy}-2-methyl-propionic acid;

2-(4-{2-[2-(4-benzofur-2-yl-phenyl)-5-methyloxazol-4-yl]ethoxy}phenoxy)-2-methylpropionic acid;

2-{5-[2-(2-biphenyl-4-yl-5-methyloxazol-4-yl)-ethoxy]-biphenyl-2-yloxy}-2-methyl-propionic acid;

2-(4-{2-[2-(4'-trifluoromethylbiphenyl-4-yl)-5-methyloxazol-4-yl]ethoxy}phenoxy)-2-methylpropionic acid;

2-{3-[2-(2-biphenyl-4-yl-5-methyloxazol-4-yl)-ethoxy]-4-butylphenoxy}-2-methylpropionic acid;

2-{5-[2-(2-biphenyl-4-yl-5-methyloxazol-4-yl)ethoxy]-2-butylphenoxy}-2-methylpropionic acid;

2-{5-[2-(2-biphenyl-3-yl-5-methyloxazol-4-yl)ethoxy]-2-butylphenoxy}-2-methylpropionic acid;

2-{5-[2-(2-biphenyl-4-yl-5-methyloxazol-4-yl)ethoxy]-2-propylphenoxy}-2-methylpropionic acid;

2-{5-[2-(2-biphenyl-3-yl-5-methyloxazol-4-yl)ethoxy]-2-propylphenoxy}-2-methylpropionic acid;

2-{4-[2-(2-biphenyl-4-yl-5-methyl-thiazol-4-yl)-ethoxy]-phenoxy}-2-methyl-propionic acid;

2-{4-[2-(2-biphenyl-3-yl-5-methyl-thiazol-4-yl)-ethoxy]-phenoxy}-2-methyl-propionic acid;

2-{4-[2-(2-biphenyl-4-yl-5-methyloxazol-4-yl)-ethylsulfanyl]-phenoxy}-2-methyl-propionic acid;

2-{4-[2-(2-biphenyl-4-yl-5-methyloxazol-4-yl)ethoxy]naphthalen-1-yloxy}-2-methyl propionic acid;

2-{4-[2-(2-biphenyl-3-yl-5-methyloxazol-4-yl)ethoxy]naphthalen-1-yloxy}-2-methyl propionic acid;

2-{4-[2-(2-biphenyl-4-yl-5-propyl-oxazol-4-yl)-ethoxy]-phenoxy}-2-methyl-propionic acid;

2-{4-[2-(2-biphenyl-4-yl-5-phenyl-oxazol-4-yl)-ethoxy]-phenoxy}-2-methyl-propionic acid;

2-{4-[2-(2-biphenyl-4-yl-5-trifluoromethyloxazol-4-yl)-ethoxy]-phenoxy}-2-methyl-propionic acid;

2-(4-{2-[2-(4'-methoxybiphenyl-4-yl)-5-methyloxazol-4-yl]ethoxy}phenoxy)-2-methylpropionic acid;

2-(4-{2-[2-(4-{5'-methylthiophen-2-yl}-phenyl)-5-methyloxazol-4-yl]ethoxy}phenoxy)-2-methylpropionic acid;

2-(4-{2-[2-(4-pyrid-3-yl-phenyl)-5-methyloxazol-4-yl]ethoxy}phenoxy)-2-methylpropionic acid;

2-(4-{2-[2-(4-pyrid-4-yl-phenyl)-5-methyloxazol-4-yl]ethoxy}phenoxy)-2-methylpropionic acid;

2-{4-[2-(2-biphenyl-4-yl-5-methyloxazol-4-yl)-ethylsulfanyl dioxide]-phenoxy}-2-methyl-propionic acid;

2-{4-[2-(2-biphenyl-4-yl-5-methyloxazol-4-yl)-ethyloxy]-2-propylphenoxy}-2-methyl-propionic acid;

2-{4-[2-(2-biphenyl-4-yl-5-methyloxazol-4-yl)-ethyloxy]-3-propylphenoxy}-ethanoic acid; and 2-{4-[2-(2-biphenyl-4-yl-5-methyloxazol-4-yl)-ethyloxy]-2-propylphenoxy}-ethanoic acid.

A preferred group of compounds of the present invention include the following compounds:

2-{4-[2-(2-biphenyl-4-yl-5-methyloxazol-4-yl)ethoxy]phenoxy}-2-methylpropionic acid;

2-{4-[2-(2-biphenyl-4-yl-5-methyloxazol-4-yl)-ethyloxy]-2-propylphenoxy}-2-methyl-propionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-propylphenoxy}-2-methylpropionic acid; and 2-{4-[2-(2-biphenyl-3-yl-5-methyloxazol-4-yl)ethoxy]phenoxy}-2-methylpropionic acid.

A more preferred compound of the present invention is 2-(4-{2-[2-(4-thiophen-2-yl-phenyl)-5-methyloxazol-4-yl]ethoxy}phenoxy)-2-methylpropionic acid.

Another group of preferred compounds of the present invention include the following:

2-{4-[2-(2-biphenyl-4-yl-5-methyloxazol-4-yl)ethoxy]naphthalen-1-yloxy}-2-methyl propionic acid; and 2-{4-[2-(2-biphenyl-4-yl-5-methyloxazol-4-yl)-ethoxy]-5,6,7,8-tetrahydronaphthalen-1-yloxy}-2-methyl propionic acid;

2-{4-[2-(2-biphenyl-3-yl-5-methyloxazol-4-yl)-ethoxy]-5,6,7,8-tetrahydronaphthalen-1-yloxy}-2-methyl propionic acid; and 2-{4-[2-(2-biphenyl-3-yl-5-methyloxazol-4-yl)ethoxy]naphthalen-1-yloxy}-2-methyl propionic acid.

Prodrugs are compounds of the present invention, which have chemically or metabolically cleavable groups and become by solvolysis or under physiological conditions the compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of formula I in a medium such as methanol with an acid or base esterification catalyst (e.g., NaOH, $H_2SO_4$). Ethyl ester prodrugs are prepared in similar fashion using ethanol in place of methanol.

Morpholinylethyl ester prodrugs may be prepared by reaction of the sodium salt of a compound of Structural Formula I (in a medium such as dimethylformamide) with 4-(2-chloroethyl)morphine hydrochloride (available from Aldrich Chemical Co., Milwaukee, Wis. USA, Item No. C4,220-3).

The term "pharmaceutically acceptable" means that the carrier, diluent, excipients and salt must be compatible with the other ingredients of the formulation, and not deleterious to the recipient thereof. Pharmaceutical formulations of the present invention are prepared by procedures known in the art using well known and readily available ingredients.

"Effective amount" means an amount of compound according to Structural Formula I, in any polymorphic form, or a salt thereof that is capable of producing its intended effect.

"Preventing" refers to reducing the likelihood that the recipient will incur or develop any of the pathological conditions described herein.

By virtue of its acidic moiety, a compound of Structural Formula I forms salts with pharmaceutically acceptable bases. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-p-phenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Certain compounds of Structural Formula I and their salts may also exist in the form of solvates, for example hydrates, and the present invention includes each solvate and mixtures thereof.

Certain compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has one or more chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may exist in more than one crystal form. Polymorphs of compounds represented by Structural Formula I form part of this invention and may be prepared by crystallization of a compound of Structural Formula I under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of Structural Formula I followed by gradual or fast cooling. The presence of polymorphs may be determined by solid probe nmr spectroscopy, ir spectroscopy, differential scanning calorimetry, powder X-ray diffraction or such other techniques.

The language a "therapeutically effective amount" or "pharmaceutically effective amount" is intended to include an amount which is sufficient to mediate a disease or condition and prevent its further progression or ameliorate the symptoms associated with the disease or condition. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR receptor, such as a PPARγ or PPARα receptor, which mediate a disease or condition. Conditions mediated by PPARα or PPARγ receptors include diabetes mellitus, cardiovascular disease, Syndrome X, obesity and gastrointestinal disease.

The compounds of Structural Formula I, and the pharmaceutically acceptable salts, solvates and hydrates thereof, have valuable pharmacological properties and can be used in pharmaceutical preparations containing the compound or pharmaceutically acceptable salts, esters or prodrugs thereof, in combination with a pharmaceutically acceptable carrier or diluent. They are useful as therapeutic substances in preventing or treating Syndrome X, diabetes mellitus and related endocrine and cardiovascular disorders and diseases in human or non-human animals. Suitable pharmaceutically acceptable carriers include inert solid fillers or diluents and sterile aqueous or organic solutions. The active compound will be present in such pharmaceutical compositions in amounts sufficient to provide the desired dosage amount in the range described herein. Techniques for formulation and administration of the compounds of the instant invention can be found in *Remington: the Science and Practice of Pharmacy,* 19$^{th}$ edition, Mack Publishing Co., Easton, Pa. (1995).

For oral administration, the compound or salts thereof can be combined with a suitable solid or liquid carrier or diluent to form capsules, tablets, pills, powders, syrups, solutions, suspensions and the like.

The tablets, pills, capsules, and the like may also contain a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The active compounds can also be administered intranasally as, for example, liquid drops or spray. For oral or nasal inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

For parental administration the compounds of the present invention, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, ethanol, polyol (e.g. glycerol, propylene glycol and liquid polyethylene glycol), propylene glycol and liquid polyethylene glycol), suitable mixtures thereof, and vegetable oils. The injectable solutions prepared in this manner can then be administered intravenously, intraperitoneally, subcutaneously, or intramuscularly, with intramuscular administration being preferred in humans.

The compounds may also be formulated in rectal compositions such as suppositories or retention enemas, e.g., containing conventional suppository bases such as cocoa butter or other glycerides.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

The effective dosage of active ingredient employed may vary depending on the particular compound employed, the mode of administration, the condition being treated and the severity of the condition being treated.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage formulation which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

A therapeutically effective amount of a compound of Structural Formula I can be used for the preparation of a medicament useful for treating Syndrome X, diabetes, treating obesity, lowering tryglyceride levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of Structural Formula I (1) reduces serum glucose levels of a patient, or more specifically HbA1c, typically by about 0.7%; (2) reduces the serum triglyceride levels of a patient, typically by about 20%; and/or (3) increases the serum HDL levels in a patient, preferably by about 30%.

Additionally, an effective amount of a compound of Structural Formula I and a therapeutically effective amount of one or more active agents selected from a group consisting of: antihyperlipidemic agent, plasma HDL-raising agents, antihypercholesterolemic agents, fibrates, vitamins, aspirin, insulin secretogogues, insulin and the like can be used together for the preparation of a medicament useful for the above-described treatments.

Preferably compounds of the invention or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Structural Formula I or salts thereof) in a unit dose of composition is a therapeutically effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Pharmaceutical formulations of the invention are prepared by combining (e.g., mixing) a therapeutically effective amount of a compound of the invention together with a pharmaceutically acceptable carrier or diluent. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of about 0.05 to about 5.0 mg/ml in a 4% dextrose/0.5% Na citrate aqueous solution.

Solid form formulations include powders, tablets and capsules. A solid carrier can be one or more substance which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Powders and tablets preferably contain from about 1 to about 99 weight percent of the active ingredient which is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

The following pharmaceutical formulations 1 through 8 are illustrative only and are not intended to limit the scope of the invention in any way. "Active Ingredient", refers to a compound according to Structural Formula I or salts thereof.

| Formulation 1 Hard gelatin capsules are prepared using the following ingredients: | |
|---|---|
| | Quantity (mg/capsule) |
| Active Ingredient | 250 |
| Starch, dried | 200 |
| Magnesium stearate | 10 |
| Total | 460 mg |

| Formulation 2 A tablet is prepared using the ingredients below: | |
|---|---|
| | Quantity (mg/tablet) |
| Active Ingredient | 250 |
| Cellulose, microcrystalline | 400 |
| Silicon dioxide, filmed | 10 |
| Stearic acid | 5 |
| Total | 665 mg |

The components are blended and compressed to form tablets each weighing 665 mg

| Formulation 3 |  |
|---|---|
| An aerosol solution is prepared containing the following components: | |
|  | Weight |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

| Formulation 4 |  |
|---|---|
| Tablets, each containing 60 mg of Active ingredient, are made as follows: | |
| Active Ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

| Formulation 5 |  |
|---|---|
| Capsules, each containing 80 mg of Active Ingredient, are made as follows: | |
| Active Ingredient | 80 mg |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

| Formulation 6 |  |
|---|---|
| Suppositories, each containing 225 mg of Active Ingredient, are made as follows: | |
| Active Ingredient | 225 mg |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

| Formulation 7 |  |
|---|---|
| Suspensions, each containing 50 mg of Active Ingredient per 5 ml dose, are made as follows: | |
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

| Formulation 8 |  |
|---|---|
| An intravenous formulation may be prepared as follows: | |
| Active Ingredient | 100 mg |
| Isotonic saline | 1,000 ml |

The solution of the above materials generally is administered intravenously to a subject at a rate of 1 ml per minute.

SYNTHESIS

Compounds in which the five membered ring is an oxazole have been synthesized by four routes. Two of the synthetic routes proceed through a 2-(bromophenyl)-4-(2-hydroxyethyl)-5-substituted-oxazole intermediate (Structural Formula XVII), the synthesis of which is depicted in Scheme I.

The first step of the synthesis of the 2-(bromophenyl)-4-(2-hydroxyethyl)-5-substituted-oxazole intermediate is a condensation of a dionemonooxime represented by Structural Formula XI with a bromobenzaldehyde represented by Structural Formula XII in the presence of an acid such as aqueous concentrated hydrochloric acid or, preferably, acetic acid which is saturated with hydrogen chloride gas. Typically, hydrogen chloride is bubbled through a solution of the dionemonooxime and the bromobenzaldehyde in acetic acid, which is held at a constant temperature of about −20° C. to about 20° C. for about 15 minutes to about 1 hour. The product of the condensation is an oxazole n-oxide represented by Structural Formula XIII.

The oxazole n-oxide is then treated with phosphorous oxychloride in an inert solvent such as dichloromethane or chloroform to form a 2-(bromophenyl)-4-chloromethyl-5-substituted-oxazole represented by Structural Formula XIV. The reaction typically is carried out at the reflux temperature of the solvent used and is complete in about 15 minutes to about 1 hour.

The 2-(bromophenyl)-4-chloromethyl-5-substituted-oxazole is then treated with a cyanide and an iodide salt to form a 2-(bromophenyl)-4-cyanomethyl-5-substituted-oxazole represented by Structural Formula XV. The reaction is typically carried out in a polar, aprotic solvent such as dimethylformamide at a temperature of about 30° C. to about 120° C. for about 1 hour to about 6 hours. Preferably, the cyanide and iodide salts are potassium cyanide and potassium iodide.

The cyano group of the a 2-(bromophenyl)-4-cyanomethyl-5-substituted-oxazole is converted to a carboxylic acid group by treatment with a alkali metal hydroxide to form a 2-(bromophenyl)-4-carboxymethyl-5-substituted-oxazole represented by Structural Formula XVI. The reaction is generally carried out in an aqueous solution at about 80° C. to about 100° C. The concentration of the alkali metal hydroxide in the aqueous solution is typically about 25% to about 85% (weight/volume). Preferably, the alkali metal hydroxide is potassium hydroxide.

The 2-(bromophenyl)-4-carboxymethyl-5-substituted-oxazole is then treated with a carboxylic acid reducing agent, such as borane or lithium aluminum hydride, to form the 2-(bromophenyl)-4-(2-hydroxyethyl)-5-substituted-oxazole intermediate represented by Structural Formula XVII. The reaction is typically carried out under anhydrous conditions in an ether solvent such as tetrahydrofuran (THF), dioxane, or ethyl ether. When borane is the reducing agent used, it typically forms a complex with the ether solvent such as a $BH_3$-THF complex. A solution having a concentration of about 0.5 M to about 1.5 M borane complex in the ether solvent is added dropwise to a solution of 0.1 M to 1.3 M of the 2-(bromophenyl)-4-carboxymethyl-5-substituted-oxazole in the ether solvent. The reaction temperature is about 20° C. to about 40° C. Typically, the reaction is complete in about 1 hour to about 5 hours.

Scheme I:
General synthesis of 2-(bromophenyl)-4-(2-hydroxyethyl)-5-substituted oxazoles represented by Structural Formula XVII.

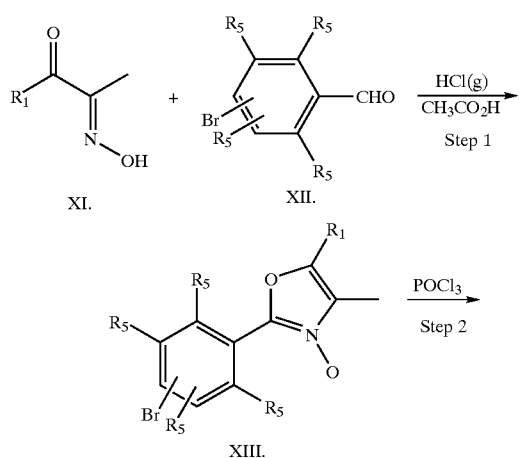

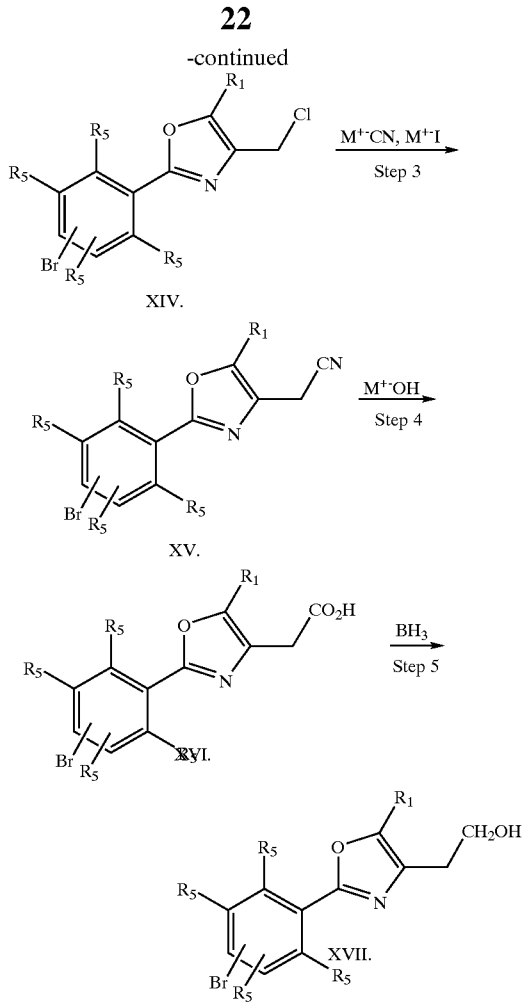

In a first synthetic route to prepare compounds represented by Structural Formula I in which the five membered ring is an oxazole ring (see Scheme II), the key intermediate represented by Structural Formula XVII can be converted into a 2-(bromophenyl-5-substituted-oxazol-4-yl)ethyl sulfonyl ester represented by Structural Formula XVIII by treatment with a sulfonyl anhydride or a sulfonyl halide such as tosyl anhydride, mesyl anhydride, tosyl chloride or mesyl chloride in the presence of a base (Scheme II, step 1). The reaction is typically carried out in an aprotic solvent such as methylene chloride in the presence of an aprotic base such as pyridine or a nucleophilic catalyst such as N,N-dimethylaminopyridine (DMAP). The reaction is complete in about 0.5 hours to about 5 hours.

The 2-(bromophenyl-5-substituted-oxazol-4-yl)ethyl sulfonyl ester is then reacted with a phenol represented by Structural Formula XIX in the presence of cesium carbonate to form a 2-(3-{2-[2-(bromophenyl)-5-substituted-oxazol-4-yl]ethoxy}-2-phenoxy)-ethanoic acid ester represented by Structural Formula XX (Scheme II, step 2). In Structural Formula XIX, $R_2$, $R_3$ and $R_4$ are as previously defined for Structural Formula I, and $R_{20}$ is a C1–C4 alkyl. The reaction is typically carried out in a polar, aprotic solvent such as dimethylformamide at about 40° C. to about 70° C. and is allowed to proceed for about 10 hours to about 24 hours. The reactants (i.e., the compounds represented by Structural Formulas XVIII and XIX) are present in about equal molar amounts or with about 0.1 M to about 0.5 M excess of the sulfonyl ester compound represented by Structural Formula XVIII. The cesium carbonate is present in about one molar equivalent to about 1.5 molar equivalents with respect to the sulfonyl ester.

The 2-(3-{2-[2-(bromophenyl)-5-substituted-oxazol-4-yl]ethoxy}-2-phenoxy)-ethanoic acid ester is then treated with an aryl boronic acid in the presence of triphenylphosphine, palladium acetate and sodium carbonate to form a 2-(3-{2-[2-(arylphenyl)-5-substituted-oxazol-4-yl]ethoxy}-2-phenoxy)-ethanoic acid ester represented by Structural Formula XXI (Scheme II, step 3). In Structural Formula XXI, Ar is a substituted or unsubstituted aryl or a substituted or unsubstituted heteroaryl. Typically, the 2-(3-{2-[2-(bromophenyl)-5-substituted-oxazol-4-yl]ethoxy}-2-phenoxy)-ethanoic acid ester (compound XX) and the arylboronic acid are present in equal molar amounts, or preferable about 0.1 to 0.5 molar excess of the arylboronic acid. The triphenylphosphine is present in about 1.5 to about 2 equivalents, the palladium acetate is present in about 0.1 to about 0.01 equivalents and the sodium carbonate is present in about 1 equivalent to about 1.5 equivalents with respect to compound XX. The reaction is generally carried out in an alcoholic solvent at about 50° C. to about 100° C. and is allowed to proceed for about 1 hour to about 5 hours.

Alternatively, the 2-(3-{2-[2-(bromophenyl)-5-substituted-oxazol-4-yl]ethoxy}-2-phenoxy)-ethanoic acid ester can be treated with an aryl tributyl tin in the presence of $Pd(PPh_3)_4$ ("Ph"0 is phenyl) to form 2-(3-{2-[2-(arylphenyl)-5-substituted-oxazol-4-yl]ethoxy}-2-phenoxy)-ethanoic acid ester.

The 2-(3-{2-[2-(arylphenyl)-5-substituted-oxazol-4-yl]ethoxy}-2-phenoxy)-ethanoic acid ester represented by Structural Formula XXI can be converted to a 2-(3-{2-[2-(arylphenyl)-5-substituted-oxazol-4-yl]ethoxy}-2-phenoxy)-ethanoic acid by treating it with a solution of an alkali metal hydroxide for about 6 hours to about 24 hours. Preferably, the alkali metal hydroxide is sodium hydroxide.

The 2-(3-{2-[2-(arylphenyl)-5-substituted-oxazol-4-yl]ethoxy}-2-phenoxy)-ethanoic acid can be converted to an aminoalkyl 2-(3-{2-[2-(arylphenyl)-5-substituted-oxazol-4-yl]ethoxy}-2-phenoxy)-ethanoic acid ester by treatment of the acid with oxalyl chloride to form an anhydride. The anhydride is then reacted with an aminoalkanol in the presence of an aprotic base to form an aminoalkyl 2-(3-{2-[2-(arylphenyl)-5-substituted-oxazol-4-yl]ethoxy}-2-phenoxy)-ethanoic acid ester.

Scheme III:

Method 1 for synthesizing compounds represented by Structural Formula XXI.

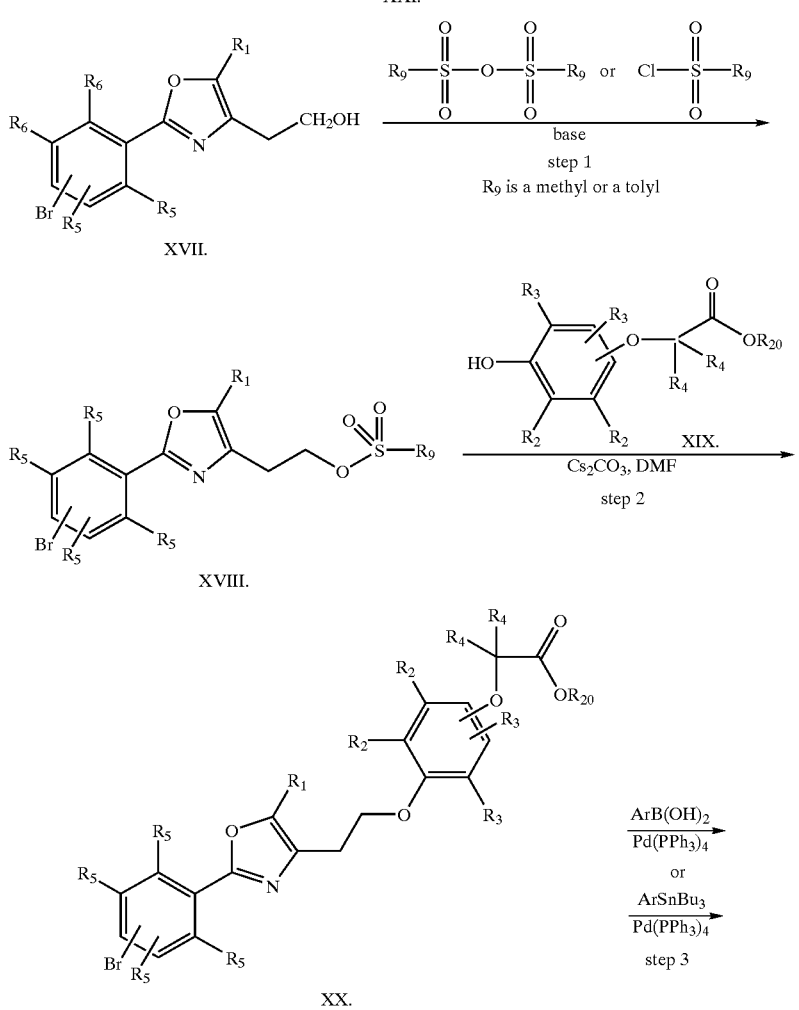

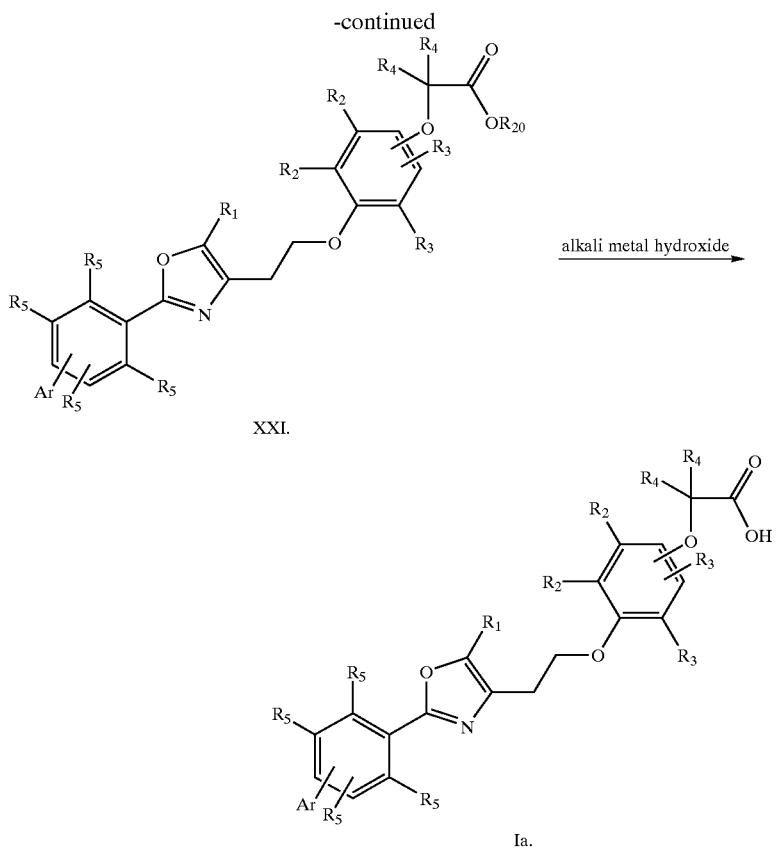

XXI.

↓ alkali metal hydroxide

Ia.

A second method of preparing the compounds represented by Structural Formula I which have an oxazole five membered ring is depicted in Scheme III. The 2-(bromophenyl)-4-(2-hydroxyethyl)-5-substituted oxazole represented by Structural Formula XVII is treated an arylboronic acid in the presence of triphenylphosphine, palladium acetate and sodium carbonate to form a 2-(arylphenyl)-4-(2-hydroxyethyl)-5-substituted oxazole represented by Structural Formula XXII. The reaction conditions are the same as those described for step 3 in Scheme II.

The 2-(arylphenyl)-4-(2-hydroxyethyl)-5-substituted oxazole is then treated with a sulfonyl anhydride or a sulfonyl chloride in the presence of a base under conditions as described for step 1 of Scheme II to form a 2-(arylphenyl-5-substituted-oxazol-4-yl)ethyl sulfonyl ester represented by Structural Formula XXIII.

The 2-(arylphenyl-5-substituted-oxazol-4-yl)ethyl sulfonyl ester is then reacted with a phenol represented by Structural Formula XIX in the presence of cesium carbonate under conditions as described for step 2 of Scheme II to form a 2-(3-{2-[2-(arylphenyl)-5-substituted-oxazol-4-yl]ethoxy}-2-phenoxy)-ethanoic acid ester represented by Structural Formula XXI.

Scheme III:
Method 2 for synthesizing compounds represented by Structural Formula XXI.

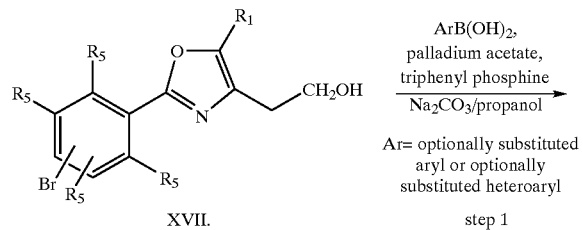

step 1

-continued

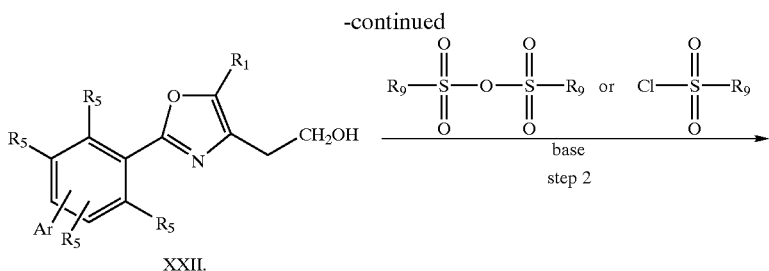

XXII.

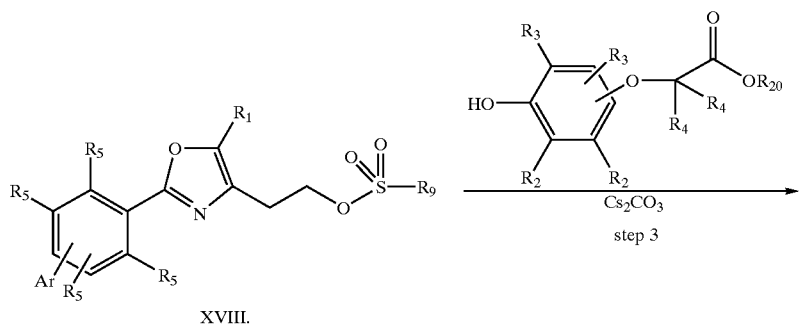

XVIII.

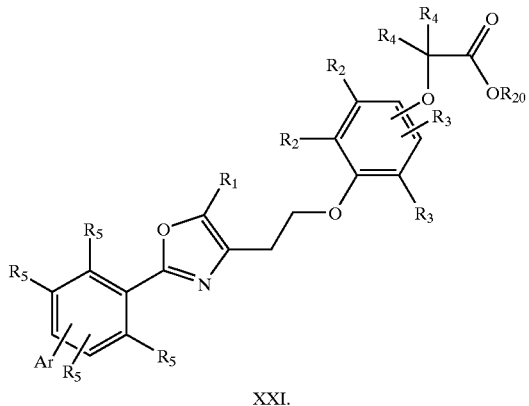

XXI.

The compound represented by Structural Formula XIX can be prepared by the method depicted in Scheme IV. In this method, the benzyloxyphenol represented by Structural Formula XXIV is reacted with a α-haloester represented by Structural Formula XXV in the presence of cesium carbonate to form a compound represented by Structural Formula XXVI. The reaction is carried out under anhydrous conditions in a polar, aprotic solvent such as dimethylformamide at about 40° C. to about 80° C. The α-haloester and the cesium carbonate are present in about 1.5 to about 2.5 molar equivalents with respect to the benzyloxyphenol. Typically, the reaction is complete in about 10 hours to about 24 hours.

The compound represented by Structural Formula XXVI is then treated to remove the benzyl protecting group to form the phenol represented by Structural Formula XIX. Methods of removing a benzyl protecting group from a phenol can be found in Green, et al., *Protective Groups in Organic Synthesis*, 2$^{nd}$ edition, (1991), John Wiley & Sons, Inc., New York, pages 156–158, the entire teachings of which are incorporated herein by reference. A preferred method of removing a benzyl protecting group is by treating the compound represented by Structural Formula XXVI with hydrogen in the presence of palladium on carbon (Pd—C) catalyst.

Scheme IV:

Method of synthesizing compounds represented by Structural Formula XIX.

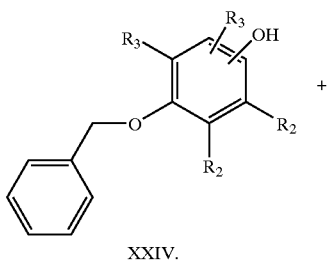

XXIV.

+

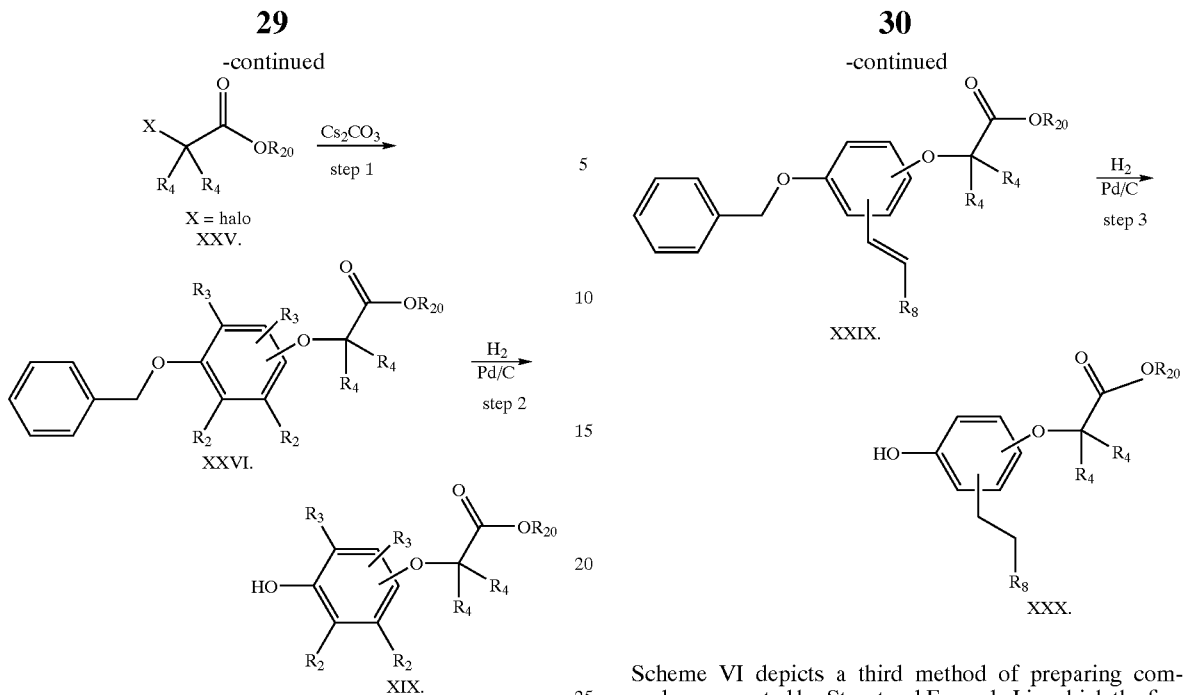

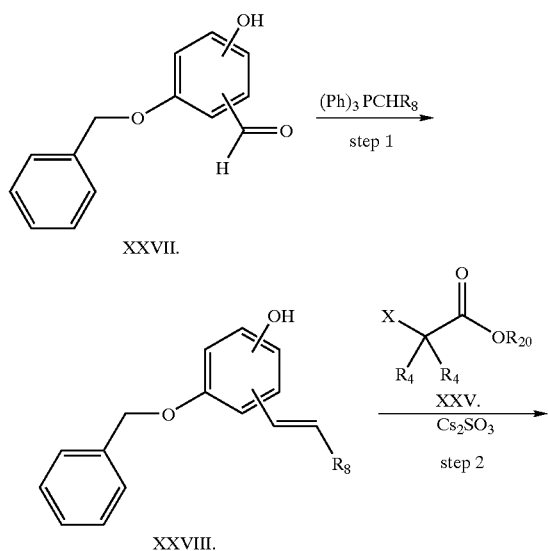

When it is desired to prepare a compound represented by Structural Formula XIX in which at least one $R_2$ or $R_3$ group is other than hydrogen, the compound can be prepared by the method depicted in Scheme V. A benzyloxy-hydroxybenzaldehyde is treated with a Wittig reagent to form an alkenyl-benzyloxyphenol represented by Structural Formula XXVIII. $R_8$ of the Wittig reagent is a C1–C5 alkyl, an aryl-C1–C5-alkyl, a cycloalkyl-C1–C3-alkyl, or a cycloalkyl. Conditions for carrying out a Wittig reaction are known to those skilled in the art. The alkenyl-benzyloxyphenol is then reacted as described in step 1 and step 2 of Scheme IV to form the compound represented by Structural Formula XXX.

Scheme VI depicts a third method of preparing compounds represented by Structural Formula I in which the five membered ring is an oxazole and the oxazole ring is substituted with a trifluoromethyl group. In step 1, the amine group of a compound represented by Structural Formula XXXI is reacted benzaldehyde in the presence of sodium triacetoxyborohydride to form the compound represented by Structural Formula XXXII. The reaction is carried out in a non-polar solvent at about 20° C. to about 30° C. and is typically complete in about 3 hours to about 8 hours. In Structural Formula XXXI, n is as defined for Structural Formula I and $R_{13}$ and $R_{14}$ are each, independently, alkyl, aryl, aryl-C1–C6-alkyl or cycloalkyl-C1–C6-alkyl.

The compound represented by Structural Formula XXXII is then reacted with an aryl acid chloride represented by Structural Formula XXXIII in the presence of a non-protic base such as triethylamine or diisopropylethylamine. The reaction is typically carried out in a non-polar solvent such as methylene chloride and is complete in about 8 hours to about 16 hours. The reaction product is a compound represented by Structural Formula XXXIV.

The ester group α to the amino group is selectively removed by treating the compound represented by Structural Formula XXXIV with sodium hydroxide to form a compound represented by Structural Formula XXXV. The reaction is typically carried out by dissolving the compound represented by Structural Formula XXXIV in an ether solvent such as dioxane, then adding a 5 N aqueous solution of sodium hydroxide. The mixture is then heated to about 50° C. to about 70° C. for about 5 hours to about 9 hours. When the reaction is complete the mixture is quenched by adding 1.0 N HCl.

The oxazole ring is then formed by treating the compound represented by Structural Formula XXXV with trifluoroacetic anhydride to form a compound represented by Structural Formula XXXVI. The reaction is carried out by dissolving the compound represented by Structural Formula XXXV in an inert, non-polar solvent such as toluene and adding pyridine. The reaction mixture is then chilled to about 10° C. and about 3 equivalents of trifluoroacetic anhydride is added. The reaction is then allowed to come to room temperature and is allowed to proceed for about 10 hours to about 16 hours, then is heated for about 8 hours to about 10 hours.

The carboxylic acid product can optionally be converted into the methyl ester by treatment with diazomethane. Example 54 was prepared by this method.
Scheme VI:
Method of preparing compounds represented by Structural Formula XXXVI.
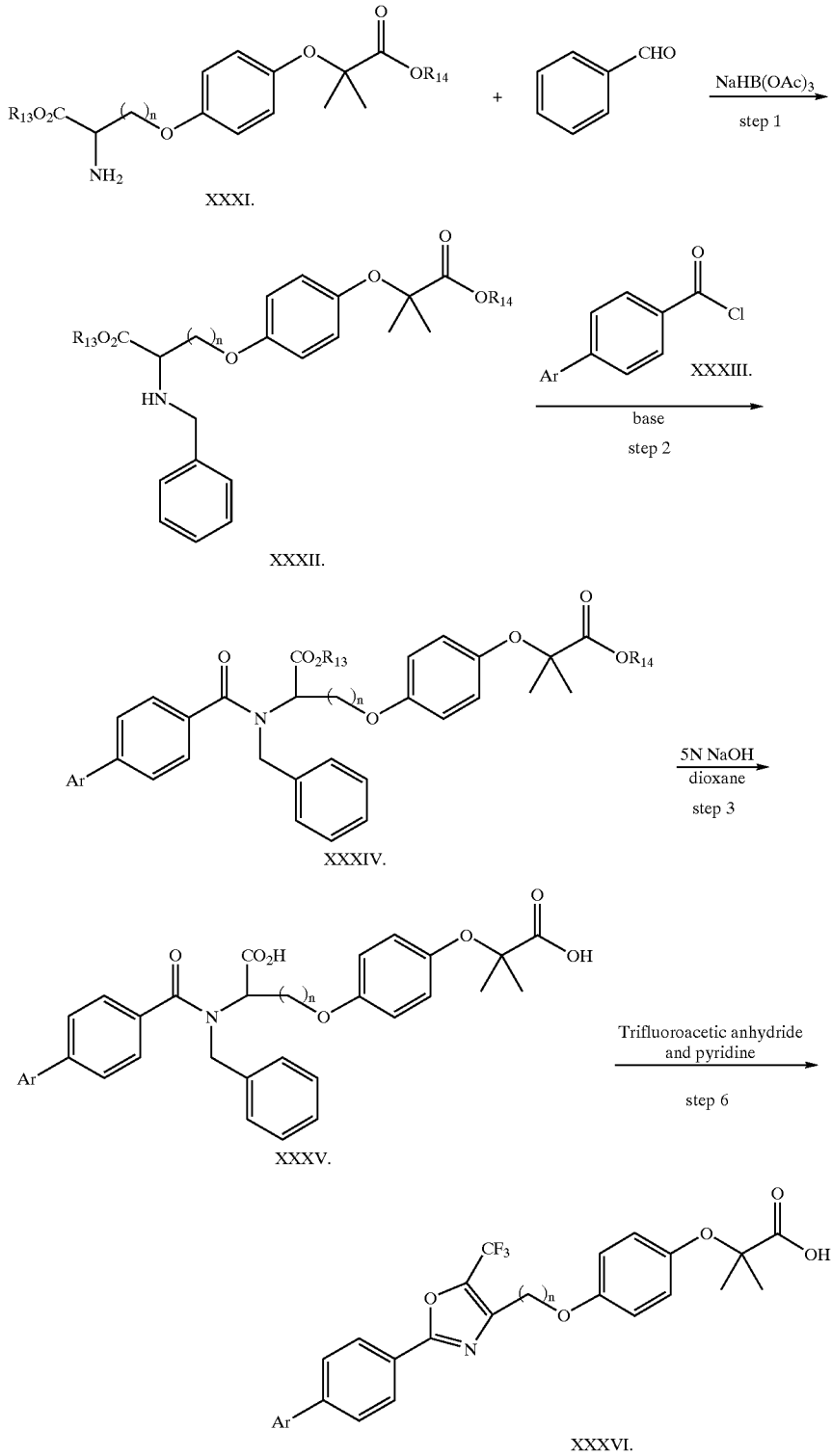

A fourth method of forming a compound represented by Structural Formula I in which the five membered ring is an oxazole ring is depicted in Scheme VII. The starting material for this synthesis is a compound represented by Structural Formula XXXVII which can be prepared by hydrolyzing the ester groups of the compound represented by Structural Formula XXXIV and removing the benzyl protecting group. Methods of hydrolyzing esters can be found in Greene, et al., *Protective Groups in Organic Synthesis*, 2nd edition, (1991), John Willey & Sons, New York, page 229–231, the entire teachings of which are incorporated herein by reference. Methods for removing a benzyl protecting group from an amine can be found in Id., page 364–366, the entire teachings of which are incorporated herein by reference.

The compound represented by Structural Formula XXXVII is reacted with an anhydride to form a compound represented by Structural Formula XXXVIII. $R_9$ in the anhydride compound is a C1–C4 alkyl or a phenyl group. The reaction is typically carried out in pyridine or a mixture of an aprotic base and an inert solvent such as dioxane or THF.

The compound represented by Structural Formula XXXVIII is then converted to the methyl ester represented by Structural Formula XXXIX. One method to form a methyl ester from a carboxylic acid is to treat the carboxylic acid with diazomethane. Other methods of forming a methyl ester from a carboxylic acid can be found in Id., pages 231–234, the entire teachings of which are incorporated herein by reference.

The oxazole ring is formed by treating the compound represented by Structural Formula XXXIX with phosphorous oxychloride to form the compound represented by Structural Formula XL. The reaction is carried out in an aprotic, polar solvent such as dimethylformamide at about 70° C. to about 110° C. The reaction is typically complete in about 15 minutes to about 1 hour.

The ester can be hydrolyzed to an acid by treatment with an alcoholic solution of sodium hydroxide. The compounds of Examples 52 and 53 were prepared using this method.

Scheme VII:

Method of preparing compounds represented by Structural Formula XL.

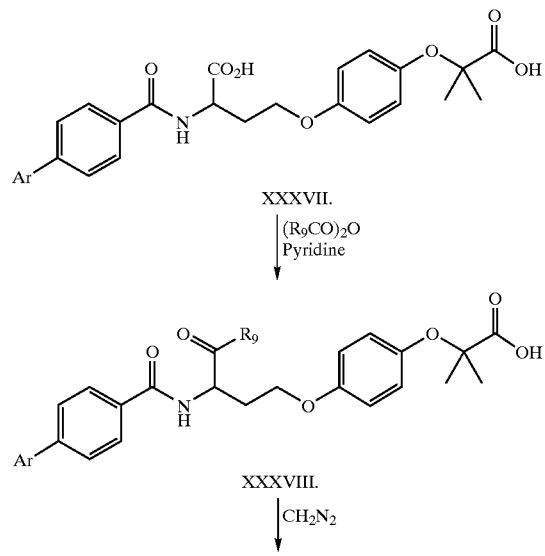

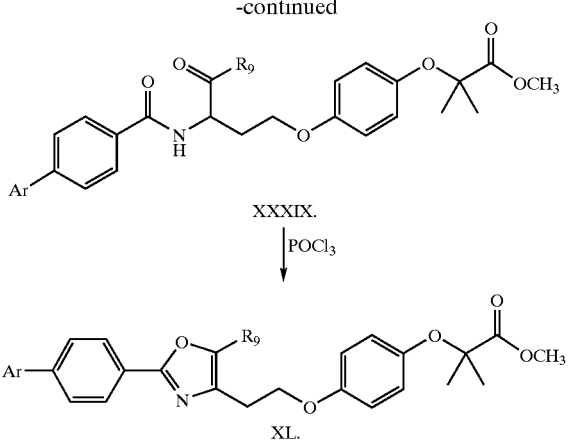

Compounds of the present invention in which the five membered ring is a thiazole were synthesized according to the method described in *Journal of Medicinal Chemistry*, (1998), 41:5037. Examples 45 and 46 further describe this method.

EXAMPLES

General

Infrared spectra were recorded on a Perkin Elmer 781 spectrometer. $^1$H NMR spectra were recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR were recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses were performed by Eli Lilly & Company Microanalytical Laboratory. High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

Example 1

2-{4-[2-(2-Biphenyl-4-yl-5-methyloxazol-4-yl)ethoxy]phenoxy}-2-methylpropionic acid

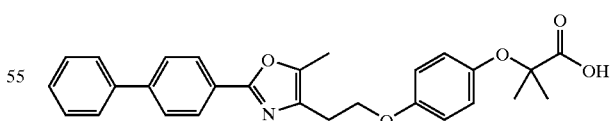

A. 4,5-Dimethyl-2-(4-bromophenyl)-oxazole oxide

A solution of 2,3-butanedione monooxime (50 g, 0.49 mol) and 4-bromo-benzaldehyde (101 g, 0.54 mol) in acetic acid (500 mL) was cooled to 0° C. and then gaseous HCl was bubbled through the solution for 35 min while the reaction was stirred in an ice bath. Diethyl ether (500 mL) was then added to the reaction to precipitate the product and the resultant slurry stirred 45 min at 0° C. before being filtered. The solids were rinsed with Et$_2$O (50 mL), taken up in water (1 L) and conc. NH$_4$OH (60 mL) added to the slurry. This mixture was extracted with CHCl$_3$, the organic layer was dried (MgSO$_4$), and the solvent removed in vacuo to give 97.4 g (74%) of 4,5-dimethyl-2-(4-bromophenyl)-oxazole oxide as a white solid. The compound should be used directly within 24–48 h: $^1$H NMR (500 MHz, CDCl$_3$) 8.34 (d, J=9.0 Hz, 2H), 7.61 (d, J=9.0 Hz, 2H), 2.35 (s, 3H), 2.20 (s, 3H); $^{13}$C (125 MHz, CDCl$_3$) 142.1, 131.9, 129.5, 126.3, 124.1, 122.2, 11.1, 6.2; IR (KBr) 1685, 1529, 1418, 1377, 1233, 1165 cm$^{-1}$; UV (EtOH)$_{max}$ 307 nm (24371); HRMS (TOF) m/z calculated for C$_{11}$H$_{11}$$^{79}$BrNO$_2$: 267.997, found 267.9951.

B. 2-(4-Bromophenyl-4-(chloromethyl)-5-methyloxazole

A solution of 4,5-dimethyl-2-(4-bromophenyl)-oxazole oxide (96.6 g, 0.36 mol) in CHCl$_3$ (0.90 L) was treated dropwise with phosphorous oxychloride (61.1 g, 0.40 mol) allowing the reaction to exotherm and then was stirred at reflux for 30 min. The reaction was then cooled to room temperature and washed with water (2×1 L). The combined aqueous washes were back extracted with CH$_2$Cl$_2$ (2×400 mL). The organic layers were dried (MgSO$_4$), and the solvent removed in vacuo to give crude product that was recrystallized from hot hexanes (300 mL), decanting the hot supernate away from a dark oily material. The remaining dark oil was agitated in additional hot hexanes (200 mL) and the combined supernates were cooled to 0° C. to crystallize the product which was isolated by filtration to give 74.2 g (72%) of 2-(4-bromophenyl-4-(chloromethyl)-5-methyloxazole as a lime-green powder: Rf=0.39 in 20% ethyl acetate/hexanes; $^1$H NMR (500 MHz, CDCl$_3$) 7.88–7.86 (m, 2H), 7.59–7.56 (m, 2H), 4.54 (s, 2H), 2.42 (s, 3H); $^{13}$C (125 MHz, CDCl$_3$) 159.2, 146.9, 133.2, 132.0, 127.6, 126.1, 124.7, 37.1, 11.5; IR (KBr) 2970, 1633, 1599, 1481, 1401, 1258, 1117, 1008 cm$^{-1}$; UV (EtOH)$_{max}$ 281 nm (21349); HRMS (FAB) m/z calculated for C$_{11}$H$_{10}$$^{79}$BrClNO: 285.9634, found 285.9641; Anal. Calculated for C$_{11}$H$_9$ClBrNO: C, 46.11; H, 3.17; N, 4.89; Cl, 12.37; Br, 27.88. Found C, 46.28; H, 3.07; N, 4.81; Cl, 12.36; Br, 27.88.

C. 2-(4-Bromophenyl)-5-methyl-4-oxazoleacetic acid

To a solution of 2-(4-bromophenyl-4-(chloromethyl)-5-methyloxazole (64.8 g, 0.23 mol) in DMF (400 mL) was added powdered potassium cyanide (22.1 g, 0.34 mol) and potassium iodide (28.6 g, 0.17 mol) and the resultant mixture was heated to 85° C. for 3.5 h. The reaction mixture was then cooled to room temperature. Potassium carbonate (5 g) was dissolved in water (800 mL) and added dropwise to the reaction to precipitate 2-(4-bromophenyl-4-(cyanomethyl)-5-methyloxazole (stir vigorously 15 min following addition) which was isolated by filtration and washed with water (2×400 mL). The crude 2-(4-bromophenyl-4-(cyanomethyl)-5-methyloxazole was carried on as is in the next step without purification. $^1$H NMR (300 MHz, CDCl$_3$) 7.85 (m, 2H), 7.58 (m, 2H), 3.64 (s, 3H), 2.43 (s, 3H).

The crude 2-(4-bromophenyl-4-(cyanomethyl)-5-methyloxazole (assume 0.22 mol) was combined with 2-methoxyethanol (630 mL) and 85% solid KOH (74.6 g, 1.33 mol) in water (360 mL) was added to the reaction. The mixture was heated to reflux for 3 h, cooled, quenched with 2 M HCl (500 mL), and extracted with CH$_2$Cl$_2$. The organic layer was dried (MgSO$_4$), and the solvent removed in vacuo, using toluene to azeotropically remove residual 2-methoxyethanol. The crude product (57.3 g) was recrystallized from toluene (450 mL) to give 39.8 g (60%) of 2-(4-bromophenyl)-5-methyl-4-oxazoleacetic acid as an off-white powder: Rf=0.23 in 10% MeOH/CH$_2$Cl$_2$; $^1$H NMR (500 MHz, CDCl$_3$) 9.00 (br s, 1H), 7.85–7.83 (m, 2H), 7.58–7.56 (m, 2H), 3.62 (s, 3H), 2.36 (s, 3H); $^{13}$C (125 MHz, CDCl$_3$) 173.8, 159.0, 146.2, 132.0, 129.1, 127.6, 125.9, 124.7, 31.5, 10.2; IR (CHCl$_3$) 2923, 1699, 1641, 1481, 1428, 1306, 1234, 1010, 829, 727 cm$^{-1}$; UV (EtOH) $_{max}$ 288 nm (19626).

D. 2-(4-Bromophenyl)-5-methyl-4-oxazoleethanol

A solution of 2-(4-bromophenyl)-5-methyl-4-oxazoleacetic acid (39.1 g, 0.13 mol) in dry THF (175 mL) was treated dropwise with borane-THF complex (227 mL of a 1.0 M solution in THF, 1.3 mol) over 2 h (reaction temperature to 35° C.). After stirring 2 h at room temperature under N$_2$, the reaction was quenched with slow addition of methanol (60 mL) and stirred overnight at room temperature. The reaction was diluted with 1 N NaOH (50 mL) and extracted with CH$_2$Cl$_2$ (2×200 mL). The organic layer was washed with H$_2$O (3×100 mL), dried (MgSO$_4$), and the solvent removed in vacuo to give 38.7 g of crude product that was recrystallized from toluene (200 mL, wash solid with cold hexanes) to give 26.9 g (72%) of 2-(4-bromophenyl)-5-methyl-4-oxazoleethanolas a white powder: Rf=0.37 in 10% MeOH/CH$_2$Cl$_2$; $^1$H NMR (500 MHz, CDCl$_3$) 7.84–7.82 (m, 2H), 7.57–7.55 (m, 2H), 3.91 (q, J=5.5 Hz, 2H), 3.14 (t, J=6 Hz, OH), 2.72 (t, J=5.5 Hz, 2H), 2.33 (s, 3H); $^{13}$C (125 MHz, CDCl$_3$) 158.7, 144.5 134.2, 131.9, 127.4, 126.4, 124.3, 61.8, 28.1, 10.1; IR (KBr) 3293, 2948, 1642, 15985, 1480, 1472, 1401, 1053, 1003, 836, 734 cm$^{-1}$; UV (EtOH)$_{max}$ 290 nm (20860); Anal. Calculated for C$_{12}$H$_{12}$BrNO$_2$: C, 51.09; H, 4.29; N, 4.96; Br, 28.32. Found C, 51.31; H, 4.06; N, 4.90; Br, 28.19.

E. 2-(Biphenyl-4-yl-5-methyl-oxazol-4-yl)ethanol 2-(4-Bromophenyl)-5-methyl-4-oxazoleethanol (10.0 g, 35.0 mmol) and phenylboronic acid (4.5 g, 38.0 mmol) were dissolved in n-propanol (120 mL) before adding triphenylphosphine (165.2 mg, 0.63 mmol), palladium acetate (46 mg, 2.1 mmol), and Na$_2$CO$_3$ (4.5 g, 42 mmol dissolved in 30 mL distilled H$_2$O). The solution was heated to reflux and stirred for 1.5 h. After cooling to ambient temperature, the mixture was concentrated under reduced pressure and then partitioned between CH$_2$Cl$_2$ (100 mL) and 1N NaOH (100 mL). The aqueous phase was extracted with CH$_2$Cl$_2$ (2×50 mL) and the combined organic phases were dried (MgSO$_4$) and concentrated under reduced pressure to provide 2-(4-biphenyl)-5-methyl-4-oxazoleethanol (9.5 g, 97% yield) as a white solid which was used directly without further purification. $^1$H NMR (500 MHz, CDCl$_3$) 8.01 (d, 2H), 7.77–7.50 (m, 4H), 7.46 (m, 2H), 7.38 (m, 1H), 3.91 (q, J=5.5 Hz, 2H), 3.18 (t, J=6 Hz, OH), 2.72 (t, J=5.5 Hz, 2H), 2.33 (s, 3H).

F. Toluene-4-sulfonic acid 2-(2-biphenyl-4-yl-5-methyl-oxazol-4-yl)ethyl ester

To a solution of 2-(biphenyl-4-yl-5-methyl-oxazol-4-yl)ethanol (15.8 g, 56.6 mmol) in CH$_2$Cl$_2$ (250 mL) at room temperature under N$_2$ was added pyridine (14.7 g, 185 mmol, 15.0 mL) and DMAP (2.03 g, 16.6 mmol) followed by portionwise addition of tosyl anhydride (24.57 g, 75.2 mmol). The reaction exothermed to 32° C. and was stirred 30 min before additional 2.3 of tosyl anhydride was added. The mixture was diluted with 100 mL of CH$_2$Cl$_2$ and stirred vigorously with 1N HCl (150 mL) for 15 min, and then the organic phase was dried (MgSO$_4$) and filtered through a pad of silica gel (100 mL, packed with CH$_2$Cl$_2$). After rinsing the silica gel with ethyl acetate (100 mL) the solution was concentrated to give toluene-4-sulfonic acid 2-(2-biphenyl-4-yl-5-methyl-oxazol-4-yl)ethyl ester as a white solid (23.3 g, 95%) which was used without further purification: Rf=0.51 in 60% ethyl acetate/hexanes; $^1$H NMR (400 MHz, CDCl$_3$) 7.97 (d, 2H), 7.70 (d, 2H), 7.66 (t, 2H), 7.65 (d, 2H), 7.51 (t, 1H), 7.42 (d, 2H), 7.24 (d, 2H), 4.37 (t, 2H), 2.88 (t, 2H), 2.37 (s, 3H), 2.26 (s, 3H).

G. 2-Methyl-2-{4-[2-(5-methyl-2-biphenyl-4-yl-oxazol-4-yl)ethoxy]phenoxy}propionic acid ethyl ester A mixture of toluene-4-sulfonic acid 2-(2-biphenyl-4-yl--methyl-oxazol-4-yl)ethyl ester (14.9 g, 34.3 mmol), 2-(4-hydroxyphenoxy)-2-methyl propionic acid ethyl ester (American Home Products U.S. Pat. No. 3,795,691 (6.15 g, 27.4 mmol) and $Cs_2CO_3$ (12.0 g, 36.8 mmol) was heated at 55° C. in DMF (110 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (600 mL $SiO_2$, 10% ethyl acetate/hexanes to 20% ethyl acetate/hexanes) to provide 2-methyl-2-{4-[2-(5-methyl-2-biphenyl-4-yl-oxazol-4 -yl)ethoxy]phenoxy}propionic acid ethyl ester (6.25 g, 47%) as a colorless, viscous oil: Rf=0.48 in 35% ethyl acetate/hexanes; $^1$H NMR (500 MHz, $CDCl_3$) δ8.05–8.03 (m, 2H), 7.67–7.64 (m, 4H), 7.46 (m, 2H), 7.38 (m, 1H), 6.83–6.77 (m, 4H), 4.22 (q, J=9.2 Hz, 2H), 4.18 (t, J=8.8 Hz, 2H), 2.97 (t, J=8.8 Hz, 2H), 2.37 (s, 3H), 1.52 (s, 6H), 1.27 (t, J=9.2 Hz, 3H).

H. 2-Methyl-2-{4-[2-(5-methyl-2-biphenyl-4-yl-oxazol-4-yl)ethoxy]phenoxy}propionic acid 2-Methyl-2-{4-[2-(5-methyl-2-biphenyl-4-yl-oxazol-4-yl)ethoxy]phenoxy}propionic acid ethyl ester (12.0 g, 24.7 mmol) was dissolved in methanol (200 mL) and 2N NaOH (150 mL) was added. The resulting cloudy solution became clear after 30 min and the reaction was stirred vigorously overnight. The solution was concentrated under reduced pressure, diluted with $H_2O$ (100 mL) and acidified to pH=1 with 5N HCl. The mixture was extracted with ethyl acetate (2×200 mL), dried ($MgSO_4$), and concentrated under reduced pressure to provide an oil. The oil (8.23 g) was recrystallized from ethyl acetate (24 mL) and hexanes (56 mL) to afford 2-methyl-2-{4-[2-(5-methyl-2-biphenyl-4-yl-oxazol-4-yl)ethoxy]phenoxy}propionic acid (7.57 g, 67%) as colorless needles after drying at 50° C. under vacuum for 6 h: Rf=0.14 in 35% ethyl acetate/hexanes; mp 123–124° C.; $^1$H NMR (400 MHz, $CDCl_3$) δ8.05 (d, J=8.0 Hz, 2H), 7.67 (d, J=8.0 Hz, 2H), 7.66–7.63 (m, 2H), 7.46 (t, J=7.6 Hz, 2H), 7.38 (t, J=7.6 Hz, 1H), 6.91–6.79 (m, 4H), 4.21 (t, J=6.4 Hz, 2H), 3.01 (t, J=6.4 Hz, 2H), 2.40 (s, 3H), 1.53 (s, 6H); MS m/e calculated. for $C_{28}H_{28}NO_5$ (M$^+$+1) 458.2, found 458.2.

Figure 2:
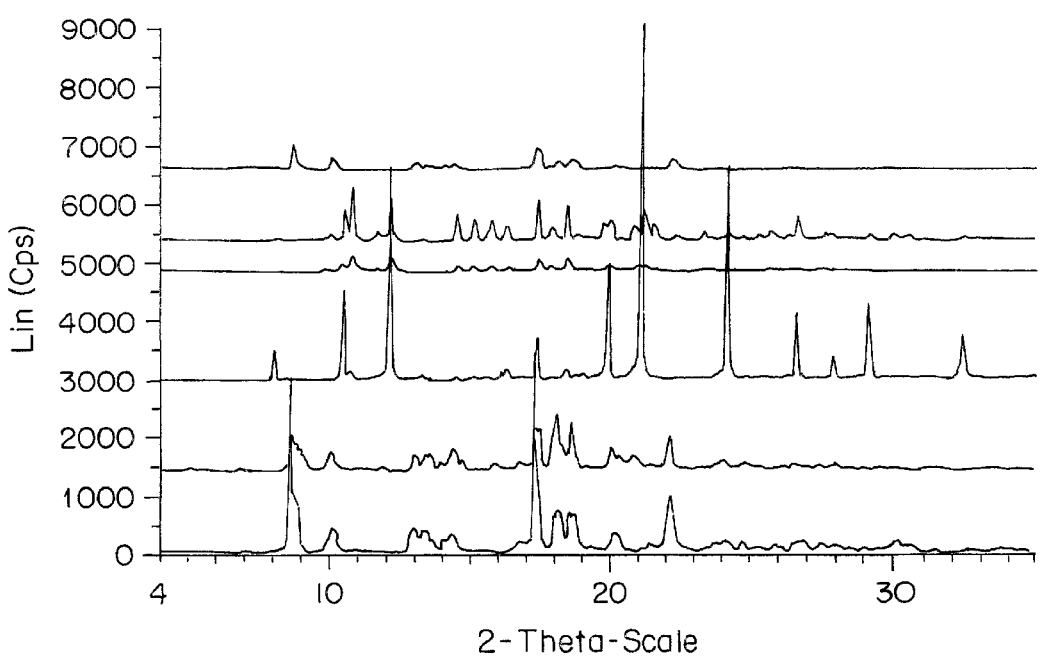
FIG. 2 is a x-ray scan of several polymorphs of 2-methyl-2-{4-[2-(5-methyl-2-biphenyl-4-yl-oxazol-4-yl)ethoxy]phenoxy}propionic acid and its salts.

2-Methyl-2-{4-[2-(5-methyl-2-biphenyl-4-yl-oxazol-4-yl)ethoxy]phenoxy}propionic acid can exist in at least two crystalline forms or polymorphs. One polymorph was formed by dissolving the compound in one volume of hot ethyl acetate, then adding two volumes of hexane while warming. Upon cooling the mixture, crystals formed which melted at 123–124° C. A second polymorph was formed by heating a solution of the compound in one volume of ethyl acetate to reflux, then adding one volume of heptane. Upon cooling the solution, crystals formed which melted at 141° C. FIGS. 1 and 2, respectively, show the results of differential scanning calorimetric analysis and x-ray crystallographic of several polymorphs of 2-methyl-2-{4-[2-(5-methyl-2-biphenyl-4-yl-oxazol-4-yl)ethoxy]phenoxy}propionic acid.

Example 2

2-(4-{2-[2-(4'-Fluorobiphenyl-4-yl)-5-methyloxazol-4-yl]ethoxy}phenoxy)-2-methylpropionic acid

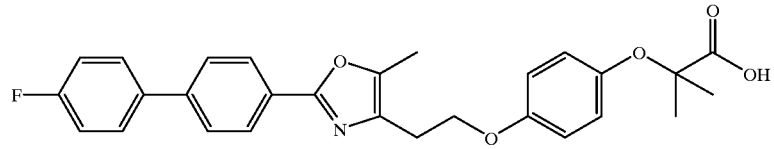

A. Toluene-4-sulfonic acid 2-[2-(4-bromophenyl)-5-methyloxazol-4-yl]ethyl ester

To a solution of 2-(4-bromophenyl)-5-methyl-4-oxazoleethanol (8.89 g, 31.5 mmol) (see Ex. 1, Part D) in $CH_2Cl_2$ (150 mL) at room temperature under $N_2$ was added pyridine (8.74 g, 110 mmol, 8.9 mL) and DMAP (0.97 g, 7.88 mmol) followed by portionwise addition of tosyl anhydride (12.7 g, 37.8 mmol). The reaction exothermed to 32° C. and was stirred 1 h before 1N HCl (200 mL) was added. The mixture was stirred vigorously 15 min, and then the organic phase was dried ($MgSO_4$) and filtered through a pad of silica gel (200 mL, packed with $CH_2Cl_2$). After rinsing the silica gel with ethyl acetate (100 mL) the solution was concentrated to toluene-4-sulfonic acid 2-[2-(4-bromophenyl)-5-methyloxazol-4-yl]ethyl ester which was used without further purification (mp 136° C.).

B. 2-(4-{2-[2-(4-Bromophenyl)-5-methyloxazol-4-yl]ethoxy}phenoxy)-2-methylpropionic acid ethyl ester A mixture of toluene-4-sulfonic acid 2-[2-(4-bromophenyl)-5-methyloxazol-4-yl]ethyl ester, 2-(4-hydroxyphenoxy)-2-methylpropanoic acid ethyl ester (American Home Products U.S. Pat. No. 3,795,691) (7.06 g, 31.5 mmol) and $Cs_2CO_3$ (13.3 g, 41.0 mmol) was heated at 55° C. in DMF (45 mL) for 18 h. The reaction was partitioned between ethyl acetate (250 mL) and $H_2O$ (250 mL), and the aqueous phase extracted with ethyl acetate (2×100 mL). The combined organic phases were dried ($MgSO_4$) and concentrated under reduced pressure to an oil which was purified by column chromatography (1500 mL $SiO_2$, hexanes to 10% ethyl acetate/hexanes) to provide 2-(4-{2-[2-(4-bromophenyl)-5-methyloxazol-4-yl]ethoxy}phenoxy)-2-methyl propionic acid ethyl ester (6.81 g, 44%) as a off-white solid: Rf=0.48 in 35% ethyl acetate/hexanes; mp 78–79° C.; $^1$H NMR (300 MHz, $CDCl_3$) δ7.85–7.82 (m, 2H), 7.57–7.53 (m, 2H), 6.83–6.75 (m, 4H), 4.22 (q, J=7.0 Hz, 2H), 4.18 (t, J=6.6 Hz, 2H), 2.94 (t, J=6.7 Hz, 2H), 2.36 (s, 3H), 1.52 (s, 6H), 1.27 (t, J=7.0 Hz, 3H) and by-product 2-(4-Bromophenyl)-5-methyl-4-vinyloxazole (1.81 g, 22%) as a white solid: $^1$H NMR (300 MHz, $CDCl_3$) δ7.92–7.87 (m, 2H), 7.58–7.55 (m, 2H), 6.54 (dd, J=17.3, 10.8 Hz, 1H), 5.94 (dd, J=17.0, 1.8 Hz, 1H), 5.30 (dd, J=10.8, 1.8 Hz, 1H), 2.41 (s, 3H).

C. 2-(4-{2-[2-(4'-Fluorobiphenyl-4-yl)-5-methyloxazol-4-yl]ethoxy}phenoxy)-2-methylpropionic acid ethyl ester To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg), 4-fluorophenyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh$_3$)$_4$ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4'-fluorobiphenyl-4-yl)-5-methyloxazol-4-yl]ethoxy}phenoxy)-2-methylpropionic acid ethyl ester.

D. 2-(4-{2-[2-(4'-Fluorobiphenyl-4-yl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4'-fluorobiphenyl-4-yl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was resolvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4'-fluorobiphenyl-4-yl)-5-methyloxazol-4-yl]ethoxy}phenoxy)-2-methylpropionic acid. $^1$H NMR (400 MHz, CDCl$_3$) 8.02 (2H, m), 7.64 (4H, m), 7.59 (2H, m), 7.13 (2H, m), 6.89 (2H, d), 6.78 (2H, d), 4.16 (2H, t), 3.00 (2H, t) 2.39 (3H, s), 1.53 (6H, s).

Example 3

2-{4-[2-(2-Biphenyl-3-yl-5-methyloxazol-4-yl)ethoxy]phenoxy}-2-methylpropionic acid

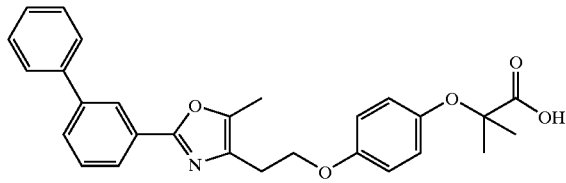

A. 2-(3-Bromophenyl)-4,5-dimethyloxazole-3-oxide

A solution of 2,3-butanedione monooxime (50 g, 0.49 mol) and 3-bromobenzaldehyde (101 g, 0.54 mol) in acetic acid (500 mL) was cooled to 0° C. and then gaseous HCl was bubbled through the solution for 35 min while the reaction was stirred in an ice bath. Diethyl ether (500 mL) was then added to the reaction to precipitate the product and the resultant slurry stirred 45 min at 0° C. before being filtered. The solids were rinsed with Et$_2$O (50 mL), taken up in water (1 L) and concentrated NH$_4$OH (60 mL) added to the slurry. This mixture was extracted with CHCl$_3$, the organic layer was dried (MgSO$_4$), and the solvent removed in vacuo to give 97.4 g (74%) of 2-(3-bromophenyl)-4,5-dimethyloxazole-3-oxide as a white solid. The compound should be used directly with 24–48 h. $^1$H NMR (300 MHz, CDCl$_3$) δ8.60 (s, 1H), 8.40 (d, J=8.0 Hz, 1H), 7.55 (d, J=8.0 Hz, 1H), 7.38 (d, J=8.0 Hz, 1H), 2.39 (s, 3H), 2.20 (s, 3H).

B. 2-(3-Bromophenyl)-4-(chloromethyl)-5-methyloxazole

A solution of 2-(3-bromophenyl)-4,5-dimethyloxazole-3-oxide (96.6 g, 0.36 mol) in CHCl$_3$ (0.90 L) was treated dropwise with phosphorous oxychloride (61.1 g, 0.40 mol) allowing the reaction to exotherm and then stirred at reflux for 30 min. The reaction was then cooled to room temperature and washed with water (2×1 L). The combined aqueous washes were back extracted with CH$_2$Cl$_2$ (2×400 mL). The organic layers were dried (MgSO$_4$), and the solvent removed in vacuo to give crude product that was recrystallized from hot hexanes (300 mL), decanting the hot supernate away from a dark oily material. The remaining dark oil was agitated in additional hot hexanes (200 mL) and the combined supernates were cooled to 0° C. to crystallize the product which was isolated by filtration to give 74.2 g (72%) of 2-(3-bromophenyl)-4-(chloromethyl)-5-methyloxazole as a lime-green powder. $^1$H NMR (300 MHz, d$_6$-DMSO) δ8.19 (s, 1H), 7.93 (d, J=8.0 Hz, 1H), 7.58 (d, J=8.0 Hz, 1H), 7.35 (t, J=8.0 Hz, 1H), 4.45 (s, 2H), 2.41 (s, 3H).

C. 2-(3-Bromophenyl)-5-methyl-4-oxazoleacetic acid

To a solution of 2-(3-bromophenyl)-4-(chloromethyl)-5-methyloxazole (64.8 g, 0.23 mol) in DMF (400 mL) was added powdered potassium cyanide (22.1 g, 0.34 mol) and potassium iodide (28.6 g, 0.17 mol) and the resultant mixture heated to 85° C. for 3.5 h. The reaction mixture was then cooled to room temperature. Potassium carbonate (5 g) was dissolved in water (800 mL) and added dropwise to the reaction to precipitate the product (stir vigorously 15 min following addition) which was isolated by filtration and washed with water (2×400 mL). The crude [2-(3-bromophenyl)-5-methyloxazole-4-yl]-acetonitrile was carried on as is in the next step without purification. $^1$H NMR (300 MHz, d$_6$-DMSO) δ8.00 (t, J=1.83 Hz, 1H), 7.90 (dt, J=8.2, 1.2 Hz, 1H), 7.70 (ddd, J=8.0, 1.8, 1.2 Hz, 1H), 7.48 (t, J=7.9 Hz, 1H), 4.01 (s, 2H), 2.41 (s, 3H.

The crude [2-(3-bromophenyl)-5-methyloxazole-4-yl]-acetonitrile (assume 0.22 mol) was combined with 2-methoxyethanol (630 mL) and 85% solid KOH (74.6 g, 1.33 mol) in water (360 mL) was added to the reaction. The mixture was heated to reflux for 3 h, cooled, quenched with 2 M HCl (500 mL), and extracted with CH$_2$Cl$_2$. The organic layer was dried (MgSO$_4$), and the solvent removed in vacuo, using toluene to azeotropically remove residual 2-methoxyethanol. The crude product (57.3 g) was recrystallized from toluene (450 mL) to give 39.8 g (60%) of 2-(3-bromophenyl)-5-methyl-4-oxazoleacetic acid as an off-white powder. $^1$H NMR (300 MHz, d$_6$-DMSO) δ7.99 (t, J=1.83 Hz, 1H), 7.88 (dt, J=8.1, 1.5 Hz, 1H), 7.65 (ddd, J=8.1, 1.8, 1.5 Hz, 1H), 7.45 (t, J=8.1 Hz, 1H), 3.50 (s, 2H), 2.35 (s, 3H).

D. 2-(3-Bromophenyl)-5-methyl-4-oxazoleethanol

A solution of 2-(3-bromophenyl)-5-methyl-4-oxazoleacetic acid (39.1 g, 0.13 mol) in dry THF (175 mL) was treated dropwise with borane-THF complex (227 mL of a 1.0 M solution in THF, 1.3 mol) over 2 h (reaction temperature to 35° C.). After stirring 2 h at room temperature under N$_2$, the reaction was quenched with slow addition of methanol (60 mL) and stirred overnight at room temperature. The reaction was diluted with 1 N NaOH (50 mL) and extracted with CH$_2$Cl$_2$ (2×200 mL). The organic layer was washed with H$_2$O (3×100 mL), dried (MgSO$_4$), and the solvent removed in vacuo to give 38.7 g of crude product that was recrystallized from toluene (200 mL, wash solid with cold hexanes) to give 26.9 g (72%) of 2-(3-bromophenyl)-5-methyl-4-oxazoleethanol as a white powder. Mp 92–93° C.; $^1$H NMR (300 MHz, d$_6$-DMSO) δ7.99 (s, 1H), 7.88 (d, J=7.7 Hz, 1H), 7.64 (d, J=7.7 Hz, 1H), 7.44 (t, J=7.7 Hz, 1H), 4.61 (t, J=5.5 Hz, OH), 3.63 (q, J=5.5 Hz, 2H), 2.60 (t, J=6.6 Hz, 2H), 2.32 (s, 3H).

E. Toluene-4-sulfonic acid 2-[2-(3-bromophenyl)-5-methyloxazol-4-yl]ethyl ester

To a solution of 2-(3-bromophenyl)-5-methyl-4-oxazoleethanol (8.89 g, 31.5 mmol) in CH$_2$Cl$_2$ (150 mL) at room temperature under N$_2$ was added pyridine (8.74 g, 110 mmol, 8.9 mL) and DMAP (0.97 g, 7.88 mmol) followed by portionwise addition of tosyl anhydride (12.7 g, 37.8 mmol). The reaction exothermed to 32° C. and was stirred 1 h before 1N HCl (200 mL) was added. The mixture was stirred vigorously 15 min, and then the organic phase was dried (MgSO$_4$) and filtered through a pad of silica gel (200 mL, packed with CH$_2$Cl$_2$). After rinsing the silica gel with ethyl acetate (100 mL) the solution was concentrated to toluene-4-sulfonic acid 2-[2-(3-bromophenyl)-5-methyloxazol-4-yl] ethyl ester which was used without further purification (mp 136° C.). $^1$H NMR (300 MHz, CDCl$_3$) δ7.99 (s, 1H), 7.80 (d, J=8.0 Hz, 1H), 7.64 (d, 8.0 Hz, 1H), 7.51 (d, J=9.0 Hz, 1H), 7.30 (t, J=8.0 Hz, 1H), 7.20 (d, J=9.0 Hz, 1H), 4.30 (t, J=7.0 Hz, 2H), 2.80 (t, J=7.0 Hz, 2H), 2.30 (s, 3H), 2.23 (s, 3H).

F. 2-(4-{2-[2-(3-Bromophenyl)-5-methyloxazol-4-yl]ethoxy}phenoxy)-2-methylpropionic acid ethyl ester A mixture of toluene-4-sulfonic acid 2-[2-(3-bromophenyl)-5-methyloxazol-4-yl]ethyl ester, 2-(4-hydroxyphenoxy)-2-methylpropanoic acid ethyl ester (American Home Products U.S. Pat. No. 3,795,691) (7.06 g, 31.5 mmol) and Cs$_2$CO$_3$ (13.3 g, 41.0 mmol) was heated at 55° C. in DMF (45 mL) for 18 h. The reaction was partitioned between ethyl acetate (250 mL) and H$_2$O (250 mL), and the aqueous phase extracted with ethyl acetate (2×100 mL). The combined organic phases were dried (MgSO$_4$) and concentrated under reduced pressure to an oil which was purified by column chromatography (1500 mL SiO$_2$, hexanes to 10% ethyl acetate/hexanes) to provide 2-(4-{2-[2-(3-bromophenyl)-5-methyloxazol-4-yl]ethoxy}phenoxy)-2-methyl propionic acid ethyl ester (6.81 g, 44%) as a off-white solid. Rf=0.39 in 1:4 ethyl acetate:hexanes; $^1$H NMR (400 MHz, CDCl$_3$) δ8.11 (t, J=1.6 Hz, 1H), 7.89–7.86 (m, 1H), 7.49 (ddd, J=8.0, 2.0, 1.2 Hz, 1H), 7.27 (t, J=8.0 Hz, 1H), 6.80–6.72 (m, 4H), 4.20 (q, J=7.2 Hz, 2H), 4.15 (t, J=6.6 Hz, 2H), 2.92 (t, J=6.6 Hz, 2H), 2.34 (s, 3H), 1.49 (s, 6H), 1.24 (t, J=7.2 Hz, 3H); MS (EI) 510.1 (M+Na)$^+$, 488.1 (M+H)$^+$.

G. 2-{4-[2-(2-Biphenyl-3-yl-5-methyloxazol-4-yl)ethoxy]phenoxy}-2-methylpropionic acid ethyl ester A solution of 2-{4-[2-(3-bromophenyl)-5-methyloxazol-4-yl]ethoxy}phenoxy)-2-methylpropionic acid ethyl ester (433 mg, 0.907 mmol) and phenylboronic acid (121.6 mg, 0.998 mmol) in toluene:ethanol (18.2 mL of a 1:1 solution) was treated with Na$_2$CO$_{3(aq)}$ (0.906 mL of a 2M solution). A nitrogen atmosphere was applied, Pd(PPh$_3$)$_4$ (52.5 mg) was added, and the orange mixture was heated at reflux for 2 h. After cooling to room temperature, the mixture was partitioned between ethyl acetate (20 mL) and H$_2$O (30 mL). The layers were separated, and the aqueous phase was back-extracted with ethyl acetate (2×10 mL). Combined organic phases were washed with brine (20 mL), dried over Na$_2$SO$_4$, and concentrated. The product was purified by silica gel chromatography (20 g SiO$_2$, 3:7 ethyl acetate:hexanes) to yield 393.7 mg (89%) as an orange oil. Rf=0.16 in 3:7 ethyl acetate:hexanes; $^1$H NMR (400 MHz, CDCl$_3$) δ8.23–8.19 (s, 1H), 7.99–7.93 (d, 1H), 7.70–7.28 (m, 7H), 6.83–6.77 (d, 2H), 6.76–6.70 (d, 2h), 4.24–4.10 (q, 2H), 4.20–4.16 (d, 2H), 3.99–3.92 (t, 2H), 2.40–2.31 (s, 3H), 1.58–1.48 (s, 6H), 1.30–1.19 (t, 3H).

H. 2-{4-[2-(2-Biphenyl-3-yl-5-methyloxazol-4-yl)ethoxy]phenoxy}-2-methylpropionic acid A stirred solution of 2-{4-[2-(2-biphenyl-3-yl-5-methyloxazol-4-yl)ethoxy]-phenoxy}-2-methyl propionic acid ethyl ester (345.2 mg, 0.711 mmol) in ethanol (8.9 mL) was treated with NaOH$_{(aq)}$ (0.854 mL of a 5M solution), and heated at reflux for 1 h. The hot solution was acidified to pH 1 with 1M HCl (6 mL). The mixture was cooled to ambient temperature, then further cooled to 0° C. before filtering the product. Following washing with H$_2$O, the product was dried under vacuum at 50° C. to yield 226.2 mg (70%) as a white, crystalline solid: Rf=0.2 in 6:4 ethyl acetate:hexanes; $^1$H NMR (400 MHz, CDCl$_3$) δ8.21 (s, 1H), 7.95 (d, J=7.2 Hz, 1H), 7.64–7.62 (m, 3H), 7.48 (t, J=7.8 Hz, 1H), 7.43 (t, J=7.8 Hz, 2H), 7.35 (t, J=7.2 Hz, 1H), 6.88–6.77 (m, 4H), 4.18 (t, J=6.4 Hz, 2H), 2.99 (t, J=6.4 Hz, 2H), 2.44 (s, 3H), 1.51 (s, 6H).

Example 4

2-Methyl-2-(4-{2-[5-methyl-2-(3-naphthalen-1-ylphenyl)oxazol-4-yl]ethoxy}-phenoxy)propionic acid

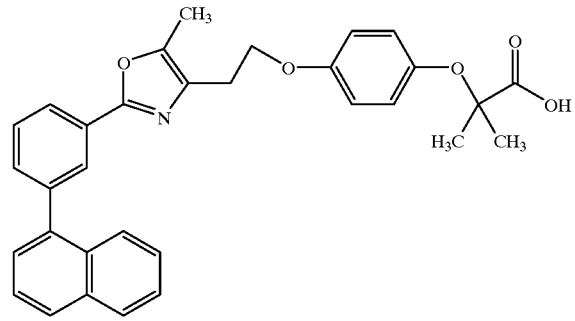

A. 2-Methyl-2-(4-{2-[5-methyl-2-(3-naphthalen-1-ylphenyl)oxazol-4-yl]ethoxy}phenoxy)propionic acid ethyl ester A solution of 2-(4-{2-[2-(3-bromophenyl)-5-methyloxazol-4-yl]ethoxy}phenoxy)-2-methylpropionic acid ethyl ester (433 mg, 0.907 mmol) (see Ex. 3, part F) and 1-naphthyleneboronic acid (0.998 mmol) in toluene:ethanol (18.2 mL of a 1:1 solution) was treated with Na$_2$CO$_{3(aq)}$ (0.906 mL of a 2M solution). A nitrogen atmosphere was applied, Pd(PPh$_3$)$_4$ (52.5 mg) was added, and the orange mixture was heated at reflux for 2 h. After cooling to room temperature, the mixture was partitioned between ethyl acetate (20 mL) and H$_2$O (30 mL). The layers were separated, and the aqueous phase was back-extracted with ethyl acetate (2×10 mL). Combined organic phases were washed with brine (20 mL), dried over Na$_2$SO$_4$, and concentrated. The product was purified by silica gel chromatography (20 g SiO$_2$, 3:7 ethyl acetate:hexanes). Rf=0.16 in 1:9 ethyl acetate:hexanes; $^1$H NMR (400 MHz, CDCl$_3$) δ8.11–8.05 (m, 2H), 7.90–7.82 (m, 3H), 7.56–7.39 (m, 6H), 6.80–6.72 (m, 4H), 4.22–4.19 (m, 4H), 2.98 (t, 2H), 2.35 (s, 3H) 1.47 (s, 3H), 1.22 (t, 6H); MS (EI) 436.5 (M+H)$^+$.

B. 2-Methyl-2-(4-{2-[5-methyl-2-(3-naphthalen-1-ylphenyl)oxazol-4-yl]ethoxy}phenoxy)propionic acid A stirred solution of 2-methyl-2-(4-{2-[5-methyl-2-(3-naphthalen-1-ylphenyl)oxazol-4-yl]ethoxy}phenoxy) propionic acid ethyl ester (0.711 mmol) in ethanol (8.9 mL)

was treated with NaOH$_{(aq)}$ (0.854 mL of a 5M solution), and heated at reflux for 1 h. The hot solution was acidified to pH 1 with 1M HCl (6 mL). The mixture was cooled to ambient temperature, then further cooled to 0° C. before filtering the product. Following washing with H$_2$O, the product was dried under vacuum at 50° C. to yield a white, crystalline solid: Rf=0.22 in 6:4 ethyl acetate:hexanes; $^1$H NMR (400 MHz, CDCl$_3$) δ8.08 (s, 1H), 8.03 (d, J=8.8 Hz, 1H), 7.90–7.82 (m, 3H), 7.53–7.39 (m, 6H), 6.86–6.75 (m, 4H), 4.16 (t, J=6.4 Hz, 2H), 2.95 (t, J=6.4 Hz, 2H), 2.35 (s, 3H), 1.47 (s, 6H); MS (EI) 508.1 (M+H)$^+$.

Example 5

2-(4-{2-[2-(4'-Formylbiphenyl-3-yl)-5-methyloxazol-4-yl]ethoxy}phenoxy)-2-methylpropionic acid

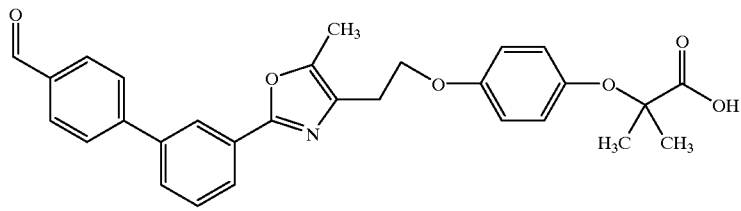

A. 2-(4-{2-[2-(4'-Formylbiphenyl-3-yl)-5-methyloxazol-4-yl]ethoxy}phenoxy)-2-methyl propionic acid ethyl ester A solution of 2-(4-{2-[2-(3-bromophenyl)-5-methyloxazol-4-yl]ethoxy}phenoxy)-2-methylpropionic acid ethyl ester (0.907 mmol) (see Ex. 3, part F) and 1-(4-formylphenyl)boronic acid (0.998 mmol) in toluene:ethanol (18.2 mL of a 1:1 solution) was treated with Na$_2$CO$_{3(aq)}$ (0.906 mL of a 2M solution). A nitrogen atmosphere was applied, Pd(PPh$_3$)$_4$ (0.045 mmol) was added, and the orange mixture was heated at reflux for 2 h. After cooling to room temperature, the mixture was partitioned between ethyl acetate (20 mL) and H$_2$O (30 mL). The layers were separated, and the aqueous phase was back-extracted with ethyl acetate (2×10 mL). Combined organic phases were washed with brine (20 mL), dried over Na$_2$SO$_4$, and concentrated. The product was purified by silica gel chromatography (20 g SiO$_2$, 3:7 ethyl acetate:hexanes). Rf=0.24 in 1:4 ethyl acetate:hexanes; $^1$H NMR (400 MHz, CDCl$_3$) δ10.03 (s, 1H), 9.21 (s, 1H), 9.02–8.94 (m, 3H), 8.81–8.78 (m, 2H), 8.46–8.41 (m, 1H), 8.36–8.30 (m, 1H), 6.79–6.71 (m, 4H), 4.23–4.16 (m, 4H), 2.94 (t, 2H), 2.37 (s, 3H), 1.26 (s, 6H), 1.24 (t, 3H); MS (EI) 514.2 (M+H)$^+$.

B. 2-(4-{2-[2-(4'-Formylbiphenyl-3-yl)-5-methyloxazol-4-yl]ethoxy}phenoxy)-2-methylpropionic acid A stirred solution of 2-(4-{2-[2-(4'-formylbiphenyl-3-yl)-5-methyloxazol-4-yl]ethoxy}phenoxy)-2-methyl propionic acid ethyl ester (0.711 mmol) in ethanol (8.9 mL) was treated with NaOH$_{(aq)}$ (0.854 mL of a 5M solution), and heated at reflux for 1 h. The hot solution was acidified to pH 1 with 1M HCl (6 mL). The mixture was cooled to ambient temperature, then further cooled to 0° C. before filtering the product. Following washing with H$_2$O, the product was dried under vacuum at 50° C. to yield a white, crystalline solid: Rf 0.14 in 6:4 ethyl acetate:hexanes; MS (EI) 486.1 (M+H)$^+$.

Example 6

3'-(4-{2-[3-(1-Carboxy-1-methylethoxy)phenoxy]ethyl}-5-methyloxazol-2-yl)-biphenyl-4-carboxylic acid

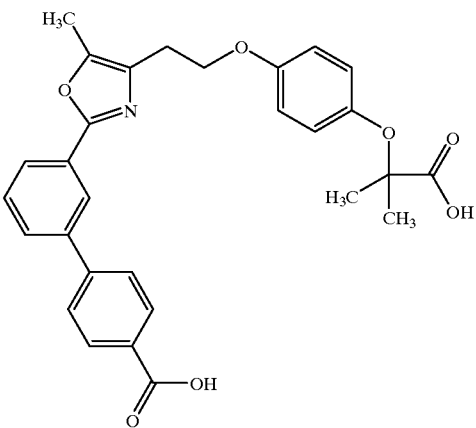

A. 3'-(4-{2-[3-(1-Ethoxycarbonyl-1-methylethoxy) phenoxy]ethyl}-5-methyloxazol-2-yl)-biphenyl-4-carboxylic acid ethyl ester A solution of 2-(4-{2-[2-(3-bromophenyl)-5-methyloxazol-4-yl]ethoxy}phenoxy)-2-methylpropionic acid ethyl ester (433 mg, 0.907 mmol) (see Ex. 3, part F) and 1-(4-carboxyphenyl)boronic acid (0.998 mmol) in toluene:ethanol (18.2 mL of a 1:1 solution) was treated with $Na_2CO_{3(aq)}$ (0.906 mL of a 2M solution). A nitrogen atmosphere was applied, $Pd(PPh_3)_4$ (52.5 mg) was added, and the orange mixture was heated at reflux for 2 h. After cooling to room temperature, the mixture was partitioned between ethyl acetate (20 mL) and $H_2O$ (30 mL). The layers were separated, and the aqueous phase was back-extracted with ethyl acetate (2×10 mL). Combined organic phases were washed with brine (20 mL), dried over $Na_2SO_4$, and concentrated. The product was purified by silica gel chromatography (20 g $SiO_2$, 3:7 ethyl acetate:hexanes). $^1$H NMR (400 MHz, $CDCl_3$) δ8.45 (br s, 1H), 8.17 (d, J=7.6 Hz, 2H), 7.93 (m, 1H), 7.76 (d, J=7.6 Hz, 2H), 7.70–7.54 (m, 2H), 6.81–6.78 (m, 4H), 4.26 (t, J=6.4 Hz, 2H), 4.22 (q, J=6.8 Hz, 2H), 3.11 (t, J=6.4 Hz, 2H), 2.42 (s, 3H), 1.51 (s, 6H), 1.27 (t, J=7.2 Hz, 3H).

B. 3'-(4-{2-[3-(1-Carboxy-1-methylethoxy)phenoxy]ethyl}-5-methyloxazol-2-yl)-biphenyl-4-carboxylic acid A stirred solution of 3'-(4-{2-[3-(1-ethoxycarbonyl-1-methylethoxy)phenoxy]ethyl}-5-methyloxazol-2-yl)-biphenyl-4-carboxylic acid ethyl ester (0.711 mmol) in ethanol (8.9 mL) was treated with $NaOH_{(aq)}$ (0.854 mL of a 5M solution), and heated at reflux for 1 h. The hot solution was acidified to pH 1 with 1M HCl (6 mL). The mixture was cooled to ambient temperature, then further cooled to 0° C. before filtering the product. Following washing with $H_2O$, the product was dried under vacuum at 50° C. to a white, crystalline solid: mp 184° C.; MS (EI) 525.2 (M+Na)$^+$, 502.2 (M+H)$^+$.

Example 7

2-[4-(2-{2-[4'-(2-Carboxyethyl)biphenyl-3-yl]-5-methyloxazol-4-yl}ethoxy)phenoxy]-2-methylpropionic acid A. 3-[3'-(4-{2-[4-(1-Ethoxycarbonyl-1-methylethoxy) phenoxy]ethyl}-5-methyloxazol-2-yl)biphenyl-4-yl] acrylic acid ethyl ester A solution of 2-(4-{2-[2-(4'-formylbiphenyl-3-yl)-5-methyloxazol-4-yl]ethoxy}-phenoxy)-2-methylpropionic acid ethyl ester (see Example 5, step A) (244 mg, 0.475 mmol) in toluene (9.5 mL) was treated with (carbethoxymethylene)triphenylphosphorane (331 mg, 0.95 mmol) and heated at reflux for 0.5 h. After cooling to room temperature, the reaction mixture was concentrated, then purified by column chromatography (25 g $SiO_2$, 1:2 ethyl acetate:hexanes) to provide the product (232 mg, 84%) as an off-white solid: Rf=0.21 in 1:4 ethyl acetate:hexanes; $^1$H NMR (400 MHz, $CDCl_3$) δ8.20 (s, 1H), 7.92 (d, 1H), 7.72–7.58 (m, 5.9H), 7.43 (t, 1H), 6.93 (d, 0.1H) 6.81–6.73 (m, 4H), 6.42 (d, 0.89H), 5.95 (d, 0.07), 4.27–4.18 (m, 6H), 2.96 (t, 2H), 2.37 (s, 3H), 1.46 (s, 6H), 1.26–1.21 (m, 6H); MS (EI) 606.2 (M+Na)$^+$, 584.2 (M+H)$^+$.

B. 2-[4-(2-{2-[4'-(2-Ethoxycarbonylethyl)biphenyl-3-yl]-5-methyloxazol-4-yl}ethoxy)phenoxy]-2-methylpropionic acid ethyl ester A solution of 3-[3'-(4-{2-[4-(1-ethoxycarbonyl-1-methylethoxy)phenoxy]ethyl}-5-methyloxazol-2-yl) biphenyl-4-yl]acrylic acid ethyl ester (202 mg, 0.346 mmol) in EtOH (35 mL) was treated with 5% Pd/C (250 mg) and hydrogenated in a Parr shaker at 60 p.s.i. for 18 h. The reaction mixture was filtered through celite, concentrated, and purified by column chromatography ($SiO_2$, 15 g, 1:2 ethyl acetate:hexanes) to provide the product (65.1 mg, 32%) as an oil: Rf=0.29 in 1:4 ethyl acetate:hexanes; $^1$H NMR (400 MHz, $CDCl_3$) δ8.19 (s, 1H), 7.91 (d, 1H), 7.60–7.54 (m, 3H), 7.43 (t, 1H), 7.28 (d, 2H) 6.80–6.71 (m, 4H), 4.22–4.15 (m, 6H), 3.00–2.92 (t, 4H), 2.42 (t, 2H), 2.37 (s, 3H), 1.39 (s, 6H), 1.28–1.20 (m, 6H); MS (EI) 608.2 (M+Na)$^+$, 586.2 (M+H)$^+$.

C. 2-[4-(2-{2-[4'-(2-Carboxyethyl)biphenyl-3-yl]-5-methyloxazol-4-yl}ethoxy)phenoxy]-2-methylpropionic acid Under nitrogen, a solution of 2-[4-(2-{2-[4'-(2-ethoxycarbonylethyl)biphenyl-3-yl]-5-methyloxazol-4-

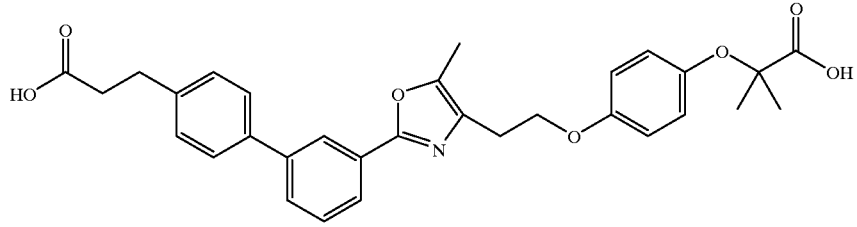

yl}ethoxy)-phenoxy]-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to give a 45% yield of a white solid. Rf=0.25 in 6:4 ethyl acetate:hexanes; $^1$H NMR (400 MHz, $CDCl_3$) δ8.19 (s, 1H), 7.83 (d, 1H), 7.60–7.54 (m, 3H), 7.42 (t, 1H), 7.26 (d, 2H) 6.82–6.71 (m, 4H), 4.18 (t, 2H), 4.18 (t, 2H), 3.00–2.82 (m, 4H), 2.37 (s, 3H), 1.42 (s, 6H); MS (EI) 552.0 (M+Na)$^+$, 530.0 (M+H)$^-$.

Example 8

2-Methyl-2-(4-{2-[5-methyl-2-(4-naphthalen-1-ylphenyl)oxazol-4-yl]ethoxy}phenoxy)propionic acid

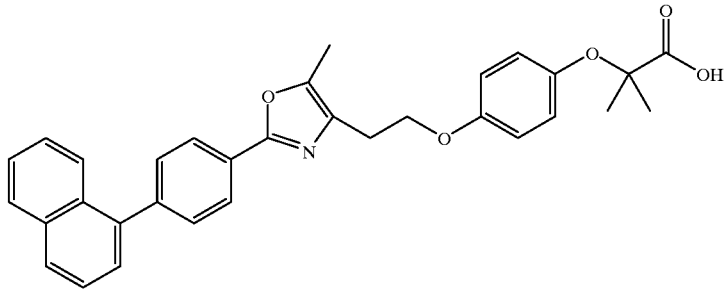

A. 2-Methyl-2-(4-{2-[5-methyl-2-(4-naphthalen-1-ylphenyl)oxazol-4-yl]ethoxy}phenoxy)propionic acid ethyl ester A solution of 2-(4-{2-[2-(4-bromophenyl)-5-methyloxazol-4-yl]ethoxy}phenoxy)-2-methyl-propionic acid ethyl ester (0.907 mmol) (see Ex. 2, part B) and 1-naphthaleneboronic acid (0.998 mmol) in toluene:ethanol (18.2 mL of a 1:1 solution) was treated with $Na_2CO_{3(aq)}$ (0.906 mL of a 2M solution). A nitrogen atmosphere was applied, $Pd(PPh_3)_4$ (52.5 mg) was added, and the orange mixture was heated at reflux for 2 h. After cooling to room temperature, the mixture was partitioned between ethyl acetate (20 mL) and $H_2O$ (30 mL). The layers were separated, and the aqueous phase was back-extracted with ethyl acetate (2×10 mL). Combined organic phases were washed with brine (20 mL), dried over $Na_2SO_4$ and concentrated. The product was purified by silica gel chromatography (20 g $SiO_2$, 3:7 ethyl acetate:hexanes) to give the desired product in 87% as an orange oil; Rf=0.46 in 1:4 ethyl acetate:hexanes; $^1H$ NMR (400 MHz, $CDCl_3$) δ8.09 (d, J=8 Hz, 2H), 7.92–7.82 (m, 3H), 7.59–7.40 (m, 6H), 6.81–6.72 (m, 4H), 4.22–4.17 (m, 4H), 2.98 (t, 2H), 2.38 (s, 3H), 1.46 (s, 6H), 1.22 (t, 3H); MS (EI) 536.3 $(M+H)^+$.

B. 2-Methyl-2-(4-{2-[5-methyl-2-(4-naphthalen-1-ylphenyl)oxazol-4-yl]ethoxy}phenoxy)propionic acid Under nitrogen, 2-methyl-2-(4-{2-[5-methyl-2-(4-naphthalen-1-ylphenyl)oxazol-4-yl]ethoxy}-phenoxy) propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to yield of a white solid. Rf=0.25 in 6:4 ethyl acetate:hexanes; $^1H$ NMR (400 MHz, $CDCl_3$) δ7.96 (d, 2H), 7.78–7.70 (m, 3H), 7.41–7.29 (m, 6H), 6.78–6.60 (m, 4H), 4.04 (t, 2H), 2.84 (t, 2H), 2.22 (s, 3H), 1.37 (s, 6H); MS (EI) 508.2 $(M+H)^+$.

Example 9

2-(4-{2-[2-(3',5'-Bis-trifluoromethylbiphenyl-4-yl)-5-methyloxazol-4-yl]ethoxy}-phenoxy)-2-methyl propionic acid

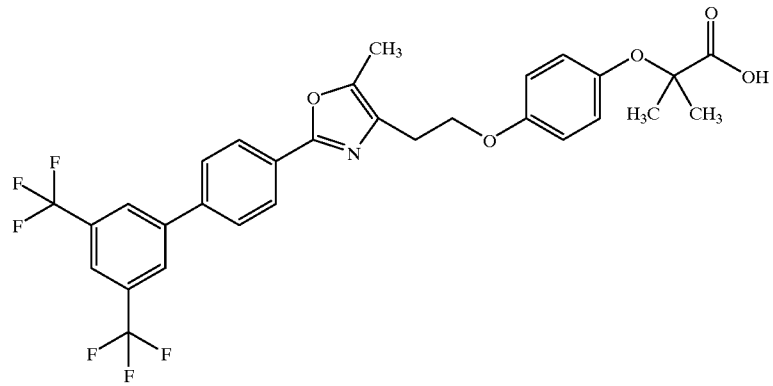

A. 2-(4-{2-[2-(3',5'-Bis-trifluoromethylbiphenyl-4-yl)-5-methyloxazol-4-yl]ethoxy}-phenoxy)-2-methyl propionic acid ethyl ester A solution of 2-(4-{2-[2-(4-bromophenyl)-5-methyloxazol-4-yl]ethoxy}phenoxy)-2-methyl-propionic acid ethyl ester (0.907 mmol) (see Ex. 2, part B) and 1–3,5 bis-trifluoromethylphenylboronic acid (0.998 mmol) in toluene:ethanol (18.2 mL of a 1:1 solution) was treated with $Na_2CO_{3(aq)}$ (0.906 mL of a 2M solution). A nitrogen atmosphere was applied, $Pd(PPh_3)_4$ (52.5 mg) was added, and the orange mixture was heated at reflux for 2 h. After cooling to room temperature, the mixture was partitioned between ethyl acetate (20 mL) and $H_2O$ (30 mL). The layers were separated, and the aqueous phase was back-extracted with ethyl acetate (2×10 mL). Combined organic phases were washed with brine (20 mL), dried over $Na_2SO_4$, and concentrated. The product was purified by silica gel chromatography (20 g $SiO_2$, 3:7 ethyl acetate:hexanes) to give the desired product. Rf=0.52 in 1:4 ethyl acetate:hexanes; $^1$H NMR (400 MHz, $CDCl_3$) δ8.12 (d, 2H), 8.03 (s, 2H), 7.83 (s, 1H), 7.62 (d, 2H), 6.81–6.74 (m, 4H), 4.22–4.16 (m, 4H), 2.97 (t, 2H), 2.38 (s, 3H), 1.43 (s, 6H), 1.22 (t, 3H); MS (EI) 622.2 $(M+H)^+$.

B. 2-(4-{2-[2-(3',5'-Bis-trifluoromethylbiphenyl-4-yl)-5-methyloxazol-4-yl]ethoxy}-phenoxy)-2-methyl propionic acid Under nitrogen, 2-(4-{2-[2-(3',5'-bis-trifluoromethylbiphenyl-4-yl)-5-methyloxazol-4-yl]ethoxy}-phenoxy)-2-methyl propionic acid ethyl ester (0.53 mmol) in ethanol (2.5 mL) and THF (2.5 mL) was treated with 2.0 N NaOH (2.0 mL). The reaction mixture was stirred at 55° C. for 1 H and concentrated in vacuo. The resulting slurry was suspended in ethyl acetate, acidified to pH 1 with 1N HCl, and partitioned. The organic layer was washed with brine, dried ($N2SO_4$), and concentrated in vacuo to yield of a white solid. Rf=0.1 in 6:4 ethyl acetate:hexanes; $^1$H NMR (400 MHz, $CDCl_3$) δ8.08 (d, 2H), 8.01 (s, 2H), 7.83 (s, 1H), 7.62 (d, 2H), 6.88–6.76 (m, 4H), 4.17 (t, 2H), 2.98 (t, 2H), 2.40 (s, 3H), 1.52 (s, 6H); MS (EI) 594.2 $(M+H)^+$.

Example 10

2-(4-{2-[2-(2'-Methoxy-biphenyl-4-yl)-5-methyloxazol-4-yl]-ethoxy}-phenoxy)-2-methylpropionic acid A. 2-(4-{2-[2-(2'-Methoxy-biphenyl-4-yl)-5-methyloxazol-4-yl]-ethoxy}-phenoxy)-2-methylpropionic acid ethyl ester A solution of 2-(4-{2-[2-(4-bromophenyl)-5-methyloxazol-4-yl]ethoxy}phenoxy)-2-methylpropionic acid ethyl ester (300 mg, 0.614 mmol) (see Ex. 2, part B), o-methoxyphenylboronic acid (140 mg, 0.921 mmol), potassium fluoride (88.6 mg, 1.84 mmol), palladium acetate (1.3 mg, 0.14 μmol), and 2-(dicyclohexylphosphino)biphenyl (4.3 mg, 12.3 μmol) were combined under $N_2$, to which anhydrous THF (1.23 mL) was added. The yellow mixture was heated at reflux for 12 h. After cooling to room temperature, the mixture was partitioned between $Et_2O$ (20 mL) and 1M NaOH (10 mL). The layers were separated, and the aqueous phase was back-extracted with $Et_2O$ (10 mL). Combined organic phases were dried over $Na_2SO_4$, and concentrated. The product was purified by silica gel chromatography (25 g $SiO_2$, 1:4 ethyl acetate:hexanes) to yield 100.5 mg (32%) as an oil. Rf=0.38 in 1:4 ethyl acetate:hexanes; $^1$H NMR (400 MHz, $CDCl_3$) δ7.97 (d, J=8.0 Hz, 2H), 7.57 (d, J=8.0 Hz, 2H), 7.33–7.29 (m, 2H), 7.01 (t, J=7.2 Hz, 1H), 6.97 (d, J=7.6 Hz, 1H), 6.80–6.74 (m, 4H), 4.20 (q, J=7.2 Hz, 2H), 4.17 (t, J=6.8 Hz, 2H), 3.80 (s, 3H), 2.94 (t, J=6.8 Hz, 2H), 2.34 (s, 3H), 1.50 (s, 6H), 1.24 (t, J=7.2 Hz, 3H); MS (EI) 538.2 $(M+Na)^+$, 516.2 $(M+H)^+$.

B. 2-(4-{2-[2-(2'-Methoxy-biphenyl-4-yl)-5-methyloxazol-4-yl]-ethoxy}-phenoxy)-2-methylpropionic acid Under nitrogen, 2-(4-{2-[2-(2'-methoxy-biphenyl-4-yl)-5-methyloxazol-4-yl]-ethoxy}-phenoxy)-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product (83.1 mg, 87%) as a solid. Rf=0.11 in 6:4 ethyl acetate:hexanes; $^1$H NMR (400 MHz, $CDCl_3$) δ7.73 (d, J=8.4 Hz, 2H), 7.35 (d, J=8.4 Hz, 2H), 7.10–7.07 (m, 2H), 6.80–6.75 (m, 2H), 6.63 (d, J=8.8 Hz, 2H), 6.52 (d, J=8.8 Hz, 2H), 3.94 (t, J=6.6 Hz, 2H), 3.58 (s, 3H), 2.71 (t, J=6.6 Hz, 2H), 2.13 (s, 3H), 1.26 (s, 6H); MS (EI) 510.1 $(M+Na)^+$, 488.1 $(M+H)^+$.

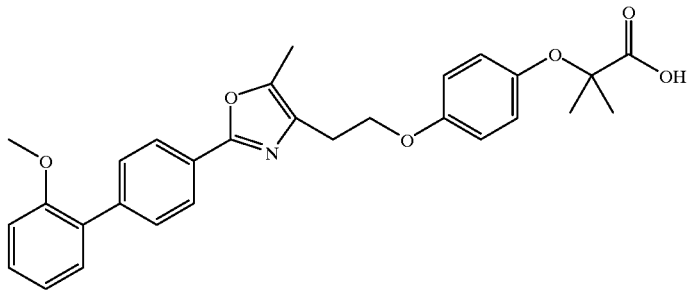

Example 11

2-Methyl-2-(4-{2-[5-methyl-2-(2'-methyl-biphenyl-4-yl)-oxazol-4-yl]-ethoxy}-phenoxy)propionic acid

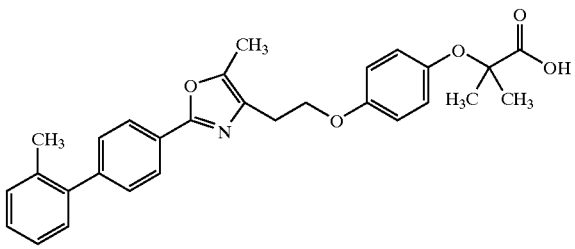

A. 2-Methyl-2-(4-{2-[5-methyl-2-(2'-methyl-biphenyl-4-yl)-oxazol-4-yl]-ethoxy}-phenoxy)propionic acid ethyl ester A solution of 2-(4-{2-[2-(4-bromophenyl)-5-methyloxazol-4-yl]ethoxy}phenoxy)-2-methylpropionic acid ethyl ester (300 mg, 0.614 mmol) (see Ex. 2, part B), 2-methylphenylboronic acid (0.921 mmol), potassium fluoride (88.6 mg, 1.84 mmol), palladium acetate (1.3 mg, 0.14 µmol), and 2-(dicyclohexylphosphino)biphenyl (4.3 mg, 12.3 µmol) were combined under $N_2$, to which anhydrous THF (1.23 mL) was added. The yellow mixture was heated at reflux for 12 h. After cooling to room temperature, the mixture was partitioned between $Et_2O$ (20 mL) and 1M NaOH (10 mL). The layers were separated, and the aqueous phase was back-extracted with $Et_2O$ (10 mL). Combined organic phases were dried over $Na_2SO_4$, and concentrated. The product was purified by silica gel chromatography (25 g $SiO_2$, 1:4 ethyl acetate:hexanes) to yield the desired product as an oil. Rf=0.44 in 1:4 ethyl acetate:hexanes; $^1$H NMR (400 MHz, $CDCl_3$) δ7.99 (d, J 8.6 Hz, 2H), 7.36 (d, J 8.6 Hz, 2H), 7.26–7.21 (m, 4H), 6.81–6.74 (m, 4H), 4.20 (t, J=6.6 Hz, 2H), 4.19 (q, J=7.2 Hz, 2H), 2.94 (t, J=6.6 Hz, 2H), 2.35 (s, 3H), 2.26 (s, 3H), 1.50 (s, 6H), 1.25 (t, J=7.2 Hz, 3H); MS (EI) 500.2 $(M+H)^-$.

B. 2-Methyl-2-(4-{2-[5-methyl-2-(2'-methyl-biphenyl-4-yl)-oxazol-4-yl]-ethoxy}-phenoxy)propionic acid Under nitrogen, 2-methyl-2-(4-{2-[5-methyl-2-(2'-methyl-biphenyl-4-yl)-oxazol-4-yl]-ethoxy}-phenoxy)propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product as a solid. Rf=0.12 in 6:4 ethyl acetate:hexanes; $^1$H NMR (400 MHz, $CDCl_3$) δ8.00 (d, J=8.6 Hz, 2H), 7.37 (d, J=8.6 Hz, 2H), 7.25–7.22 (m, 4H), 6.87 (d, J=9.2 Hz, 2H), 6.79 (d, J=9.2 Hz, 2H), 4.19 (t, J=6.4 Hz, 2H), 2.98 (t, J 6.4 Hz, 2H), 2.37 (s, 3H), 2.25 (s, 3H), 1.49 (s, 6H); MS (EI) 472.2 $(M+H)^+$.

Example 12

2-Methyl-2-(4-{2-[5-methyl-2-(2'-trifluoromethyl-biphenyl-4-yl)-oxazol-4-yl]-ethoxy}-phenoxy) propionic acid

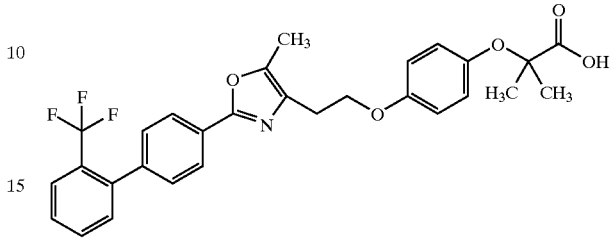

A. 2-Methyl-2-(4-{2-[5-methyl-2-(2'-trifluoromethyl-biphenyl-4-yl)-oxazol-4-yl]-ethoxy}-phenoxy)propionic acid ethyl ester A solution of 2-(4-{2-[2-(4-bromophenyl)-5-methyloxazol-4-yl]ethoxy}phenoxy)-2-methylpropionic acid ethyl ester (300 mg, 0.614 mmol) (see Ex. 2, part B), 2-trifluoromethylphenylboronic acid (0.921 mmol), potassium fluoride (88.6 mg, 1.84 mmol), palladium acetate (1.3 mg, 0.14 µmol), and 2-(dicyclohexylphosphino)biphenyl (12.3 µmol) were combined under $N_2$, to which anhydrous THF (1.23 mL) was added. The yellow mixture was heated at reflux for 12 h. After cooling to room temperature, the mixture was partitioned between $Et_2O$ (20 mL) and 1M NaOH (10 mL). The layers were separated, and the aqueous phase was back-extracted with $Et_2O$ (10 mL). Combined organic phases were dried over $Na_2SO_4$, and concentrated. The product was purified by silica gel chromatography (25 g $SiO_2$, 1:4 ethyl acetate:hexanes) to yield the desired product as an oil. Rf=0.47 in 1:4 ethyl acetate:hexanes; $^1$H NMR (400 MHz, $CDCl_3$) δ7.98 (d, J=8.4 Hz, 2H), 7.73 (d, J=7.6 Hz, 1H), 7.55 (t, J=7.6 Hz, 1H), 7.46 (t, J=7.6 Hz, 1H), 7.36 (d, J=8.4 Hz, 2H), 7.32 (d, J=7.6 Hz, 1H), 6.80–6.73 (m, 4H), 4.20 (q, J=7.2 Hz, 2H), 4.17 (t, J=6.6 Hz, 2H), 2.94 (t, J=6.6 Hz, 2H), 2.35 (s, 3H), 1.50 (s, 6H), 1.24 (t, J=7.2 Hz, 3H); MS (EI) 554.1 $(M+H)^+$.

B. 2-Methyl-2-(4-{2-[5-methyl-2-(2'-trifluoromethyl-biphenyl-4-yl)-oxazol-4-yl]-ethoxy}-phenoxy)propionic acid Under nitrogen, 2-methyl-2-(4-{2-[5-methyl-2-(2'-trifluoromethyl-biphenyl-4-yl)-oxazol-4-yl]-ethoxy}-phenoxy)propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product as a solid. Rf=0.10 in 6:4 ethyl acetate:hexanes; $^1$H NMR MHz, $CDCl_3$) δ7.99 (d, J=8.4 Hz, 2H), 7.73 (d, J=8.0 Hz, 1H), 7.55 (t, J=7.6 Hz, 1H), 7.46 (t, J=7.5 Hz, 1H), 7.37 (d, J=8.4 Hz, 2H), 7.32 (d, J=7.6 Hz, 1H), 6.87 (d, J=8.8 Hz, 2H), 6.75 (d, J=8.8 Hz, 2H), 4.14 (t, J=6.6 Hz, 2H), 2.98 (t, J=6.6 Hz, 2H), 2.37 (s, 3H), 1.51 (s, 6H); MS (EI) 548.1 $(M+Na)^+$, 526.2 $(M+H)^+$.

Example 13

2-(4-{2-[2-(2'-Fluorobiphenyl-4-yl)-5-methyloxazol-4-yl]-ethoxy}-phenoxy)-2-methylpropionic acid

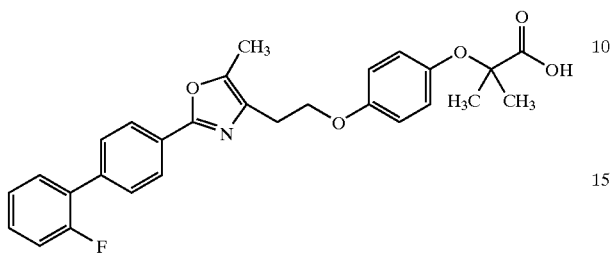

A. 2-(4-{2-[2-(2'-Fluoro-biphenyl-4-yl)-5-methyloxazol-4-yl]-ethoxy}-phenoxy)-2-methylpropionic acid ethyl ester A solution of 2-(4-{2-[2-(4-bromophenyl)-5-methyloxazol-4-yl]ethoxy}phenoxy)-2-methylpropionic acid ethyl ester (300 mg, 0.614 mmol) (see Ex. 2, part B), 2-fluorophenylboronic acid (0.921 mmol), potassium fluoride (88.6 mg, 1.84 mmol), palladium acetate (1.3 mg, 0.14 µmol), and 2-(dicyclohexylphosphino)biphenyl (4.3 mg, 12.3 µmol) were combined under $N_2$, to which anhydrous THF (1.23 mL) was added. The yellow mixture was heated at reflux for 12 h. After cooling to room temperature, the mixture was partitioned between $Et_2O$ (20 mL) and 1M NaOH (10 mL). The layers were separated, and the aqueous phase was back-extracted with $Et_2O$ (10 mL). Combined organic phases were dried over $Na_2SO_4$, and concentrated. The product was purified by silica gel chromatography (25 g $SiO_2$, 1:4 ethyl acetate:hexanes) to yield the desired product as an oil. Rf=0.48 in 1:4 ethyl acetate:hexanes; $^1$H NMR (400 MHz, $CDCl_3$) δ8.01 (d, J=8.0 Hz, 2H), 7.60 (d, J=8 Hz, 2H), 7.47–7.42 (m, 1H), 7.34–7.28 (m, 1H), 7.22–7.11 (m, 2H), 6.81–6.73 (m, 4H), 4.20 (q, J=6.8 Hz, 2H), 4.17 (t, J=6.6 Hz, 2H), 2.94 (t, J=6.6 Hz, 2H), 2.35 (s, 3H), 1.50 (s, 6H), 1.24 (t, J=6.8 Hz, 3H); MS (EI) 504.2 $(M+H)^+$.

B. 2-(4-{2-[2-(2'-Fluorobiphenyl-4-yl)-5-methyloxazol-4-yl]-ethoxy}-phenoxy)-2-methylpropionic acid Under nitrogen, 2-(4-{2-[2-(2'-fluoro-biphenyl-4-yl)-5-methyloxazol-4-yl]-ethoxy}-phenoxy)-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product as a solid. Rf=0.11 in 6:4 ethyl acetate:hexanes; $^1$H NMR (400 MHz, $CDCl_3$) δ8.02 (d, J=8.4 Hz, 2H), 7.60 (d, J=8.4 Hz, 2H), 7.46–7.42 (m, 1H), 7.32–7.28 (m, 1H), 7,22–7.12 (m, 2H), 6.87 (d, J=9.2 Hz, 2H), 6.76 (d, J=9.2 Hz, 2H), 4.15 (t, J=6.6 Hz, 2H), 2.98 (t, J=6.6 Hz, 2H), 2.37 (s, 3H), 1.51 (s, 6H); MS (EI) 498.1 $(M+Na)^+$, 476.1 $(M+H)^+$.

Example 14

2-(4-{2-[2-(2',6'-Difluorobiphenyl-4-yl)-5-methyloxazol-4-yl]-ethoxy}-phenoxy)-2-methylpropionic acid

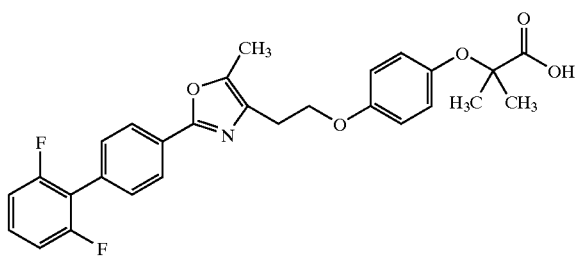

A. 2-(4-{2-[2-(2',6'-Difluoro-biphenyl-4-yl)-5-methyloxazol-4-yl]-ethoxy}-phenoxy)-2-methylpropionic acid ethyl ester A solution of 2-(4-{2-[2-(4-bromophenyl)-5-methyloxazol-4-yl]ethoxy}-phenoxy)-2-methylpropionic acid ethyl ester (300 mg, 0.614 mmol) (see Ex. 2, part B), 2,6-difluorophenylboronic acid (0.921 mmol), potassium fluoride (88.6 mg, 1.84 mmol), palladium acetate (1.3 mg, 0.14 µmol), and 2-(dicyclohexylphosphino)biphenyl (4.3 mg, 12.3 µmol) were combined under $N_2$, to which anhydrous THF (1.23 mL) was added. The yellow mixture was heated at reflux for 12 h. After cooling to room temperature, the mixture was partitioned between $Et_2O$ (20 mL) and 1M NaOH (10 mL). The layers were separated, and the aqueous phase was back-extracted with $Et_2O$ (10 mL). Combined organic phases were dried over $Na_2SO_4$, and concentrated. The product was purified by silica gel chromatography (25 g $SiO_2$, 1:4 ethyl acetate:hexanes) to yield the desired product as an oil. $^1$H NMR (400 MHz, $CDCl_3$) δ8.02 (d, J=8.0 Hz, 2H), 7.51 (d, J=8 Hz, 2H), 7.34–7.28 (m, 1H), 6.98–6.91 (m, 2H), 6.81–6.73 (m, 4H), 4.20 (q, J=6.8 Hz, 2H), 4.17 (t, J=6.6 Hz, 2H), 2.93 (t, J=6.6 Hz, 2H), 2.33 (s, 3H), 1.50 (s, 6H), 1.24 (t, J=6.8 Hz, 3H); MS (EI) 522.2 $(M+H)^+$.

B. 2-(4-{2-[2-(2',6'-Difluorobiphenyl-4-yl)-5-methyloxazol-4-yl]-ethoxy}-phenoxy)-2-methylpropionic acid Under nitrogen, 2-(4-{2-[2-(2',6'-difluoro-biphenyl-4-yl)-5-methyloxazol-4-yl]-ethoxy}-phenoxy)-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product as a solid. $^1$H NMR (400 MHz, $CDCl_3$) δ8.05 (d, J=8.0 Hz, 2H), 7.54 (d, J=8.0 Hz, 2H), 7.34–7.28 (m, 1H), 7.02–6.98 (m, 2H), 6.91–6.78 (m, 4H), 4.17 (t, J=6.6 Hz, 2H), 2.97 (t, J=6.6 Hz, 2H), 2.39 (s, 3H), 1.53 (s, 6H); MS (EI) 494.5 $(M+H)^+$.

Example 15

2-(4-{2-[2-(2',6'-Dichloro-biphenyl-4-yl)-5-methyloxazol-4-yl]-ethoxy}-phenoxy)-2-methylpropionic acid

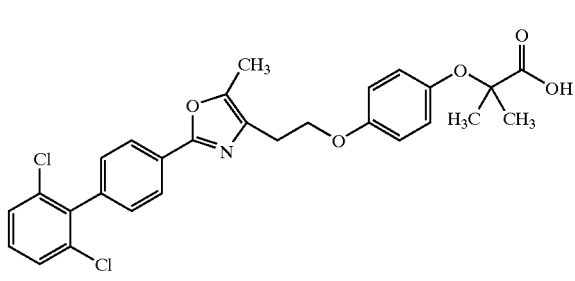

A. 2-(4-{2-[2-(2',6'-Dichloro-biphenyl-4-yl)-5-methyloxazol-4-yl]-ethoxy}-phenoxy)-2-methylpropionic acid ethyl ester A solution of 2-(4-{2-[2-(4-bromophenyl)-5-methyloxazol-4-yl]ethoxy}phenoxy)-2-methylpropionic acid ethyl ester (300 mg, 0.614 mmol) (see Ex. 2, part B), 2,6-dichlorophenylboronic acid (0.921 mmol), potassium fluoride (88.6 mg, 1.84 mmol), palladium acetate (1.3 mg, 0.14 μmol), and 2-(dicyclohexylphosphino)biphenyl (4.3 mg, 12.3 μmol) were combined under $N_2$, to which anhydrous THF (1.23 mL) was added. The yellow mixture was heated at reflux for 12 h. After cooling to room temperature, the mixture was partitioned between $Et_2O$ (20 mL) and 1M NaOH (10 mL). The layers were separated, and the aqueous phase was back-extracted with $Et_2O$ (10 mL). Combined organic phases were dried over $Na_2SO_4$, and concentrated. The product was purified by silica gel chromatography (25 g $SiO_2$, 1:4 ethyl acetate:hexanes) to yield the desired product as an oil. Rf=0.50 in 1:4 ethyl acetate:hexanes; MS (EI) 554.2 $(M+H)^+$.

B. 2-(4-{2-[2-(2',6'-Dichloro-biphenyl-4-yl)-5-methyloxazol-4-yl]-ethoxy}-phenoxy)-2-methylpropionic acid Under nitrogen, 2-(4-{2-[2-(2',6'-dichloro-biphenyl-4-yl)-5-methyloxazol-4-yl]-ethoxy}-phenoxy)-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product as a solid. Rf=0.11 in 6:4 ethyl acetate:hexanes; $^1$H NMR (400 MHz, $CDCl_3$) δ8.03 (d, J=8.4 Hz, 2H), 7.36 (d, J=8.0 Hz, 2H), 7.29 (d, J=8.4 Hz, 1H), 7.18 (d, J=8.0 Hz, 1H), 6.84 (d, J=8.8 Hz, 2H), 6.74 (d, J=8.8 Hz, 2H), 4.14 (t, J=6.6 Hz, 2H), 2.95 (t, J=6.6 Hz, 2H), 2.34 (s, 3H), 1.47 (s, 6H); MS (EI) 550.2 $(M+Na)^+$, 526.2 $(M+H)^+$.

Example 16

2-(4-{2-[2-(4'-tert-Butylcarbamoylbiphenyl-3-yl)-5-methyloxazol-4-yl]ethoxy}phenoxy)-2-methyl propionic acid

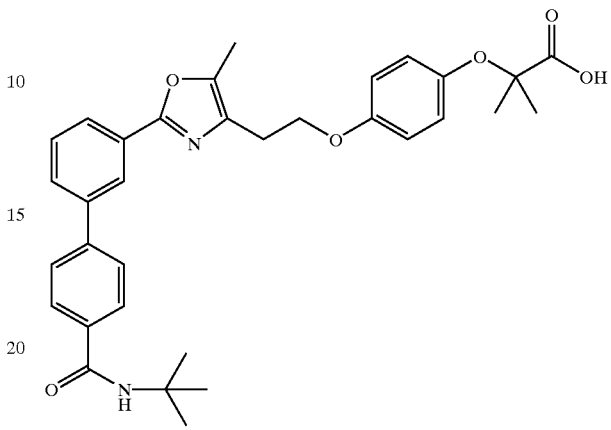

A. 2-(4-{2-[2-(4'-tert-Butylcarbamoylbiphenyl-3-yl)-5-methyloxazol-4-yl]ethoxy}phenoxy)-2-methyl propionic acid ethyl ester 3'-(4-{2-[3-(1-Ethoxycarbonyl-1-methylethoxy)phenoxy]ethyl}-5-methyloxazol-2-yl)-biphenyl-4-carboxylic acid ethyl ester (30 mg, 0.057 mmol) (see Ex. 6, part A), 1-hydroxybenzotriazole (15 mg, 0.11 mmol), and 1-(3-dimethylaminopropyl)-3-ethylcarbodiimide hydrochloride (22 mg, 0.11 mmol) were combined in DMF (1 mL) under $N_2$ and then t-butyl amine (8 mg, 0.11 mmol, 20 μL) was added. After 6 h, the solution was partitioned between ethyl acetate (10 mL) and 1N HCl (10 mL). The organic phase was washed with brine (1×), dried ($MgSO_4$), filtered and concentrated to a yellow-brown oil. The product was purified by flash chromatography (20 mL $SiO_2$, 35% ethyl acetate/hexanes to 50% ethyl acetate/hexanes) and obtained as a clear, colorless oil (21 mg, 64%): $^1$H NMR (400 MHz, $CDCl_3$) δ8.22 (t, J=1.2 Hz, 1H), 7.97 (dt, J=8.4, 1.2 Hz, 1H), 7.82–7.68 (m, 4H), 7.63 (dt, J=8.4, 1.2 Hz, 1H), 7.51 (t, J=7.2 Hz, 1H), 6.83–6.77 (m, 4H), 6.01 (br s, 1H), 4.22 (q, J=6.8 Hz, 2H), 4.20 (t, J=6.4 Hz, 2H), 2.97 (t, J=6.4 Hz, 2H), 2.38 (s, 3H), 1.52 (s, 6H), 1.27 (t, J=7.2 Hz, 3H); MS (EI) 585.2 $(M+H)^+$.

B. 2-(4-{2-[2-(4'-tert-Butylcarbamoylbiphenyl-3-yl)-5-methyloxazol-4-yl]ethoxy}phenoxy)-2-methyl propionic acid Under nitrogen, 2-(4-{2-[2-(4'-tert-butylcarbamoylbiphenyl-3-yl)-5-methyloxazol-4-yl]ethoxy}phenoxy)-2-methyl propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product as a solid. $^1$H NMR (400 MHz, $d_6$-DMSO) δ8.12 (t, J=1.2 Hz, 1H), 7.90–7.73 (m, 6H), 7.56 (t, J=7.2 Hz, 1H), 6.82–6.74 (m, 4H), 4.17 (t, J=6.4 Hz, 2H), 2.90 (t, J=6.4 Hz, 2H), 2.34 (s, 3H), 1.36 (s, 6H); MS (EI) 557.2 $(M+H)^+$.

Example 17

2-[4-(2-{2-[4-(3,5-Dimethyl-isoxazol-4-yl)-phenyl]-5-methyloxazol-4-yl}-ethoxy)-phenoxy]-2-methylpropionic acid

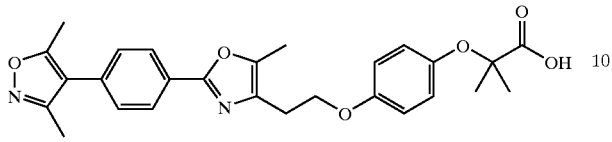

A. 2-[4-(2-{2-[4-(3,5-Dimethyl-isoxazol-4-yl)-phenyl]-5-methyloxazol-4-yl}-ethoxy)-phenoxy]-2-methylpropionic acid ethyl ester A solution of 2-(4-{2-[2-(4-bromophenyl)-5-methyloxazol-4-yl]ethoxy}phenoxy)-2-methyl-propionic acid ethyl ester (907 mmol) (see Ex. 2, part B) and 3,5-dimethylisoxazole-4-boronic acid (0.998 mmol) in toluene:ethanol (18.2 mL of a 1:1 solution) was treated with $Na_2CO_{3(aq)}$ (0.906 mL of a 2M solution). A nitrogen atmosphere was applied, $Pd(PPh_3)_4$ (52.5 mg) was added, and the orange mixture was heated at reflux for 2 h. After cooling to room temperature, the mixture was partitioned between ethyl acetate (20 mL) and $H_2O$ (30 mL). The layers were separated, and the aqueous phase was back-extracted with ethyl acetate (2×10 mL). Combined organic phases were washed with brine (20 mL), dried over $Na_2SO_4$, and concentrated. The product was purified by silica gel chromatography (20 g $SiO_2$, 3:7 ethyl acetate:hexanes) to yield the product in 92% yield as an oil; Rf=0.16 in 1:4 ethyl acetate:hexanes; $^1H$ NMR (400 MHz, $CDCl_3$) δ7.99 (d, J=8.4 Hz, 2H), 7.27 (d, J=8.4 Hz, 2H), 6.78 (d, J=8.8 Hz, 2H), 6.73 (d, J=8.8 Hz, 2H), 7.06–7.01 (m, 2H), 4.8 (q, J=7.2 Hz, 2H), 4.15 (t, J=6.4 Hz, 2H), 2.92 (t, J=6.4 Hz, 2H), 2.39 (s, 3H), 2.33 (s, 3H), 2.25 (s, 3H), 1.48 (s, 6H), 1.23 (t, J=7.2 Hz, 3H); MS (EI) 528.2 (M+Na)+5.05.2 (M+H)+.

B. 2-[4-(2-{2-[4-(3,5-Dimethyl-isoxazol-4-yl)-phenyl]-5-methyloxazol-4yl}-ethoxy)-phenoxy]-2-methylpropionic acid Under nitrogen, 2-[4-(2-{2-[4-(3,5-dimethyl-isoxazol-4-yl)-phenyl]-5-methyloxazol-4-yl}-ethoxy)-phenoxy]-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product in 86% yield. Rf=0.10 in 6:4 ethyl acetate:hexanes; $^1H$ NMR (400 MHz, $CDCl_3$) δ8.02 (d, J=8.8 Hz, 2H), 7.29 (d, J=8.8 Hz, 2H), 6.88 (d, J=8.8 Hz, 2H), 6.77 (d, J=8.8 Hz 2H), 4.17 (t, J=6.6 Hz, 2H), 2.97 (t, J=6.6 Hz, 2H), 2.41 (s, 3H), 2.37 (s, 3H), 2.77 (s, 3H), 1.50 (s, 6H); MS (EI) 499.2 (M+Na)+, 477.3 (M+H)+.

Example 18

2-Methyl-2-[4-(2-{5-methyl-2-[4-(1H-pyrrol-2-yl)-phenyl]-oxazol-4-yl}-ethoxy)-phenoxy]propionic acid

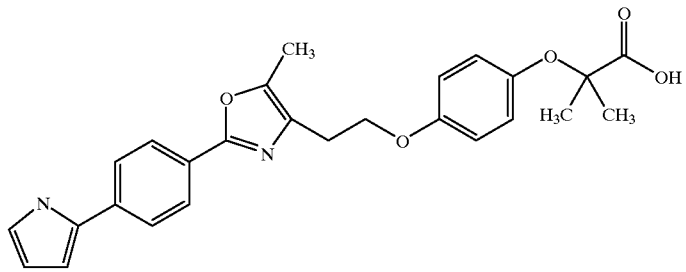

A. 2-[4-(4-{2-[4-(1-Ethoxycarbonyl-1-methyl-ethoxy)-phenoxy]-ethyl}-5-methyloxazol-2-yl)-phenyl]-pyrrole-1-carboxylic acid tert-butyl ester A solution of 2-(4-{2-[2-(4-bromophenyl)-5-methyloxazol-4-yl]ethoxy}phenoxy)-2-methyl-propionic acid ethyl ester (907 mmol) (see Ex. 2, part B) and 1-(t-butoxycarbonyl)pyrrole-2-boronic acid (0.998 mmol) in toluene: ethanol (18.2 mL of a 1:1 solution) was treated with $Na_2CO_{3(aq)}$ (0.906 mL of a 2M solution). A nitrogen atmosphere was applied, $Pd(PPh_3)_4$ (52.5 mg) was added, and the orange mixture was heated at reflux for 2 h. After cooling to room temperature, the mixture was partitioned between ethyl acetate (20 mL) and $H_2O$ (30 mL). The layers were separated, and the aqueous phase was back-extracted with ethyl acetate (2×10 mL). Combined organic phases were washed with brine (20 mL), dried over $Na_2SO_4$, and concentrated. The product was purified by silica gel chromatography (20 g $SiO_2$, 3:7 ethyl acetate:hexanes) to yield the product in 92% yield as an oil; Rf=0.50 in 1:4 ethyl acetate:hexanes; $^1H$ NMR (400 MHz, $CDCl_3$) δ7.92 (d, J=8.0 Hz, 2H), 7.37 (d, J=8.0 Hz, 2H), 7.34 (t, J=2.4 Hz, 1H), 6.79 (d, J=9.4 Hz, 2H), 6.74 (d, J=9.4 Hz, 2), 6.21 (d, J=2.4 Hz, 2H), 4.20 (q, J=6.8 Hz, 2H), 4.16 (t, J=6.8 Hz, 2H), 2.93 (d, J=6.8 Hz, 2H), 2.34 (s, 3H), 1.49 (s, 6H), 1.33 (s, 9H), MS (EI) 598.2 (M+Na)+, 575.2 (M+H)+.

B. 2-Methyl-2-[4-(2-{5-methyl-2-[4-(1H-pyrrol-2-yl)-phenyl]-oxazol-4-yl}-ethoxy)-phenoxy]propionic acid Under nitrogen, 2-[4-(2-{2-[4-(3,5-dimethyl-isoxazol-4-yl)-phenyl]-5-methyloxazol-4-yl}-ethoxy)-phenoxy]-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to yield the desired product. Rf=0.09 in 6:4 ethyl acetate:hexanes; $^1$H NMR (400 MHz, $CDCl_3$) δ7.93 (d, J=8.0 Hz, 2H), 7.67–7.61 (m, 1H), 7.49 (d, J=8.0 Hz, 2H), 7.43 (m, 3H), 6.86 (d, J=9.6 Hz, 2H), 6.77 (d, J=9.6 Hz, 2H), 6.59–6.58 (m, 1H), 6.31–6.28 (m, 1H) 4.16 (t, J=6.6 Hz, 2H), 2.95 (t, J=6.6 Hz, 2H), 2.35 (s, 3H), 2.19 (s, 3H), 1.49 (s, 6H); MS (EI) 469.2 $(M+Na)^+$, 447.3 $(M+H)^+$.

Example 19

2-Methyl-2-(4-{2-[5-methyl-2-(4-pyrimidin-2-yl-phenyl)-oxazol-4-yl]-ethoxy}-phenoxy)-propionic acid

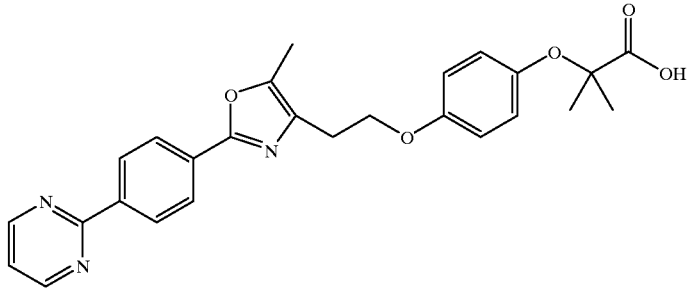

A. 2-Methyl-2-[4-(2-{5-methyl-2-[4,4,5,5-tetramethyl-[1,3,2]dioxaborolan-2-yl)-phenyl]-oxazol-4-yl}-ethoxy)-phenoxy]-propionic acid ethyl ester A flask charged with 2-(4-{2-[2-(4-bromophenyl)-5-methyl-oxazol-4-yl]-ethoxy}-phenoxy)-2-methylpropionic acid ethyl ester (3.00 g, 6.155 mmol), potassium acetate (1.81 g, 18.466 mmol), and bis(pinacolato)diboron (1,87 g, 7.387 mmole) in dimethylsulfoxide (31.2 mL) was flushed and purged with nitrogen three times. [1,1'-Bis(diphenylphosphino)-ferrocene]dichloro palladium(II) complex with dichloromethane (1:1) (905 mg, 1.108 mmol) was then added. After being stirred at 80° C. for 2 h, the reaction was checked by HPLC. The product was extracted with dichloromethane (60 mL) and washed with water. The aqueous layer was back extracted with dichloromethane (60 mL). The combined organic layers were washed with water (50 mL), dried over NaCl, and the solvent was removed in vacuo. Flash chromatography using hexanes, 10% ethyl acetate, 20% ethyl acetate, then 40% ethyl acetate provided product in quantitative yield: $^1$H NMR (400 MHz, $CDCl_3$) δ7.94(d, 2H), 7.82 (d, 2H), 6.76 (d, 2H), 6.73 (d, 2H), 4.22 (q, 2H), 4.18 (t, 2H), 2.93 (t, 2H), 2.33 (s, 3H), 1.47 (s, 6H), 1.31 (s, 12H), 1.21 (t, 3H); MS (EI) 536.3 $(M+H)^+$.

B. 2-Methyl-2-(4-{2-[5-methyl-2-(4-pyrimidin-2-yl-phenyl)-oxazol-4-yl]-ethoxy}-phenoxy)-propionic acid ethyl ester A 50 mL flask was charged with 2-methyl-2-[4-(2-{5-methyl-2-[4-(4,4,5,5-tetramethyl-[1,3,2]dioxaborolan-2-yl)-phenyl]-oxazol-4-yl})-ethoxy)-phenoxy]-propionic acid ethyl ester (198 mg, 0.371 mmol), 2-bromopyrimidine (54 mg, 338 mmol), and 5 mL of isopropanol. The flask was purged with $N_2$ three times. After 20 min, palladium acetate (3.0 mg, 0.04 mmol) and triphenylphosphine (3.5 mg, 0.04 mmol) were added. Following addition of a solution of sodium carbonate (43 mg in 1 mL $H_2O$), the mixture was heated to 86° C. for 4 h. The solvent was removed under reduced pressure and the remaining residue taken up in $CH_2Cl_2$ (25 mL) and extracted with 0.5 N NaOH (25 mL). The aqueous layer was back extracted with an additional 25 mL $CH_2Cl_2$ and the organic layers combined. The organic layer was washed with 1 N NaOH (25 mL) and $H_2O$ (25 mL) and then dried and concentrated in vacuo. Flash chromatography provided 45.7 mg (28%) of desired product as a clear oil: $^1$H NMR (400 MHz, $CDCl_3$) δ8.76 (d, 1H), 8.45 (d, 2H), 8.06 (d, 2H), 7.15 (t, 2H), 6.76 (d, 2H), 6.71 (d, 2H), 4.18 (q, 2H), 4.14 (t, 2H), 2.93 (t, 2H), 2.33 (s, 3H), 1.45 (s, 6H), 1.21 (t, 3H); MS (EI) 488.3 $(M+H)^+$.

C. 2-Methyl-2-(4-{2-[5-methyl-2-(4-pyrimidin-2-yl-phenyl)-oxazol-4-yl]-ethoxy}-phenoxy)-propionic acid Under nitrogen, 2-methyl-2-(4-{2-[5-methyl-2-(4-pyrimidin-2-yl-phenyl)-oxazol-4-yl]-ethoxy}-phenoxy)-propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to yield the desired product. $^1$H NMR (400 MHz, $CDCl_3$) δ8.76 (d, 1H), 8.45 (d, 2H), 8.06 (d, 2H), 7.15 (t, 2H), 6.76 (d, 2H), 6.71 (d, 2H), 4.14 (t, 2H), 2.93 (t, 2H), 2.33 (s, 3H), 1.45 (s, 6H); MS (EI) 460.3 $(M+H)^+$.

Example 20

2-Methyl-2-(4-{2-[5-methyl-2-(4-pyrimidin-5-yl-phenyl)-oxazol-4-yl]-ethoxy}-phenoxy)-propionic acid

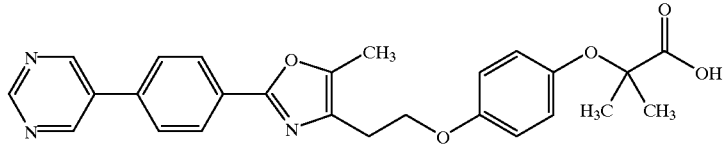

A. 2-Methyl-2-(4-{2-[5-methyl-2-(4-pyrimidin-5-yl-phenyl)-oxazol-4-yl]-ethoxy}-phenoxy)-propionic acid ethyl ester A 50 mL flask was charged with 2-methyl-2-[4-(2-{5-methyl-2-[4-(4,4,5,5-tetramethyl-[1,3,2]dioxaborolan-2-yl)-phenyl]-oxazol-4-yl}-ethoxy)-phenoxy]-propionic acid ethyl ester (198 mg, 0.371 mmol), 5-bromopyrimidine (54 mg, 338 mmol), and 5 mL of isopropanol. The flask was purged with $N_2$ three times. After 20 min, palladium acetate (3.0 mg, 0.04 mmol) and triphenylphosphine (3.5 mg, 0.04 mmol) were added. Following addition of a solution of sodium carbonate (43 mg in 1 mL $H_2O$), the mixture was heated to 86° C. for 4 h. The solvent was removed under reduced pressure and the remaining residue taken up in $CH_2Cl_2$ (25 mL) and extracted with 0.5 N NaOH (25 mL). The aqueous layer was back extracted with an additional 25 mL $CH_2Cl_2$ and the organic layers combined. The organic layer was washed with 1 N NaOH (25 mL) and $H_2O$ (25 mL) and then dried and concentrated in vacuo. Flash chromatography provided the desired product. $^1$H NMR (400 MHz, $CDCl_3$) δ9.23 (s, 1H), 9.20 (s, 2H), 8.16 (d, 2H), 7.65 (d, 2H), 6.88 (d, 2H), 6.75 (d, 2H), 4.21 (q, 2H), 4.20 (t, 2H), 3.00 (t, 2H), 2.39 (s, 3H), 1.48 (s, 6H), 1.21 (t, 3H); MS (EI) 4.88.1 $(M+H)^+$.

B. 2-Methyl-2-(4-{2-[5-methyl-2-(4-pyrimidin-5-yl-phenyl)-oxazol-4-yl]-ethoxy}-phenoxy)-propionic acid Under nitrogen, 2-methyl-2-(4-{2-[5-methyl-2-(4-pyrimidin-5yl-phenyl)-oxazol-4-yl]-ethoxy}-phenoxy)-propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to yield the desired product. $^1$H NMR (400 MHz, $CDCl_3$) δ9.23 (s, 1H), 9.20 (s, 2H), 8.16 (d, 2H), 7.65 (d, 2H), 6.86 (d, 2H), 6.76 (d, 2H), 4.20 (t, 2H), 3.00 (t, 2H), 2.39 (s, 3H), 1.48 (s, 6H); MS (EI) 460.2 $(M+H)^+$.

Example 21

2-{3-[2-(2-Biphenyl-4-yl-5-methyloxazol-4-yl)ethoxy]phenoxy}-2-methylpropionic acid

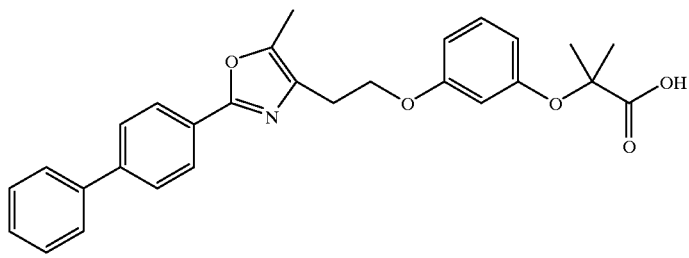

A. 2-{3-[2-(2-Biphenyl-4-yl-5-methyloxazol-4-yl)ethoxy]phenoxy}-2-methylpropionic acid ethyl ester A mixture of the toluene-4-sulfonic acid 2-(2-biphenyl-4-yl-5-methyloxazol-4-yl)ethyl ester (24 g, 66.9 mmol) and 2-(3-hydroxyphenoxy)-2-methylpropanoic acid ethyl ester (Columbia University WO 9731530) (12.5 g, 55.71 mmol) and $Cs_2CO_3$ (22.7 g, 69.6 mmol) was heated at 55° C. in DMF (45 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (1500 mL $SiO_2$, 10% ethyl acetate/hexanes to 20% ethyl acetate/hexanes) to provide 2-{3-[2-(2-biphenyl-4-yl-5-methyloxazol-4-yl)ethoxy]phenoxy}-2-methylpropionic acid ethyl ester. Rf=0.63 in 35% ethyl acetate/hexanes; $^1$H NMR (400 MHz, $CDCl_3$) δ8.03–8.00 (m, 2H), 7.65–7.60 (m, 4H), 7.43 (t, J 7.2 Hz, 2H), 7.34 (tt, J=7.2, 1.2 Hz, 1H), 7.07 (t, J 8.0 Hz, 1H), 6.52 (ddd, J=8.0, 2.4, 1.2 Hz, 1H), 6.43 (t, J=2.4 Hz, 1H), 6.36 (ddd, J=8.0, 2.4, 1.2 Hz, 1H), 4.20 (q, J=6.8 Hz, 2H), 4.18 (t, J=6.4 Hz, 2H), 2.95 (t, J=6.4 Hz, 2H), 2.36 (s, 3H), 1.56 (s, 6H), 1.21 (t, J=6.8 Hz, 3H).

B. 2-{3-[2-(2-Biphenyl-4-yl-5-methyloxazol-4-yl)ethoxy]phenoxy}-2-methylpropionic acid Under nitrogen, 2-{3-[2-(2-biphenyl-4-yl-5-methyloxazol-4-yl)ethoxy]phenoxy}-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the product in 99% yield as a white solid: $^1$H NMR (400 MHz, $CDCl_3$) δ8.05–8.03 (m, 2H), 7.68–7.66 (m, 2H), 7.65–7.63 (m, 2H), 7.47 (t, J=7.6 Hz, 2H), 7.38 (tt, J=7.2 1.6 Hz, 1H), 7.14 (t, J=8.4 Hz, 1H), 6.69 (t, J=2.4 Hz, 1H), 6.61 (dd, J=8.0, 2.8 Hz, 1H), 6.54 (dd, J=7.6, 2.4 Hz, 1H), 4.20 (q, J=7.2 Hz, 2H), 2.95 (t, J=7.2 Hz, 2H), 2.37 (s, 3H), 1.56 (s, 6H).

Example 22

2-{3-[2-(2-Biphenyl-3-yl-5-methyloxazol-4-yl)ethoxy]phenoxy}-2-methylpropionic acid

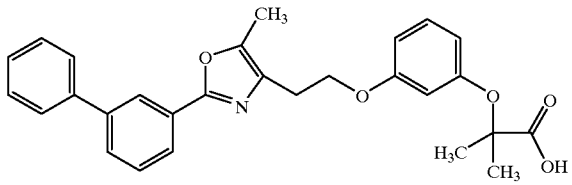

A. 2-(3-Biphenyl)-5-methyl-4-oxazoleethanol 2-(3-Bromophenyl)-5-methyl-4-oxazoleethanol (35.0 mmol) (see Ex. 3, part D) and phenylboronic acid (4.5 g, 38.0 mmol) were dissolved in n-propanol (120 mL) before adding triphenylphosphine (165.2 mg, 0.63 mmol), palladium acetate (46 mg, 2.1 mmol), and $Na_2CO_3$ (4.5 g, 42 mmol) dissolved in 30 mL distilled $H_2O$). The solution was heated to reflux and stirred for 1.5 h. After cooling to ambient temperature, the mixture was concentrated under reduced pressure and then partitioned between $CH_2Cl_2$ (100 mL) and 1N NaOH (100 mL). The aqueous phase was extracted with $CH_2Cl_2$ (2×50 mL) and the combined organic phases were dried ($MgSO_4$) and concentrated under reduced pressure to provide the desired product which was used directly without further purification. $^1$H NMR ($CDCl_3$) δ6.42 (d, J=8.6 Hz, 2H), 6.38 (d, J=8.6 Hz, 2H), 4.20 (q, J=7.2 Hz, 2H), 2.61 (t, J=6.0 Hz, 2H), 2.55 (t, J=6.0 Hz, 2H), 1.6 (m, 4H), 1.49 (s, 6H), 1.23 (t, J=7.2 Hz, 3H); MS (ES+) m/e (% relative intensity) 301.1 (28), 279.2 (M$^+$+1, 49), 233.1 (100), 205.1 (470), 165.1 (88).

B. Toluene-4-sulfonic acid 2-(2-biphenyl-3-yl-5-methyloxazol-4-yl)ethyl ester

To a solution of 2-(3-biphenyl)-5-methyl-4-oxazoleethanol (31.5 mmol) in $CH_2Cl_2$ (150 mL) at room temperature under $N_2$ was added pyridine (8.74 g, 110 mmol, 8.9 mL) and DMAP (0.97 g, 7.88 mmol) followed by portionwise addition of tosyl anhydride (12.7 g, 37.8 mmol). The reaction exothermed to 32° C. and was stirred 1 h before 1N HCl (200 mL) was added. The mixture was stirred vigorously 15 min, and then the organic phase was dried ($MgSO_4$) and filtered through a pad of silica gel (200 mL, packed with $CH_2Cl_2$). After rinsing the silica gel with ethyl acetate (100 mL) the solution was concentrated to Toluene-4-sulfonic acid 2-(2-biphenyl-3-yl-5-methyloxazol-4-yl) ethyl ester which was used without further purification. $^1$H NMR (400 MHz, $CDCl_3$) δ8.06 (s, 1H), 7.80 (d, J=8.0 Hz, 1H), 7.6 (m, 5H), 7.4 (m, 4H), 7.12 (d, J=8.4 Hz, 2H), 4.28 (t, J=6.0 Hz, 2H), 2.79 (t, J=6.0 Hz, 2H), 2.28 (s, 3H), 2.12 (s, 3H); MS (ES+) m/e (% relative intensity) 436.1 (44), 435.1 (70), 434.1 (M$^+$+1, 100).

C. 2-{3-[2-(2-Biphenyl-3-yl-5-methyloxazol-4-yl)ethoxy]phenoxy}-2-methylpropionic acid ethyl ester A mixture of the toluene-4-sulfonic acid 2-(2-biphenyl-3-yl-5-methyloxazol-4-yl)ethyl ester (66.9 mmol) and 2-(3-hydroxyphenoxy)-2-methylpropanoic acid ethyl ester (Columbia University WO 9731530) (12.5 g, 55.71 mmol) and $Cs_2CO_3$ (22.7 g, 69.6 mmol) was heated at 55° C. in DMF (45 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (1500 mL $SiO_2$, 10% ethyl acetate/hexanes to 20% ethyl acetate/hexanes) to provide 2-{3-[2-(2-biphenyl-3-yl-5-methyloxazol-4-yl)ethoxy]phenoxy}-2-methylpropionic acid ethyl ester. Rf=0.50 in 20% ethyl acetate/hexanes; $^1$H NMR (400 MHz, $CDCl_3$) δ8.18 (s, 1H), 7.95 (d, 1H), 7.65–7.59 (m, 3H), 7.44–7.39 (m, 3H), 7.36 (t, 1H), 7.08 (t, 1H), 6.55 (d, 1H), 6.41 (s, 1H), 6.37 (d, 1H), 4.20–4.14 (m, 4H), 2.97 (t, 2H), 2.38 (s, 3H), 1.57 (s, 6H), 1.20 (t, 3H); MS (EI) 508.2 (M+Na)$^+$, 486.2 (M+H)$^+$.

D. 2-{3-[2-(2-Biphenyl-3-yl-5-methyloxazol-4-yl)ethoxy]phenoxy}-2-methylpropionic acid Under nitrogen, 2-{3-[2-(2-biphenyl-3-yl-5-methyloxazol-4-yl)ethoxy]phenoxy}-2-methylpropionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the desired product. mp 67–71° C.; Rf=0.09 in 60% ethyl acetate/hexanes; $^1$H NMR (400 MHz, $CDCl_3$) δ8.22 (s, 1H), 7.91 (d, J=7.2 Hz, 1H), 7.65–7.63 (m, 3H), 7.51–7.41 (m, 3H), 7.35 (t, J=7.2 Hz, 1H), 7.13 (t, J=8.0 Hz, 1H), 6.72 (s, 1H), 6.38 (d, J=8.0 Hz, 1H), 6.53 (d, J=8.0 Hz), 4.19 (t, J=7.4 Hz, 2H), 2.92 (t, J=7.4 Hz, 2H), 2.36 (s, 3H), 1.58 (s, 6H); MS (EI) 479.9 (M+Na)$^+$, 457.9 (M+H)$^+$.

Example 23

2-{3-[2-(2-Biphenyl-4-yl-5-methyloxazol-4-yl)-ethoxy]-2-propyl-phenoxy}-2-methyl-propionic acid

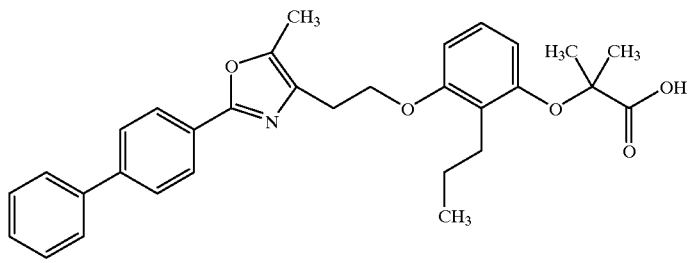

A. 2-{3-[2-(2-Biphenyl-4-yl-5-methyloxazol-4-yl)-ethoxy]-2-propyl-phenoxy}-2-methyl-propionic acid ethyl ester A mixture of the toluene-4-sulfonic acid 2-(biphenyl-4-yl-5-methyloxazol-4-yl ester (66.9 mmol) (see Ex. 1, part F) and 2-(3-hydroxy-2-propylphenoxy)-2-methylpropanoic acid ethyl ester (55.71 mmol) and $Cs_2CO_3$ (22.7 g, 69.6 mmol) was heated at 55° C. in DMF (45 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (1500 mL $SiO_2$, 10% ethyl acetate/hexanes to 20% ethyl acetate/hexanes) to provide 2-{3-[2-(2-biphenyl-4-yl-5-methyloxazol-4-yl)-ethoxy]-2-propyl-phenoxy}-2-methyl-propionic acid ethyl ester. Rf=0.28 in 20% ethyl acetate/hexanes; $^1$H NMR (400 MHz, $CDCl_3$) δ7.92 (d, J=8.0 Hz, 1H), 7.74 (d, J=8.0 Hz, 1H), 7.67 (d, J=7.6 Hz, 3H), 7.43 (t, J=7.2 Hz, 1H), 7.34 (t, J=7.6 Hz, 2H), 6.95 (t, J=8.4 Hz, 1H), 6.56 (d, J=8.4 Hz, 1H), 6.24 (d, J=8.4 Hz, 1H), 4.26–4.20 (m, 4H), 3.00 (t, J=6.4 Hz, 2H), 2.61 (t, J=7.6 Hz, 2H), 2.42 (s, 3H), 1.59 (s, 6H), 1.47 (sextet, J=7.2 Hz, 2H), 1.23 (t, J=7.2 Hz, 3H), 0.90 (t, J=7.6 Hz, 3H).

B. 2-{3-[2-(2-Biphenyl-4-yl-5-methyloxazol-4-yl)-ethoxy]-2-propyl-phenoxy}-2-methyl-propionic acid Under nitrogen, 2-{3-[2-(2-biphenyl-4-yl-5-methyloxazol-4-yl)-ethoxy]-2-propyl-phenoxy}-2-methyl-propionic acid ethyl ester (0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried ($Na_2SO_4$), and concentrated in vacuo to provide the desired product. Rf=0.22 in 70% ethyl acetate/hexanes; $^1$H NMR (400 MHz, $d_6$-DMSO) δ7.92 (d, J=8.0 Hz, 1H), 7.74 (d, J=8.0 Hz, 1H), 7.67 (d, J=7.6 Hz, 3H), 7.43 (t, J=7.2 Hz, 1H), 7.34 (t, J=7.6 Hz, 2H), 6.95 (t, J=8.4 Hz, 1H), 6.56 (d, J=8.4 Hz, 1H), 6.24 (d, J=8.4 Hz, 1H), 4.13 (t, J=6.4 Hz, 2H), 2.87 (t, J=6.4 Hz, 2H), 2.41 (t, J=7.6 Hz, 2H), 2.32 (s, 3H), 1.40 (s, 6H), 1.23 (sextet, J=7.2 Hz, 2H), 0.71 (t, J=7.6 Hz, 3H), Example 24

2-{4-[2-(2-Biphenyl-4-yl-5-methyloxazol-4-yl)-ethoxy]-2-methylphenoxy}-2-methylpropionic acid mixture was cooled and partitioned between water (30 mL) and ether (75 mL). The organic layer was washed with brine (15 mL). The aqueous layers were back-extracted with ethyl acetate (30 mL), and the organic layer was washed with brine (20 mL). The combined organic layers were dried ($Na_2SO_4$) and concentrated to a brown oil. The crude product was purified by flash chromatography using hexanes:ethyl acetate (2.5:1) to give a pale yellow solid (3.04 g, 89%): mp 65° C.; $^1$H NMR (400 MHz, $CDCl_3$) δ1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30–7.43 (m, 6H); MS (ES) m/e 343.1 [M+1].

B. 2-(4-Hydroxy-2-methyl-phenoxy)-2-methyl-propionic acid ethyl ester

2-Methyl-2-{2-methyl-4-[2-(5-methyl-2-phenyloxazol-4-yl)ethoxy]phenoxy}propionic acid (9.00 g, 26.3 mmol) in ethanol (250 mL) was treated with 5% Pd/C (1.25 g) and hydrogen (60 psi, room temperature, overnight). Additional 5% Pd/C (1.25 g) was added, and the reaction was continued for 6 h at 40° C. The mixture was filtered and concentrated to a tan oil (6.25 g). This oil contained 9 mol% of 2-(4-Hydroxy-2-hydroxymethyl-phenoxy)-2-methyl-propionic acid ethyl ester. $^1$H NMR (400 MHz, $CDCl_3$) δ1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

C. 2-{4-[2-(2-Biphenyl-4-yl-5-methyloxazol-4-yl)-ethoxy]-2-methylphenoxy}-2-methylpropionic acid ethyl ester A mixture of 2-(4-hydroxy-2-methyl-phenoxy)-2-methyl-propionic acid ethyl ester (4.50 g, 18.9 mmol), toluene-4-sulfonic acid 2-(5-methyl-2-biphenyl-4-yl-oxazol-4-yl) ethyl (8.43 g, 23.6 mmol) (see Ex. 1, part F), and $Cs_2CO_3$ (7.68 g, 23.6 mmol) was heated at 55° C. in DMF (45 mL) for 20 h. Additional toluene-4-sulfonic acid 2-(5-methyl-2-biphenyl-4-yl-oxazol-4-yl) ethyl (7.86 mmol) and $Cs_2CO_3$ (2.56 g, 7.86 mmol) were added, and the mixture was heated at 55° C. in DMF (45 mL) for 6 h. The reaction mixture cooled and partitioned between ethyl acetate (200 mL) and $H_2O$ (100 mL). The organic layer was washed with brine (50 mL). The aqueous layers were extracted further with ethyl acetate (200 mL). The combined organic layers were dried ($Na_2SO_4$) and concentrated. The crude product was purified by flash chromatography using hexanes:ethyl acetate (6:1 to 4:1) to give an oil. Rf=0.47 in 35% Ethyl acetate/hexanes; $^1$H NMR (400 MHz, $CDCl_3$) δ8.06–8.04 (m, 2H), 7.68–7.62 (m, 4H), 7.45 (t, J=7.2 Hz, 2H), 7.36 (tt, J=7.2, 1.6 Hz, 1H),

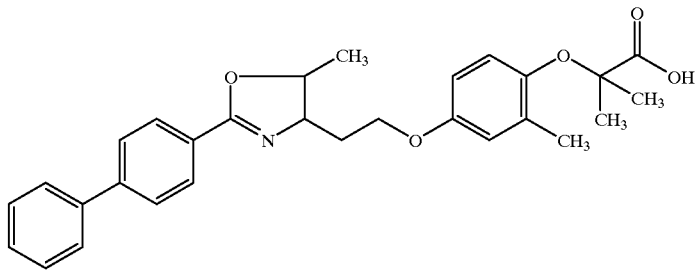

A. 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm. (1975), 308 (5), 339–346) (2.28 g, 10.0 mmol), ethyl bromoisobutyrate (2.2 mL, 15 mmol), and cesium carbonate (3.26 g, 10.0 mmol) in dry DMF (25 mL) were heated at 80° C. for 18 h. The reaction 6.72 (d, J=2.8 Hz, 1H), 6.68 (d, J=8.8 Hz, 1H), 6.60 (dd, J=8.8, 2.8 Hz, 1H), 4.25 (q, J=6.8 Hz, 2H), 4.20 (t, J=6.4 Hz, 2H), 2.96 (t, J=6.8 Hz, 2H), 2.38 (s, 3H), 2.21 (s, 3H), 1.53 (s, 6H), 1.28 (t, J=6.8 Hz, 3H).

D. 2-{4-[2-(2-Biphenyl-4-yl-5-methyloxazol-4-yl)-ethoxy]-2-methylphenoxy}-2-methylpropionic acid A solution of 2-{4-[2-(2-biphenyl-4-yl-5-methyloxazol-4-yl)-ethoxy]-2-methylphenoxy}-2-methylpropionic acid ethyl ester (11.8 mmol) in THF (30 mL) and methanol (60 mL) was treated with 5N aqueous NaOH (20 mL). The solution was heated at 55° C. for 1 h, cooled to ambient temperature, and concentrated in vacuo. The residue was treated with ice water (20 mL), acidified with 5N aqueous HCl (25 mL), and extracted with ethyl acetate (200 mL). The organic layer was washed with brine (40 mL), dried ($Na_2SO_4$), and concentrated to yield the desired product. mp 122–123° C.; $^1$H NMR (400 MHz, $CDCl_3$) δ8.07 (d, J=8.8 Hz, 2H), 7.67 (d, J=8.8 Hz, 2H), 7.62 (dt, J=6.8, 1.2 Hz, 2H), 7.45 (tt, J=6.8, 1.2 Hz, 2H), 7.37 (tt, J=7.2, 2.0 Hz, 1H), 6.82 (d, J=8.8 Hz, 1H), 6.71 (d, J=3.2 Hz, 1H), 6.57 (dd, J=8.8, 3.2 Hz, 1H), 4.16 (t, J=6.4 Hz, 2H), 3.82 (t, J=6.4 Hz, 2H), 2.40 (s, 3H), 2.21 (s, 3H), 1.56 (s, 6H).

Example 25

2-{4-[2-(2-Biphenyl-4-yl-5-methyloxazol-4-yl)-ethoxy]-2-cyclohexylmethyl-phenoxy}-2-methyl-propionic acid

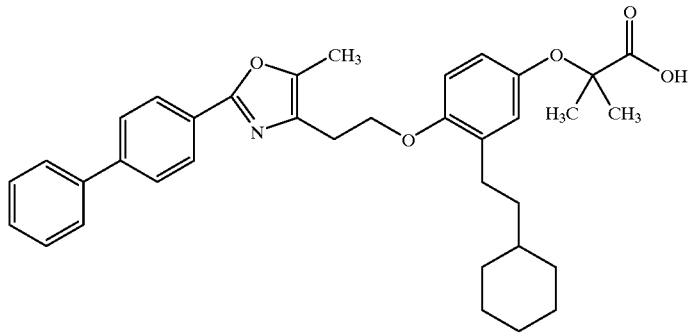

A. (4-Benzyloxy-2-cyclohexylmethylphenoxy)acetic acid ethyl ester

4-Benzyloxy-2-cyclohexylmethylphenol (1,77 mmol) was dissolved in anhydrous DMF (4 mL), followed by the addition of ethyl bromoacetate (0.29 mL, 2.65 mmol), and cesium carbonate (0.75 g, 2.30 mmol). The mixture was then heated for 18 h (55° C.). The reaction mixture was then cooled and concentrated in vacuo. The crude residue was partitioned between ethyl acetate (70 mL) and water (40 mL). The organic layer was washed with brine, dried ($Na_2SO_4$), and removed in vacuo to give the desired product.

B. (2-Cyclohexylmethyl-4-hydroxyphenoxy)acetic acid ethyl ester

A solution of (4-benzyloxy-2-cyclohexylmethylphenoxy) acetic acid ethyl ester (1.77 mmol) in ethanol (15 mL) was treated with 5% Pd/C (70 mg) and hydrogen (60 psi) at ambient temperature for 18 h. The mixture was filtered and concentrated in vacuo to give the desired product.

C. 2-{4-[2-(2-Biphenyl-4-yl-5-methyloxazol-4-yl)-ethoxy]-2-cyclohexylmethylphenoxy}-2-methyl-propionic acid ethyl ester A mixture of (2-cyclohexylmethyl-4-hydroxyphenoxy) acetic acid ethyl ester (1.29 mmol), toluene-4-sulfonic acid 2-(5-methyl-2-biphenyl-4-yl-oxazol-4-ly)ethyl ester (1.55 mmol) (see Ex. 1, part F), and cesium carbonate (0.55 g, 1.7 mmol) in anhydrous DMF (4 mL) was heated for 18 h (55° C.). The mixture was concentrated in vacuo, and the residue was partitioned between ethyl acetate (100 mL) and water (50 mL), washed with brine (50 mL), dried ($Na_2SO_4$), and removed in vacuo to give a crude oil which was purified using radial chromatography eluting with 10–15% ethyl acetate/hexanes to give 2-{4-[2-(2-biphenyl-4-yl-5-methyloxazol-4-yl)-ethoxy]-2-cyclohexylmethyl-phenoxy}-2-methyl-propionic acid ethyl ester, MS (ES) m/e 582.3 (M+1).

D. 2-{4-[2-(2-Biphenyl-4-yl-5-methyloxazol-4-yl)-ethoxy]-2-cyclohexylmethyl-phenoxy}-2-methyl-propionic acid A solution of 2-{4-[2-(2-biphenyl-4-yl-5-methyloxazol-4-yl)-ethoxy]-2-cyclohexylmethyl-phenoxy}-2-methyl-propionic acid ethyl ester (0.54 mmol) in ethanol (10 mL) was treated with 2.5 N aqueous NaOH (0.4 mL), and heated at 55° C. for 2 h. The reaction was cooled to ambient temperature and concentrated down to near dryness. The residue was then diluted with ethyl acetate (40 mL) and water (20 mL) and acidified to pH 1 with 1N aqueous HCl. The organic layer was washed with brine (20 mL), dried ($Na_2SO_4$) and concentrated in vacuo to give 2-{4-[2-(2-biphenyl-4-yl-5-methyloxazol-4-yl)-ethoxy]-2-cyclohexylmethyl-phenoxy}-2-2-methyl-propionic acid. $^1$H NMR (400 MHz, $CDCl_3$) δ8.03–8.05 (m, 2H), 7.67 (d, 2H, J=8.8 Hz) 7.62 (d, 2H, 6.8 Hz), 7.47–7.43 (m, 2H), 7.35–7.39 (m, 1H), 6.77 (d, 1H, J=8.8 Hz), 6.67 (d, 1H, J=2.9 Hz), 6.62 (dd, 1H, J=8.8 Hz, J=2.9 Hz), 4.18 (t, 2H, J=6.4 Hz), 3.00 (t, 2H, J=6.4 Hz), 2.40 (s, 3H), 1.62–1.66 (m, 5H), 1.53 (s, 6H), 1.25 (s, 2H), 1.13–1.18 (m, 4H), 0.85–0.97 (m, 2H), MS (ES) m/e 554.2 (M+1).

Example 26

2-{4-[2-(2-Biphenyl-3-yl-5-methyloxazol-4-yl)-ethoxy]-2-cyclohexylmethyl-phenoxy}-2-methyl-propionic acid

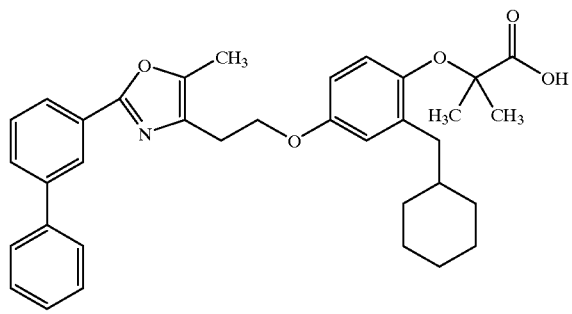

A. 2-{4-[2-(2-Biphenyl-3-yl-5-methyloxazol-4-yl)-ethoxy]-2-cyclohexylmethyl-phenoxy}-2-methyl-propionic acid ethyl ester A mixture of (2-cyclohexylmethyl-4-hydroxyphenoxy) acetic acid ethyl ester (1.29 mmol) (see Ex. 25, part B), toluene-4-sulfonic acid 2-(5-methyl-2-biphenyl-3-yl-oxazol-4-ly)ethyl ester (1.55 mmol) (see Ex. 22, part B), and cesium carbonate (0.55 g, 1.7 mmol) in anhydrous DMF (4 mL) was heated for 18 h (55° C.). The mixture was concentrated in vacuo, and the residue was partitioned between ethyl acetate (100 mL) and water (50 mL), washed with brine (50 mL), dried (Na₂SO₄), and removed in vacuo to give a crude oil which was purified using radial chromatography eluting with 10–15% ethyl acetate/hexanes to give 2-{4-[2-(2-biphenyl-3-yl-5-methyloxazol-4-yl)-ethoxy-]-2-cyclohexylmethyl-phenoxy}-2-methyl-propionic acid ethyl ester, MS (ES) m/e 582.3 (M+1).

B. 2-{4-[2-(2-Biphenyl-3-yl-5-methyloxazol-4-yl)-ethoxy]-2-cyclohexylmethyl-phenoxy}-2-methyl-propionic acid A solution of 2-{4-[2-(2-biphenyl-3-yl-5-methyloxazol-4-yl)-ethoxy]-2-cyclohexylmethyl-phenoxy}-2-methyl-propionic acid ethyl ester (0.54 mmol) in ethanol (10 mL) was treated with 2.5 N aqueous NaOH (0.4 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na₂SO₄) and concentrated in vacuo to give 2-{4-[2-(2-biphenyl-3-yl-5-methyloxazol-4-yl)-ethoxy]-2-cyclohexylmethyl-phenoxy}-2-methyl-propionic acid. ¹H NMR (400 MHz, CDCl₃) δ8.23 (s, 1H), 7.95 (dd, 1H, J=7.8 Hz, J=1.0 Hz) 7.64–7.69 (m, 3H), 7.50–7.54 (m, 1H), 7.46 (t, 2H, J=7.6 Hz), 7.37–7.39 (m, 1H), 6.77 (d, 1H, J=8.3 Hz), 6.66 (d, 1H, J=3.4 Hz), 6.62 (dd, 1H, J=8.8 Hz, J=2.9 Hz), 4.17 (t, 2H, J=6.4 Hz), 3.03 (t, 2H, J=6.4 Hz), 2.41 (s, 3H), 1.62–1.65 (m, 5H), 1.52 (s, 6H), 1.44 (s, 2H), 1.15–1.19 (m, 4H), 0.85–0.91 (m, 2H), MS (ES) m/e 554.2 (M+1).

Example 27

2-(4-{2-[2-(4-Thiophen-2-yl-phenyl)-5-methyloxazol-4-yl]ethoxy}phenoxy)-2-methylpropionic acid

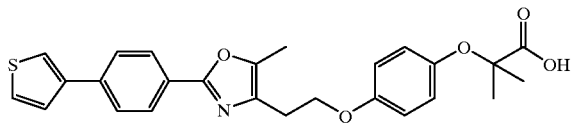

A. 2-(4-{2-[2-(4-Thiophen-2-yl-phenyl)-5-methyloxazol-4-yl]ethoxy}phenoxy)-2-methylpropionic acid ethyl ester To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, part B), 2-thiophenyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh₃)₄ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4-thiophen-2-yl-phenyl)-5-methyloxazol-4-yl]ethoxy}phenoxy)-2-methylpropionic acid ethyl ester.

B. 2-(4-{2-[2-(4-Thiophen-2-yl-phenyl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4-thiophen-2-yl-phenyl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4-thiophen-2-yl-phenyl)-5-methyloxazol-4-yl]ethoxy}phenoxy)-2-methylpropionic acid. ¹H NMR (400 MHz, CDCl) 8.74 (2H, m), 8.39 (2H, d), 8.26 (1H, m), 8.16 (2H, m), 7.64 (2H, d), 7.55 (2H, d), 4.18 (2H, t), 3.00 (2H, t) 2.39 (3H, s), 1.53 (6H, s)

Example 28

2-{4-[2-(2-Biphenyl-4-yl-5-methyloxazol-4-yl)ethoxy]-2-phenethylphenoxy}-2-methylpropionic acid

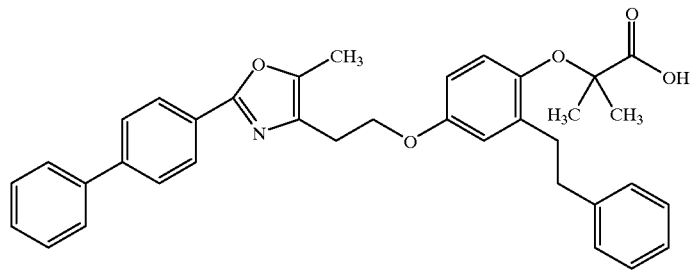

A. (4-Benzyloxy-2-phenethylphenoxy)acetic acid ethyl ester

4-Benzyloxy-2-phenethylphenol (1,77 mmol) was dissolved in anhydrous DMF (4 mL), followed by the addition of ethyl bromoacetate (0.29 mL, 2.65 mmol), and cesium carbonate (0.75 g, 2.30 mmol). The mixture was then heated for 18 h (55° C.). The reaction mixture was then cooled and concentrated in vacuo. The crude residue was partitioned between ethyl acetate (70 mL) and water (40 mL). The organic layer was washed with brine, dried (Na$_2$SO$_4$), and removed in vacuo to give the desired product.

B. (2-Phenethyl-4-hydroxyphenoxy)acetic acid ethyl ester

A solution of (4-benzyloxy-2-phenethylphenoxy)acetic acid ethyl ester (1.77 mmol) in ethanol (15 mL) was treated with 5% Pd/C (70 mg) and hydrogen (60 psi) at ambient temperature for 18 h. The mixture was filtered and concentrated in vacuo to give the desired product.

C. 2-{4-[2-(2-Biphenyl-4-yl-5-methyloxazol-4-yl)ethoxy]-2-phenethylphenoxy}-2-methylpropionic acid ethyl ester A mixture of (2-phenethyl-4-hydroxyphenoxy)acetic acid ethyl ester (1.29 mmol), toluene-4-sulfonic acid 2-(5-methyl-2-biphenyl-4-yl-oxazol-4-ly)ethyl ester (1.55 mmol) (see Ex. 1, part F), and cesium carbonate (0.55 g, 1.7 mmol) in anhydrous DMF (4 mL) was heated for 18 h (55° C.). The mixture was concentrated in vacuo, and the residue was partitioned between ethyl acetate (100 mL) and water (50 mL), washed with brine (50 mL), dried (Na$_2$SO$_4$), and removed in vacuo to give a crude oil which was purified using radial chromatography eluting with 10–15% ethyl acetate/Hexanes to give 2-{4-[2-(2-biphenyl-4-yl-5-methyloxazol-4-yl)ethoxy]-2-phenethylphenoxy}-2-methylpropionic acid ethyl ester. MS (ES) m/e 590 (M+1).

D. 2-{4-[2-(2-Biphenyl-4-yl-5-methyloxazol-4-yl)ethoxy]-2-phenethylphenoxy}-2-methylpropionic acid A solution of 2-{4-[2-(2-biphenyl-4-yl-5-methyloxazol-4-yl)ethoxy]-2-phenethylphenoxy}-2-methylpropionic acid ethyl ester (0.54 mmol) in ethanol (10 mL) was treated with 2.5 N aqueous NaOH (0.4 mL), and heated at 55° C. for 2 h. The reaction was cooled to ambient temperature and concentrated down to near dryness. The residue was then diluted with ethyl acetate (40 mL) and water (20 mL) and acidified to pH 1 with 1N aqueous HCl. The organic layer was washed with brine (20 mL), dried (Na$_2$SO$_4$) and concentrated in vacuo to give 2-{4-[2-(2-biphenyl-4-yl-5-methyloxazol-4-yl)ethoxy]-2-phenethylphenoxy}-2-methylpropionic acid. $^1$H NMR (400 MHz, CDCl$_3$) δ8.06 (d, J=1.5 Hz, 2H), 8.05 (d, J=2.0 Hz, 2H), 7.69 (d, J=2.0 Hz, 2H), 7.67–7.36 (m, 3H), 7.28–7.15 (m, 5H), 6.77–6.73 (m, 2H), 6.62 (dd, J=8.8, 2.9 Hz, 1H), 4.16 (t, J=6.4 Hz, 2H), 3.01 (t, J=6.4 Hz, 2H), 2.86 (s, 4H, 2.41 (s, 3H), 1.55 (s, 6H), MS (ES) m/e 562 M+1).

Example 29

2-{4-[2-(2-Biphenyl-3-yl-5-methyloxazol-4-yl)ethoxy]-2-phenethylphenoxy}-2-methylpropionic acid

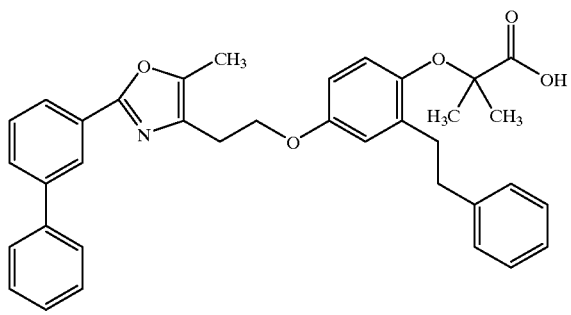

A. 2-{4-[2-(2-Biphenyl-3-yl-5-methyloxazol-4-yl)ethoxy]-2-phenethylphenoxy}-2-methylpropionic acid ethyl ester A mixture of (2-phenethyl-4-hydroxyphenoxy)acetic acid ethyl ester (1.29 mmol), toluene-4-sulfonic acid 2-(5-methyl-2-biphenyl-3-yl-oxazol-4,1-yl)ethyl ester (1.55 mmol) (see Ex. 22, part B), and cesium carbonate (0.55 g, 1.7 mmol) in anhydrous DMF (4 mL) was heated for 18 h (55° C.). The mixture was concentrated in vacuo, and the residue was partitioned between ethyl acetate (100 mL) and water (50 mL), washed with brine (50 mL), dried (Na$_2$SO$_4$), and removed in vacuo to give a crude oil which was purified using radial chromatography eluting with 10–15% ethyl acetate/hexanes to give 2-{4-[2-(2-biphenyl-4-yl-5-methyloxazol-4-yl)ethoxy]-2-phenethylphenoxy}-2-methylpropionic acid ethyl ester. MS (ES) m/e 590 (M+1).

B. 2-{4-[2-(2-Biphenyl-3-yl-5-methyloxazol-4-yl)ethoxy]-2-phenethylphenoxy}-2-methylpropionic acid ethyl ester A solution of 2-{4-[2-(2-biphenyl-3-yl-5-methyloxazol-4-yl)ethoxy]-2-phenethylphenoxy}-2-methylpropionic acid ethyl ester (0.54 mmol) in ethanol (10 mL) was treated with 2.5 N aqueous NaOH (0.4 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na$_2$SO$_4$) and concentrated in vacuo to give 2-{4-[2-(2-biphenyl-3-yl-5-methyloxazol-4-yl)ethoxy]-2-phenethylphenoxy}-2-methylpropionic acid. $^1$H NMR (400 MHz, CDCl$_3$) δ8.18 (d, J=2.0 Hz, 1H), 7.91 (d, J=7.8 Hz, 1H), 7.61 (dd, J=7.8, 2.9 Hz, 3H), 7.48–7.30 (m, 4H), 7.24–7.10 (m, 5H), 6.73–6.68 (m, 2H), 6.57 (dd, J=8.8, 2.9 Hz, 1H), 4.10 (t, J=6.4 Hz, 2H), 2.97 (t, J=6.4 Hz, 2H), 2.81 (s, 4H), 2.36 (s, 3H), 1.50 (s, 9H), MS (ES) m/e 562 M+1).

A. 4-[2-(4-Benzyloxy-2-propylphenoxy)ethyl]-5-methyl-2-phenyloxazole

A mixture of 4-benzyloxy-2-propylphenol (3.89 mmol), toluene-4-sulfonic acid 2-(5-methyl-2-biphenyl-4-yl-oxazol-4-ly) ethyl ester (4.67 mmol) (see Ex. 1, part F) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried (Na$_2$SO$_4$), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-2-propylphenoxy)ethyl]-5-methyl-2-phenyloxazole.

B. 3-Propyl-4-[2-(5-methyl-2-biphenyl-4-yl-oxazole-4-yl)ethoxy]phenol

A solution of 4-[2-(4-benzyloxy-2-propylphenoxy)ethyl]-5-methyl-2-phenyloxazole (3.16 mmol) in ethanol (100 mL) was treated with 5% Pd/C (160 mg) and hydrogen (60 psi) at ambient temperature for 18 h. The mixture was filtered and concentrated in vacuo to give a tan solid.

C. 2-{4-[2-(2-Biphenyl-4-yl-5-methyloxazol-4-yl)ethoxy]-3-propylphenoxy}-2-methylpropionic acid ethyl ester A mixture of 3-propyl-4-[2-(5-methyl-2-biphenyl-4-yl-oxazole-4-yl)ethoxy]phenol (0.90 mmol), ethyl 2-bromo-2-methylpropanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried (Na$_2$SO$_4$), and removed in vacuo to give a crude oil which was purified using radial chromatography eluting with 2% ethyl acetate/Dichloromethane to give 2-{4-[2-(2-biphenyl-4-yl-5-methyloxazol-4-yl)ethoxy]-3-propylphenoxy}-2-methylpropionic acid ethyl ester, $^1$H NMR (400 MHz, CDCl$_3$) δ8.04 (dd, J=8.3 Hz, 2H) 7.67 (d, J=3.4 Hz, 1H), 7.65 (dd, J=6.8, 2.0 Hz, 7.62 (d, J=2.9 Hz, 1H), 7.45 (t, J=6.6

Hz, 2H), 7.37 (t, J=7.8 Hz, 2H), 6.72–6.61 (m, 3H), 4.25 (q, J=7.1 Hz, 2H), 4.20 (t, J=6.6 Hz, 2H), 2.95 (t, J=7 Hz, 2H), 2.48, (t, J=7 Hz, 1H), 2.38 (s, 3H), 1.53–1.48 (m, 8H), 1.25 (t, J=7 Hz, 3H), 0.88 (t, J=7.1 Hz, 3H); MS (FIA) m/e 528 (M+1).

D. 2-{4-[2-(2-Biphenyl-4-yl-5-methyloxazol-4-yl)ethoxy]-3-propylphenoxy}-2-methylpropionic acid A solution of 2-{4-[2-(2-biphenyl-4-yl-5-methyloxazol-4-yl)ethoxy]-3-propylphenoxy}-2-methylpropionic acid ethyl ester, (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na$_2$SO$_4$) and concentrated in vacuo to give 2-{4-[2-(2-Biphenyl-4-yl-5-methyloxazol-4-yl)ethoxy]-3-propylphenoxy}-2-methylpropionic acid $^1$H NMR (400 MHz, CDCl$_3$) δ8.06 (d, J=8.3 Hz, 2H), 7.67 (d, J=8.3 Hz, 2H), 7.63 (d, J=8.3 Hz, 2H), 7.46 (t, J=7.6 Hz, 2H), 7.32 (t, J=7.3 Hz, 1H), 6.72 (s, 3H), 4.21 (t, J=6.4 Hz, 2H), 3.02 (t, J=6.1 Hz, 2H), 2.50 (t, J=7.6 Hz, 2H), 2.41 (s, 3H), 1.52 (s, 6H), 1.31–1.24 (m, 2H), 0.88 (t, J=7.3 Hz, 3H); MS (ES) m/e 500 (M+1).

Example 31

2-{4-[2-(2-Biphenyl-4-yl-5-methyloxazol-4-yl)ethoxy]-3-butylphenoxy}-2-methylpropionic acid C. 2-{4-[2-(2-Biphenyl-4-yl-5-methyloxazol-4-yl)ethoxy]-3-butylphenoxy}-2-methylpropionic acid ethyl ester A mixture of 3-butyl-4-[2-(5-methyl-2-biphenyl-4-yl-oxazole-4-yl)ethoxy]phenol (0.90 mmol), ethyl 2-bromo-2-methylpropanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried (Na$_2$SO$_4$), and removed in vacuo to give a crude oil which was purified using radial chromatography eluting with 2% ethyl acetate/dichloromethane to give 2-{4-[2-(2-biphenyl-4-yl-5-methyloxazol-4-yl)ethoxy]-3-butylphenoxy}-2-methylpropionic acid ethyl ester. $^1$H NMR (400 MHz, CDCl$_3$) δ8.04 (d, J=8.3 Hz, 2H), 7.66 (d, J=8.3 Hz, 2H), 7.63 (d, J=8.3 Hz, 2H), 7.46 (t, J=7.6 Hz, 2H), 7.37 (t, J=7.3 Hz, 1H), 6.71 (d, J=8.8 Hz, 1H), 6.69 (br s, 2H), 6.64 (dd, J=8.8, 2.9 Hz, 1H), 4.25–4.19 (m, 4H), 2.97 (t, J=6.4 Hz, 2H), 2.50 (t, J=7.5 Hz, 2H), 2.38 (s, 3H), 1.52 (s, 6H), 1.46 (quintet, J=7.6 Hz, 2H), 1.31 (t, J=7.1 Hz, 3H), 0.88 (t, J=7 Hz, 3H); Rf=0.16 (25% ethyl acetate/hexanes).

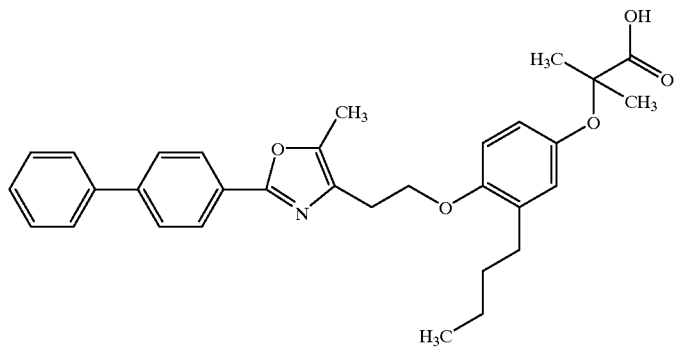

A. 4-[2-(4-Benzyloxy-2-butylphenoxy)ethyl]-5-methyl-2-biphenyl-4-yl-oxazole

A mixture of 4-benzyloxy-2-butylphenol (3.89 mmol), toluene-4-sulfonic acid 2-(5-methyl-2-biphenyl-4-yl-oxazol-4-ly) ethyl ester (4.67 mmol) (see Ex. 1, part F) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried (Na$_2$SO$_4$), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-2-butylphenoxy)ethyl]-5-methyl-2-biphenyl-4-yl-oxazole.

B. 3-Butyl-4-[2-(5-methyl-2-biphenyl-4-yl-oxazole-4-yl)ethoxy]phenol

A solution of 4-[2-(4-benzyloxy-2-butylphenoxy)ethyl]-5-methyl-2-biphenyl-4-yl-oxazole (3.16 mmol) in ethanol (100 mL) was treated with 5% Pd/C (160 mg) and hydrogen (60 psi) at ambient temperature for 18 h. The mixture was filtered and concentrated in vacuo to give 3-butyl-4-[2-(5-methyl-2-biphenyl-4-yl-oxazole-4-yl)ethoxy]phenol as a tan solid.

D. 2-{4-[2-(2-Biphenyl-4-yl-5-methyloxazol-4-yl)ethoxy]-3-butylphenoxy}-2-methylpropionic acid A solution of 2-{4-[2-(2-biphenyl-4-yl-5-methyloxazol-4-yl)ethoxy]-3-butylphenoxy}-2-methylpropionic acid ethyl ester (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na$_2$SO$_4$) and concentrated in vacuo to give 2-{4-[2-(2-biphenyl-4-yl-5-methyloxazol-4-yl)ethoxy]-3-butylphenoxy}-2-methylpropionic acid. $^1$H NMR (400 MHz, CDCl$_3$) δ8.04 (d, J=8.3 Hz, 2H), 7.68–7.62 (m, 4H), 7.46 (t, J=6.6 Hz, 2H), 7.38 (t, J=7.3 Hz, 1H), 6.74 (s, 3H), 4.21 (t, J=6.1 Hz, 2H), 3.01 (t, J=6.4 Hz, 2H), 2.40 (s, 3H), 1.52–1.43 (m, 8H), 1.32–1.24 (m, 2H), 0.87 (t, J=7.3 Hz, 3H); MS (ES) m/e 514 (M+1).

Example 32

2-{4-[2-(2-Biphenyl-3-yl-5-methyloxazol-4-yl)ethoxy]-3-butylphenoxy}-2-methylpropionic acid

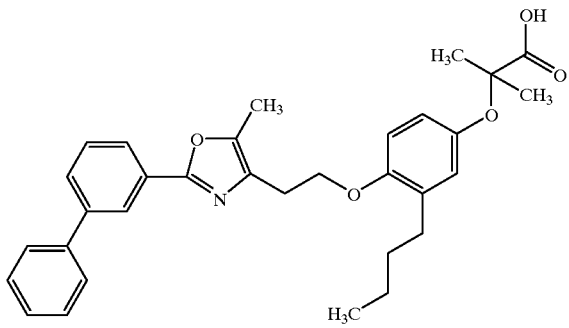

A. 4-[2-(4-Benzyloxy-2-butylphenoxy)ethyl]-5-methyl-2-biphenyl-3-yl-oxazole

A mixture of 4-benzyloxy-2-butylphenol (3.89 mmol), toluene-4-sulfonic acid 2-(5-methyl-2-biphenyl-3-yl-oxazol-4-ly) ethyl ester (4.67 mmol) (see Ex. 22, part B) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried ($Na_2SO_4$), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-2-butylphenoxy)ethyl]-5-methyl-2-biphenyl-3-yl-oxazole.

B. 3-Butyl-4-[2-(5-methyl-2-biphenyl-3-yl-oxazole-4-yl)ethoxy]phenol

A solution of 4-[2-(4-benzyloxy-2-butylphenoxy)ethyl]-5-methyl-2-biphenyl-3-yl-oxazole (3.16 mmol) in ethanol (100 mL) was treated with 5% Pd/C (160 mg) and hydrogen (60 psi) at ambient temperature for 18 h. The mixture was filtered and concentrated in vacuo to give 3-butyl-4-[2-(5-methyl-2-biphenyl-3-yl-oxazole-4-yl)ethoxy]phenol as a tan solid.

C. 2-{4-[2-(2-Biphenyl-3-yl-5-methyloxazol-4-yl)ethoxy]-3-butylphenoxy}-2-methylpropionic acid ethyl ester A mixture of 3-butyl-4-[2-(5-methyl-2-biphenyl-3-yl-oxazole-4-yl)ethoxy]phenol (0.90 mmol), ethyl 2-bromo-2-methylpropanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried ($Na_2SO_4$), and removed in vacuo to give a crude oil which was purified using radial chromatography eluting with 2% ethyl acetate/dichloromethane to give 2-{4-[2-(2-biphenyl-3-yl-5-methyloxazol-4-yl)ethoxy]-3-butylphenoxy}-2-methylpropionic acid ethyl ester. $^1$H NMR (400 MHz, $CDCl_3$) δ8.22 (d, J=1.5 Hz, 1H), 7.95 (dd, J=7.8, 1.5 Hz, 1H), 7.67–7.62 (m, 3H), 7.51–7.44 (m, 3H), 7.37 (t, J=6.8 Hz, 1H), 6.72–6.69 (m, 2H), 6.64 (dd, J=8.8, 2.9 Hz, 1H), 4.25–4.19 (m, 4H), 2.97 (t,J=6.6 Hz, 2H), 2.50 (t, J=7.6 Hz, 2H), 2.38 (s, 3H), 1.52 (s, 6H), 1.51–1.43 (m, 2H), 1.33–1.23 (m, 5H), 0.85 (t, J=7 Hz, 3H); Rf=0.24 (2% ethyl acetate/dichloromethane).

D. 2-{4-[2-(2-Biphenyl-3-yl-5-methyloxazol-4-yl)ethoxy]-3-butylphenoxy}-2-methylpropionic acid A solution of 2-{4-[2-(2-biphenyl-3-yl-5-methyloxazol-4-yl)ethoxy]-3-butylphenoxy}-2-methylpropionic acid ethyl ester (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried ($Na_2SO_4$) and concentrated in vacuo to give 2-{4-[2-(2-biphenyl-4-yl-5-methyloxazol-4-yl)ethoxy]-3-butylphenoxy}-2-methylpropionic acid. $^1$H NMR (400 MHz, $CDCl_3$) δ8.2 (d, J=1.5 Hz, 1H), 7.95 (d, J=7.8 Hz, 1H), 7.66–7.63 (m, 3H), 7.52–7.35 (m, 4H), 6.73 (d, J=2.9 Hz, 3H), 4.20 (t, J=6.1 Hz, 2H), 3.02 (t, J=6.1 Hz, 2H), 2.52 (t, J=7.6 Hz, 2H), 2.40 (s, 3H), 1.51–1.42 (m, 8H), 1.29 (quintet, J=7.2 Hz, 2H), 0.86 (t, J=7.1 Hz, 3H); MS (ES) m/e 514 (M+1).

Example 33

2-{4-[2-(2-Biphenyl-4-yl-5-methyloxazol-4-yl)ethoxy]-3-phenethylphenoxy}-2-methylpropionic acid

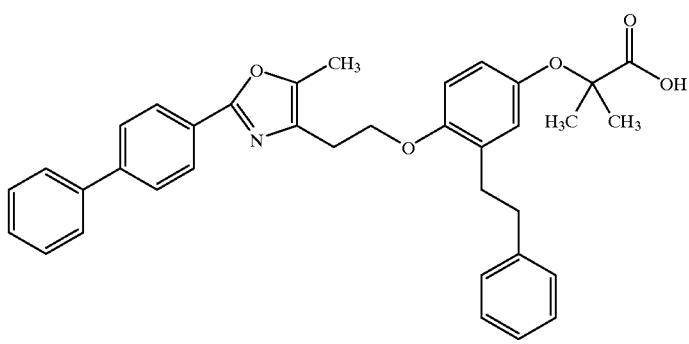

A. 4-[2-(4-Benzyloxy-2-phenethylphenoxy)ethyl]-5-methyl-2-phenyloxazole

A mixture of 4-benzyloxy-2-phenethylphenol (3.89 mmol), toluene-4-sulfonic acid 2-(5-methyl-2-biphenyl-4-yl-oxazol-4-ly) ethyl ester (4.67 mmol) (see Ex. 1, part F) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried ($Na_2SO_4$), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-2-phenethylphenoxy)ethyl]-5-methyl-2-phenyloxazole.

B. 3-Phenethyl-4-[2-(5-methyl-2-biphenyl-4-yl-oxazole-4-yl)ethoxy]phenol

A solution of 4-[2-(4-benzyloxy-2-phenethylphenoxy)ethyl]-5-methyl-2-phenyloxazole (3.16 mmol) in ethanol (100 mL) was treated with 5% Pd/C (160 mg) and hydrogen (60 psi) at ambient temperature for 18 h. The mixture was filtered and concentrated in vacuo to give a tan solid.

C. 2-{4-[2-(2-Biphenyl-4-yl-5-methyloxazol-4-yl)ethoxy]-3-phenethylphenoxy}-2-methylpropionic acid ethyl ester A mixture of 3-phenethyl-4-[2-(5-methyl-2-biphenyl-4-yl-oxazole-4-yl)ethoxy]phenol (0.90 mmol), ethyl 2-bromo-2-methylpropanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried ($Na_2SO_4$), and removed in vacuo to give a crude oil which was purified using radial chromatography eluting with 2% ethyl acetate/dichloromethane to give 2-{4-[2-(2-Biphenyl-4-yl-5-methyloxazol-4-yl)ethoxy]-3-phenethylphenoxy}-2-methylpropionic acid ethyl ester. $^1$H NMR (400 MHz, $CDCl_3$) δ8.03 (d, J=8.3 Hz, 2H), 7.64 (t, J=8.3 Hz, 4H), 7.46 (t, J=7.6 Hz, 2H), 7.37 (t, J=7.3 Hz, 1H), 7.26–7.17 (m, 2H), 7.13 (dd, J=12.3, 7.3 Hz, 3H), 4.24–4.19 (m, 4H), 2.98 (t, J=6.6 Hz, 2H), 2.81 (s, 4H), 2.32 (s, 3H), 1.48 (s, 6H). 1.27 (t, J=7.1 Hz, 3H), MS (ES) m/e 590 (M+1).

D. 2-{4-[2-(2-Biphenyl-4-yl-5-methyloxazol-4-yl)ethoxy]-3-phenethylphenoxy}-2-methylpropionic acid A solution of 2-{4-[2-(2-biphenyl-4-yl-5-methyloxazol-4-yl)ethoxy]-3-phenethylphenoxy}-2-methylpropionic acid ethyl ester (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to ph=1 with 1N aqueous HCl. The organic layer was washed with brine (20 mL), dried ($Na_2SO_4$) and concentrated in vacuo to give 2-{4-[2-(2-biphenyl-4-yl-5-methyloxazol-4-yl)ethoxy]-3-phenethylphenoxy}-2-methylpropionic acid. $^1$H NMR (400 MHz, $CDCl_3$) δ8.03 (d, J=8.3 Hz, 2H), 7.67–7.62 (m, 4H), 7.46 (t, J=7.6 Hz, 2H), 7.37 (t, J=7.3 Hz, 1H), 7.26–7.21 (m, 3H), 7.15 (t, J=7.3 Hz, 1H), 7.08 (d, J=6.8 Hz, 2H), 6.76 (d, J=1.5 Hz, 2H), 6.64 (s, 1H), 4.24 (t, J=6.4 Hz, 2H), 3.00 (t, J=6.4 Hz, 2H), 2.87–2.79 (m, 4H), 2.35 (s, 3H), 1.43 (s, 6H), MS (ES) m/e 562 (M+1).

Example 34

2-{4-[2-(2-Biphenyl-4-yl-5-methyloxazol-4-yl)ethoxy]-3-cyclohexylmethylphenoxy}-2-methylpropionic acid

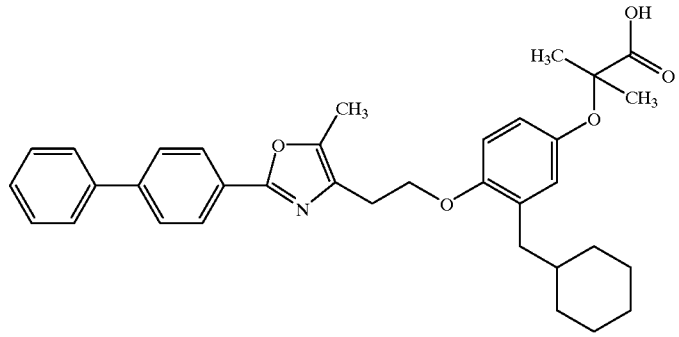

A. 4-[2-(4-Benzyloxy-2-cyclohexylmethylphenoxy)ethyl]-5-methyl-2-phenyloxazole

A mixture of 4-benzyloxy-2-cyclohexylmethylphenol (3.89 mmol), toluene-4-sulfonic acid 2-(5-methyl-2-biphenyl-4-yl-oxazol-4-ly) ethyl ester (4.67 mmol) (see Ex. 1, part F) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried ($Na_2SO_4$), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-2-cyclohexylmethylphenoxy)ethyl]-5-methyl-2-phenyloxazole.

B. 3-Cyclohexylmethyl-4-[2-(5-methyl-2-biphenyl-4-yl-oxazole-4-yl)ethoxy]phenol

A solution of 4-[2-(4-benzyloxy-2-cyclohexylmethylphenoxy)ethyl]-5-methyl-2-phenyloxazole (3.16 mmol) in ethanol (100 mL) was treated with 5% Pd/C (160 mg) and hydrogen (60 psi) at ambient temperature for 18 h. The mixture was filtered and concentrated in vacuo to give a tan solid.

C. 2-{4-[2-(2-Biphenyl-4-yl-5-methyloxazol-4-yl)ethoxy]-3-cyclohexylmethylphenoxy}-2-methylpropionic acid ethyl ester A mixture of 3-cyclohexylmethyl-4-[2-(5-methyl-2-biphenyl-4-yl-oxazole-4-yl)ethoxy]phenol (0.90 mmol), ethyl 2-bromo-2-methylpropanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried ($Na_2SO_4$), and removed in vacuo to give a crude oil which was purified using radial chromatography eluting with 2% ethyl acetate/dichloromethane to give 2-{4-[2-(2-biphenyl-4-yl-5-methyloxazol-4-yl)ethoxy]-3-cyclohexylmethylphenoxy}-2-methylpropionic acid ethyl ester. $^1$H NMR (400 MHz, $CDCl_3$) δ8.04 (d, J=8.8 Hz, 2H), 7.65 (q, J=8.3 Hz, 4H), 7.46 (t, J=7.6 Hz, 2H), 7.37 (t, J=7.3 Hz, 1H), 6.72–6.64 (m, 3H), 4.25–4.18 (m, 4H), 2.96 (t, J=6.4 Hz, 2H), 2.40 (s, 3H), 2.38 (t, J=7.3 Hz, 2H), 1.59–1.55 (m, 11H), 1.47–1.42 (m, 1H), 1.27 (t, J=7.1 Hz, 3H), 1.13–1.05 (m, 3H), 0.88–0.75 (m, 2H), MS (ES) m/e 582 (M+1).

D. 2-{4-[2-(2-Biphenyl-4-yl-5-methyloxazol-4-yl)ethoxy]-3-cyclohexylmethylphenoxy}-2-methylpropionic acid A solution of 2-{4-[2-(2-biphenyl-4-yl-5-methyloxazol-4-yl)ethoxy]-3-cyclohexylmethylphenoxy}-2-methylpropionic acid ethyl ester (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried ($Na_2SO_4$) and concentrated in vacuo to give 2-{4-[2-(2-Biphenyl-4-yl-5-methyloxazol-4-yl)ethoxy]-3-cyclohexylmethylphenoxy}-2-methylpropionic acid. $^1$H NMR (400 MHz, $CDCl_3$) δ8.04 (d, J=8.3 Hz, 2H), 7.65 (dd. J=8.8, 2.2 Hz, 4H), 7.46 (t, J=7.6 Hz, 2H), 7.37 (t, J=6.6 Hz, 1H), 6.74 (s, 2H). 6.70 (s, 1H), 4.21 (t, J=6.4 Hz, 2H), 3.00 (t, J=5.9 Hz, 2H), 2.46–2.36 (m, 5H), 1.67–1.51 (m, 11H), 1.47–1.42 (m, 1H), 1.18–1.09 (m, 3H), 0.85–0.83 (m, 2H), MS (ES) m/e 554 (M+1).

Example 35

2-{2-Benzyl-4-[2-(2-biphenyl-3-yl-5-methyloxazol-4-yl)-ethoxy]-phenoxy}-2-methyl-propionic acid

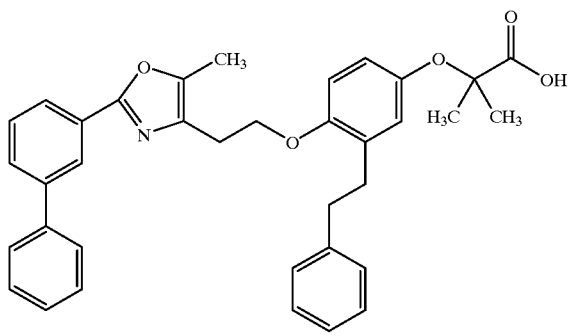

A. 4-Benzyloxy-2-(hydroxy-phenyl-methyl)-phenol

A solution of phenol (Kappe, T.; Witoszynskyj, T. Arch. Pharm. (1975), 308 (5), 339–346) (1.14 g, 5.00 mmol) in THF (15 mL) was cooled in a dry ice/acetone bath and treated dropwise with phenyllithium (7.5 mL, 13.5 mmol, 1.8M in cyclohexane/ethyl ether 70/30). The reaction mixture was allowed to warm gradually to ambient temperature. After 18 h, the reaction was quenched with aqueous saturated $NH_4Cl$ solution (1 mL) and partitioned between ethyl acetate (50 mL) and 1N HCl (20 mL). The organic layer was washed with brine (75 mL), dried ($Na_2SO_4$), and concentrated to a brown oil (2.3 g). The crude product was purified by flash chromatography using hexanes:ethyl acetate (3:1 to 2:1) to give a pale yellow oil (1.42 g, 93%): $^1$H NMR (400 MHz, $CDCl_3$) δ2.79 (s, 1H), 4.92 (s, 2H), 5.95, (s, 1H), 6.51 (s, 1H), 6.81 (d, 3H, J=1.5 Hz), 7.28–7.38 (s, 10H); MS (ES) m/e 305 [M−1].

B. 2-[4-Benzyloxy-2-(hydroxy-phenyl-methyl)-phenoxy]-2-methyl-propionic acid ethyl ester 4-Benzyloxy-2-(hydroxy-phenyl-methyl)-phenol (690 mg, 2.25 mmol) and $Cs_2CO_3$ (734 mg, 2.25 mmol) in DMF (7 mL) was treated with ethyl bromoisobutyrate (0.66 mL, 4.5 mmol) and heated at 55° C. for 16 h. Additional bromo ester (0.40 mL, 1.23 mmol) and $Cs_2CO_3$ (400 mg, 1.23 mmol) were added and the reaction mixture was heated for 40 h. The mixture was cooled and partitioned between ethyl acetate (30 mL) and $H_2O$ (10 mL). The organic layer was washed with brine (10 mL), dried ($Na_2SO_4$), and concentrated. The crude product was purified by flash chromatography using hexanes:ethyl acetate to give a pale yellow oil (615 mg, 65%): $^1$H NMR (400 MHz, $CDCl_3$) δ1.21 (t, 3H, J=7.3 Hz), 1.39 (s, 3H), 1.43 (s, 3H), 4.19 (q, 2H, J=7.3 Hz), 4.97 (s 2H), 6.00 (s, 1H), 6.61 (d, 1H, J=8.8 Hz), 6.74 (dd, 2H, J=3.2, 9.0 Hz), 6.96 (d, 1H, J=2.9 Hz), 7.22–7.39 (m, 10).

C. 2-(2-Benzyl-4-hydroxy-phenoxy)-2-methyl-propionic acid ethyl ester

A solution of 2-[4-benzyloxy-2-(hydroxy-phenyl-methyl)-phenoxy]-2-methyl-propionic acid ethyl ester (1.67 g, 3.97 mmol maximum) in ethanol (50 mL) was treated with 5% Pd/C (0.42 g) and hydrogen (60 psi, room temperature, 18 h). The mixture was filtered and concentrated to a viscous colorless oil (1.15 g, 91%): $^1$H NMR (400 MHz, $CDCl_3$) δ1.32 (t, 3H, J=7.1 Hz), 1.51 (s, 6H), 3.99 (s, 2H), 4.30 (q, 2H, J=7.0 Hz), 4.93 (brs, 1H), 6.58–6.66 (m, 3H), 7.22–7.34 (m, 5H); MS (ES) m/e 315 [M+1].

D. 2-{2-Benzyl-4-[2-(2-biphenyl-3-yl-5-methyloxazol-4-yl-ethoxy]phenoxy}-2-methylpropionic acid ethyl ester A mixture of 2-(2-benzyl-4-hydroxy-phenoxy)-2-methyl-propionic acid ethyl ester (1.14 g, 3.63 mmol), toluene-4-sulfonic acid 2-(5-methyl-2- biphenyl-3-yl-oxazol-4-yl) ethyl ester) (see Ex. 22, part B) (4.71 mmol), and $Cs_2CO_3$ (1.77 g, 5.45 mmol) was heated at 55° C. in DMF (10 mL) for 72 h. The reaction mixture cooled and partitioned between ethyl acetate (30 mL) and $H_2O$ (10 mL). The organic layer was washed with brine (15 mL). The organic layer was dried ($Na_2SO_4$) and concentrated. The crude product was purified by flash chromatography using hexanes:ethyl acetate (8:1) to give an oil. $^1$H NMR (400 MHz, $CDCl_3$) δ8.21 (s, 1H), 7.94 (dd, 1H, J=7.8, 1.0 Hz), 7.64 (t, 3H, J=9.8 Hz), 7.51–7.44 (m, 3H), 7.37 (t, 1H, J=7.3 Hz), 7.26–7.14 (m, 5H), 6.66 (s, 1H), 6.61 (s, 2H), 4.22 (q, 2H, J=7.2 Hz), 4.15 (t, 2H, J=6.8 Hz), 3.94 (s, 2H), 2.93 (t, 2H, J=6.6 Hz), 2.35 (s, 3H), 1.42 (s, 6H), 1.25 (t, 3H, J=7.1 Hz), MS (ES) m/e 576 (M+1).

E. 2-{2-Benzyl-4-[2-(2-biphenyl-3-yl-5-methyloxazol-4-yl)-ethoxy]-phenoxy}-2-methyl-propionic acid A solution of 2-{2-benzyl-4-[2-(2-biphenyl-3-yl-5-methyloxazol-4-yl-ethoxy]phenoxy}-2-methylpropionic acid ethyl ester (2.30 mmol) in THF (15 mL) and methanol (30 mL) was treated with 2.5N aqueous NaOH (10 mL). The solution was heated at 55° C. for 2 h, cooled to ambient temperature, and concentrated in vacuo. The residue was acidified with 5N aqueous HCl (5 mL) and partitioned between ethyl acetate (125 mL) and $H_2O$ (25 mL). The organic layer was washed with brine (50 mL), dried ($Na_2SO_4$), and concentrated to a give 2-{2-Benzyl-4-[2-(2-biphenyl-3-yl-5-methyloxazol-4-yl)-ethoxy]-phenoxy}-2-methyl-propionic acid: $^1$H NMR (400 MHz, $CDCl_3$) δ8.21 (d, 1H, J=1.5 Hz), 7.94 (dd, 1H, J=7.6, 1.2 Hz), 7.67–7.63 (m, 3H), 7.52–7.37 (m, 3H), 7.37 (t, 1H, J=6.8 Hz), 7.31–7.14 (m, 5H), 6.79 (d, 1H, J=8.8 Hz), 6.71 (d, 1H, J=2.9 Hz), 6.65 (dd, 1H, J=8.8, 2.9 Hz), 4.15 (t, 2H, J=6.6 Hz), 3.93 (s, 2H), 2.98 (t, 2H, J=6.1 Hz), 2.37 (s, 3H), 1.45 (s, 6H), MS (ES) m/e 548 (M+1).

Example 36

2-{2-Benzyl-4-[2-(2-biphenyl-4-yl-5-methyloxazol-4-yl)-ethoxy]-phenoxy}-2-methyl-propionic acid

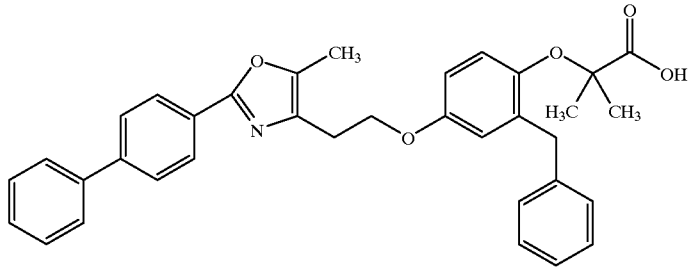

A. 2-{4-[2-(2-Biphenyl-4-yl-5-methyloxazol-4-yl)-ethoxy]-2-cyclohexylmethyl-phenoxy}-2-methyl-propionic acid ethyl ester A mixture of 2-(2-benzyl-4-hydroxy-phenoxy)-2-methyl-propionic acid ethyl ester (1.14 g, 3.63 mmol) (see Ex. 35, part C), toluene-4-sulfonic acid 2-(5-methyl-2-biphenyl-4-yl-oxazol-4-yl)ethyl ester (4.71 mmol) (see Ex. 1, part F), and $Cs_2CO_3$ (1.77 g, 5.45 mmol) was heated at 55° C. in DMF (10 mL) for 72 h. The reaction mixture cooled and partitioned between ethyl acetate (30 mL) and $H_2O$ (10 mL). The organic layer was washed with brine (15 mL). The organic layer was dried ($Na_2SO_4$) and concentrated. The crude product was purified by flash chromatography using hexanes:ethyl acetate (8:1) to give 2-{4-[2-(2-biphenyl-4-yl-5-methyloxazol-4-yl)-ethoxy]-2-cyclohexylmethyl-phenoxy}-2-methyl-propionic acid ethyl ester: MS (ES) m/e 582.3 (M+1).

B. 2-{2-Benzyl-4-[2-(2-biphenyl-4-yl-5-methyloxazol-4-yl)-ethoxy]-phenoxy}-2-methyl-propionic acid A solution of 2-{4-[2-(2-biphenyl-4-yl-5-methyloxazol-4-yl)-ethoxy]-2-cyclohexylmethyl-phenoxy}-2-methyl-propionic acid ethyl ester (2.30 mmol) in THF (15 mL) and methanol (30 mL) was treated with 2.5N aqueous NaOH (10 mL). The solution was heated at 55° C. for 2 h, cooled to ambient temperature, and concentrated in vacuo. The residue was acidified with 5N aqueous HCl (5 mL) and partitioned between ethyl acetate (125 mL) and $H_2O$ (25 mL). The organic layer was washed with brine (50 mL), dried ($Na_2SO_4$), and concentrated to a give 2-{2-benzyl-4-[2-(2-biphenyl-4-yl-5-methyloxazol-4-yl)-ethoxy]-phenoxy}-2-methyl-propionic acid. $^1$H NMR (400 MHz, $CDCl_3$) δ8.03–8.05 (m, 2H), 7.68 (d, 2H, J=8.3 Hz), 7.62 (d, 2H, J=6.8 Hz), 7.46 (t, 2H, J=7.3 Hz), 7.30–7.38 (m, 1H), 7.23–7.27 (m, 2H), 7.18 (d, 1H, J=7.3 Hz), 7.14 (d, 2H, J=8.3 Hz), 6.78 (d, 1H, J=9.3 Hz), 6.70 (d, 1H, J=2.9 Hz), 6.66 (dd, 1H, J=8.8 Hz, J=2.9 Hz), 4.16 (t, 2H, J=6.4 Hz), 3.92 (s, 2H), 3.00 (t, 2H, J=6.4 Hz), 2.38 (s, 3H), 1.45 (s, 6H), MS (ES) m/e 554.2 (M+1).

Example 37

2-(4-{2-[2-(4-Benzofur-2-yl-phenyl)-5-methyloxazol-4-yl]ethoxy}phenoxy)-2-methylpropionic acid

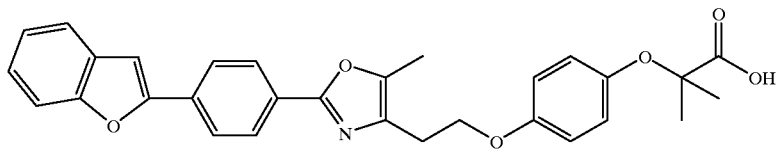

A. 2-(4-{2-[2-(4-Benzofur-2-yl-phenyl)-5-methyloxazol-4-yl]ethoxy}phenoxy)-2-methylpropionic acid ethyl ester To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, Part B), 2-benzofuryl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. $Pd(PPh_3)_4$ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4-benzofur-2-yl-phenyl)-5-methyloxazol-4-yl]ethoxy}phenoxy)-2-methylpropionic acid ethyl ester.

B. 2-(4-{2-[2-(4-Benzofur-2-yl-phenyl)-5-methyloxazol-4-yl]ethoxy}phenoxy)-2-methylpropionic acid To a 20 mL round-bottomed flask equipped for magnetic stirring and fitted with a reflux condenser was added 2-(4-

{2-[2-(4-benzofur-2-yl-phenyl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4-benzofur-2-yl-phenyl)-5-methyloxazol-4-yl]ethoxy}phenoxy)-2-methylpropionic acid. $^1$H NMR (400 MHz, CDCl$_3$) 8.04 (2H, d), 7.92 (2H, d), 7.58 (2H,dd), 7.26 (2H, m), 6.91(2H, d), 6.79 (2H, d), 4.17 (2H, t), 3.00 (2H, t) 2.39 (3H, s), 1.53 (6H, s).

Example 38

2-{5-[2-(2-Biphenyl-4-yl-5-methyloxazol-4-yl)-ethoxy]-biphenyl-2-yloxy}-2-methyl-propionic acid

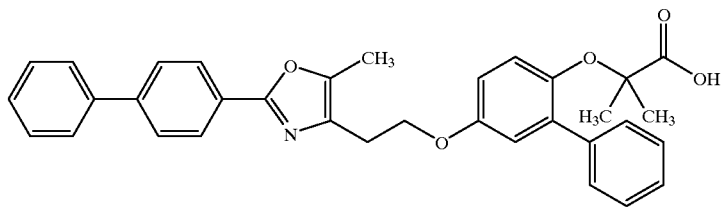

A. 2-(4-Benzyloxy-2-bromo-phenoxy)-2-methyl-propionic acid ethyl ester

A mixture of 4-benzyloxy-2-bromo-phenol (9.37 g, 33.6 mmol) and Cs$_2$CO$_3$ (21.9 g, 67.2 mmol) in DMF (80 mL) was treated with ethyl bromoisobutyrate (15 mL, 100 mmol) and heated at 55° C. for 18 h. The reaction mixture was cooled and partitioned between ethyl acetate (250 mL) and H$_2$O (100 mL). The organic layer was washed with brine (75 mL), dried (Na$_2$SO$_4$), and concentrated. The crude product was purified by flash chromatography using CH$_2$Cl$_2$:hexanes (2:3 to 3:2) to give a pale yellow oil (4.58 g, 35%): $^1$H NMR (400 MHz, CDCl$_3$) δ1.29 (t, 3H, J=7.1 Hz), 1.57 (s, 6H), 4.25 (q, 2H, J=7.1 Hz), 4.98 (s, 2H), 6.79 (dd, 1H, J=3.2, 9.1 Hz), 6.89 (d, 1H, J=8.8 Hz), 7.17 (d, 1H, J=3.4 Hz), 7.32–7.40 (m, 5H); MS (ES) m/e # [M+1].

B. 2-(5-Benzyloxy-biphenyl-2-yloxy)-2-methyl-propionic acid ethyl ester 2-(4-Benzyloxy-2-bromo-phenoxy)-2-methyl-propionic acid ethyl ester (3.00 g, 7.63 mmol) and phenyl boronic acid (1.12 g, 9.15 mmol) were dissolved in toluene (75 mL)/ethanol (75 mL). The solution was degassed (2x), and tetrakis(triphenylphosphine)palladium (70 mg, 0.061 mmol) was added followed by aqueous 2M Na$_2$CO$_3$ solution (7.63 mL, 15.3 mmol). The reaction mixture was degassed (2x) and heated to reflux under argon for 16 h. The reaction mixture cooled and partitioned between ethyl acetate (200 mL) and H$_2$O (75 mL). The organic layer was washed with brine (75 mL), dried (Na$_2$SO$_4$), and concentrated to a light brown oil (3.58 g). The crude product was used directly in the next reaction: $^1$H NMR (400 MHz, CDCl$_3$) δ1.266 (t, 3H, J=7.1 Hz), 1.273 (s, 6H), 4.20 (q, 2H, J=7.1 Hz), 5.03 (s, 2H), 6.82 (dd, 1H, J=3.2, 9.0 Hz), 6.92 (d, 1H, J=8.8 Hz), 6.97 (d, 1H, J=3.0 Hz), 7.28–7.44 (m, 8H), 7.51–7.60 (m, 2H); MS (ES) m/e # [M+1].

C. 2-(5-Hydroxy-biphenyl-2-yloxy)-2-methyl-propionic acid

A solution of 2-(5-benzyloxy-biphenyl-2-yloxy)-2-methyl-propionic acid ethyl ester (3.58 g, 7.63 mmol maximum) in ethanol (75 mL) was treated with 5% Pd/C (3.0 g) and hydrogen (balloon, room temperature, 16 h). The mixture was filtered and concentrated to a viscous colorless oil (2.44 g, 107%): $^1$H NMR (400 MHz, CDCl$_3$) δ1.25 (t, 3H, J=7.1 Hz), 1.27 (s, 6H), 4.20 (q, 2H, J=7.3 Hz), 4.95 (brs, 1H), 6.67 (dd, 1H, J=3.4, 8.8 Hz), 6.81 (d, 1H, J=3.4 Hz), 6.88(d, 1H, J=8.8 Hz), 7.30(dt, 1H, J=1.5, 7.3 Hz), 7.37 (dt, 2H, J=1.5, 7.3 Hz), 7.52 (dd, 2H, J=1.5, 6.8 Hz).

D. 2-{5-[2-(2-Biphenyl-4-yl-5-methyloxazol-4-yl)-ethoxy]-biphenyl-2-yloxy}-2-methyl-propionic acid A mixture of 2-(5-hydroxy-biphenyl-2-yloxy)-2-methyl-propionic acid (80 mg, 0.26 mmol), toluene-4-sulfonic acid 2-(5-methyl-2-biphenyl-4-yl-oxazol-4-yl)ethyl ester (0.22 mmol) (see Ex. 1, part F), and 1,5,7-triazobicyclo[4.4.0]dec-5-ene bound to polystyrene (200 mg, 2.6 mmol/g resin, Fluka) was diluted with absolute EtOH (2 mL) and was heated at 65–70° C. for 20 h. The warm mixture was filtered through a cotton plug, and the resin was washed with EtOH (2 mL). The combined filtrates were treated with aqueous 5N NaOH (0.3 mL), heated at 55° C. for 1.5 h, cooled to ambient temperature, and concentrated in vacuo. The residue was treated with ice water (1 mL) and acidified with 5N aqueous HCl (0.5 mL). The mixture with CH$_2$Cl$_2$ (1 mL) was transferred to a ChemElute cartridge (3 g) and eluted with CH$_2$Cl$_2$. The eluent was concentrated to crude product which was purified by mass guided HPLC to afford a white foam. $^1$H NMR (400 MHz, CDCl$_3$) δ1.26 (s, 6H), 2.44 (s, 3H), 3.10 (t, 2H, J=5.9 Hz), 4.28 (t, 2H, J=6.1 Hz), 6.81 (dd, 1H, J=2.9, 8.8 Hz), 6.86 (d, 1H, J=2.9 Hz), 7.01 (d, 1H, J=8.8 Hz), 7.30–7.48 (m, 8H), 7.63 (d, 2H, J=7.3 Hz), 7.70 (d, 2H, J=8.3 Hz), 8.11 (d, 2H, J=8.3 Hz); MS (ES) m/e [M−1].

Example 39

2-(4-{2-[2-(4'-Trifluoromethylbiphenyl-4-yl)-5-methyloxazol-4-yl]ethoxy}phenoxy)-2-methylpropionic acid

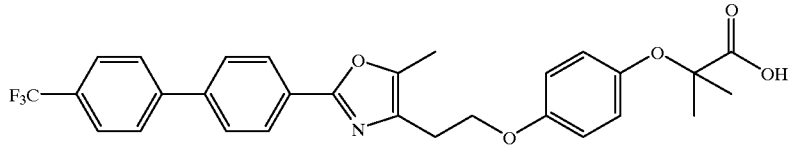

A. 2-(4-{2-[2-(4'-Trifluoromethylbiphenyl-4-yl)-5-methyloxazol-4-yl]ethoxy}phenoxy)-2-methylpropionic acid ethyl ester To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, Part B), 4-trifluoromethylphenyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh$_3$)$_4$ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4'-trifluoromethylbiphenyl-4-yl)-5-methyloxazol-4-yl]ethoxy}phenoxy)-2-methylpropionic acid ethyl ester.

B. 2-(4-{2-[2-(4'-Trifluoromethylbiphenyl-4-yl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4'-trifluoromethylbiphenyl-4-yl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4'-trifluoromethylbiphenyl-4-yl)-5-methyloxazol-4-yl]ethoxy}phenoxy)-2-methylpropionic acid. $^1$H NMR (400 MHz, CDCl$_3$) 8.04 (2H, d), 7.92 (2H, d), 7.58 (2H,dd), 7.26 (2H, m), 6.91(2H, d), 6.79 (2H, d), 4.17 (2H, t), 3.00 (2H, t) 2.39 (3H, s), 1.53 (6H, s).

Example 40

2-{3-[2-(2-Biphenyl-4-yl-5-methyloxazol-4-yl)-ethoxy]-4-butylphenoxy}-2-methylpropionic acid

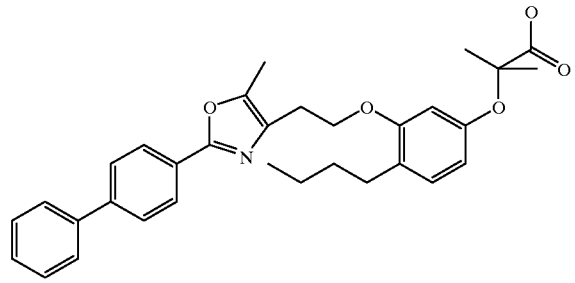

A. 5-Benzyloxy-2-but-1-enylphenol

To a flame dried 500 mL 3-neck flask under an atmosphere of argon, was charged n-propyltriphenylphosphonium bromide (12.66 g, 32.85 mmol) dissolved in anhydrous THF (85 mL), followed by the dropwise addition of n-butyllithium 16.4 mL, 26.28 mmol). The dark red mixture was stirred at ambient temperature for 1 h. 15 min. Next 4-benzyloxy-2-hydroxybenzaldehyde (1.5 g, 6.57 mmol) (*Synth. Commun.*, 26(3), 593–601, (1996) was added followed by the addition of anhydrous dichloromethane (27 mL). The mixture was stirred at ambient temperature for 18 h. The solvents were removed in vacuo, and the residue was partitioned between ethyl acetate and water (500 mL each). The organic layer was washed with brine (500 mL), dried (Na$_2$SO$_4$), and concentrated in vacuo. The crude product was purified using the Biotage FlashElute chromatography system using a 65M normal phase cartridge, eluting with 15% ethyl acetate/Hex to give a yellow solid (1.50 g, 90%). $^1$H NMR (400 MHz, CDCl$_3$) δ7.43–7.30 (m, 5H), 7.19 (d, J=8.3 Hz, 1H), 6.52 (dd, J=8.8, 2.4 Hz, 1H), 6.46 (d, J=2.4 Hz, 1H), 6.43 (s, 1H), 6.14–6.07 (m, 1H), 5.03 (s, 2H), 4.98 (s, 1H), 2.25 (quintet, J=7.6 Hz, 2H), 1.09 (t, J=7.3 Hz, 3H), MS (ES) m/e 255 (M+1).

B. 4-[2-(5-Benzyloxy-2-but-1-enylphenoxy)ethyl]-5-methyl-2-biphenyl-4-yl-oxazole A mixture of 5-benzyloxy-2-but-1-enylphenol (0.090 g, 0.35 mmol), toluene-4-sulfonic acid 2-(5-methyl-2-biphenyl-4-yl-oxazol-4-ly)ethyl ester (0.46 mmol) (see Ex. 1, part F) and cesium carbonate (0.173 g, 0.53 mmol) in anhydrous DMF (0.5 mL) was heated for 18 h at 55° C. The mixture was concentrated in vacuo, and the residue was partitioned between ethyl acetate (60 mL) and water (40 mL), washed with brine (50 mL), dried (Na$_2$SO$_4$), and removed in vacuo to give a crude oil which was purified using radial chromatography eluting with 5% ethyl acetate/hexanes to give a white solid C. 4-Butyl-3-[2-(5-methyl-2-biphenyl-4-yl-oxazol-4-yl)ethoxy]phenol A solution of 4-[2-(5-Benzyloxy-2-but-1-enylphenoxy)ethyl]-5-methyl-2-biphenyl-4-yl-oxazole (0.34 mmol) in ethanol (10 mL) was treated with 5% Pd/C (30 mg) under a balloon containing hydrogen at ambient temperature for 24 h. The mixture was filtered and concentrated in vacuo to give a white solid.

D. 2-{3-[2-(2-Biphenyl-4-yl-5-methyloxazol-4-yl)-ethoxy]-4-butylphenoxy}-2-methylpropionic acid ethyl ester A mixture of 4-butyl-3-[2-(5-methyl-2-biphenyl-4-yl-oxazol-4-yl)ethoxy]phenol (0.313 mmol), ethyl bromoisobutyrate (0.18 mL, 1.25 mmol) and cesium carbonate (0.41 g, 1.25 mmol) in anhydrous DMF (2 mL) was heated for 18 h at 55° C. The mixture was concentrated in vacuo, and the residue was partitioned between ethyl acetate (50 mL) and water (40 mL), washed with brine, dried ($Na_2SO_4$), and removed in vacuo to give a crude oil which was purified using radial chromatography eluting with 5–15% ethyl acetate/hexanes to give a yellow oil (0.12 g, 68%). $^1$H NMR (400 MHz, $CDCl_3$) δ8.04 (dd, J=6.9, 1.7 Hz, 2H), 7.65 (q, J=7.8 Hz, 4H), 7.46 (t, J=7.6 Hz, 2H), 7.37 (t, J=7.3 Hz, 1H), 6.91 (d, J=8.3 Hz, 1H), 6.46 (d, J=2.4 Hz, 1H), 6.29 (dd, J=8.1, 2.2 Hz, 1H), 4.25–4.18 (m, 4H), 2.98 (t, J=6.4 Hz, 2H), 2.48 (t, J=7.8 Hz, 2H), 2.39 (s, 3H), 1.57 (s, 6H), 1.44 (penta, J=7.6 Hz, 2H), 1.33–1.24 (m, 5H), 0.86 (t, J=7.1 Hz, 3H), MS (ES) m/e 542 (M+1).

E. 2-{3-[2-(2-Biphenyl-4-yl-5-methyloxazol-4-yl)-ethoxy]-4-butylphenoxy}-2-methylpropionic acid A solution of 2-{3-[2-(2-biphenyl-4-yl-5-methyloxazol-4-yl)-ethoxy]-4-butylphenoxy}-2-methylpropionic acid ethyl ester (0.12 g, 0.258 mmol) in ethanol (3 mL) was treated with 2 N aqueous NaOH (0.64 mL), and heated at 55° C. for 8 h. The reaction was cooled to ambient temperature and concentrated down to near dryness. The residue was then diluted with ethyl acetate (25 mL) and water (20 mL) and acidified to pH 1 with 1N aqueous HCl. The organic layer was washed with brine (20 mL), dried ($Na_2SO_4$) and concentrated in vacuo to give a white solid (0.10 g, 88%). $^1$H NMR (400 MHz, $CDCl_3$) δ8.05 (d, J=8.3 Hz, 2H), 7.69 (d, J=8.3 Hz, 2H), 7.64 (d, J=7.3 Hz, 2H), 7.47 (t, J=7.8 Hz, 2H), 7.38 (t, J=7.3 Hz, 1H), 7.00 (d, J=8.3 Hz, 1H), 6.81 (s, 1H), 6.50 (d, J=8.3 Hz, 1H), 4.24 (t, J=7.6 Hz, 2H), 2.93 (t, J=7.6 Hz, 2H), 2.40 (s, 3H), 1.60 (s, 6H), 1.51 (penta, J=7.6 Hz, 2H), 1.39–1.26 (m, 2H), 0.91 (t, J=7.3 Hz, 3H), MS (ES) m/e 514 (M+1).

Example 41

2-{5-[2-(2-Biphenyl-4-yl-5-methyloxazol-4-yl)ethoxy]-2-butylphenoxy}-2-methylpropionic acid A. 2-(5-Benzyloxy-2-but-1-enylphenoxy)-2-methylpropionic acid ethyl ester 5-Benzyloxy-2-but-1-enylphenol (0.70 g, 2.75 mmol) (see Ex. 40, part A) was dissolved in anhydrous DMF (12 mL), followed by the addition of ethyl bromoisobutyrate (1.62 mL, 11.0 mmol), and cesium carbonate (3.58 g, 11.0 mmol). The mixture was then heated for 18 h (55° C.). The reaction mixture was then cooled and concentrated in vacuo. The crude residue was partitioned between ethyl acetate (70 mL) and water (40 mL). The organic layer was washed with brine, dried ($Na_2SO_4$), and removed in vacuo. The crude residue was purified using radial chromatography, eluting with 5% ethyl acetate/hexanes to give 0.77 g (76%) of a colorless oil. $^1$H NMR (400 MHz, $CDCl_3$) δ7.41–7.28 (m, 6H), 6.65–6.59 (m, 2H), 6.40 (d, J 2.4 Hz, 1H), 6.14–6.07 (m, 1H), 4.99 (s, 2H), 4.22 (q, J=7.2 Hz, 2H), 2.22 (quintet, J=7.6 Hz, 2H), 1.56 (s, 6H), 1.26 (t, J=7.1 Hz, 3H), 1.08 (t, J=7.6 Hz, 3H), MS (ES) m/e 369 (M+1).

B. 2-(2-Butyl-5-hydroxyphenoxy)-2-methylpropionic acid ethyl ester

A solution of 2-(5-Benzyloxy-2-but-1-enylphenoxy)-2-methylpropionic acid ethyl ester (0.76 g, 2.06 mmol) in ethanol (50 mL) was treated with 5% Pd/C (0.10 g) and hydrogen (60 psi) at ambient temperature for 6 h. The mixture was filtered and concentrated in vacuo to give a colorless oil (0.52 g, 90%). $^1$H NMR (400 MHz, $CDCl_3$) δ6.96 (d, J=7.8 Hz, 1H), 6.37 (dd, J=8.3, 2.4 Hz, 1H), 6.20 (s, 1H), 4.66 (br s, 1H), 4.24 (q, J=7.2 Hz, 2H), 2.53 (t, J=7.8 Hz, 2H), 1.60 (s, 6H), 1.53 (quintet, J=7.6 Hz, 2H), 1.34 (sextet, J=7.3 Hz, 2H), 1.25 (t, J=7.1 Hz, 3H), 0.92 (t, J=7.3 Hz, 3H), MS (ES) m/e 281 (M+l).

C. 2-{5-[2-(2-Biphenyl-4-yl-5-methyloxazol-4-yl)ethoxy]-2-butylphenoxy}-2-methylpropionic acid The following example exemplifies the general procedure for the parallel synthesis of analogs utilizing the DynaVac carousel. To a 50 mL glass tube with screw cap and nitrogen inlet were charged 2-(2-butyl-5-hydroxyphenoxy)-2-methylpropionic acid ethyl ester, (0.050 g, 0.178 mmol), toluene-4-sulfonic acid 2-(5-methyl-2-bipheny-4-yl-loxazol-4-yl)ethyl ester (0.187 mmol) (see Ex. 1, part F), and powdered potassium carbonate (0.050 g, 0.36 mmol) in 1 mL of absolute ethanol. The mixture was heated to reflux for 18 h. MS analysis of the reaction indicated that 2-{5-[2-(2-biphenyl-4-yl-5 -methyloxazol-4-yl)ethoxy]-2-butylphenoxy}-2-methylpropionic acid ethyl ester, MS (ES) m/e 542 (M+1). had formed. Next 0.4 mL of 5 N sodium hydoxide was added and the reaction was heated for 3 h at 55° C. The ethanol was removed in vacuo and the residue was treated with 1 mL of 5N hydrochloric acid and 1 mL of dichloromethane and poured into a 3 mL ChemElute column to remove the aqueous layer. The column was eluted with additional dichloromethane until nothing UV active remained on the column. The solvent was removed in vacuo.

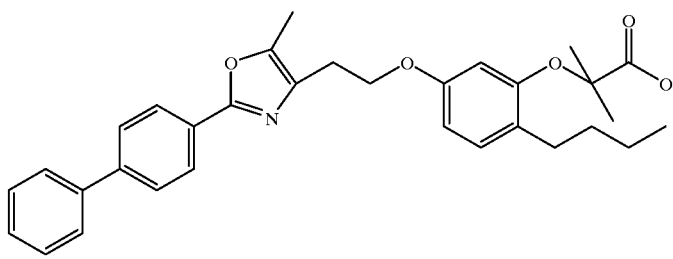

The crude residue was purified by mass-directed reverse phase HPLC to provide 2-{5-[2-(2-biphenyl-4-yl-5-methyloxazol-4-yl)ethoxy]-2-butylphenoxy}-2-methylpropionic acid. $^1$H NMR (400 MHz, CDCl$_3$) δ8.06 (d, J=8.3 Hz, 2H), 7.70 (d, J=8.3 Hz, 2H), 7.64 (d, J=8.3 Hz, 2H), 7.47 (t, J=7.6 Hz, 2H), 7.39 (t, J=7.3 Hz, 1H), 7.04 (d, J=8.3 Hz, 1H), 6.69 (d, J=2.4 Hz, 1H), 6.53 (dd, J=8.3, 2.4 Hz, 1H), 4.20 (t, J=7.6 Hz, 2H), 2.94 (t, J=7.6 Hz, 2H), 2.55 (t, J=7.8 Hz, 2H), 2.38 (s, 3H), 1.64 (s, 6H), 1.55 (quintet, J=7.7 Hz, 2H), 1.35 (sextet, J=7.5 Hz, 2H), 0.93 (t, J=7.3 Hz, 3H), MS (ES) m/e 514 (M+1).

Example 42

2-{5-[2-(2-Biphenyl-3-yl-5-methyloxazol-4-yl)ethoxy]-2-butylphenoxy}-2-methylpropionic acid

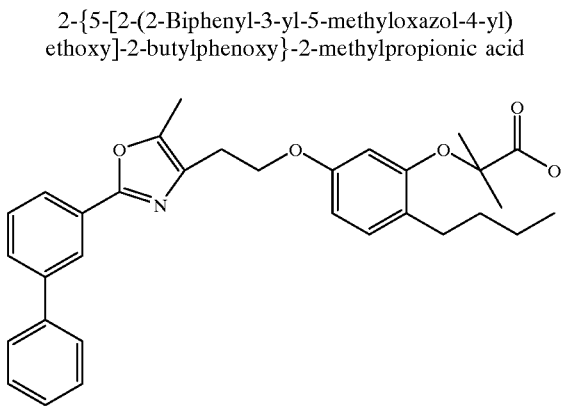

To a 50 mL glass tube with screw cap and nitrogen inlet were charged 2-(2-butyl-5-hydroxyphenoxy)-2-methylpropionic acid ethyl ester, (0.050 g, 0.178 mmol) (see Example 41, Part B), toluene-4-sulfonic acid 2-(5-methyl-2-bipheny-3-yl-loxazol-4-yl)ethyl ester (0.187 mmol) (see Ex. 22, part B), and powdered potassium carbonate (0.050 g, 0.36 mmol) in 1 mL of absolute ethanol. The mixture was heated to reflux for 18 h. MS analysis of the reaction indicated that 2-{5-[2-(2-biphenyl-3-yl-5-methyloxazol-4-yl)ethoxy]-2-butylphenoxy}-2-methylpropionic acid ethyl ester, MS (ES) m/e 542 (M+1) had formed. Next 0.4 mL of 5N sodium hydoxide was added and the reaction was heated for 3 h at 55° C. The ethanol was removed in vacuo and the residue was treated with 1 mL of 5N hydrochloric acid and 1 mL of dichloromethane and poured into a 3 mL ChemElute column to remove the aqueous layer. The column was eluted with additional dichloromethane until nothing UV active remained on the column. The solvent was removed in vacuo. The crude residue was purified by mass-directed reverse phase HPLC to provide 2-{5-[2-(2-biphenyl-3-yl-5-methyloxazol-4-yl)ethoxy]-2-butylphenoxy}-2-methylpropionic acid. $^1$H NMR (400 MHz, CDCl$_3$) δ8.27 (s, 1H), 7.95 (d, J=7.8 Hz, 1H), 7.70–7.68 (m, 3H), 7.53 (t, J=7.8 Hz, 1H), 7.46 (t, J=7.6 Hz, 2H), 7.38 (t, J=7.3 Hz, 1H), 7.04 (d, J=8.3 Hz, 1H), 6.72 (d, J=2.0 Hz, 1H), 6.53 (dd, J=8.3, 2.4 Hz, 1H), 4.20 (t, J=7.8 Hz, 2H), 2.94 (t, J=7.8 Hz, 2H), 2.56 (t, J=7.8 Hz, 2H), 2.38 (s, 3H), 1.64 (s, 6H), 1.54 (quintet, J=7.5 Hz, 2H), 1.35 (sextet, J=7.3 Hz, 2H), 0.93 (t, J=7.3 Hz, 3H), MS (ES) m/e 514 (M+1).

Example 43

2-{5-[2-(2-Biphenyl-4-yl-5-methyloxazol-4-yl)ethoxy]-2-propylphenoxy}-2-methylpropionic acid

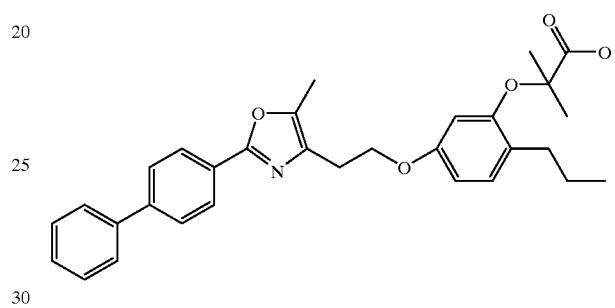

To a 50 mL glass tube with screw cap and nitrogen inlet were charged 2-(2-propyl-5-hydroxyphenoxy)-2-methylpropionic acid ethyl ester, (0.178 mmol) (see Ex. 41, part B), toluene-4-sulfonic acid 2-(5-methyl-2-bipheny-4-yl-loxazol-4-yl)ethyl ester (0.187 mmol) (see Ex. 1, part F), and powdered potassium carbonate (0.050 g, 0.36 mmol) in 1 mL of absolute ethanol. The mixture was heated to reflux for 18 h. MS analysis of the reaction indicated that 2-{5-[2-(2-biphenyl-4-yl-5-methyloxazol-4-yl)ethoxy]-2-propylphenoxy}-2-methylpropionic acid ethyl ester, MS (ES) m/e 528 (M+1) had formed. Next 0.4 mL of 5N sodium hydoxide was added and the reaction was heated for 3 h at 55° C. The ethanol was removed in vacuo and the residue was treated with 1 mL of 5N hydrochloric acid and 1 mL of dichloromethane and poured into a 3 mL ChemElute column to remove the aqueous layer. The column was eluted with additional dichloromethane until nothing UV active remained on the column. The solvent was removed in vacuo. The crude residue was purified by mass-directed reverse phase HPLC to provide 2-{5-[2-(2-biphenyl-4-yl-5-methyloxazol-4-yl)ethoxy]-2-propylphenoxy}-2-methylpropionic acid(508988). $^1$H NMR (400 MHz, CDCl3) δ8.06 (dd, J=8.8, 2.0 Hz, 2H), 7.71–7.63 (m, 4H), 7.47 (t, J 6.6 Hz, 2H), 7.39 (t J=7.3 Hz, 1H), 7.04 (d, J=8.3 Hz, 1H), 6.68 (d, J=2.4 Hz, 1H), 6.53 (dd, J=8.3, 2.4 Hz, 1H), 4.20 (t, J=7.6 Hz, 2H), 2.95 (t, J=7.3 Hz, 2H), 2.53 (t, J=7.6 Hz, 2H), 2.38 (s, 3H), 1.64 (s, 6H), 1.59 (sextet, J=7.5 Hz, 2H), 0.94 (t, J=7.3 Hz, 3H), MS (ES) m/e 500 (M+1).

Example 44

2-{5-[2-(2-Biphenyl-3-yl-5-methyloxazol-4-yl)ethoxy]-2-propylphenoxy}-2-methylpropionic acid

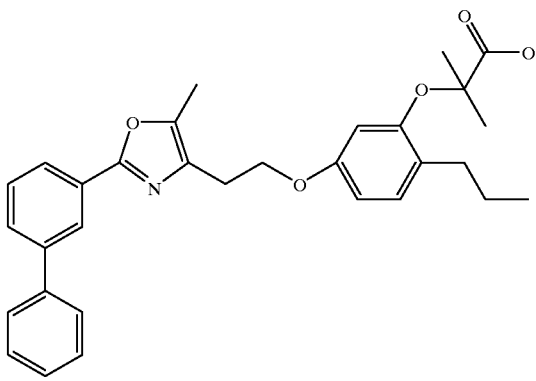

To a 50 mL glass tube with screw cap and nitrogen inlet were charged 2-(2-propyl-5-hydroxyphenoxy)-2-methylpropionic acid ethyl ester, (0.178 mmol), toluene-4-sulfonic acid 2-(5-methyl-2-biphenyl-3-yl-1oxazol-4-yl)ethyl ester (0.187 mmol) (see Ex. 22, part B), and powdered potassium carbonate (0.050 g, 0.36 mmol) in 1 mL of absolute ethanol. The mixture was heated to reflux for 18 h. MS analysis of the reaction indicated that 2-{5-[2-(2-biphenyl-3-yl-5-methyloxazol-4-yl)ethoxy]-2-propylphenoxy}-2-methylpropionic acid, MS (ES) m/e 528 (M+1) had formed. Next 0.4 mL of 5N sodium hydroxide was added and the reaction was heated for 3 h at 55° C. The ethanol was removed in vacuo and the residue was treated with 1 mL of 5N hydrochloric acid and 1 mL of dichloromethane and poured into a 3 mL ChemElute column to remove the aqueous layer. The column was eluted with additional dichloromethane until nothing UV active remained on the column. The solvent was removed in vacuo. The crude residue was purified by mass-directed reverse phase HPLC to provide 2-{5-[2-(2-biphenyl-3-yl-5-methyloxazol-4-yl)ethoxy]-2-propylphenoxy}-2-methylpropionic acid. $^1$H NMR (400 MHz, CDCl$_3$) δ8.27 (s, 1H), 7.96 (d, J=7.8 Hz, 1H), 7.73 (d, J=7.8 Hz, 1H), 7.66 (d, J=7.8 Hz, 2H), 7.55 (t, J=7.8 Hz, 1H, ), 7.47 (t, J=7.3 Hz, 2H), 7.39 (t, J=7.3 Hz, 1H), 7.03 (d, J=8.3 Hz, 1H), 6.60 (s, 1H), 6.53–6.50 (m, 1H), 4.21 (t, J=6.8 Hz, 2H), 3.00 (t, J=6.8 Hz, 2H), 2.52 (t, J=7.6 Hz, 2H), 2.42 (s, 3H), 1.62 (s, 6H), 1.57 (sextet, J=7.6 Hz, 2H), 0.92 (t, J=7.3 Hz, 3H), MS (ES) m/e 500 (M+1).

Example 45

2-{4-[2-(2-Biphenyl-4-yl-5-methyl-thiazol-4-yl)-ethoxy]-phenoxy}-2-methyl-propionic acid

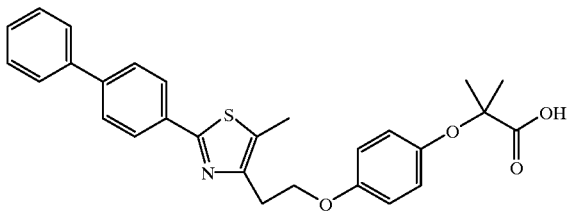

A. Biphenyl-4-carbothioic acid amide

According to a modification of Taylor, et al., *J. Am. Chem. Soc.* 82:2656–2657 (1960), a mixture of commercially available 4-cyanobiphenyl (10.7 g, 60 mmol) and thoiacetamide (9.0 g, 119 mmol) in 4N HCl dioxane (30 mL) was heated to a gently reflux. After 3 h, the reaction was cooled and poured into saturated NaHCO$_3$ (400 mL). After setting for a few hours, the mixture was heated and filtered hot. The brown solid which was not water soluble was collected and dried to give 11.2 g (87%) crude product. The product was used without further purification. $^1$H NMR (DMSO-d$_6$) δ7.35–8.07 (m, 9H), 9.63 (br s, 2H); MS (m/e) 214 (M+H).

B. (2-Biphenyl-4-yl-5-methyl-thiazol-4-yl)-acetic acid methyl ester

Biphenyl-4-carbothioic acid amide (7.3 g) in toluene was heated at reflux for 1 h in a flask equipped with a Dean-Stark trap. After 1.2 mL water was obtained, the dry thioamide (6.0 g, 28 mmol) and 4-bromo-3-oxo-pentanoic acid methyl ester (9.0 g, 43 mmol) were heated in toluene (200 mL) for 3 h. The cooled reaction was concentrated and purified by short path chromatography (400 g silica gel, 15% ethyl acetate/hexanes, then 20% ethyl acetate/hexanes). The fractions that contained pure product were concentrated to yield 3.53 g (39%) ester as a red foam: $^1$H NMR (CDCl$_3$) δ2.50 (s, 3H), 3.77 (s, 3H), 3.86 (s, 2H), 7.36–7.68 (m, 7H), 7.98 (d, 2H); MS (m/e) 324 (M+H)

C. 2-(2-Biphenyl-4-yl-5-methyl-thiazol-4-yl)-ethanol

According to the general method of Collins et al, *J. Med. Chem.*, 41:5037–5054 (1998), a THF (100 mL) solution of (2-biphenyl-4-yl-5-methyl-thiazol-4-yl)-acetic acid methyl ester (3.5 g, 16 mmol) was cooled to 0° C. and a 1M LiAlH$_4$ (16 mL, 16 mmol) was added slowly. After stirring at room temperature for 45 min, tlc (15% ethyl acetate/hexane) showed that all the starting ester had been consumed. The reaction was cooled and carefully quenched with 4 mL water, 2.6 mL 5N NaOH and 2 mL water. The light tan solid was filter and dried to give 3.29 g crude product. Recrystallization (60 mL toluene) gave 2.36 g (50%) alcohol as an orange solid: mp 138.5° C.; $^1$H NMR (CDCl$_3$) δ2.46 (s, 3H), 2.95 (t, 2H), 3.73 (br t, 1H), 4.03 (t, 2H), 7.36–7.54 (m, 3H), 7.64–7.72 (m, 4H), 7.97 (d, 2H); MS (m/e) 296 (M+H).

D. 2-{4-[2-(2-Biphenyl-4-yl-5-methyl-thiazol-4-yl)-ethoxy]-phenoxy}-2-methyl-propionic acid ethyl ester To a solution of 2-(2-biphenyl-4-yl-5-methyl-thiazol-4-yl)-ethanol (31.5 mmol) in CH$_2$Cl$_2$ (150 mL) at room temperature under N$_2$ was added pyridine (8.74 g, 110 mmol, 8.9 mL) and DMAP (0.97 g, 7.88 mmol) followed by portionwise addition of tosyl anhydride (12.7 g, 37.8 mmol). The reaction exothermed to 32° C. and was stirred 1 h before 1N HCl (200 mL) was added. The mixture was stirred vigorously 15 min, and then the organic phase was dried (MgSO$_4$) and filtered through a pad of silica gel (200 mL, packed with CH$_2$Cl$_2$). After rinsing the silica gel with ethyl acetate (100 mL) the solution was concentrated to toluene-4-sulfonic acid 2-(2-biphenyl-4-yl-5-methyl-thiazol-4-yl)-ethyl ester in 94% yield which was used without further purification. MS (m/e) 450 (MH). A mixture of toluene-4-sulfonic acid 2-(2-biphenyl-4-yl-5-methyl-thiazol-4-yl)-ethyl ester (6.2 mmol), Cs$_2$CO$_3$ (1.8 g, 5.5 mmol) and phenol (1.0 g, 4.4 mmol) in DMF (100 mL) was warmed at 55° C. for 18 h. The reaction was partitioned between ethyl acetate/water. The organic solution was washed a second time with water and then dried (MgSO$_4$). After concentration, 3.2 g crude product was obtained. Purification by flash column chromatography (15% ethyl acetate/hexane) gave 420 mg (19%) ester as a colorless oil: $^1$H NMR (CDCl$_3$) δ1.17 (t, 3H), 1.46 (s, 6H), 2.40 (s, 3H), 3.12 (t, 2H), 4.16 (q, 2H), 4.22 (t, 2H), 6.66–6.78 (m, 4H), 7.26–7.4 (m, 3H), 7.55–7.61 (m, 4H), 7.88 (d, 2H); MS (m/e) 502 (M+H).

E. 2-{4-[2-(2-Biphenyl-4-yl-5-methyl-thiazol-4-yl)-ethoxy]-phenoxy}-2-methyl-propionic acid A sample of 2-{4-[2-(2-biphenyl-4-yl-5-methyl-thiazol-4-yl)-ethoxy]-phenoxy}-2-methyl-propionic acid ethyl ester (400 mg, 0.8 mmol) was dissolved in EtOH (15 mL) and 5N NaOH (5 mL) added. The reaction was warmed at 40° C. for 1.5 h and then cooled to room temperature. After removing some of the EtOH, the reaction was acidified with HCl. After stirring in an ice-bath for 1 h, the yellow solid was collected and dried to give 328 mg (87%) acid as a yellow powder, mp 174° C., MS (m/e) 474 (MH); $^1$H NMR (CDCl$_3$) δ1.53 (s, 6H), 2.57 (s, 3H), 3.48 (t, 2H), 4.44 (t, 2H), 6.80 (d, 2H), 6.91 (d, 2H), 7.40–7.54 (m, 3H), 7.51 (d, 2H), 7.64 (d, 2H), 8.26 (d, 2H).

Example 46

2-{4-[2-(2-Biphenyl-3-yl-5-methyl-thiazol-4-yl)-ethoxy]-phenoxy}-2-methyl-propionic acid

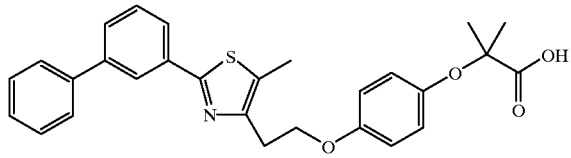

A. 2-{4-[2-(2-Biphenyl-3-yl-5-methyl-thiazol-4-yl)-ethoxy]-phenoxy}-2-methyl-propionic acid ethyl ester To a solution of 2-(2-biphenyl-3-yl-5-methyl-thiazol-4-yl)-ethanol (2.58 g, 8.73 mmol), 2-(4-hydroxy-phenoxy)-2-methyl-propionic acid ethyl ester (1.9 6 g, 8.73 mmol), and triphenylphosphine (2.2 9 g, 8.73 mmol) in 90 mL tetrahydrofuran was added diisopropylazodicarboxylate (1.76 g, 8.73 mmol) dropwise over 30 min. After stirring 24 h, the solution was diluted with ethyl acetate, washed with water and brine, dried over magnesium sulfate, filtered and concentrated to an orange oil. Silica gel chromatography (100 g silica gel, 15% ethyl acetate/hexanes) afforded 470 mg (11% yield) of 2-{4-[2-(2-biphenyl-3-yl-5-methyl-thiazol-4-yl)-ethoxy]-phenoxy}-2-methyl-propionic acid ethyl ester as a colorless oil. $^1$H NMR (400MHz, CDCl$_3$) δ8.06 (s, 1H), 7.81 (d, 1H), 7.62 (d, 2H), 7.57 (d, 1H), 7.46–7.42 (m, 3H), 7.37–7.34 (m, 1H), 6.80–6.74 (m, 4H), 4.235 (t, 2H), 4.20 (q, 2H), 3.15 (t, 2H), 2.44 (s, 3H), 1.49 (s, 6H), 1.24 (t, 3H). MS EI$^+$(m/e) 502.1

B. 2-{4-[2-(2-Biphenyl-3-yl-5-methyl-thiazol-4-yl)-ethoxy]-phenoxy}-2-methyl-propionic acid To 2-{4-[2-(2-biphenyl-3-yl-5-methyl-thiazol-4-yl)-ethoxy]-phenoxy}-2-methyl-propionic acid ethyl ester (470 mg, 0.94 mmol) in tetrahydrofuran (10 mL) and methanol (2 mL) was added 2 mL of a 5N NaOH solution. After 24 h, the solution was concentrated in vacuo. The residue was partioned between ethyl acetate and 1N hydrochloric acid. The ethyl acetate layer was dried over magnesium sulfate, filtered and concentrated to afford 385 mg (87% yield) of 2-{4-[2-(2-biphenyl-3-yl-5-methyl-thiazol-4-yl)-ethoxy]-phenoxy}-2-methyl-propionic acid as a white solid. $^1$H NMR (400MHz, CDCl$_3$) δ8.04 (s, 1H), 7.78 (d, 1H), 7.61–7.55 (m, 3H), 7.45–7.40 (m, 3H), 7.35–7.31 (m, 1H), 6.86–6.82 (m, 2H), 6.79–6.76 (m, 2H), 4.24 (t, 2H), 3.16 (t, 2H), 2.43 (s, 3H), 1.46 (s, 6H). MS EI+(m/e) 474.1.

Example 47

2-{4-[2-(2-Biphenyl-4-yl-5-methyloxazol-4-yl)-ethylsulfanyl]-phenoxy}-2-methyl-propionic acid

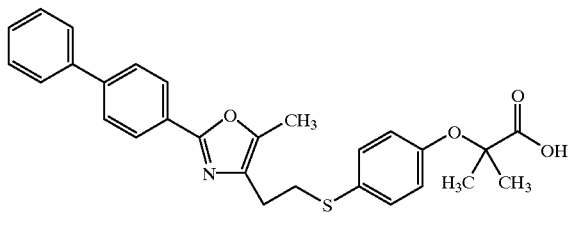

A. 2-(4-Dimethylthiocarbamoyloxy-phenoxy)-2-methyl-propionic acid ethyl ester

A DMF (100 mL) solution of 2-(4-hydroxyphenoxy)-2-methyl propionic acid ethyl ester (15.2 g, 67.7 mmol) and DABCO (15.2 g, 135.5 mmol) was charged dropwise with N,N-dimethylthiocarbamoyl chloride (16.7 g, 135.5 mmol) in 20 mL DMF over 15 min. The reaction was stirred at room temperature for 18 h and then quenched with water. The reaction was partitioned between water (1L) and ethyl acetate (500 mL) and the organic layer washed with iN HCl (500 mL). After drying (MgSO$_4$) and concentration, the crude product was obtained as a tan oil. Purification by flash chromatography (15% ethyl acetate/hexane) provided the product (15.8 g, 75%) as a pale yellow oil: $^1$H NMR (CDCl$_3$) δ1.32 (t, 3H), 1.65 (s, 6H), 3.37 (s, 3H), 3.50 (s, 3H), 4.30 (q, 2H), 6.93 (dd, 4H); MS (m/e) 312.

B. 2-(4-Dimethylcarbamoylsulfanyl-phenoxy)-2-methyl-propionic acid ethyl ester

Neat 2-(4-dimethylthiocarbamoyloxyphenoxy)-2-methyl propionic acid ethyl ester (15 g, 48.2 mmol) was heated at 200° C. for 1 h. TLC (20% ethyl acetate/hexane) showed that no reaction had occurred. The temperature was raised to 240° C. for 30 min. By TLC, all starting material was gone and there was significant decomposition. Purification by short plug column (20% ethyl acetate/hexane) followed by prep HPLC gave the product (2.6 g) as a pale yellow oil: $^1$H NMR (CDCl$_3$) δ1.27 (t, 3H), 1.63 (s, 6H), 3.05 (br s, 6H), 4.24 (q, 2H), 6.86 (d, 2H), 7.35 (d, 2H); MS (m/e) 312.

C. 2-Methyl-2-{4-[2-(5-methyl-2-phenyloxazol-4-yl)ethylsulfanyl]phenoxy}propionic acid ethyl ester Freshly prepared sodium ethoxide (from 50 mg (2.2 mmol) Na) was charged with 2-(4-Dimethylcarbamoylsulfanyl-phenoxy)-2-methyl-propionic acid ethyl ester (420 mg, 1.35 mmol) and refluxed for 3 h. Toluene-4-sulfonic acid 2-(5-methyl-2-biphenyl-4-yl-oxazol-4-yl)-ethyl ester (2.2 mmol) was added and the mixture was refluxed for another 3 h. The reaction was cooled and concentrated. The residue was shaken with ethyl acetate/water. After a second water wash, the organic layer was dried (MgSO$_4$) and concentrated to give 500 mg crude product.

D. 2-{4-[2-(2-Biphenyl-4-yl-5-methyloxazol-4-yl)-ethylsulfanyl]-phenoxy}-2-methyl-propionic acid 2-Methyl-2-{4-[2-(5-methyl-2-biphenyl-4-yl-oxazol-4-yl)ethylsulfanyl]phenoxy}propionic acid ethyl ester (0.23 mmol) was dissolved in EtOH (10 mL) and 5N NaOH (0.5 mL) was added. The reaction was stirred overnight at room temperature. The reaction was acidified with 5N HCl and the product was extracted into ethyl acetate, dried (MgSO$_4$) and concentrated to give 96 mg crude product.

Example 48

2-{4-[2-(2-Biphenyl-4-yl-5-methyloxazol-4-yl)ethoxy]naphthalen-1-yloxy}-2-methyl propionic acid

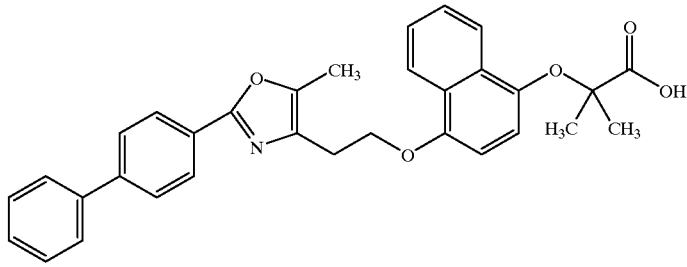

A. 2-(4-Hydroxy-naphthalen-1-yloxy)-2-methyl-propionic acid ethyl ester

A solution of naphthalene-1,4-diol (30.0 g, 187 mmol) was prepared in DMF (60 mL, anhydrous), cooled to 0° C., and treated with NaH (7.50 g of a 60% solution in oil, 188 mmol) in portions, over a 5 min period. The ice bath was removed and the mixture stirred for 30 min. The resulting black suspension was treated with ethyl 2-bromoisobutyrate (27.6 mL, 188 mmol) and stirred at 95° C. for 18 h. The mixture was cooled to room temperature, then poured into cracked ice containing HCl (1 N aqueous, 200 mL). The aqueous layer was extracted with ethyl ether (3×500 mL) and the organic layers washed with brine (100 mL), dried (MgSO$_4$), filtered, and the filtrate evaporated (40° C., 20 mm Hg). The residue was chromatographed on SiO$_2$ (Biotage, 65M column; 18% ethyl acetate/hexanes) to afford a total of 19.2 g of 2-(4-hydroxy-naphthalen-1-yloxy)-2-methyl-propionic acid ethyl ester as a black oil 37% yield: R$_f$=0.31 (20% ethyl acetate/hexanes); $^1$H NMR (CDCl$_3$) δ8.2 (m, 1H), 8.1 (m, 1H), 7.5 (m, 2H), 6.62 (dd, J=15.4, 8.4 Hz, 2H), 4.22 (q, J=7.2 Hz, 2H), 1.60 (s, 6H), 1.21 (t, J=7.2 Hz, 3H); MS (ES+) m/e (% relative intensity) 275.1 (M$^+$+1, 21), 230.1 (33), 229.0 (100), 201.0 (60).

B. 2-{4-[2-(2-Biphenyl-4-yl-5-methyloxazol-4-yl)-ethoxy]-naphthalen-1-yloxy}-2-methyl propionic acid ethyl ester A solution of 2-(4-hydroxy-naphthalen-1-yloxy)-2-methyl-propionic acid ethyl ester (450 mg, 1.64 mmol) and toluene-4-sulfonic acid 2-(2-biphenyl-4-yl-5-methyloxazol-4-yl) ethyl ester (1.96 mmol) (see Ex. 1, part F) was prepared in DMF (4 mL, anhydrous) under N$_2$, treated with Cs$_2$CO$_3$ (638 mg, 1.96 mmol), and stirred at 60° C. for 18 h. The solution was poured into 1/1 H$_2$O/brine and extracted twice with 2/1 ethyl acetate/toluene. The organic layers were washed with brine, dried (MgSO$_4$), filtered, and the filtrate evaporated (40° C., 20 mm Hg) to a residue. The residue was chromatographed on SiO$_2$ (Biotage, 40 L column; 20% ethyl acetate/hexanes) to afford 2-{4-[2-(2-Biphenyl-4-yl-5-methyloxazol-4-yl)-ethoxy]-naphthalen-1-yloxy}-2-methyl propionic acid ethyl ester. $^1$H NMR (400 MHz, CDCl$_3$) δ8.2 (m 2H), 8.01 (d, J=8.8 Hz, 2H), 7.6 (m, 4H), 7.4 (m, 4H), 7.3 (m, 1H), 6.69 (d, J=8.4 Hz, 1H), 6.64 (d, J=8.4 Hz, 1H), 4.35 (t, J=6.4 Hz, 2H), 4.21 (q, J=7.2 Hz, 2H), 3.08 (t, J=6.4 Hz, 2H), 2.38 (s, 3H), 1.60 (s, 6H), 1.23 (t, J=7.2 Hz, 3H); MS (ES+) m/e (% relative intensity) 538.2 (9), 537.2 (47), 536.2 (M$^+$+1, 100).

C. 2-{4-[2-(2-Biphenyl-4-yl-5-methyloxazol-4-yl)ethoxy]naphthalen-1-yloxy}-2-methyl propionic acid A solution of 2-{4-[2-(2-biphenyl-4-yl-5-methyloxazol-4-yl)-ethoxy]-naphthalen-1-yloxy}-2-methyl propionic acid ethyl ester (91 μmol) was prepared in THF (10 mL) and methanol (2 mL), treated with NaOH (2.0 mL of a 1 N aqueous solution, 2.0 mmol), and stirred for 4 h. The solution was acidified with HCl (400 μL, 5 N aqueous, 2.0 mmol), and partitioned between water and ethyl acetate. The layers were separated and the organic layer dried (MgSO$_4$), filtered, and the filtrate evaporated (40° C., 20 mm Hg). The residue was triturated with ethyl ether to afford 260 mg (2 crops) of 2-{4-[2-(2-biphenyl-4-yl-5-methyloxazol-4-yl)ethoxy]naphthalen-1-yloxy}-2-methyl propionic acid. $^1$H NMR (400 MHz, CDCl$_3$) δ8.1 (m, 2H), 8.03 (d, J=8.0 Hz, 2H), 7.62 (d, J=8.0 Hz, 2H), 7.58 (d, J=7.2 Hz, 2H), 7.4 (m, 4H), 7.32 (t, J=7.6 Hz, 1H), 6.88 (d, J=8.4 Hz, 1H), 6.6 (d, J=8.4 Hz, 1H), 4.29 (t, J=6.2 Hz, 2H), 3.13 (t, J=6.2 Hz, 2H), 2.43 (s, 3H), 1.62 (s, 6H); MS (ES+) m/e (% relative intensity) 509.2 (35), 508.2 (M$^+$+1, 100).

Example 49

2-{4-[2-(2-Biphenyl-3-yl-5-methyloxazol-4-yl)ethoxy]naphthalen-1-yloxy}-2-methyl propionic acid

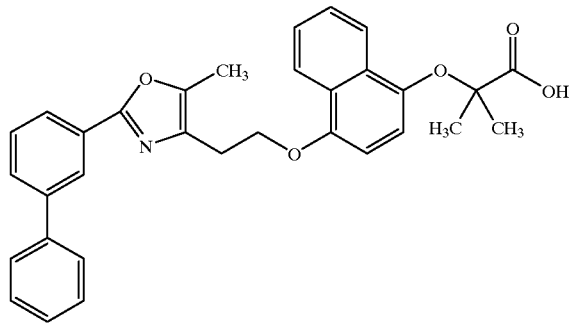

A. 2-{4-[2-(2-Biphenyl-3-yl-5-methyloxazol-4-yl)-ethoxy]-naphthalen-1-yloxy}-2-methyl-propionic acid ethyl ester A solution of 2-(4-hydroxy-naphthalen-1-yloxy)-2-methyl-propionic acid ethyl ester (450 mg, 1.64 mmol) (see Example 48, part A) and toluene-4-sulfonic acid 2-(2-biphenyl-3-yl-5-methyloxazol-4-yl) ethyl ester (1.96 mmol) (see Ex. 22, part B) was prepared in DMF (4 mL, anhydrous) under N$_2$, treated with Cs$_2$CO$_3$ (638 mg, 1.96 mmol), and stirred at 60° C. for 18 h. The solution was poured into 1/1 H$_2$O/brine and extracted twice with 2/1 ethyl acetate/toluene. The organic layers were washed with brine, dried (MgSO$_4$), filtered, and the filtrate evaporated (40° C., 20 mm Hg) to a residue. The residue was chromatographed on SiO$_2$ (Biotage, 40 L column; 20% ethyl acetate/hexanes) to afford 2-{4-[2-(2-biphenyl-3-yl-5-methyloxazol-4-yl)-ethoxy]-naphthalen-1-yloxy}-2-methyl-propionic acid ethyl ester.

¹H NMR (400 MHz, CDCl₃) δ 8.2 (m 2H), 8.01 (d, J=8.8 Hz, 2H), 7.6 (m, 4H), 7.4 (m, 4H), 7.3 (m, 1H), 6.68 (d, J=8.4 Hz, 1H), 6.63 (d, J=8.4 Hz, 1H), 4.35 (t, J=6.6 Hz, 2H), 4.21 (q, J=7.2 Hz, 2H), 3.08 (t, J=6.6 Hz, 2H), 2.38 (s, 3H), 1.59 (s, 6H), 1.20 (t, J=7.2 Hz, 3H); MS (ES+) m/e (% relative intensity) 538.2 (12), 537.2 (47), 536.2 (M⁺+1, 100).

B. 2-{4-[2-(2-Biphenyl-3-yl-5-methyloxazol-4-yl)ethoxy]naphthalen-1-yloxy}-2-methyl propionic acid A solution of 2-{4-[2-(2-biphenyl-3-yl-5-methyloxazol-4-yl)-ethoxy]-naphthalen-1-yloxy}-2-methyl-propionic acid ethyl ester (91 μmol) was prepared in THF (10 mL) and methanol (2 mL), treated with NaOH (2.0 mL of a 1 N aqueous solution, 2.0 mmol), and stirred for 4 h. The solution was acidified with HCl (400 μL, 5 N aqueous, 2.0 mmol), and partitioned between water and ethyl acetate. The layers were separated and the organic layer dried (MgSO₄), filtered, and the filtrate evaporated (40° C., 20 mm Hg). The residue was triturated with ethyl ether to afford 260 mg (2 crops) of 2-{4-[2-(2-biphenyl-3-yl-5-methyloxazol-4-yl)ethoxy]naphthalen-1-yloxy}-2-methyl propionic acid. ¹H NMR (400 MHz, CDCl₃) δ 8.1 (t, J=1.6 Hz, 1H), 8.13 (dt, J=8.0, 2.0 Hz, 2H), 7.91 (dt, J=8.4, 1.6 Hz, 1H), 7.6 (m, 3H), 7.4 (m, 5H), 7.32 (t, J=7.6 Hz, 1H), 6.87 (d, J=8.2 Hz, 1H), 6.59 (d, J=8.4 Hz, 1H), 4.23 (t, J=6.0 Hz, 2H), 3.16 (t, J=6.0 Hz, 2H), 2.45 (s, 3H), 1.62 (s, 6H); MS (ES+) m/e (% relative intensity) 509.2 (53), 508.2 (M⁺+1, 100).

Example 50

2-{4-[2-(2-Biphenyl-4-yl-5-methyloxazol-4-yl)-ethoxy]-5,6,7,8-tetrahydronaphthalen-1-yloxy}-2-methyl propionic acid

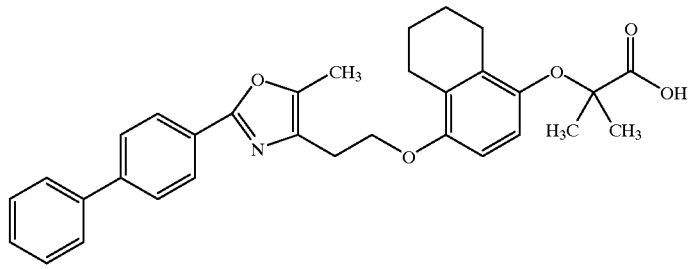

A. 5,6,7,8-Tetrahydronaphthalene-1,4-diol

A solution of naphthalene-1,4-diol (4.00 g, 25.0 mmol) was prepared in ethanol (95 mL) and acetic acid (25 mL), treated with PtO₂ (0.60 g, 2.6 mmol), charged with H₂ (60 psig), and shaken for 18 h at 40° C. The catalyst was filtered off and the filtrate evaporated (40° C., 20 mm Hg). The residue was dissolved in ethyl acetate (100 mL) and washed with NaHCO₃ (saturated aqueous, 100 mL), brine (100 mL), dried (MgSO₄), filtered, and the filtrate evaporated (40° C., 20 mm Hg) to afford a total of 2.6 g of 5,6,7,8-tetrahydronaphthalene-1,4-diol as a black solid, 63% yield: ¹H NMR (CDCl₃) δ 6.45 (s, 2H), 2.6 (m, 4H), 1.9 (m, 4H); MS (ES+) m/e (% relative intensity) 327.2 (100), 165.1 (M⁺+1, 26).

B. 2-(4-Hydroxy-5,6,7,8-tetrahydronaphthalen-1-yloxy)-2-methyl propionic acid ethyl ester A solution of 5,6,7,8-tetrahydronaphthalene-1,4-diol (2.60 g, 15.8 mmol) was prepared in DMF (20 mL, anhydrous), cooled to 0° C., and treated with NaH (0.63 g of a 60% solution in oil, 15.8 mmol) in one portion. The ice bath was removed and the mixture stirred for 30 min. The resulting black suspension was treated with ethyl 2-bromoisobutyrate (2.33 mL, 15.9 mmol) and stirred at 100° C. for 18 h. The mixture was cooled to room temperature, then poured into cracked ice containing HCl (1 N aqueous, 20 mL). The aqueous layer was extracted with ethyl ether (3×50 mL) and the organic layers washed with brine (100 mL), dried (MgSO₄), filtered, and the filtrate evaporated (40° C., 20 mm Hg). The residue was chromatographed on SiO₂ (Biotage, 40 L column; 15% ethyl acetate/hexanes) to afford a total of 1.2 g of 2-(4-hydroxy-5,6,7,8-tetrahydro-naphthalen-1-yloxy)-2-methyl-propionic acid ethyl ester as a black oil 27% yield: R_f=0.27 (15% ethyl acetate in hexanes); ¹H NMR (CDCl₃) δ 6.42 (d, J=8.6 Hz, 2H), 6.38 (d, J=8.6 Hz, 2H), 4.20 (q, J=7.2 Hz, 2H), 2.61 (t, J=6.0 Hz, 2H), 2.55 (t, J=6.0 Hz, 2H), 1.6 (m, 4H), 1.49 (s, 6H), 1.23 (t, J=7.2 Hz, 3H); MS (ES+) m/e (% relative intensity) 301.1 (28), 279.2 (M⁺+1, 49), 233.1 (100), 205.1 (470), 165.1 (88).

C. 2-{4-[2-(2-Biphenyl-4-yl-5-methyloxazol-4-yl)-ethoxy]-5,6,7,8-tetrahydronaphthalen-1-yloxy}-2-methyl propionic acid ethyl ester A solution of 2-(4-hydroxy-5,6,7,8-tetrahydronaphthalen-1-yloxy)-2-methyl propionic acid ethyl ester (400 mg, 1.44 mmol) and toluene-4-sulfonic acid 2-(2-biphenyl-4-yl-5-methyloxazol-4-yl) ethyl ester (1.70 mmol) (see Ex. 1, part F) was prepared in DMF (4 mL, anhydrous) under N₂, treated with Cs₂CO₃ (555 mg, 1.70 mmol), and stirred at 55° C. for 24 h, then stirred over the week end at room temperature. The solution was poured into dilute aqueous HCl and extracted twice with ethyl acetate. The organic layers were washed with brine, dried (MgSO₄), filtered, and the filtrate evaporated (40° C., 20 mm Hg) to a residue. The residue was chromatographed on SiO₂ (Biotage, 40S column; 15% ethyl acetate/hexanes) to afford 2-{4-[2-(2-biphenyl-4-yl-5-methyloxazol-4-yl)-ethoxy]-5,6,7,8-tetrahydronaphthalen-1-yloxy}-2-methyl propionic acid ethyl ester. ¹H NMR (400 MHz, CDCl₃) δ 8.00 (d, J=8.0 Hz, 2H), 7.6 (m, 4H), 7.41 (t, J 7.6 Hz, 2H), 7.3 (t, J=7.6 Hz, 1H), 6.4 (m, 2H), 4.20 (q, J=7.2 Hz, 2H), 4.13 (t, J=6.4 Hz, 2H), 2.93 (t, J=6.4 Hz, 2H), 2.6 (m, 4H), 2.34 (s, 3H), 1.7 (m, 4H), 1.48 (s, 6H), 1.22 (t, J=7.2 Hz, 3H); MS (ES+) m/e (% relative intensity) 542.4 (12), 541.3 (51), 540.3 (M⁺+1, 100).

D. 2-{4-[2-(2-Biphenyl-4-yl-5-methyloxazol-4-yl)-ethoxy]-5,6,7,8-tetrahydronaphthalen-1-yloxy}-2-methyl propionic acid A solution of 2-{4-[2-(2-biphenyl-4-yl-5-methyloxazol-4-yl)-ethoxy]-5,6,7,8-tetrahydronaphthalen-1-yloxy}-2-methyl propionic acid ethyl ester (755 μmol) was prepared in THF (10 mL) and methanol (3 mL), treated with NaOH (3.0 mL of a 1 N aqueous solution, 3.0 mmol), and stirred for 18 h. The solution was acidified with HCl (1.0 mL, 5 N aqueous, 5.0 mmol), and partitioned between water and ethyl acetate. The layers were separated and the organic layer was washed with brine, dried (MgSO$_4$), filtered, and the filtrate evaporated (40° C., 20 mm Hg). The resulting solid was recrystallized from ethyl acetate/hexanes to afford 179 mg (2 crops) of 2-{4-[2-(2-biphenyl-4-yl-5-methyloxazol-4-yl)-ethoxy]-5,6,7,8-tetrahydronaphthalen-1-yloxy}-2-methyl propionic acid. $^1$H NMR (400 MHz, CDCl$_3$) δ8.01 (d, J=8.2 Hz, 2H), 7.63 (d, J=8.2 Hz, 2H), 7.59 (d, J=7.6 Hz, 2H), 7.41 ((t, J=7.6 Hz,, 2H), 7.33 (t, J=7.6 Hz, 1H), 6.64 (d, J=8.8 Hz, 1H), 6.52 (d, J=8.8 Hz, 1H), 4.13 (t, J=6.2 Hz, 2H), 3.00 (t, J=6.2 Hz, 2H), 2,6 (m, 4H), 2.37 (s, 3H), 1.7 (m, 4H), 1.51 (s, 6H); MS (ES+) m/e (% relative intensity) 513.3 (35), 512.3 (M$^+$+1, 100).

Example 51

2-{4-[2-(2-Biphenyl-3-yl-5-methyloxazol-4-yl)-ethoxy]-5,6,7,8-tetrahydronaphthalen-1-yloxy}-2-methyl propionic acid

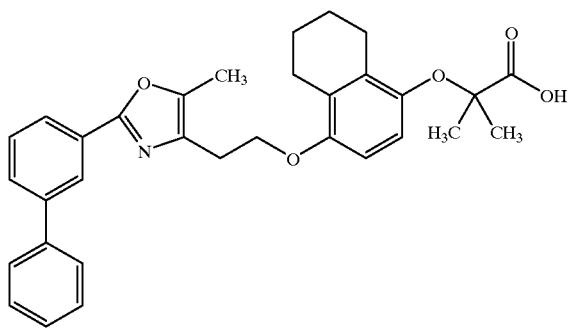

A. 2-{4-[2-(2-Biphenyl-3-yl-5-methyloxazol-4-yl)-ethoxy]-5,6,7,8-tetrahydronaphthalen-1-yloxy}-2-methyl-propionic acid ethyl ester A solution of 2-(4-hydroxy-5,6,7,8-tetrahydronaphthalen-1-yloxy)-2-methyl propionic acid ethyl ester (400 mg, 1.44 mmol) (see Example 50, Part B) and toluene-4-sulfonic acid 2-(2-biphenyl-3-yl-5-methyloxazol-4-yl) ethyl ester (1.70 mmol) was prepared in DMF (4 mL, anhydrous) under N$_2$, treated with Cs$_2$CO$_3$ (555 mg, 1.70 mmol), and stirred at 55° C. for 24 h, then stirred over the week end at room temperature. The solution was poured into dilute aqueous HCl and extracted twice with ethyl acetate. The organic layers were washed with brine, dried (MgSO$_4$), filtered, and the filtrate evaporated (40° C., 20 mm Hg) to a residue. The residue was chromatographed on SiO$_2$ (Biotage, 40S column; 15% ethyl acetate/hexanes) to afford 2-{4-[2-(2-biphenyl-3-yl-5-methyloxazol-4-yl)-ethoxy]-5,6,7,8-tetrahydronaphthalen-1-yloxy}-2-methyl-propionic acid ethyl ester. $^1$H NMR (400 MHz, CDCl$_3$) δ8.2 (s, 1H), 7.91 (d, J=7.2 Hz, 1H), 7.60 (t, J=8.4 Hz, 3H), 7.45 (t, J=7.6 Hz, 1H), 7.41 (t, J=7.6 Hz, 2H), 7.32 (t, J=8.4 Hz, 1H), 6.43 (m, 2H), 4.2 (m, 2H), 4.13 (t, J=6.4 Hz, 2H), 2.93 (t, J=6.4 Hz, 2H), 2.6 (m, 4H), 2.34 (s, 3H), 1.7 (m, 4H), 1.49 (s, 3H), 1.47 (s, 3H), 1.2 (m, 3H); MS (ES+) m/e (% relative intensity) 542.4 (13), 541.3 (60), 540.3 (M$^+$+1, 100).

B. 2-{4-[2-(2-Biphenyl-3-yl-5-methyloxazol-4-yl)-ethoxy]-5,6,7,8-tetrahydronaphthalen-1-yloxy}-2-methyl propionic acid A solution of 2-{4-[2-(2-biphenyl-3-yl-5-methyloxazol-4-yl)-ethoxy]-5,6,7,8-tetrahydronaphthalen-1-yloxy}-2-methyl-propionic acid ethyl ester (755 µmol) was prepared in THF (10 mL) and methanol (3 mL), treated with NaOH (3.0 mL of a 1 N aqueous solution, 3.0 mmol), and stirred for 18 h. The solution was acidified with HCl (1.0 mL, 5 N aqueous, 5.0 mmol), and partitioned between water and ethyl acetate. The layers were separated and the organic layer was washed with brine, dried (MgSO$_4$), filtered, and the filtrate evaporated (40° C., 20 mm Hg). The resulting solid was recrystallized from ethyl acetate/hexanes to afford 179 mg (2 crops) of 2-{4-[2-(2-biphenyl-3-yl-5-methyloxazol-4-yl)-ethoxy]-5,6,7,8-tetrahydronaphthalen-1-yloxy}-2-methyl propionic acid. $^1$H NMR (400 MHz, CDCl$_3$) δ8.20 (s, 1H), 7.91 (d, J=7.6 Hz, 1H), 7.6 (m, 3H), 7.46 (t, J=7.6 Hz, 1H), 7.41 (t, J=7.6 Hz, 2H), 7.32 (t, J=7.2 Hz, 1H), 6.63 (d, J=8.8 Hz, 1H), 6.51 (d, J=8.8 Hz, 1H), 4.12 (t, J=6.2 Hz, 1H), 3.01 (t, J=6.2 Hz, 2H), 2.6 (m, 4H), 2.37 (s, 3H), 1.7 (m, 4H), 1.51 (s, 6H); MS (ES+) m/e (% relative intensity) 513.3 (47), 512.2 (M$^+$+1, 100).

Example 52

2-{4-[2-(2-Biphenyl-4-yl-5-propyl-oxazol-4-yl)-ethoxy]-phenoxy}-2-methyl-prop ionic acid

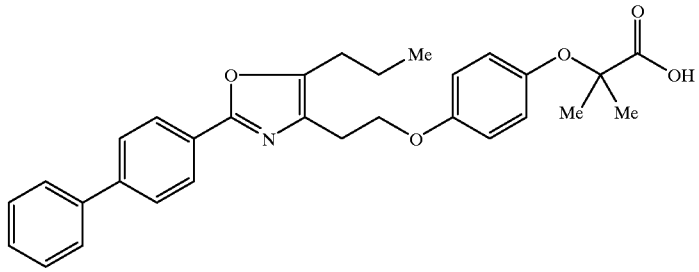

A. 2-(4-{3-[(Biphenyl-4-carbonyl)-amino]-4-oxo-heptyloxy}-phenoxy)-2-methyl-propionic acid A sample of 2-[(biphenyl-4-carbonyl)-amino]-4-[4-(1-carboxy-1-methyl-ethoxy)-phenoxy]-butyric acid (676 mg, 1.42 mmol) was dissolved in pyridine (2.53 mL, 42.5 mmol, 30 equiv.) followed by butyric anhydride (4.45 mL, 26.9 mmol, 19 equiv.) then warmed with magnetic stirring at 90° C. for 1 hour. Upon cooling to room temperature, 1 N HCl (50 mL) was added and the mixture stirred for 1 hour. The mixture was then extracted with ethyl acetate (3×100 mL). The combined organic phases were concentrated under reduced pressure to yield 4.75 gm of an oil which was heavily contaminated with butyric acid. Purification was effected upon esterification in the following step. HPLC RT[1]=2.60 min.

[1] Isocratic method (80% Acetonitrile/0.03M Phosphate buffer); Flow rate: 1.5 mL/min; Column: Zorbax SB-C18 4.6×250 mm 5-micron; 220 nm detection.

B. 2-{4-(3-[(Biphenyl-4-carbonyl)-amino]-4-oxo-heptyloxy}-phenoxy)-2-methyl-propionic acid methyl ester A sample mixture of 2-(4-{3-[(biphenyl-4-carbonyl)-amino]-4-oxo-heptyloxy}-phenoxy)-2-methyl-propionic acid and butyric acid (4.75 g) was dissolved in ethyl ether (50 mL) followed by slow addition of a diazomethane solution prepared as follows:

A sample of 1-methyl-3-nitro-1-nitrosoguanidine (9.51 gm, 64.7 mmol) was slowly added to a stirring mixture of 5 N KOH (13 mL) and ethyl ether (100 mL) at room temperature. The biphasic mixture was stirred for an additional 10 minutes followed by separation of the phases. The organic phase was used as is.

The reaction mixture was then concentrated to an oil and passed through a column of silica eluting with 40% ethyl acetate/hexanes. The product-containing eluent was concentrated under reduced pressure to yield 535 mg (73%) of an oil. HPLC RT[1]=3.86 min; $^1$H NMR (400 MHz, CDCl$_3$) δ7.89 (d, J=8.3 Hz, 2H), 7.68–7.61 (m, 4H), 7.48–7.37 (m, 3H), 6.80 (t, J=8.8 Hz, 2H), 6.71 (t, J=8.8 Hz, 2H), 4.90 (m, 1H), 4.07–3.97 (m, 1H), 3.77 (s, 3H), 2.78–2.70 (m, 1H) 2.63–2.55 (m, 2H), 2.42–2.32 (m, 1H) 1.74–1.65 (m, 2H), 1.53 (s, 6H), 0.97 (t, J=7.3 Hz, 3H).

[1] Isocratic method (80% Acetonitrile/0.03M Phosphate buffer); Flow rate: 1.5 mL/min; Column: Zorbax SB-C18 4.6×250 mm 5-micron; 220 nm detection.

C. 2-{4-[2-(2-Biphenyl-4-yl-5-propyl-oxazol-4-yl)-ethoxy]-phenoxy}-2-methyl-propionic acid methyl ester A sample of 2-(4-{3-[(biphenyl-4-carbonyl)-amino]-4-oxo-heptyloxy}-phenoxy)-2-methyl-propionic acid methyl ester (514 mg, 0.99 mmol) was dissolved in 6 mL of dry DMF followed by addition of phosphorus oxychloride (0.28 mL, 2.88 mmol, 3 equiv.). The mixture was heated at 90° C. for 20 minutes under a nitrogen atmosphere. The reaction mixture was then allowed to cool to room temperature followed by addition of cold water (10 mL) and additional stirring for 10 minutes. Sufficient 1.0 N NaOH was then added to achieve neutral pH. The mixture was partitioned between ethyl ether (100 mL) and water (50 mL). The aqueous layer was back-extracted with ethyl ether (100 mL) and the organic phases combined, which were then washed with 5% aq LiCl, dried over NaCl, and concentrated in vacuo to yield an oil which was immediately subjected to silica gel chromatography (ethyl acetate/hexanes) to yield 484 mg (98%) of an oil. HPLC RT[1]=12.70 min; $^1$H NMR (400 MHz, CDCl$_3$) δ8.02 (d, J=8.3 Hz, 2H), 7.64–7.58 (m, 4H), 7.43–7.33 (m, 3H), 6.78–6.72 (m, 4H), 4.17 (t, J=6.3 Hz, 2H), 3.73 (s, 3H), 2.94 (t, J=6.3 Hz, 2H), 2.66 (t, J=7.3 Hz, 2H), 1.73–1.67 (m, 2H), 1.48 (s, 6H), 0.97 (t, J=7.3 Hz, 3H); MS (EI) 500.1 (M+H)$^+$.

[1] Isocratic method (80% Acetonitrile/0.03M Phosphate buffer); Flow rate: 1.5 mL/min; Column: Zorbax SB-C18 4.6×250 mm 5-micron; 220 nm detection.

D. 2-{4-[2-(2-Biphenyl-4-yl-5-propyl-oxazol-4-yl)-ethoxy]-phenoxy}-2-methyl-propionic acid A sample of 2-{4-[2-(2-biphenyl-4-yl-5-propyl-oxazol-4-yl)-ethoxy]-phenoxy}-2-methyl-propionic acid methyl ester (484 mg, 0.97 mmol) was dissolved in ethanol (5 mL) followed by addition of 5.0 N NaOH (2 mL). The mixture was warmed with magnetic stirring at 50° C. for two hours. The reaction mixture was then allowed to cool to room temperature then partitioned between 50 mL of methylene chloride and 15 mL of 1.0 N HCl. The organic phase was separated, dried over sodium chloride and concentrated in vacuo to yield 384 mg (82%) of a glassy solid. HPLC RT[1]=6.37 min; $^1$H NMR (400 MHz, CDCl$_3$) δ8.01 (d, J=8.3 Hz, 2H), 7.63–7.58 (m, 4H), 7.43–7.33 (m, 3H), 6.86 (d, J=9.3 Hz, 2H), 6.73 (d, J=9.3 Hz, 2H), 4.13 (t, J=6.3 Hz, 2H), 2.97 (t, J=6.3 Hz, 2H), 2.66 (t, J=7.3 Hz, 2H), 1.73–1.68 (m, 2H), 1.49 (s, 6H), 0.98 (t, J=7.3 Hz, 3H); MS (EI) 486.33 (M+H)$^+$, 484.37 (M−H)$^−$.

[1] Isocratic method (80% Acetonitrile/0.03M Phosphate buffer); Flow rate: 1.5 mL/min; Column: Zorbax SB-C18 4.6×250 mm 5-micron; 220 nm detection.

Example 53

2-{4-[2-(2-Biphenyl-4-yl-5-phenyl-oxazol-4-yl)-ethoxy]-phenoxy}-2-methyl-propionic acid

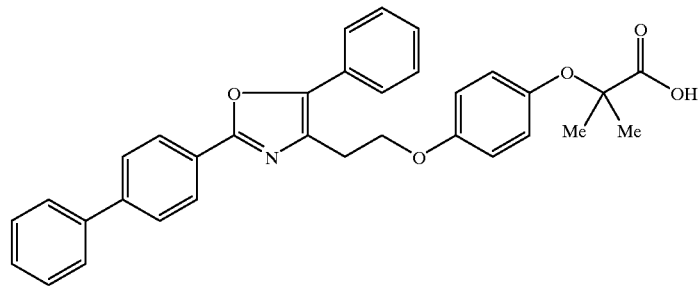

A. 2-(4-{3-[(Biphenyl-4-carbonyl)-amino]-4-oxo-4-phenyl-butoxy}-phenoxy)-2-methyl-propionic acid A sample of 2-[(biphenyl-4-carbonyl)-amino]-4-[4-(1-carboxy-1-methyl-ethoxy)-phenoxy]-butyric acid (500 mg, 1.05 mmol) was dissolved in pyridine (3.4 mL, 41.9 mmol, 30 equiv.) followed by benzoic anhydride (711 mg, 3.14 mmol, 3 equiv.) then warmed with magnetic stirring at 90° C. for 10 hours. The reaction mixture was then allowed to cool to room temperature then partitioned by addition of 1.0 N HCl (50 mL) and methylene chloride (50 mL). The organic phase was dried over sodium chloride, and then concentrated under reduced pressure to 1.10 g of an oil. The material was carried forward without further purification or characterization. HPLC RT[1]=2.36 min.

[1] Isocratic method (80% Acetonitrile/0.03M Phosphate buffer); Flow rate: 1.5 mL/min; Column: Zorbax SB-C18 4.6×250 mm 5-micron; 220 nm detection.

B. 2-(4-{3-[(Biphenyl-4-carbonyl)-amino]-4-oxo-4-phenyl-butoxy}-phenoxy)-2-methyl-propionic acid methyl ester A sample of 2-(4-{3-[(biphenyl-4-carbonyl)-amino]-4-oxo-4-phenyl-butoxy}-phenoxy)-2-methyl-propionic acid (563 mg, 1.05 mmol) was dissolved in methylene chloride (10 mL) followed by slow addition of a diazomethane solution prepared as follows:

A sample of 1-methyl-3-nitro-1-nitrosoguanidine (1.08 g, 7.33 mmol) was slowly added to a stirring mixture of 5.0 N KOH (1.3 mL) and ethyl ether (25 mL) at room temperature. The biphasic mixture was stirred for an additional 10 minutes followed by separation of the phases. The organic phase was used as is.

The reaction mixture was then concentrated to an oil under reduced pressure and the crude product thus obtained was subjected to silica gel chromatography (ethyl acetate/hexanes) to yield 422 mg (73%) of an oil. HPLC RT[1]=4.02 min; $^1$H NMR (400 MHz, CDCl$_3$) δ8.04 (d, J=8.8 Hz, 2H), 7.89 (d, J=8.8 Hz, 2H), 7.64 (d, J=8.8 Hz, 2H), 7.59–7.33 (m, XXX H), 6.73 (d, J=9.3 Hz, 2H), 6. d, J=9.3 Hz, 2H), 5.94–5.90 (m, 1H), 4.04–3.92 (m, 2H), 2.62–2.54 (m, 1H), 2.31–2.23 (m, 1H), 1.48 (m, 6H); MS (EI) 552.3 (M+H)$^+$.

[1] Isocratic method (80% Acetonitrile/0.03M Phosphate buffer); Flow rate: 1.5 mL/min; Column: Zorbax SB-C18 4.6×250 mm 5-micron; 220 nm detection.

C. 2-{4-[2-(2-Biphenyl-4-yl-5-phenyl-oxazol-4-yl)-ethoxy]-phenoxy}-2-methyl-propionic acid methyl ester A sample of 2-(4-{3-[(biphenyl-4-carbonyl)-amino]-4-oxo-4-phenyl-butoxy}-phenoxy)-2-methyl-propionic acid methyl ester (422 mg, 0.765 mmol) was dissolved in 5 mL of dry DMF followed by addition of phosphorus oxychloride (0.21 mL, 2.29 mmol, 3 equiv.). The mixture was heated at 90° C. for 20 minutes under a nitrogen atmosphere. The reaction mixture was then allowed to cool to room temperature followed by addition of cold water (10 mL) and additional stirring for 10 minutes. The mixture was partitioned between methylene chloride (50 mL) and water (50 mL). The organic phase was dried over sodium chloride then concentrated under reduced pressure. The crude product was purified by silica gel chromatography (ethyl acetate/hexanes) to yield 362 mg (89%) of an oil. HPLC RT[1]=13.78 min; $^1$H NMR (400 MHz, CDCl) δ8.16 (d, J=8.8 Hz, 2H), 7.78 (d, J=8.8 Hz, 2H), 7.68 (d, J=8.8Hz, 2H), 7.61 (d, J=8. Hz, 2H), 7.47–7.33 (m, 6H), 6.75 (m, 4H), 4.36 (t, J=6.8 Hz, 2H), 3.72 (s, 3H), 3.29 (t, J=6.8 Hz, 2H), 1.48 (s, 6H).

[1] Isocratic method (80% Acetonitrile/0.03M Phosphate buffer); Flow rate: 1.5 mL/min; Column: Zorbax SB-C18 4.6×250 mm 5-micron; 220 nm detection.

D. 2-{4-[2-(2-Biphenyl-4-yl-5-phenyl-oxazol-4-yl)-ethoxy]-phenoxy}-2-methyl-propionic acid A sample of 2-{4-[2-(2-biphenyl-4-yl-5-phenyl-oxazol-4-yl)-ethoxy]-phenoxy}-2-methyl-propionic acid methyl ester (360 mg, 0.675 mmol) was dissolved in a mixture of dioxane (2 mL) and ethanol (3 mL) followed by addition of 5.0 N NaOH (1.4 mL). The mixture was warmed with magnetic stirring at 50° C. for two hours. The reaction mixture was cooled to room temperature and then acidified with 1.0 N HCl to pH <3. The mixture was then extracted with methylene chloride (2×50 mL). The combined organic phases were dried over sodium chloride and concentrated under reduced pressure to yield 347 mg (99%) of a glassy solid. HPLC RT[1]=2.63 min; $^1$H NMR (400 MHz, CDCl$_3$) δ8.11 (d, J=8.8 Hz, 2H), 7.78 (d, J=8.8 Hz, 2H), 7.66 (d, J=8.8 Hz, 2H), 7.60 (d, J=8. Hz, 2H), 7.46–7.34 (m, 6H), 6.87 (d, J=9.3 Hz, 2H), 6.76 (d, J=9.3 Hz, 2H), 4.32 (t, J=6.8 Hz, 2H), 3.29 (t, J=6.8 Hz, 2H), 1.50 (s, 6H); MS (EI) 520.30 (M+H)$^+$.

[1] Isocratic method (80% Acetonitrile/0.03M Phosphate buffer); Flow rate: 1.5 mL/min; Column: Zorbax SB-C18 4.6×250 mm 5-micron; 220 nm detection.

Example 54

2-{4-[2-(2-Biphenyl-4-yl-5-trifluoromethyloxazol-4-yl)-ethoxy]-phenoxy}-2-methyl-propionic acid

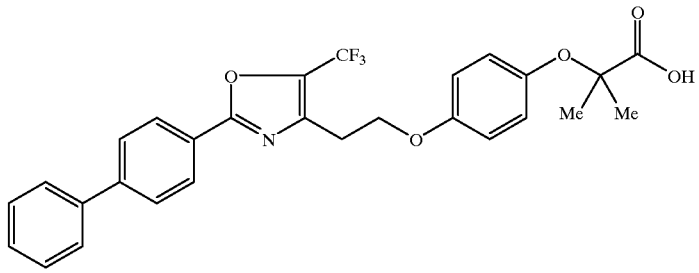

A. 2-Benzylamino-4-[4-(1-ethoxycarbonyl-1-methyl-ethoxy)-phenoxy]-butyric acid ethyl ester A sample of 2-amino-4-[4-(1-ethoxycarbonyl-1-methyl-ethoxy)-phenoxy]-butyric acid ethyl ester (612 mg, 1.73 mmol) and benzaldehyde (220 mg, 2.08 mmol) was dissolved in 10 mL of methylene chloride followed by addition of sodium triacetoxyborohydride (550 mg, 2.60 mmol). After 4 hours of stirring at room temperature the reaction mixture was partitioned between additional methylene chloride (50 mL) and 0.1 N HCl (50 mL). The pH of the mixture was then adjusted to ~13 with 1.0 N NaOH and the layers separated. The aqueous later was extracted with additional methylene chloride (25 mL). The combined organic phases were dried over sodium chloride, then concentrated under reduced pressure. The crude product was purified by silica gel chromatography (ethyl acetate/hexanes) to yield 492 mg of product (64%) as an oil. HPLC RT[1]=2.78 min; $^1$H NMR (400 MHz, CDCl$_3$) δ7.28–7.18 (m, 5H), 6.79–6.76 (m, 2H), 6.70–6.68 (m, 2 H), 4.22–4.12 (m, 4H), 4.08–4.02 (m, 1H), 3.99–3.91 (m, 1H), 3.83–3.80 (d, J=12.7 Hz, 1H), 3.65–3.62 (d, J=12.7 Hz, 1H), 3.49–3.47 (m, 1H), 2.17–2.09 (m, 1H), 2.00–1.92 (m, 1H), 1.49 (s, 6H), 1.26–1.20 (m, 6H).

[1] Isocratic method (80% Acetonitrile/0.03M Phosphate buffer); Flow rate: 1.5 mL/min; Column: Zorbax SB-C18 4.6×250 mm 5-micron; 220 nm detection.

B. 2-[Benzyl-(biphenyl-4-carbonyl)-amino]-4-[4-(1-ethoxycarbonyl-1-methyl-ethoxy)-phenoxy]-butyric acid ethyl ester A sample of 2-benzylamino-4-[4-(1-ethoxycarbonyl-1-methyl-ethoxy)-phenoxy]-butyric acid ethyl ester (490 mg, 1.10 mmol) was dissolved in 10 mL of methylene chloride followed by addition of triethylamine (0.31 mL, 2.21 mmol) and biphenyl-4-carbonyl chloride (287 mg, 1.33 mmol). The reaction was allowed to stir at room temperature for 12 hours then partitioned between additional methylene chloride (50 mL) and 0.1 N HCl (50 mL). The organic phase was dried over sodium chloride, then concentrated under reduced pressure to yield 687 mg (100%) of an oil. HPLC RT[1]=7.65 min; $^1$H NMR (400 MHz, CDCl$_3$) δ7.60–7.20 (m, 14H), 6.77–6.46 (m, 4H), 4.91–4.45 (m, 2H), 4.19–3.66 (m, 7H), 2.78–2.12 (m, 2H), 1.49 (s, 6H), 1.25–1.22 (m, 6H).

[1] Isocratic method (80% Acetonitrile/0.03M Phosphate buffer); Flow rate: 1.5 mL/min; Column: Zorbax SB-C18 4.6×250 mm 5-micron; 220 nm detection.

C. 2-[Benzyl-(biphenyl-4-carbonyl)-amino]-4-[4-(1-carboxy-1-methyl-ethoxy)-phenoxy]-butyric acid A sample of 2-[benzyl-(biphenyl-4-carbonyl)-amino]-4-[4-(1-ethoxycarbonyl-1-methyl-ethoxy)-phenoxy]-butyric acid ethyl ester (687 mg, 1.10 mmol) was dissolved in 5 mL of dioxane followed by addition of 5.0 N NaOH (2.3 mL, 11.6 mmol). The mixture was magnetically stirred and heated at 60° C. for 7 hours. The reaction mixture was allowed to cool to room temperature followed by addition of 1.0 N HCl (12 mL, 12 mmol) then partitioned by addition of methylene chloride (50 mL). The organic phase was separated, dried over sodium chloride and concentrated under reduced pressure to yield 690 mg (~100%) of a glassy solid. HPLC RT[1]=2.24 min; $^1$H NMR (400 MHz, CDCl$_3$) δ12.82 (broad s, 2H), 7.70–7.75 (m, 4H), 7.45–7.17 (m, 10H), 6.75–6.48 (m, 4H), 2.24–2.00 (m, 2H), 1.39 (s, 6H); MS (EI) 568.31 (M+H)$^+$.

[1] Isocratic method (80% Acetonitrile/0.03M Phosphate buffer); Flow rate: 1.5 mL/min; Column: Zorbax SB-C18 4.6×250 mm 5-micron; 220 nm detection.

D. 2-{4-[2-(2-Biphenyl-4-yl-5-trifluoromethyloxazol-4-yl)-ethoxy]-phenoxy}-2-methyl-propionic acid methyl ester A sample of 2-[benzyl-(biphenyl-4-carbonyl)-amino]-4-[4-(1-carboxy-1-methyl-ethoxy)-phenoxy]-butyric acid (625 mg, 1.10 mmol) was dissolved in 5 mL of toluene followed by addition of pyridine (0.54 mL, 6.61 mmol, 6 equiv.). The reaction mixture was chilled to 0° C. and trifluoroacetic anhydride (0.47 mL, 3.30 mmol, 3 equiv.) was then added. The reaction mixture was allowed to stir at room temperature for 12 hours followed by heating at reflux for 9 hours. The reaction mixture was then allowed to cool to room temperature followed by partitioning between water (50 mL) and methylene chloride (50 mL). The organic phase was dried over sodium chloride, and concentrated under reduced pressure to yield 563 mg of a glassy solid. To effect purification the crude material, 2-{4-[2-(2-biphenyl-4-yl-5-trifluoromethyloxazol-4-yl)-ethoxy]-phenoxy}-2-methyl-propionic acid, was converted to its methyl ester derivative, chromatographed on silica, then saponified as follows:

A sample of the crude 2-{4-[2-(2-biphenyl-4-yl-5-trifluoromethyloxazol-4-yl)-ethoxy]-phenoxy}-2-methyl-propionic acid, (563 mg, 1.10 mmol) was dissolved in methylene chloride (2 mL) followed by slow addition of a diazomethane solution prepared as follows:

A sample of 1-methyl-3-nitro-1-nitrosoguanidine (324 mg, 2.20 mmol) was slowly added to a stirring mixture of 5.0 N KOH (0.44 mL. 2.20 mmol) and ethyl ether (15 mL) at room temperature. The biphasic mixture was stirred for an additional 10 minutes followed by separation of the phases. The organic phase was used as is.

The reaction mixture was then concentrated to an oil under reduced pressure and the crude product thus obtained was subjected to silica gel chromatography (ethyl acetate/hexanes) to yield 141 mg (25%) of an oil. HPLC RT[1]=11.73 min; $^1$H NMR (400 MHz, CDCl$_3$) δ8.01 (d, J=8.3 Hz, 2H), 7.67 (d, J=8.3 Hz, 2H), 7.60 (d, J=8.3 Hz, 2H), 7.45–7.41 (m, 2H), 7.37–7.34 (m, 1H), 6.78–6.73 (m, 4H), 4.22 (t, J=6.8 Hz, 2H), 3.72 (s, 3H), 3.14 (t, J=6.8 Hz, 2H), 1.48 (s, 6H); MS (EI) 526.3 (M+H)$^+$.

[1] Isocratic method (80% Acetonitrile/0.004M Phosphate buffer); Flow rate: 1.5 mL/min; Column: Zorbax SB-C18 4.6×250 mm 5-micron; 220 nm detection.

E. 2-{4-[2-(2-Biphenyl-4-yl-5-trifluoromethyloxazol-4-yl)-ethoxy]-phenoxy}-2-methyl-propionic acid A sample of 2-{4-[2-(2-biphenyl-4-yl-5-trifluoromethyloxazol-4-yl)-ethoxy]-phenoxy}-2-methyl-propionic acid methyl ester (141 mg, 0.21 mmol) was dissolved in ethanol (2 mL) followed by addition of 5.0 N NaOH (0.6 mL). The mixture was warmed with magnetic stirring at 50° C. for one hour. The reaction mixture was then allowed to cool to room temperature then acidified with 1.0 N HCl (3 mL) then extracted with methylene chloride (50 mL). The organic phase was separated, dried over sodium chloride and concentrated under reduced pressure to yield 134 mg (98%, 24% overall) of a glassy solid. HPLC RT[1]=5.90 min; $^1$H NMR (400 MHz, CDCl$_3$) δ8.08 (d, J=8.3 Hz, 2H), 7.67 (d, J=8.3 Hz, 2H), 7.60 (d, J=8.3 Hz, 2H), 7.45–7.36 (m, 3H), 6.86 (d, J=9.3 Hz, 2H), 6.78 (d, J=9.3 Hz, 2H), 4.24 (t, J=6.3 Hz, 2H), 3.15 (t, J=6.3 Hz, 2H), 1.48 (s, 6H); MS (EI) 511.95 (M+H)$^+$.

[1] Isocratic method (80% Acetonitrile/0.004M Phosphate buffer); Flow rate: 1.5 mL/min; Column: Zorbax SB-C18 4.6×250 mm 5-micron; 220 nm detection.

Example 55

2-(4-{2-[2-(4'-Methoxybiphenyl-4-yl)-5-methyloxazol-4-yl]ethoxy}phenoxy)-2-methylpropionic acid

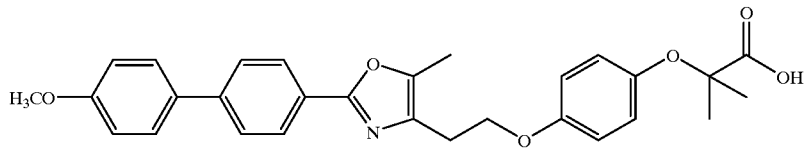

A. 2-(4-{2-[2-(4'-Methoxybiphenyl-4-yl)-5-methyloxazol-4-yl]ethoxy}phenoxy)-2-methylpropionic acid ethyl ester To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, Part B), 4-methoxyphenyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh$_3$)$_4$ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4'-methoxybiphenyl-4-yl)-5-methyloxazol-4-yl]ethoxy}phenoxy)-2-methylpropionic acid ethyl ester.

B. 2-(4-{2-[2-(4'-Methoxybiphenyl-4-yl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4'-methoxybiphenyl-4-yl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4'-methoxybiphenyl-4-yl)-5-methyloxazol-4-yl]ethoxy}phenoxy)-2-methylpropionic acid. ¹H NMR (400 MHz, CDCl₃) 8.02 (2H, m), 7.64 (4H, m), 7.01(2H, m), 6.97 (2H, m), 6.91 (2H, m), 6.79 (2H, d), 4.20 (2H, t), 3.86 (3H, s), 3.00 (2H, t) 2.39 (3H, s), 1.52 (6H, s).

Example 56

2-(4-{2-[2-(4-{5 '-Methylthiophen-2-yl}-phenyl)-5-methyloxazol-4-yl]ethoxy}phenoxy)-2-methylpropionic acid

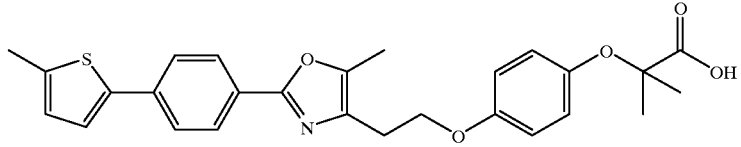

A. 2-(4-{2-[2-(4-{5'-Methylthiophen-2-yl}-phenyl)-5-methyloxazol-4-yl]ethoxy}phenoxy)-2-methylpropionic acid ethyl ester To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, Part B), 5-methyl-2-thiophenyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh₃)₄ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4-{5'-methylthiophen-2-yl}-phenyl)-5-methyloxazol-4-yl]ethoxy}phenoxy)-2-methylpropionic acid ethyl ester.

B. 2-(4-{2-[2-(4-{5'-Methylthiophen-2-yl}-phenyl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4-{5 '-methylthiophen-2-yl}-phenyl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4-{5'-methylthiophen-2-yl}-phenyl)-5-methyloxazol-4-yl]ethoxy}phenoxy)-2-methylpropionic acid. ¹H NMR (400 MHz, CDCl₃) 7.94 (2H, d), 7.59 (2H, d), 7.19 (1H, m), 6.89 (2H, d), 6.79 (3H, m), 4.16 (2H, t), 2.99 (2H, t), 2.51 (3H, s), 2.37 (3H, s), 1.53 (6H, s).

Example 57

2-(4-{2-[2-(4-Pyrid-3-yl-phenyl)-5-methyloxazol-4-yl]ethoxy}phenoxy)-2-methylpropionic acid

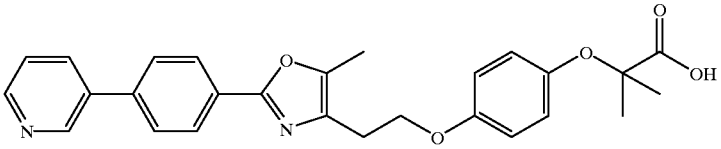

A. 2-(4-{2-[2-(4-Pyrid-3-yl-phenyl)-5-methyloxazol-4-yl]ethoxy}phenoxy)-2-methylpropionic acid To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, Part B), 3-pyridyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh₃)₄ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4-pyrid-3-yl-phenyl)-5-methyloxazol-4-yl]ethoxy}phenoxy)-2-methylpropionic acid ethyl ester.

B. 2-(4-{2-[2-(4-Pyrid-3-yl-phenyl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4-pyrid-3-yl-phenyl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4-pyrid-3-yl-phenyl)-5-methyloxazol-4-yl]ethoxy}phenoxy)-2-methylpropionic acid. $^1$H NMR (400 MHz, CDCl$_3$) 8.91 (1H, m), 8.61 (1H, m), 8.08 (2H, m), 7.94 (1H, m), 7.64 (2H, d), 7.45 (1H, m), 7.38 (1H, m), 6.91 (2H, m), 6.78 (2H, m), 4.20 (2H, t), 3.00 (2H, t) 2.39 (3H, s), 1.54 (6H, s).

Example 58

2-(4-{2-[2-(4-Pyrid-4-yl-phenyl)-5-methyloxazol-4-yl]ethoxy}phenoxy)-2-methylpropionic acid

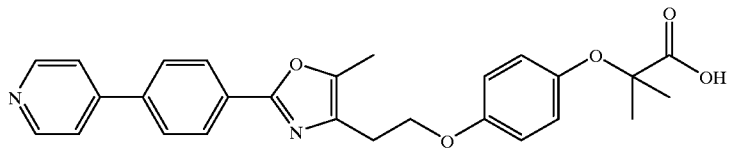

A. 2-(4-{2-[2-(4-Pyrid-4-yl-phenyl)-5-methyloxazol-4-yl]ethoxy}phenoxy)-2-methylpropionic acid To a 25 mL round-bottomed flask equipped for magnetic stirring and fitted with a reflux condenser was added 2-(4-{2-[2-(4-bromophenyl)-5-methyloxazol-4-yl]ethoxy}phenoxy)-2-methyl propionic acid ethyl ester (0.410 mmoles, 200 mg) (see Ex. 2, Part B), 4-pyridyl boronic acid (0.451 mmoles), toluene (5 mL), ethanol (5 mL), and sodium carbonate (0.819 mmoles, 0.410 mL of a 2M solution). This mixture was vacuum degassed and nitrogen was added in at a positive pressure. Pd(PPh$_3$)$_4$ (catalytic, spatula tip) was added and the reaction was heated to reflux for 3 h. Distilled water was added to the mixture. Subsequently, this was extracted with ethyl acetate and washed with brine. The organic layer was collected, filtered over a thin pad of silica gel, and concentrated in-vacuo. The crude mixture was then purified by chromatography on silica gel affording 2-(4-{2-[2-(4-pyrid-4-yl-phenyl)-5-methyloxazol-4-yl]ethoxy}phenoxy)-2-methylpropionic acid ethyl ester.

B. 2-(4-{2-[2-(4-Pyrid-4-yl-phenyl)-5-methyloxazol-4-yl]ethoxy}phenoxy)-2-methylpropionic acid To a 20 mL round-bottomed flask equipped for magnetic stirring and fitted with a reflux condenser was added 2-(4-{2-[2-(4-pyrid-4-yl-phenyl)-5-methyloxazol-4-yl]ethoxy}phenoxy)-2-methylpropionic acid ethyl ester (0.268 mmoles), lithium hydroxide (0.535 mmoles, 0.268 mL of a 2N solution), and ethanol (5 mL). This solution was heated to reflux for 2 h. Distilled water was added to the mixture and the pH was adjusted to 3 using a 1N HCl solution. The organic layer was extracted with ethyl acetate, washed with brine, and concentrated in-vacuo. This crude oil was re-solvated in pure ethyl acetate and filtered over a pad of Celite. The filtrate was concentrated in-vacuo, and the crude oil was crystallized using acetonitrile. The crystals were collected and dried in-vacuo affording 2-(4-{2-[2-(4-pyrid-3-yl-phenyl)-5-methyloxazol-4-yl]ethoxy}phenoxy)-2-methylpropionic acid. $^1$H NMR (400 MHz, CDCl$_3$) 7.99 (2H, d), 7.66 (2H, d), 7.45 (2H, m), 7.53 (1H, m), 7.42 (1H, m), 6.90 (2 h, m), 6.78 (2H, m), 4.17 (2H, t), 2.99 (2H, t) 2.39 (3H, s), 1.53 (6H, s).

Example 59

2-{4-[2-(2-Biphenyl-4-yl-5-methyloxazol-4-yl)-ethylsulfonyl]-phenoxy}-2-methyl-propionic acid

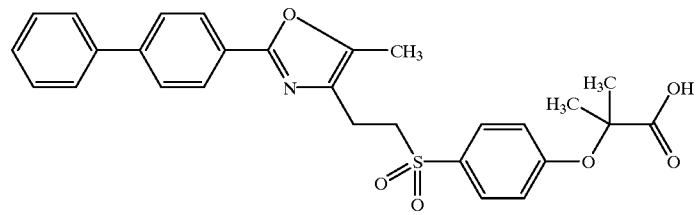

2-{4-[2-(2-biphenyl-4-yl-5-methyl-2-phenyl-oxazol-4-yl)-ethylsulfanyl]-phenoxy}-2-methylpropionic acid (31 mg, 0.078 mmol) was mixed with 8 mL 1/1 methanol/water. Solid oxone (100 mg, 0.16 mmol) was added and the reaction was stirred at room temperature for 2 h. The methanol was allowed to evaporate overnight and the white precipitate was collected and washed with water. After drying in a vacuum oven the product was obtained as a light tan solid. ¹H NMR (CDCl₃) δ1.67 (s, 6H), 2.38 (s, 3H), 3.05 (t, 2H), 3.55 (t, 2H), 6.96 (d, 2H), 7.48 (m, 3H), 7.81 (d, 2H), 7.92 (m, 2H); MS (EI+) 506.1 (M+1).

Example 60

2-{4-[2-(2-Biphenyl-4-yl-5-methyloxazol-4-yl)-ethyloxy]-2-propylphenoxy}-2-methyl-propionic acid

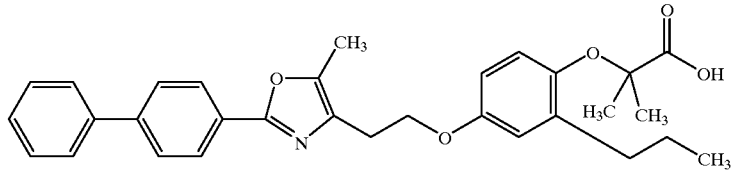

A. 4-[2-(4-Benzyloxy-3-propylphenoxy)ethyl]-5-methyl-2-phenyloxazole

A mixture of 4-benzyloxy-3-propylphenol (3.89 mmol), toluene-4-sulfonic acid 2-(5-methyl-2-biphenyl-4-yl-oxazol-4-ly) ethyl ester (4.67 mmol) (see Ex. 1, part F) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried (Na₂SO₄), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-3-propylphenoxy)ethyl]-5-methyl-2-phenyloxazole.

B. 2-Propyl-4-[2-(5-methyl-2-biphenyl-4-yl-oxazole-4-yl)ethoxy]phenol

A solution of 4-[2-(4-benzyloxy-3-propylphenoxy)ethyl]-5-methyl-2-phenyloxazole (3.16 mmol) in ethanol (100 mL) was treated with 5% Pd/C (160 mg) and hydrogen (60 psi) at ambient temperature for 18 h. The mixture was filtered and concentrated in vacuo to give a tan solid.

C. 2-{4-[2-(2-Biphenyl-4-yl-5-methyloxazol-4-yl)ethoxy]-2-propylphenoxy}-2-methylpropionic acid ethyl ester A mixture of 2-propyl-4-[2-(5-methyl-2-biphenyl-4-yl-oxazole-4-yl)ethoxy]phenol (0.90 mmol), ethyl 2-bromo-2-methylpropanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried (Na₂SO₄), and removed in vacuo to give a crude oil which was purified using radial chromatography eluting with 2% ethyl acetate/dichloromethane to give 2-{4-[2-(2-biphenyl-4-yl-5-methyloxazol-4-yl)ethoxy]-2-propylphenoxy}-2-methylpropionic acid ethyl ester, ¹H NMR (400 MHz, CDCl₃), δ8.04 (d, J=8.3 Hz, 2H), 7.65 (dd, J=11.0, 8.1 Hz, 4H), 7.46 (t, J=7.6 Hz, 2H), 7.37 (t, J=7.3 Hz, 1H), 6.70 (d, J=2.9 Hz, 1H), 6.64–6.57 (m, 2H), 4.27–4.17 (m, 4H), 2.96 (t, J=6.8 Hz, 2H), 2.54 (t, J=7.1 Hz, 2H), 2.38 (s, 3H), 1.59 (quintet, 7.6 Hz, 2H), 1.53 (s, 6H), 1.26 (t, J=6.8 Hz, 3H), 0.93 (t, J=7.3 Hz, 3H), MS (ES) m/e 528 (M+1).

D. 2-{4-[2-(2-Biphenyl-4-yl-5-methyloxazol-4-yl)ethoxy]-3-propylphenoxy}-2-methylpropionic acid A solution of 2-{4-[2-(2-biphenyl-4-yl-5-methyloxazol-4-yl)ethoxy]-3-propylphenoxy}-2-methylpropionic acid ethyl ester, (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na₂SO₄) and concentrated in vacuo to give 2-{4-[2-(2-Biphenyl-4-yl-5-methyloxazol-4-yl)ethoxy]-3-propylphenoxy}-2-methylpropionic acid ¹H NMR (400 MHz, CDCl₃), δ8.04 (dd, J=6.6, 1.7 Hz, 2H), 7.68–7.62 (m, 4H), 7.47–7.44 (m, 2H), 7.39–7.35 (m, 1H), 6.78 (d, J=8.8 Hz, 1H), 6.72 (d, J=2.9 Hz, 1H), 6.61 (dd, J=8.8, 2.9 Hz, 1H), 4.18 (t, J=6.6 Hz, 2H), 2.99 (t, J=6.6 Hz, 2H), 2.53 (t, J=7.8 Hz, 2H), 2.39 (s, 3H), 1.59 (quintet, J=7.5 Hz, 2H), 1.55 (s, 6H), 0.94 (t, J=7.3 Hz, 3H), MS (ES) m/e 500 M+1).

Example 61

{4-[2-(2-Biphenyl-4-yl-5-methyl-oxazol-4-yl)-ethoxy]-3-propyl-phenoxy}-acetic acid

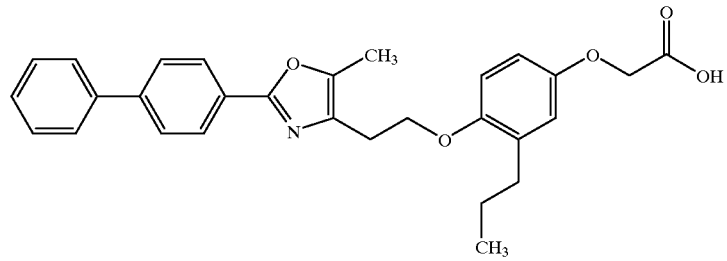

A. 4-[2-(4-Benzyloxy-2-propylphenoxy)ethyl]-5-methyl-2-phenyloxazole

A mixture of 4-benzyloxy-2-propylphenol (3.89 mmol), toluene-4-sulfonic acid 2-(5-methyl-2-biphenyl-4-yl-oxazol-4-ly) ethyl ester (4.67 mmol) (see Ex. 1, part F) and cesium carbonate (1.65 g 5.06 mmol) in anhydrous DMF (8 mL) was heated for 18 h at 55° C. The mixture was concentrated in vacuo, and the residue was partitioned between ethyl acetate (100 mL) and water (50 mL), washed with brine (50 mL), dried (Na₂SO₄), and removed in vacuo to give a crude oil which was purified using the Biotage FlashElute chromatography system using a 40 L normal phase cartridge, eluting with 10–15% ethyl acetate/hexanes to give 4-[2-(4-benzyloxy-3-propylphenoxy)ethyl]-5-methyl-2-phenyloxazole.

B. 3-Propyl-4-[2-(5-methyl-2-biphenyl-4-yl-oxazole-4-yl)ethoxy]phenol

A solution of 4-[2-(4-benzyloxy-2-propylphenoxy)ethyl]-5-methyl-2-phenyloxazole (3.16 mmol) in ethanol (100 mL) was treated with 5% Pd/C (160 mg) and hydrogen (60 psi) at ambient temperature for 18 h. The mixture was filtered and concentrated in vacuo to give a tan solid.

C. 2-{4-[2-(2-Biphenyl-4-yl-5-methyloxazol-4-yl)ethoxy]-3-propylphenoxy}-ethanoic acid ethyl ester A mixture of 3-propyl-4-[2-(5-methyl-2-biphenyl-4-yl-oxazole-4-yl)ethoxy]phenol (0.90 mmol), ethyl 2-bromoethanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried (Na$_2$SO$_4$), and removed in vacuo to give a crude oil which was purified using radial chromatography eluting with 2% ethyl acetate/dichloromethane to give 2-{4-[2-(2-biphenyl-4-yl-5-methyloxazol-4-yl)ethoxy]-2-propylphenoxy}ethanoic acid ethyl ester, $^1$H NMR (400 MHz, CDCl$_3$) δ8.04 (d, J=8.3 Hz, 2H), 7.62–7.67 (m, 4H), 7.41–7.45 (m, 2H), 7.37–7.40 (m, 1H), 6.80 (d, J=9.8 Hz, 1H), 6.75 (d, J=3.4 Hz, 1H), 6.66 (dd, J=3.4, 9.8 Hz, 1H), 4.54 (s, 2H), 4.20–4.27 (m, 4H), 2.98 (t, J=6.4 Hz, 2H), 2.50 (t, J=7.6 Hz, 2H), 2.39 (s, 3H), 1.53 (q, J=7.8 Hz, 2H), 1.29 (t, J=7.3 Hz, 3H), 0.89 (t, J=7.3 Hz, 3H); MS (ES) m/e 500.1 (M+1).

D. 2-{4-[2-(2-Biphenyl-4-yl-5-methyloxazol-4-yl)ethoxy]-2-propylphenoxy }-2-ethanoic acid A solution of 2-{4-[2-(2-biphenyl-4-yl-5-methyloxazol-4-yl)ethoxy]-2-propylphenoxy}ethanoic acid ethyl ester, (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na$_2$SO$_4$) and concentrated in vacuo to give 2-{4-[2-(2-biphenyl-4-yl-5-methyloxazol-4-yl)ethoxy]-3-propylphenoxy}-2-methylpropionic acid $^1$H NMR (400 MHz, CDCl$_3$) δ8.03 (d, J=7.8 Hz, 2H), 7.62–7.68 (m, 4H), 7.46 (t, J=7.8 Hz, 2H), 7.37–7.40 (m, 1H), 6.76 (d, J=3.4 Hz, 1H), 6.75 (d, J=9.8 Hz, 1H), 6.65 (dd, J=3.4, 9.8 Hz, 1H) 4.58 (s, 2H), 4.17 (t, J=6.4 Hz, 2H), 3.00 (t, J=6.4 Hz, 2H), 2.51 (t, J=7.6 Hz, 2H), 2.40 (s, 3H), 1.52 (q, J=7.8 Hz, 2H), 0.89 (t, J=7.3 Hz, 3H); MS (ES) m/e 472.2 (M+1).

Example 62

{4-[2-(2-Biphenyl-4-yl-5-methyl-oxazol-4-yl)-ethoxy]-2-propyl-phenoxy}-acetic acid

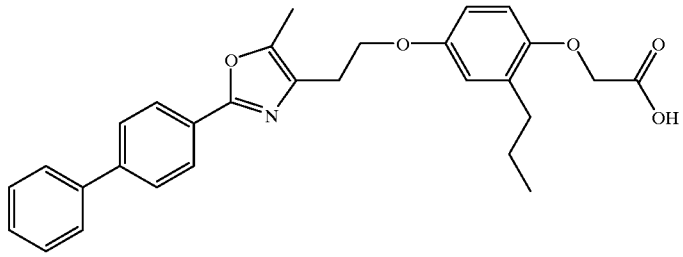

A. 2-{4-[2-(2-Biphenyl-4-yl-5-methyloxazol-4-yl)ethoxy]-2-propylphenoxy}-ethanoic acid ethyl ester A mixture of 2-propyl-4-[2-(5-methyl-2-biphenyl-4-yl-oxazole-4-yl)ethoxy]phenol (0.90 mmol) (see Ex. 60, part B), ethyl 2-bromoethanoate (2.25 mmol) and cesium carbonate (0.45 g, 1.38 mmol) in anhydrous DMF (4 mL) was heated for 24 h at 55° C. The mixture was concentrated in vacuo, and the residue was partitioned between ethyl acetate (50 mL) and water (40 mL), washed with brine, dried (Na$_2$SO$_4$), and removed in vacuo to give a crude oil which was purified using radial chromatography eluting with 2% ethyl acetate/dichloromethane to give 2-{4-[2-(2-biphenyl-4-yl-5-methyloxazol-4-yl)ethoxy]-2-propylphenoxy}ethanoic acid ethyl ester, $^1$H NMR (400 MHz, CDCl$_3$) δ8.05 (d, J=8.3 Hz, 2H), 7.67 (d, J=8.3 Hz, 2H), 7.62 (d, J=8.3 Hz, 2H), 7.44 (t, J=7.5 Hz, 2H), 7.36 (t, J=7.3 Hz, 1H), 6.72 (brs, 1H), 6.64 (brs, 2H), 4.59 (s, 2H), 4.54 (q, J=7.3 Hz, 2H), 4.20 (t, J=6.6 Hz, 2H), 2.97 (t, J=6.8 Hz, 2H), 2.58–2.61 (m, 2H), 2.38 (s, 3H), 1.61 (sextet, J=7.3 Hz, 2H), 1.27 (t, J=7.3 Hz, 3H), 0.93 (t, J=7.3 Hz, 3H).

B. 2-{4-[2-(2-Biphenyl-4-yl-5-methyloxazol-4-yl)ethoxy]-3-propylphenoxy}-2-ethanoic acid A solution of 2-{4-[2-(2-biphenyl-4-yl-5-methyloxazol-4-yl)ethoxy]-3-propylphenoxy}ethanoic acid ethyl ester, (0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with ethyl acetate (40 mL) and water (20 mL) and acidified to pH=1 with 1N aqueous HCl. The organic layer was washed with brine (20 mL), dried (Na$_2$SO$_4$) and concentrated in vacuo to give 2-{4-[2-(2-biphenyl-4-yl-5-methyloxazol-4-yl)ethoxy]-3-propylphenoxy}-2-methylpropionic acid $^1$H NMR (400 MHz, CDCl$_3$) δ8.06 (d, J=7.8 Hz, 2H), 7.67 (d, J=8.3 Hz, 2H), 7.62 (d, J=8.3 Hz, 2H), 7.45 (t, J=8.3 Hz, 2H), 7.36 (t, J=7.8 Hz, 1H), 6.76 (d, J=2.4 Hz, 1H), 6.66 (d, J=8.3 Hz, 1H), 6.60 (dd, J=2.7, 8.3 Hz, 1H), 4.59 (s, 2H), 4.15 (t, J=5.9 Hz, 2H), 3.00 (t, J=5.9 Hz, 2H), 2.59 (t, J=7.8 Hz, 2H), 2.39 (s, 3H), 1.60 (sextet, J=7.3 Hz, 2H), 0.93 (t, J=7.3 Hz, 3H); MS (ES) m/e 472.3 (M+1).

Example 63

2-(4-{2-[2-(4'-Fluorobiphenyl-3-yl)-5-methyloxazol-4-yl]ethoxy}phenoxy)-2-methyl-propionic acid

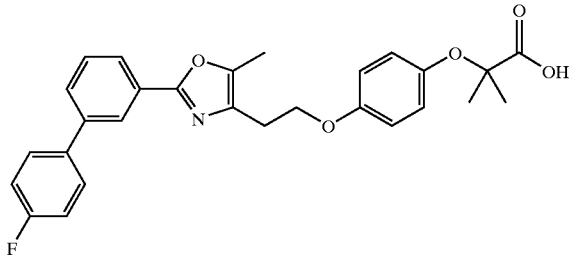

A. 2-(4-{2-[2-(4'-Fluorobiphenyl-3-yl)-5-methyloxazol-4-yl]ethoxy}phenoxy)-2-methyl-propionic acid ethyl ester A mixture of toluene-4-sulfonic acid 2-(2-[4'-fluorobiphen-3-yl]-methyl-oxazol-4-yl)ethyl ester (34.3 mmol), 2-(4-hydroxyphenoxy)-2-methylpropanoic acid ester (27.4 mmol) and $Cs_2CO_3$ (12.0 g, 36.8 mmol) was heated at 55° C. in DMF (110 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (600 mL $SiO_2$, 10% ethyl acetate/hexanes to 20% ethyl acetate/hexanes) to provide 2-(4-{2-[2-(4'-fluorobiphenyl-3-yl)-5-methyloxazol-4-yl]ethoxy}phenoxy)-2-methyl-propionic acid ethyl ester (6.25 g, 47%) as a colorless, viscous oil: Rf=0.51 in 1:4 ethyl acetate:hexanes; $^1$H NMR (400 MHz, $CDCl_3$) δ8.16 (t, J=1.6 Hz, 1H), 7.62 (dt, J=7.6 Hz, J=1.6 Hz, 1H), 7.62–7.56 (m, 3H), 7.48 (t, J=7.6 Hz, 2H), 7.16–7.11 (m, 2H), 6.83–6.76 (m, 4H), 4.22 (q, J=7.2 Hz, 2H), 4.21 (t, J=6.4 Hz, 2H), 2.96 (t, J=6.4 Hz, 2H), 2.38 (s, 3H), 1.52 (s, 6H), 1.26 (t, J=7.2 Hz, 3H); MS (EI) 526.3 (M+Na)$^-$, 504.3 (M+H)$^+$.

B. 2-(4-{2-[2-(4'-Fluorobiphenyl-3-yl)-5-methyloxazol-4-yl]ethoxy}phenoxy)-2-methyl-propionic acid 2-Methyl-2-{4-[2-(5-methyl-2-[4'-fluorobiphenyl-3-yl]-oxazol-4-yl)ethoxy]phenoxy}propionic acid ethyl ester (24.7 mmol) was dissolved in methanol (200 mL) and 2N NaOH (150 mL) was added. The resulting cloudy solution became clear after 30 min and the reaction was stirred vigorously overnight. The solution was concentrated under reduced pressure, diluted with $H_2O$ (100 mL) and acidified to pH=1 with 5N HCl. The mixture was extracted with ethyl acetate (2×200 mL), dried ($MgSO_4$), and concentrated under reduced pressure to provide an oil. The oil (8.23 g) was recrystallized from ethyl acetate (24 mL) and hexanes (56 mL) to afford 2-(4-{2-[2-(4'-fluorobiphenyl-3-yl)-5-methyloxazol-4-yl]ethoxy}phenoxy)-2-methyl-propionic acid (7.57 g, 67%) as colorless needles after drying at 50° C. under vacuum for 6 h: Rf=0.12 in 6:4 ethyl acetate:hexanes; $^1$H NMR (400 MHz, DMSO-$d_6$) δ8.02 (s, 1H), 7.88 (d, J=7.6 Hz, 1H), 7.77–7.73 (m, 3H), 7.57 (t, J=7.6 Hz, 1H), 7.30 (t, J=9.2 Hz, 2H), 6.83 (d, J=9.2 Hz, 2H), 6.78 (d, J,=9.2 Hz, 2H), 4.14 (t, J=6.4 Hz, 2H), 2.90 (t, J=6.4 Hz, 2H), 2.35 (s, 3H), 1.39 (s, 6H); MS (EI) 476.2 (M+H)$^+$, 474.2 (M-H)$^-$.

Example 64

2-{4-[2-(2-Biphenyl-3-yl-5-methyl-oxazol-4-yl)-ethoxy]-phenoxy}-2-methyl-3-phenyl-propionic acid

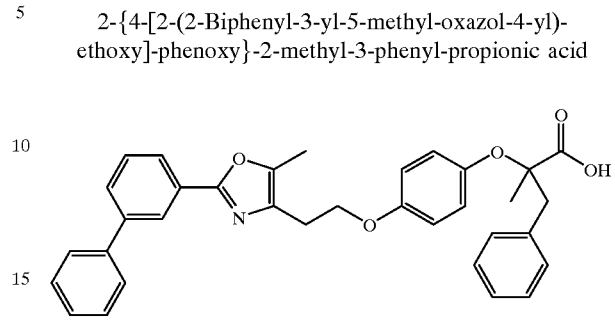

A. 2-{4-[2-(2-Biphenyl-3-yl-5-methyl-oxazol-4-yl)-ethoxy]-phenoxy}-2-methyl-3-phenyl-propionic acid ethyl ester A mixture of toluene-4-sulfonic acid 2-(2-biphen-3-yl-methyl-oxazol-4-yl)ethyl ester (34.3 mmol), 2-(4-hydroxyphenoxy)-2-benzylpropanoic acid ester (27.4 mmol) and $CS_2CO_3$ (12.0 g, 36.8 mmol) was heated at 55° C. in DMF (110 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (600 mL $SiO_2$, 10% ethyl acetate/hexanes to 20% ethyl acetate/hexanes) to provide 2-{4-[2-(2-biphenyl-3-yl-5-methyl-oxazol-4-yl)-ethoxy]-phenoxy}-2-methyl-3-phenyl-propionic acid ethyl esteras a colorless, viscous oil.

B. 2-{4-[2-(2-Biphenyl-3-yl-5-methyl-oxazol-4-yl)-ethoxy]-phenoxy}-2-methyl-3-phenyl-propionic acid 2-{4-[2-(2-Biphenyl-3-yl-5-methyl-oxazol-4-yl)-ethoxy]-phenoxy}-2-methyl-3-phenyl-propionic acid ethyl ester (24.7 mmol) was dissolved in methanol (200 mL) and 2N NaOH (150 mL) was added. The resulting cloudy solution became clear after 30 min and the reaction was stirred vigorously overnight. The solution was concentrated under reduced pressure, diluted with $H_2O$ (100 mL) and acidified to pH=1 with 5N HCl. The mixture was extracted with ethyl acetate (2×200 mL), dried ($MgSO_4$), and concentrated under reduced pressure to provide an oil. The oil (8.23 g) was recrystallized from ethyl acetate (24 mL) and hexanes (56 mL) to afford 2-{4-[2-(2-biphenyl-3-yl-5-methyl-oxazol-4-yl)-ethoxy]-phenoxy}-2-methyl-3-phenyl-propionic acid as colorless needles after drying at 50° C. under vacuum for 6 h: $^1$H NMR (400 MHz, $CDCl_3$) δ8.23–8.21 (m, 1H), 7.94 (d, 1H, J=7.43 Hz), 7.65 (dd, 3H, J=7.04 Hz, J=1.17 Hz), 7.50 (t, 1H, J=7.63 Hz), 7.45 (t, 2H, J=7.04 Hz), 7.38–7.28 (m, 1H), 7.28–7.25 (m, 5H), 6.84 (d, 2H, J=8.99 Hz), 6.75 (d, 2H, J=8.99 Hz), 4.16 (t, 2H, J=6.45 Hz), 3.31 (d, 1H, J=13.69 Hz), 3.14 (d, 1H, J=13.69 Hz), 3.01 (t, 2H, J=6.45 Hz), 2.40 (s, 3H), 1.34 (s, 3H); HRMS (ES$^+$) m/z exact mass calculated for $C_{34}H_{32}NO_5$ 534.2280, found 534.2278.

Example 65

2-Methyl-2-(4-{2-[5-methyl-2-(3-thiophen-2-yl-phenyl)-oxazol-4-yl]-ethoxy}-phenoxy)-3-phenyl-propionic acid

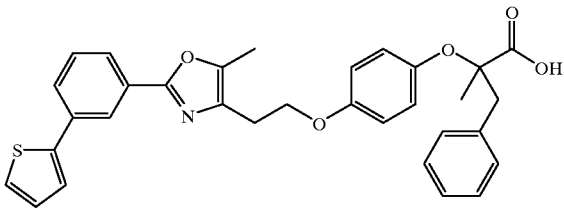

A. 2-Methyl-2-(4-{2-[5-methyl-2-(3-thiophen-2-yl-phenyl)-oxazol-4-yl]-ethoxy}-phenoxy)-3-phenyl-propionic acid ethyl ester A mixture of toluene-4-sulfonic acid 2-(2-thiophen-2-yl-phen-3-yl-methyl-oxazol-4-yl)ethyl ester (34.3 mmol), 2-(4-hydroxyphenoxy)-2-benzylpropanoic acid ester (27.4 mmol) and $Cs_2CO_3$ (12.0 g, 36.8 mmol) was heated at 55° C. in DMF (110 mL) for 18 h. The reaction was partitioned between ethyl acetate (160 mL) and $H_2O$ (180 mL), and the aqueous phase extracted with ethyl acetate (150 mL). The combined organic phases were dried ($MgSO_4$) and concentrated under reduced pressure to an oil which was purified by column chromatography (600 mL $SiO_2$, 10% ethyl acetate/hexanes to 20% ethyl acetate/hexanes) to provide 2-Methyl-2-(4-{2-[5-methyl-2-(3-thiophen-2-yl-phenyl)-oxazol-4-yl]-ethoxy}-phenoxy)-3-phenyl-propionic acid ethyl ester as a colorless, viscous oil.

B. 2-Methyl-2-(4-{2-[5-methyl-2-(3-thiophen-2-yl-phenyl)-oxazol-4-yl]-ethoxy}-phenoxy)-3-phenyl-propionic acid 2-Methyl-2-(4-{2-[5-methyl-2-(3-thiophen-2-yl-phenyl)-oxazol-4-yl]-ethoxy}-phenoxy)-3-phenyl-propionic acid ethyl ester (24.7 mmol) was dissolved in methanol (200 mL) and 2N NaOH (150 mL) was added. The resulting cloudy solution became clear after 30 min and the reaction was stirred vigorously overnight. The solution was concentrated under reduced pressure, diluted with $H_2O$ (100 mL) and acidified to pH 1 with 5N HCl. The mixture was extracted with ethyl acetate (2×200 mL), dried ($MgSO_4$), and concentrated under reduced pressure to provide an oil. The oil (8.23 g) was recrystallized from ethyl acetate (24 mL) and hexanes (56 mL) to afford 2-Methyl-2-(4-{2-[5-methyl-2-(3-thiophen-2-yl-phenyl)-oxazol-4-yl]-ethoxy}-phenoxy)-3-phenyl-propionic acid as colorless needles after drying at 50° C. under vacuum for 6 h: $^1$H NMR (400 MHz, $CDCl_3$) δ8.22 (t, 1H, J=1.56 Hz), 7.87 (d, 1H, J=7.82 Hz), 7.66–7.64 (m, 1H), 7.45 (d, 1H, J=7.82 Hz), 7.41–7.40 (m, 1H), 7.31–7.25 (m, 6H), 7.09 (dd, 1H, J=5.08 Hz, J=3.52 Hz), 6.84 (d, 2H, J=9.38 Hz), 6.76 (d, 2H, J=9.38 Hz), 4.17 (t, 2H, J=6.45 Hz), 3.30 (d, 1H, J=13.69 Hz), 3.15 (d, 1H, J=13.69 Hz), 3.01 (t, 2H, J=6.45 Hz), 2.40 (s, 3H), 1.35 (s, 3H); HRMS ($ES^+$) m/z exact mass calculated for $C_{32}H_{30}NO_5S$ 540.1857, found 540.1857.

Example 66

2-{4-[2-(2-Biphenyl-4-yl-5-methyl-oxazol-4-yl)-ethoxy]-phenoxy}-2-methyl-propionic acid 2-dimethylamino-ethyl ester hydrochloride

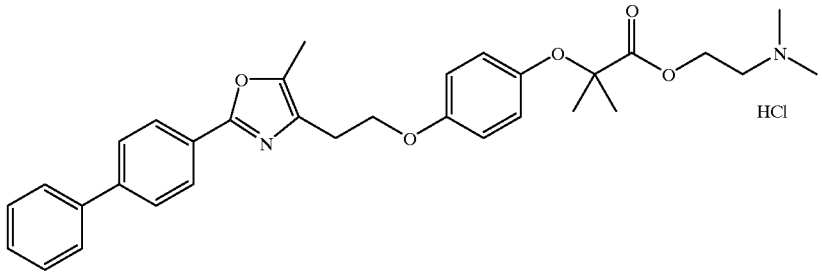

A solution of 2-{4-[2-(2-biphenyl-4-yl-5-methyl-oxazol-4-yl)-ethoxy]-phenoxy}-2-methyl-propionic acid (508 mg, 1.11 mmol) was prepared in $CH_2Cl_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in $CH_2Cl_2$ (5 mL) and treated with 2-dimethylaminoethanol (170 μL, 1.69 mmol), triethyl amine (230 μL, 1.65 mmol), and DMAP (1 crystal). After stirring for 1 h at room temperature, the solution was poured into water containing $K_2CO_3$ (200 mg, 1.45 mmol) and extracted with $CH_2Cl_2$ (2×50 mL). The organic layers were dried ($MgSO_4$), filtered, and the filtrate evaporated (40° C., 20 mm Hg). The residue was chromatographed on $SiO_2$ (biotage 40 L, acetone) to afford an oil, which was dissolved in ethyl ether (25 mL) and treated with hydrogen chloride (2 mL of a 1 N solution in ethyl ether, 2 mmol) to afford 440 mg of 2-{4-[2-(2-biphenyl-4-yl-5-methyl-oxazol-4-yl)-ethoxy]-phenoxy}-2-methyl-propionic acid 2-dimethylamino-ethyl ester hydrochloride as a white powder, 70% yield: TLC (free base), $R_f$=0.24 (acetone); $^1$H NMR (400 MHz, DMSO-$d_6$) δ10.1 (bs, 1H), 7.93 (d, J=8.4 Hz, 2H), 7.75 (d, J=8.4 Hz, 2H), 7.67 (d, J=8.4 Hz, 2H), 7.50 (t, J=7.6 Hz, 2H), 7.34 (t, J=7.6 Hz, 1H), 6.8 (m, 4H), 4.38 (t, J=5.2 Hz, 2H), 4.11 (t, J=6.4 Hz, 2H), 3.34 (dt, J=5.2, 4.8 Hz, 2H), 2.86 (d, J=6.4 Hz, 2H), 2.70 (s, 3H), 2.69 (s, 3H), 2.31 (s, 3H), 1.41 (s, 6H); MS (ES) m/e (% relative intensity) 531.3 ($M^+$+3, 12), 530.3 ($M^+$+2, 47), 529.3 ($M^+$+1, 100).

Example 67

2-{4-[2-(2-Biphenyl-4-yl-5-methyl-oxazol-4-yl)-ethoxy]-phenoxy}-2-methyl-propionic acid 3-dimethylamino-propyl ester hydrochloride

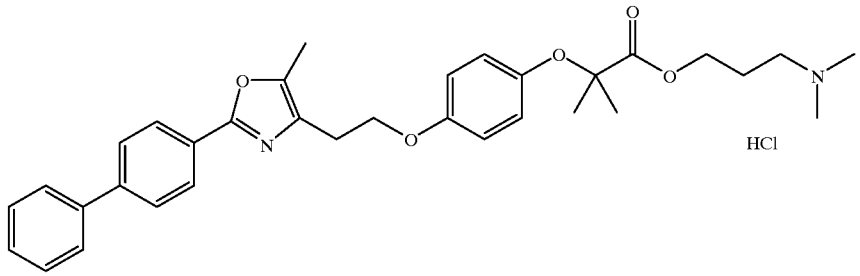

A solution of 2-{4-[2-(2-biphenyl-4-yl-5-methyl-oxazol-4-yl)-ethoxy]-phenoxy}-2-methyl-propionic acid (1.11 mmol) was prepared in CH$_2$Cl$_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in CH$_2$Cl$_2$ (5 mL) and treated with 3-dimethylaminopropanol (1.69 mmol), triethyl amine (230 μL, 1.65 mmol), and DMAP (1 crystal). After stirring for 1 h at room temperature, the solution was poured into water containing K$_2$CO$_3$ (200 mg, 1.45 mmol) and extracted with CH$_2$Cl$_2$ (2×50 mL). The organic layers were dried (MgSO$_4$), filtered, and the filtrate evaporated (40° C., 20 mm Hg). The residue was chromatographed on SiO$_2$ (biotage 40 L, acetone) to afford an oil, which was dissolved in ethyl ether (25 mL) and treated with hydrogen chloride (2 mL of a 1 N solution in ethyl ether, 2 mmol) to afford 440 mg of 2-{4-[2-(2-biphenyl-4-yl-5-methyl-oxazol-4-yl)-ethoxy]-phenoxy}-2-methyl-propionic acid 3-dimethylamino-propyl ester hydrochloride as a white powder. $^1$H NMR (400 MHz, DMSO-d$_6$) δ10.0 (bs, 1H), 7.93 (d, J=8.4 Hz, 2H), 7.75 (d, J=8.4 Hz, 2H), 7.67 (d, J=7.6 Hz, 2H), 7.43 (t, J=7.8 Hz, 2H), 7.34 (t, J=7.6 Hz, 1H), 6.80 (d, J=9.2 Hz, 2H), 6.71 (d, J=9.2 Hz, 2H), 4.1 (m, 4H), 2.9 (m, 4H), 2.64 (s, 6H), 2.31 (s, 3H), 1.9 (m, 2H), 1.41 (s, 6H); MS (ES) m/e (% relative intensity) 545.3 (M$^+$+3, 7), 544.3 (M$^+$+2, 37), 543.3 (M$^+$+1, 100).

Example 68

2-{4-[2-(2-Biphenyl-4-yl-5-methyl-oxazol-4-yl)-ethoxy]-phenoxy}-2-methyl-propionic acid 4-dimethylamino-butyl ester hydrochloride

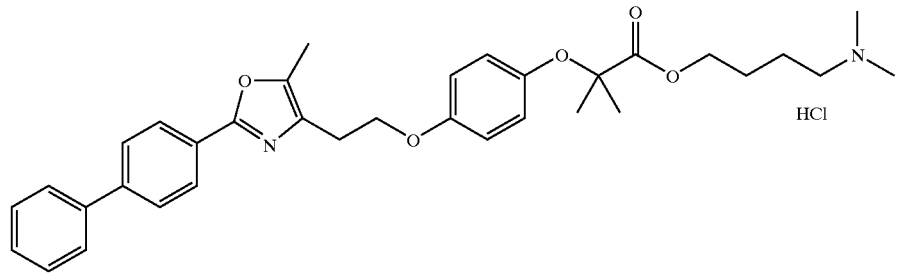

A solution of 2-{4-[2-(2-biphenyl-4-yl-5-methyl-oxazol-4-yl)-ethoxy]-phenoxy}-2-methyl-propionic acid (1.11 mmol) was prepared in CH$_2$Cl$_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in CH$_2$Cl$_2$ (5 mL) and treated with 4-dimethylaminobutanol (1.69 mmol), triethyl amine (230 μL, 1.65 mmol), and DMAP (1 crystal). After stirring for 1 h at room temperature, the solution was poured into water containing K$_2$CO$_3$ (200 mg, 1.45 mmol) and extracted with CH$_2$Cl$_2$ (2×50 mL). The organic layers were dried (MgSO$_4$), filtered, and the filtrate evaporated (40° C., 20 mm Hg). The residue was chromatographed on SiO$_2$ (biotage 40 L, acetone) to afford an oil, which was dissolved in ethyl ether (25 mL) and treated with hydrogen chloride (2 mL of a 1 N solution in ethyl ether, 2 mmol) to afford 2-{4-[2-(2-biphenyl-4-yl-5-methyl-oxazol-4-yl)-ethoxy]-phenoxy}-2-methyl-propionic acid 4-dimethylamino-butyl ester hydrochloride as a white powder after recrystallization from 2-butanone/hexanes, 21% yield: TLC (free base), R$_f$=0.09 (acetone); $^1$H NMR (400 MHz, DMSO-d$_6$) δ10.4 (bs, 1H), 7.88 (d, J=8.4 Hz, 2H), 7.71 (d, J=8.4 Hz, 2H), 7.62 (d, J=7.6 Hz, 2H), 7.39 (t, J=7.6 Hz, 2H), 7.30 (t, J=7.4 Hz, 1H), 6.76 (d, J=9.0 Hz, 2H), 6.67 (d, J=9.0 Hz, 2H), 4.06 (t, J=6.2 Hz, 4H), 2.8 (m, 4H), 2.56 (s, 6H), 2.27 (s, 3H), 1.9 (m, 2H), 1.36 (s, 6H), MS (ES) m/e (% relative intensity) 559.3 (M$^+$+3, 19), 558.3 (M$^+$+2, 74), 557.3 (M$^+$1, 100).

Example 69

2-{4-[2-(2-Biphenyl-4-yl-5-methyl-oxazol-4-yl)-ethoxy]-phenoxy}-2-methyl-propionic acid 2-morpholin-4-yl-ethyl ester hydrochloride

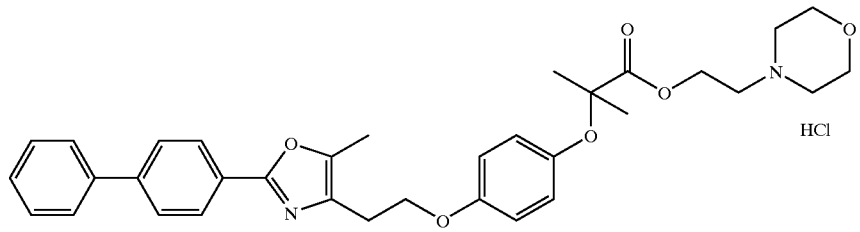

A solution of 2-{4-[2-(2-biphenyl-4-yl-5-methyl-oxazol-4-yl)-ethoxy]-phenoxy}-2-methyl-propionic acid (1.11 mmol) was prepared in CH$_2$Cl$_2$ (5 mL, anhydrous) and treated sequentially with oxalyl chloride (125 µL, 1.43 mmol) and DMF (1 drop). This solution was stirred for 1 h at room temperature, then concentrated (40° C., 20 mm Hg). The residue was dissolved in CH$_2$Cl$_2$ (5 mL) and treated with 2-morpholin-4-yl-ethanol (1.69 mmol), triethyl amine (230 µL, 1.65 mmol), and DMAP (1 crystal). After stirring for 1 h at room temperature, the solution was poured into water containing K$_2$CO$_3$ (200 mg, 1.45 mmol) and extracted with CH$_2$Cl$_2$ (2×50 mL). The organic layers were dried (MgSO$_4$), filtered, and the filtrate evaporated (40° C., 20 mm Hg). The residue was chromatographed on SiO$_2$ (biotage 40 L, acetone) to afford an oil, which was dissolved in ethyl ether (25 mL) and treated with hydrogen chloride (2 mL of a 1 N solution in ethyl ether, 2 mmol) to afford 445 mg of 2-{4-[2-(2-biphenyl-4-yl-5-methyl-oxazol-4-yl)-ethoxy]-phenoxy}-2-methyl-propionic acid 2-morpholin-4-yl-ethyl ester hydrochloride as a white powder $^1$H NMR (400 MHz, DMSO-d$_6$) δ10.80 (bs, 1H), 7.94 (d, J=8.8 Hz, 2H), 7.77 (d, J=8.8 Hz, 2H), 7.69 (d, J=7.6 Hz, 2H), 7.45 (t, J=7.6 Hz, 2H), 7.36 (t, J=7.6 Hz, 1H), 6.79 (q, J=8.8 Hz, 4H), 4.44 (bs, 2H), 4.13 (t, J=6.4 Hz, 2H), 3.80–3.63 (m, 4H), 3.41 (bs, 2H), 3.26–3.23 (m, 2H), 3.09–2.95 (m, 2H), 2.88 (t, J=6.4 Hz, 2H), 2.34 (s, 3H), 1.44 (s, 6H). MS (ES) m/e 571.2 (M$^+$1).

Example 70

2-{4-[2-(2-Biphenyl-4-yl-5-methyl-oxazol-4-yl)-ethoxy]-phenoxy}-2-methyl-propionic acid 2-piperidin-1-yl-ethyl ester hydrochloride

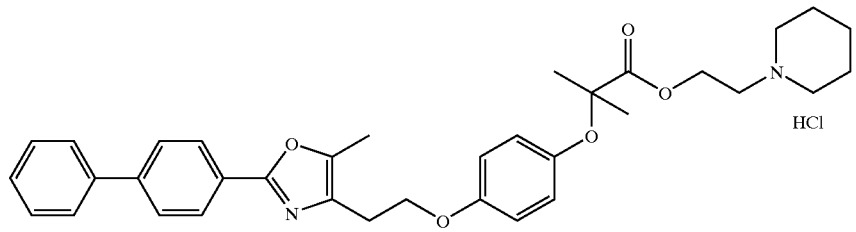

A solution of 2-{4-[2-(2-biphenyl-4-yl-5-methyl-oxazol-4-yl)-ethoxy]-phenoxy}-2-methyl-propionic acid (1.11 mmol) was prepared in CH$_2$Cl$_2$ (5 mL, anhydrous) and treated sequentially with oxalyl chloride (125 µL, 1.43 mmol) and DMF (1 drop). This solution was stirred for 1 h at room temperature, then concentrated (40° C., 20 mm Hg). The residue was dissolved in CH$_2$Cl$_2$ (5 mL) and treated with 2-piperidin-1-yl-ethanol (1.69 mmol), triethyl amine (230 µL, 1.65 mmol), and DMAP (1 crystal). After stirring for 1 h at room temperature, the solution was poured into water containing K$_2$CO$_3$ (200 mg, 1.45 mmol) and extracted with CH$_2$Cl$_2$ (2×50 mL). The organic layers were dried (MgSO$_4$), filtered, and the filtrate evaporated (40° C., 20 mm Hg). The residue was chromatographed on SiO$_2$ (biotage 40 L, acetone) to afford an oil, which was dissolved in ethyl ether (25 mL) and treated with hydrogen chloride (2 mL of a 1 N solution in ethyl ether, 2 mmol) to afford 2-{4-[2-(2-Biphenyl-4-yl-5-methyl-oxazol-4-yl)-ethoxy]-phenoxy}-2-methyl-propionic acid 2-piperidin-1-yl-ethyl ester hydrochloride as a white powder in 62% yield: $^1$H NMR (400 MHz, DMSO-d$_6$) δ10.07 (bs, 1H), 7.94 (d, J=8.8 Hz, 2H), 7.77 (d, J=8.8 Hz, 2H), 7.69 (d, J=7.2 Hz, 2H), 7.45 (t, J=7.6 Hz, 2H), 7.36 (t, J=7.6 Hz, 1H), 6.83–6.74 (m, 4H), 4.42 (t, J=5.2 Hz, 2H), 4.13 (t, J=6.4 Hz, 2H), 3.32–3.23 (m, 4H), 2.88 (t, J=6.4 Hz, 2H), 2.83–2.74 (m, 2H), 2.34 (s, 3H), 1.68–1.54 (m, 5H), 1.44 (s, 6H), 1.28–1.19 (m, 1H). MS (ES) m/e 568.9 (M$^+$1).

Example 71

2-{4-[2-(2-Biphenyl-4-yl-5-methyl-oxazol-4-yl)-ethoxy]-phenoxy}-2-methyl-propionic acid 2-diethylamino-ethyl ester hydrochloride

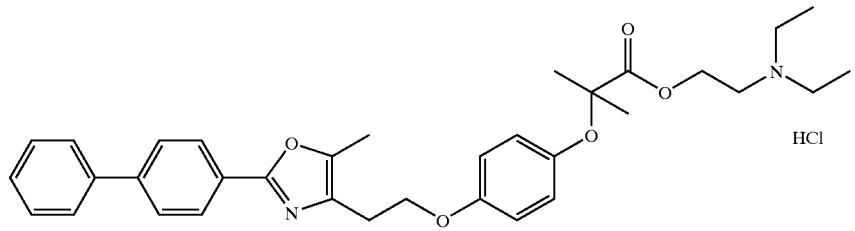

A solution of 2-{4-[2-(2-biphenyl-4-yl-5-methyl-oxazol-4-yl)-ethoxy]-phenoxy}-2-methyl-propionic acid (1.11 mmol) was prepared in CH$_2$Cl$_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in CH$_2$Cl$_2$ (5 mL) and treated with 2-diethylamino-ethanol (1.69 mmol), triethyl amine (230 μL, 1.65 mmol), and DMAP (1 crystal). After stirring for 1 h at room temperature, the solution was poured into water containing K$_2$CO$_3$ (200 mg, 1.45 mmol) and extracted with CH$_2$Cl$_2$ (2×50 mL). The organic layers were dried (MgSO$_4$), filtered, and the filtrate evaporated (40° C., 20 mm Hg). The residue was chromatographed on SiO$_2$ (biotage 40 L, acetone) to afford an oil, which was dissolved in ethyl ether (25 mL) and treated with hydrogen chloride (2 mL of a 1 N solution in ethyl ether, 2 mmol) to afford 2-{4-[2-(2-biphenyl-4-yl-5-methyl-oxazol-4-yl)-ethoxy]-phenoxy}-2-methyl-propionic acid 2-diethylamino-ethyl ester hydrochloride as a white powder in 58% yield: $^1$H NMR (400 MHz, DMSO-d$_6$) δ10.07 (bs, 1H), 7.94 (d, J=8.4 Hz, 2H), 7.77 (d, J=8.4 Hz, 2H), 7.69 (d, J=7.6 Hz, 2H), 7.45 (t, J=7.6 Hz, 2H), 7.36 (t, J=7.6 Hz, 1H), 6.83–6.75 (m, 4H), 4.40 (t, J=5.2 Hz, 2H), 4.13 (t, J=6.4 Hz, 2H), 3.37–3.33 (m, 2H), 3.07–3.01 (m, 4H), 2.88 (t, J=6.4 Hz, 2H), 2.34 (s, 3H), 1.43 (s, 6H), 1.12 (t, J=7.2 Hz, 6H). MS (ES) m/e 557.4 (M$^+$+1).

Example 72

2-{4-[2-(2-Biphenyl-4-yl-5-methyl-oxazol-4-yl)-ethoxy]-phenoxy}-2-methyl-propionic acid 3-dimethylamino-prop-2-yl ester hydrochloride

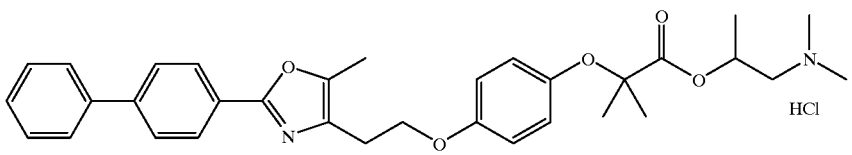

A solution of 2-{4-[2-(2-biphenyl-4-yl-5-methyl-oxazol-4-yl)-ethoxy]-phenoxy}-2-methyl-propionic acid (1.11 mmol) was prepared in CH$_2$Cl$_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in CH$_2$Cl$_2$ (5 mL) and treated with 3-dimethylaminopropan-2-ol (1.69 mmol), triethyl amine (230 μL, 1.65 mmol), and DMAP (1 crystal). After stirring for 1 h at room temperature, the solution was poured into water containing K$_2$CO$_3$ (200 mg, 1.45 mmol) and extracted with CH$_2$Cl$_2$ (2×50 mL). The organic layers were dried (MgSO$_4$), filtered, and the filtrate evaporated (40° C., 20 mm Hg). The residue was chromatographed on SiO$_2$ (biotage 40 L, acetone) to afford an oil, which was dissolved in ethyl ether (25 mL) and treated with hydrogen chloride (2 mL of a 1 N solution in ethyl ether, 2 mmol) to afford 2-{4-[2-(2-biphenyl-4-yl-5-methyl-oxazol-4-yl)-ethoxy]-phenoxy}-2-methyl-propionic acid 3-dimethylamino-prop-2-yl ester hydrochloride as a white powder in 40% yield: $^1$H NMR (400 MHz, DMSO-d$_6$) δ10.0 (bs, 1H), 7.94 (d, J=8.3 Hz, 2H), 7.76 (d, J=8.3 Hz, 2H), 7.69 (d, J=6.8 Hz, 2H), 7.45 (t, J=7.8 Hz, 2H), 7.34 (t, J=6.8 Hz, 1H), 6.81 (d, J=10.2 Hz, 2H), 6.78 (d, J=10.2 Hz, 2H), 4.99 (m, 1H), 4.12 (t, J=6.4 Hz, 2H), 3.25 (m, 2H), 2.87 (t, J=6.4 Hz, 2H), 2.32 (s, 6H), 2.16 (s, 3H), 1.39 (s, 3H), 1.37 (s, 3H), 1.19 (d, J=6.3 Hz, 3H); MS (ES) m/e (% relative intensity) 545.3 (M$^+$+3, 7), 544.3 (M$^+$+2, 37), 543.3 (M$^+$+1, 100).

Example 73

2-{4-[2-(2-Biphenyl-4-yl-5-methyl-oxazol-4-yl)-ethoxy]-phenoxy}-2-methyl-propionic acid 3-diethylamino-propyl ester hydrochloride

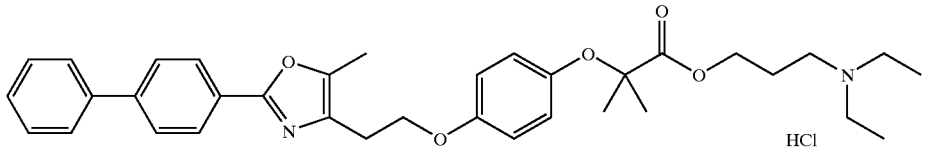

A solution of 2-{4-[2-(2-biphenyl-4-yl-5-methyl-oxazol-4-yl)-ethoxy]-phenoxy}-2-methyl-propionic acid (1.11 mmol) was prepared in $CH_2Cl_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in $CH_2Cl_2$ (5 mL) and treated with 3-diethylaminopropanol (1.69 mmol), triethyl amine (230 μL, 1.65 mmol), and DMAP (1 crystal). After stirring for 1 h at room temperature, the solution was poured into water containing $K_2CO_3$ (200 mg, 1.45 mmol) and extracted with $CH_2Cl_2$ (2×50 mL). The organic layers were dried ($MgSO_4$), filtered, and the filtrate evaporated (40° C., 20 mm Hg). The residue was chromatographed on $SiO_2$ (biotage 40 L, acetone) to afford an oil, which was dissolved in ethyl ether (25 mL) and treated with hydrogen chloride (2 mL of a 1 N solution in ethyl ether, 2 mmol) to afford 2-{4-[2-(2-biphenyl-4-yl-5-methyl-oxazol-4-yl)-ethoxy]-phenoxy}-2-methyl-propionic acid 3-diethylamino-propyl ester hydrochloride as a white powder in 47% yield. $^1H$ NMR (400 MHz, DMSO-$d_6$) δ11.0 (bs, 1H), 7.94 (d, J=8.4 Hz, 2H), 7.76 (d, J=8.4 Hz, 2H), 7.68 (d, J=8.3 Hz, 2H), 7.47 (t, J=7.8 Hz, 2H), 7.36 (t, J=7.8 Hz, 1H), 6.79 (d, J=9.3 Hz, 2H), 6.71 (d, J=9.3 Hz, 2H), 4.11 (t, J=6.4 Hz, 2H), 4.06 (t, J=6.4 Hz, 2H), 2.87 (t, J=6.4 Hz, 2H), 2.25 (t, J=6.4 Hz, 2H), 2.33 (s, 3H), 2.25 (t, J=6.4 Hz, 2H), 1.59 (p, J=6.4, 2H), 1.40 (s, 6H), 0.82 (t, J=6.4 Hz, 6H); MS (ES) m/e (% relative intensity) 573.3 ($M^+$+3, 16), 572.3 ($M^+$+2, 70), 571.3 ($M^+$+1, 100).

Example 74

2-{4-[2-(2-Biphenyl-4-yl-5-methyl-oxazol-4-yl)-ethoxy]-phenoxy}-2-methylpropionic acid 3-(1-piperidnyl)-propyl ester hydrochloride A solution of2-{4-[2-(2-biphenyl-4-yl-5-methyl-oxazol-4-yl)-ethoxy]-phenoxy}-2-methylpropionic acid (1.11 mmol) was prepared in $CH_2Cl_2$ (5 mL, anhydrous) and treated sequentially with oxalyl chloride (125 μL, 1.43 mmol) and DMF (1 drop). This solution was stirred for 1 h at room temperature, then concentrated (40° C., 20 mm Hg). The residue was dissolved in $CH_2Cl_2$ (5 mL) and treated with 3-(1-piperidinyl)-propanol (1.69 mmol), triethyl amine (230 μL, 1.65 mmol), and DMAP (1 crystal). After stirring for 1 h at room temperature, the solution was poured into water containing $K_2CO_3$ (200 mg, 1.45 mmol) and extracted with $CH_2Cl_2$ (2×50 mL). The organic layers were dried ($MgSO_4$), filtered, and the filtrate evaporated (40° C., 20 mm Hg). The residue was chromatographed on $SiO_2$ (biotage 40 L, acetone) to afford an oil, which was dissolved in ethyl ether (25 mL) and treated with hydrogen chloride (2 mL of a 1 N solution in ethyl ether, 2 mmol) to afford 2-{4-[2-(2-biphenyl-4-yl-5-methyl-oxazol-4-yl)-ethoxy]-phenoxy}-2-methylpropionic acid 3-(1-piperidnyl)-propyl ester hydrochloride as a white powder in 53% yield. $^1H$ NMR (400 MHz, DMSO-$d_6$) δ10.7 (bs, 1H), 7.94 (d, J=8.3 Hz, 2H), 7.77 (d, J=8.3 Hz, 2H), 7.69 (d, J=7.3 Hz, 2H), 7.45 (t, J=7.8 Hz, 2H), 7.37 (t, J=7.3 Hz, 1H), 6.79 (d, J=8.8 Hz, 2H), 6.71 (d, J=8.8 Hz, 2H), 4.11 (t, J=6.4 Hz, 2H), 4.04 (t, J=6.4 Hz, 2H), 2.87 (t, J=6.4 Hz, 2H), 2.25 (t, J=6.4 Hz, 2H), 2.33 (s, 3H), 2.16 (br m, 6H), 1.63 (p, J=6.4, 2H), 1.41 (s, 6H), 1.38 (br. m, 4H), 1.27 (br. M, 2H); MS (ES) m/e (% relative intensity) 585.3 ($M^+$+3, 16), 584.3 ($M^+$2, 67), 583.3 ($M^+$+1, 100).-

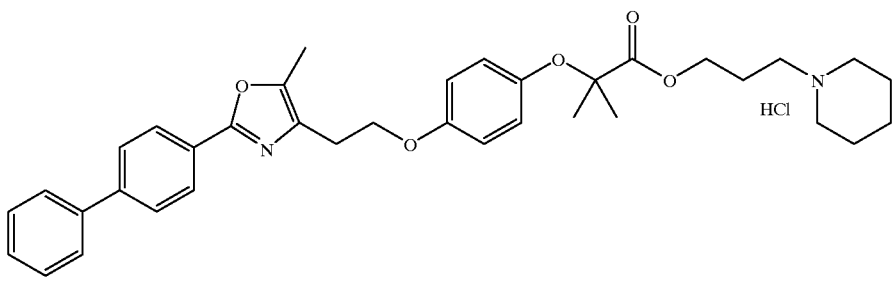

The following compounds were prepared using the methods described above:

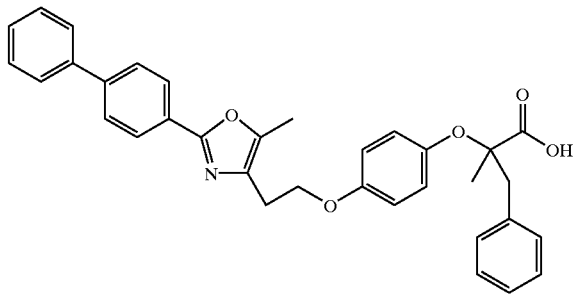
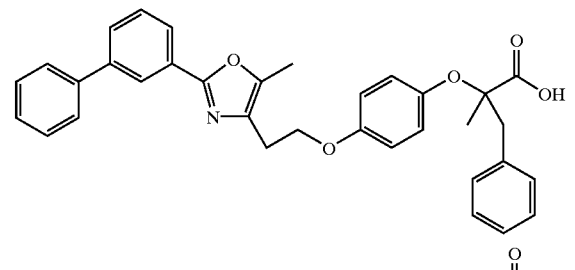
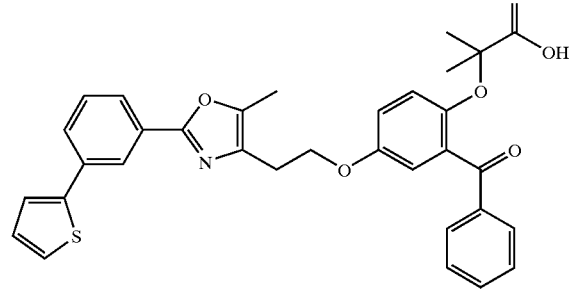
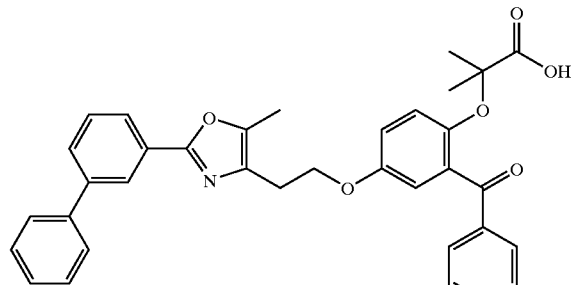
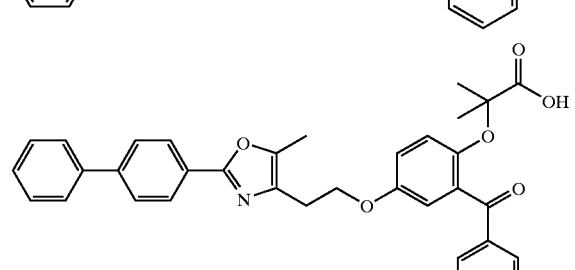
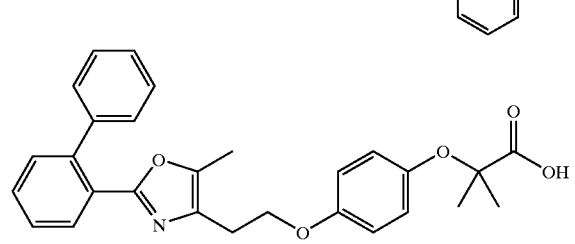

The in vitro potency of compounds in modulating PPARγ and PPARα receptors may be determined by the procedures detailed below.

Example 75
Binding and Cotransfection Studies

DNA-dependent binding (ABCD binding) was carried out using SPA technology with PPAR receptors. Tritium-labeled PPARγ and PPARα agonists were used as radioligands for generating displacement curves and $IC_{50}$ values with compounds of the invention. Cotransfection assays were carried out in CV-1 cells. The reporter plasmid contained an acyl-CoA oxidase (AOX) PPRE and TK promoter upstream of the luciferase reporter cDNA. Appropriate PPARs and RXRα were constitutively expressed using plasmids containing the CMV promoter. For PPARα and PPARβ, interference by endogenous PPARγ in CV-1 cells was an issue. In order to eliminate such interference, a GAL4 chimeric system was used in which the DNA binding domain of the transfected PPAR was replaced by that of GAL4, and the GAL4 response element was utilized in place of the AOX PPRE. Cotransfection efficacy was determined relative to PPARα agonist and PPARβ agonist reference molecules. Efficacies were determined by computer fit to a concentration-response curve, or in some cases at a single high concentration of agonist (10 μM). For binding or cotransfection studies with receptors other than PPARs, similar assays were carried out using appropriate ligands, receptors, reporter constructs, etc., for that particular receptor.

These studies were carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention were compared with corresponding data for marketed compounds that act on either huPPARα or huPPARγ.

Binding and cotransfection data for representative compounds of the invention are compared with corresponding data for reference compounds in Table 1.

TABLE 1

Comparison of binding $IC_{50}$ values and cotransfection efficacy data of compounds of the invention to reference compounds.

| | huPPARα | | huPPARγ | |
| --- | --- | --- | --- | --- |
| Example | $IC_{50}$ (nM) | CTF Efficacy (%) | $IC_{50}$ (Nm) | CTF Efficacy (%) |
| 10 | 350 | 111 | 1063 | 80 |
| 13 | 475 | 84 | 928 | 100 |
| 14 | 155 | 90 | 457 | 84 |
| 18 | 539 | 97 | 1790 | 145 |
| 21 | 97 | 92 | 532 | 70 |
| 25 | 125 | 104 | 81 | 71 |
| 26 | 78 | 111 | 33 | 73 |
| 28 | 172 | 93 | 140 | 63 |
| 32 | 47 | 91 | 12 | 60 |
| 34 | 193 | 180 | 227 | 55 |
| 35 | 65 | 90 | 24 | 61 |
| 36 | 140 | 140 | 62 | 92 |
| 46 | 447 | 122 | 268 | 142 |
| 47 | 371 | 90 | 1534 | 126 |
| Troglitazone | 94,500 | 0 | 1180 | 80 |
| Fenofibric acid | 68,000 | 16 | 125,000 | 0 |

Example 76
Evaluation of Triglyceride and Cholesterol Levels in Hu apoAI Transgenic Mice Five to six week old male mice, transgenic for human apoAI [C57B1/6-tgn(apoa1)1 rub, Jackson Laboratory, Bar Harbor, Me.] were housed five per cage (10"×20"×8" with aspen chip bedding) with food (Purina 5001) and water available at all times. After an acclimation period of 2 weeks, animals were individually identified by ear notches, weighed, and assigned to groups based on body weight. Beginning the following morning, mice were dosed daily by oral gavage for 7 days using a 20 gauge, 1½ curved disposable feeding needle (Popper & Sons). Treatments were test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice were weighed and dosed. Three hours after dosing, animals were anesthetized by inhalation of isoflurane (2–4%; Abbott Laboratories, Chicago, Ill.) and blood obtained via cardiac puncture (0.7–1.0 ml). Whole blood was transferred to serum separator tubes (Vacutainer SST), chilled on ice, and permitted to clot. Serum was obtained after centrifugation at 4° C. and frozen until analysis for triglycerides, total cholesterol, compound levels, and serum lipoprotein profile by fast protein liquid chromatography (FPLC) coupled to an inline detection system. After sacrifice by cervical dislocation, the liver, heart and epididymal fat pads were excised and weighed.

The animals dosed with vehicle had average triglycerides values of 60–80 mg/dl, which were reduced by the positive control fenofibrate (33–58 mg/dl with a mean reduction of 37%). The animals dosed with vehicle had average total serum cholesterol values of 148–180 mg/dl, which were increased by fenofibrate (190–280 mg/dl, with a mean elevation of 41%. The percentage decrease in triglyceride serum levels in mice receiving a compound of the invention over mice receiving vehicle are reported in Table 2. When subject to FPLC analysis, pooled sera from vehicle-treated hu apoAI transgenic mice had a high a density lipoprotein cholesterol (HDLc) peak area which ranged from 47 v-sec to 62 v-sec. Fenofibrate increased the amount of HDLc (68–96 v-sec with a mean percent increase of 48%). Test compounds are reported in terms of percent increase in the area under the curve as indicated in Table 3.

TABLE 2

Percent decrease of triglyceride serum levels in mice receiving a compound of the invention over mice receiving vehicle.

| Example | % Triglyceride Decrease |
|---|---|
| 1 | 62.2 |
| 3 | 51.2 |
| 8 | 31.8 |
| 12 | 37.6 |
| 14 | 67.5 |
| 21 | 60.5 |
| 22 | 73.6 |
| 24 | 62.3 |
| 27 | 37.2 |
| 30 | 51.3 |
| 31 | 66.7 |
| 38 | 53.3 |
| 46 | 16.4 |
| 48 | 43.7 |
| 49 | 48.7 |
| 50 | 53.9 |
| 51 | 41.6 |
| 60 | 40.8 |
| 62 | 45.5 |

TABLE 3

Percent increase of HDLc serum levels in mice receiving a compound of the invention over mice receiving vehicle.

| Example | % HDLc Increase |
|---|---|
| 1 | 160 |
| 3 | 69 |
| 8 | 41 |
| 12 | 29 |
| 14 | 66 |
| 21 | 204 |
| 22 | 191 |
| 24 | 72 |
| 27 | 57 |
| 30 | 92 |
| 31 | 217 |
| 38 | 34 |
| 46 | 26 |
| 48 | 89 |
| 49 | 34 |
| 50 | 95 |
| 51 | 53 |
| 60 | 38 |
| 62 | 56 |

Example 77

Evaluation of Glucose Levels in db/db Mice

Five week old male diabetic (db/db) mice [C57B1Ks/j-m+/+Lepr(db), Jackson Laboratory, Bar Harbor, Me.] or lean littermates (DB/?) were housed 6 per cage (10"×20"×8" with aspen chip bedding) with food (Purina 5015) and water available at all times. After an acclimation period of 2 weeks, animals were individually identified by ear notches, weighed, and bled via the tail vein for determination of initial glucose levels. Blood was collected (100 µl) from unfasted animals by wrapping each mouse in a towel, cutting the tip of the tail with a scalpel, and milking blood from the tail into a heparinized capillary tube (Fisher) balanced on the edge of the bench. Sample was discharged into a heparinized microtainer with gel separator (VWR) and retained on ice. Plasma was obtained after centrifugation at 4° C. and glucose measured immediately. Remaining plasma was frozen until the completion of the experiment, when glucose and triglycerides were assayed in all samples. Animals were grouped based on initial glucose levels and body weights. Beginning the following morning, mice were dosed daily by oral gavage for 7 days using a 20 gauge, 1½" curved disposable feeding needle. Treatments were test compounds (30 mg/,kg), a positive control agent (30 mg/kg) or vehicle [1% carboxymethylcellulose (w/v)/0.25% Tween80 (w/v); 0.3 ml/mouse]. On day 7, mice were weighed and bled (tail vein) 3 hours after dosing. Twenty-four hours after the $7^{th}$ dose (i.e., day 8), animals were bled again (tail vein). Samples obtained from conscious animals on days 0, 7 and 8 were assayed for glucose. After the 24 hour bleed, animals were weighed and dosed for the final time. Three hours after dosing on day 8, animals were anesthetized by inhalation of isoflurane and blood obtained via cardiac puncture (0.5–0.7 ml). Whole blood was transferred to serum separator tubes, chilled on ice and permitted to clot. Serum was obtained after centrifugation at 4° C. and frozen until analysis for compound levels. After sacrifice by cervical dislocation, the liver, heart and epididymal fat pads were excised and weighed. The animals dosed with vehicle had average triglycerides values of 170–230 mg/dl, which were reduced by the positive PPARα (70–120 mg/dl with a mean reduction of 50%). Male db/db mice were hyperglycemic (average glucose of 680–730 mg/dl on the $7^{th}$ day of treatment), while lean animals had average glucose levels between 190–230 mg/dl. Treatment with the positive control agent reduced glucose significantly (350–550 mg/dl with a mean decrease towards normalization of 56%). Test compounds are reported in Table 4 in terms of glucose normalization (i.e., 100% normalization would be glucose levels in treated db/db mice which did not differ from lean values.

Glucose was measured calorimetrically using commercially purchased reagents (Sigma #315–500). According to the manufacturers, the procedures were modified from published work (McGowan, M. W., Artiss, J. D., Strandbergh, D. R. & Zak, B. *Clin Chem*, 20:470–5 (1974) and Keston, A. Specific colorimetric enzymatic analytical reagents for glucose. *Abstract of papers* 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. *Ann Clin Biochem*, 6:24 (1969)). The absorbance of the dye produced is linearly related to the analyte in the sample. The assays were further modified in our laboratory for use in a 96 well format. Standards (Sigma #339-11, Sigma #16-11, and Sigma #CC0534 for glucose, triglycerides and total cholesterol, respectively), quality control plasma (Sigma #A2034), and samples (2 or 5 μl/well) were measured in duplicate using 200 μl of reagent. An additional aliquot of sample, pipetted to a third well and diluted in 200 μl water, provided a blank for each specimen. Plates were incubated at room temperature (18, 15, and 10 minutes for glucose, triglycerides and total cholesterol, respectively) on a plate shaker (DPC Micormix 5) and absorbance read at 500 nm (glucose and total cholesterol) or 540 nm (triglycerides) on a plate reader (Wallac Victor 1420). Sample absorbances were compared to a standard curve (100–800, 10–500, and 100–400 mg/dl for glucose, triglycerides and total cholesterol, respectively). Values for the quality control sample were always within the expected range and the coefficient of variation for samples was below 10%. All samples from an experiment were assayed at the same time to minimize inter-assay variability.

Serum lipoproteins were separated and cholesterol quantitated with an in-line detection system. Sample was applied to a Superose® 6 HR 10/30 size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C. water bath. The colored product produced in the presence of cholesterol was monitored in the flow stream at 505 nm and the analog voltage from the monitor was converted to a digital signal for collection and analysis. The change in voltage corresponding to change in cholesterol concentration was plotted vs time and the area under the curve corresponding to the elution of VLDL, LDL and HDL was calculated using Perkin Elmer Turbochrome software.

TABLE 4

Percent glucose normalisation values in db/db mice.

| Example | Glucose Normalisation |
|---------|----------------------|
| 1 | 90 |
| 3 | 93 |
| 8 | 19 |

TABLE 4-continued

Percent glucose normalisation values in db/db mice.

| Example | Glucose Normalisation |
|---------|----------------------|
| 12 | 44 |
| 14 | 134 |
| 21 | 95 |
| 22 | 102 |
| 24 | 55 |
| 27 | 20 |
| 30 | 69 |
| 31 | 89 |
| 38 | 59 |
| 46 | 29 |
| 48 | 31 |
| 49 | 39 |
| 50 | 42 |
| 51 | 31 |
| 60 | 68 |
| 62 | 36 |

EQUIVALENTS

While this invention has been particularly shown and described with references to preferred embodiments thereof, it will be understood by those skilled in the art that various changes in from and details may be made therein without departing from the scope of the invention encompassed by the appended claims.

What is claimed is:

1. A compound represented by the following structural formula:

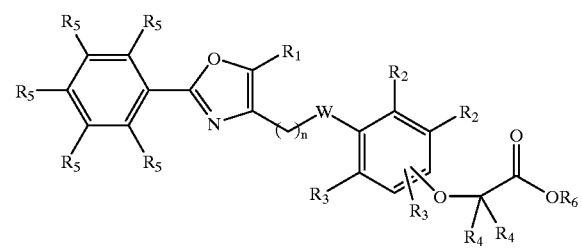

and pharmaceutically acceptable salts thereof, wherein:

n is 2, 3, or 4;

W is O, S, or $SO_2$;

$R^1$ is H, a C1–C4 alkyl, phenyl or trifluoromethyl;

$R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, an aryl-C1–C6 alkyl, a cycloalkyl-C1–C4 alkyl, an aryl, or a cycloalkyl;

$R_4$ are each, independently, H, a C1–C4 alkyl, an aryl, or benzyl;

$R_5$ are each, independently, H or a substituted or unsubstituted aryl, provided that at least one $R_5$ is a substituted or unsubstituted aryl; and $R_6$ is H, a C1–C4 alkyl, or an aminoalkyl.

2. The compound of claim 1, wherein the compound is represented by the following structural formula:

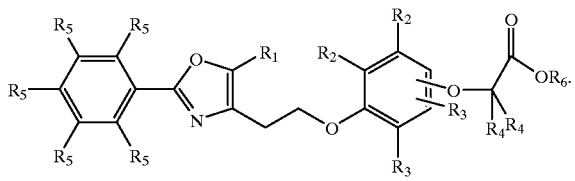

3. The compound of claim 2, wherein one $R_5$ is phenyl.

4. The compound of claim 3, wherein the compound is represented by the following structural formula:

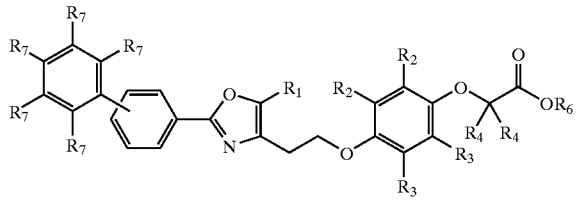

wherein, $R_7$ are each, independently, H, halo, a C1–C6 alkyl, trifluoromethyl, a C1–C6 alkoxy, C(O)OH, C(O)NHC(CH$_3$)$_3$, (CH$_2$)$_2$C(O)OH, or CHO.

5. The compound of claim 4, wherein $R_1$ and each $R_4$ are methyl.

6. The compound of claim 4, wherein the compound is represented by the following structural formula:

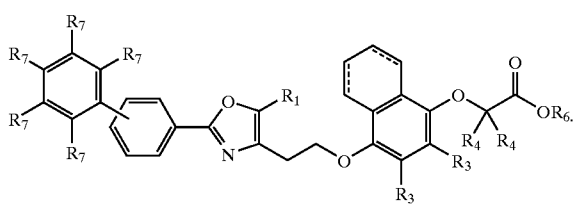

7. The compound of claim 6, wherein the compound is selected from the group consisting of:
2-{4-[2-(2-biphenyl-4-yl-5-methyloxazol-4-yl)ethoxy]naphthalen-1-yloxy}-2-methyl propionic acid; and
2-{4-[2-(2-biphenyl-4-yl-5-methyloxazol-4-yl)-ethoxy]-5,6,7,8-tetrahydronaphthalen-1-yloxy}-2-methyl propionic acid;
2-{4-[2-(2-biphenyl-3-yl-5-methyloxazol-4-yl)-ethoxy]-5,6,7,8-tetrahydronaphthalen-1-yloxy}-2-methyl propionic acid; and
2-{4-[2-(2-biphenyl-3-yl-5-methyloxazol-4-yl)ethoxy]naphthalen-1-yloxy}-2-methyl propionic acid.

8. The compound of claim 4, wherein the compound is represented by the following structural formula:

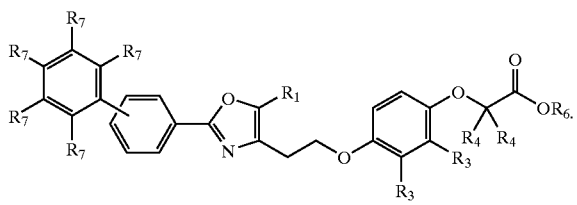

9. The compound of claim 8, wherein $R_1$ and each $R_4$ are methyl.

10. The compound of claim 9, wherein the compound is selected from the group consisting of:

2-{4-[2-(2-biphenyl-4-yl-5-methyloxazol-4-yl)ethoxy]phenoxy}-2-methylpropionic acid;
2-{4-[2-(2-biphenyl-4-yl-5-methyloxazol-4-yl)-ethyloxy]-2-propylphenoxy}-2-methyl-propionic acid;
2-{4-[2-(2-biphenyl-4-yl-5-methyloxazol-4-yl)-ethoxy]-2-methylphenoxy}-2-methylpropionic acid;
2-{4-[2-(2-biphenyl-4-yl-5-methyloxazol-4-yl)ethoxy]-3-butylphenoxy-2-methylpropionic acid;
2-{4-[2-(2-biphenyl-4-yl-5-methyloxazol-4-yl)ethoxy]-3-propylphenoxy}-2-methylpropionic acid; and
2-{4-[2-(2-biphenyl-3-yl-5-methyloxazol-4-yl)ethoxy]phenoxy}-2-methylpropionic acid.

11. A pharmaceutical composition, comprising a pharmaceutically acceptable carrier and at least one compound represented by the following structural formula:

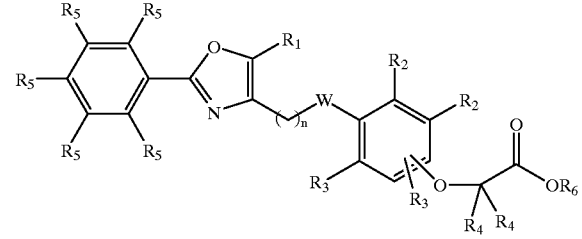

and pharmaceutically acceptable salts thereof, wherein:

n is 2, 3, or 4;

W is O, S, or SO$_2$;

$R_1$ is H, a C1–C4 alkyl, phenyl or trifluoromethyl;

$R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, an aryl-C1–C6 alkyl, a cycloalkyl-C1–C4 alkyl, an aryl, or a cycloalkyl;

$R_4$ are each, independently, H, a C1–C4 alkyl, an aryl, or benzyl;

$R_5$ are each, independently, H or a substituted or unsubstituted aryl, provided that at least one $R_5$ is a substituted or unsubstituted aryl; and $R_6$ is H, a C1–C4 alkyl, or an aminoalkyl.

12. The pharmaceutical composition of claim 11, wherein the compound is represented by the following structural formula:

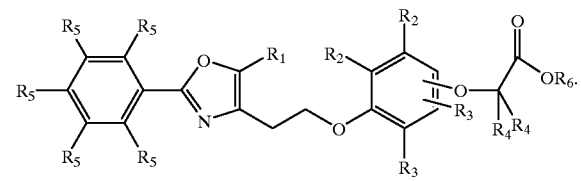

13. The pharmaceutical composition of claim 12, wherein one $R_5$ is phenyl.

14. The pharmaceutical composition of claim 13, wherein the compound is represented by the following structural formula:

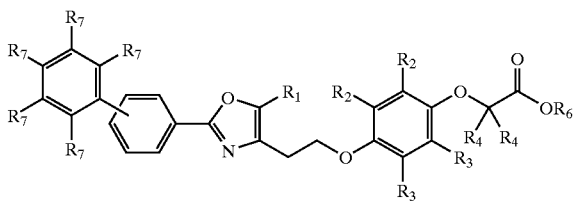

wherein, $R_7$ are each, independently, H, halo, a C1–C6 alkyl, trifluoromethyl, a C1–C6 alkoxy, C(O)OH, C(O)NHC(CH$_3$)$_3$, (CH$_2$)$_2$C(O)OH, or CHO.

15. The pharmaceutical composition of claim 14, wherein $R_1$ and each $R_4$ are methyl.

16. The pharmaceutical composition of claim 14, wherein the compound is represented by the following structural formula:

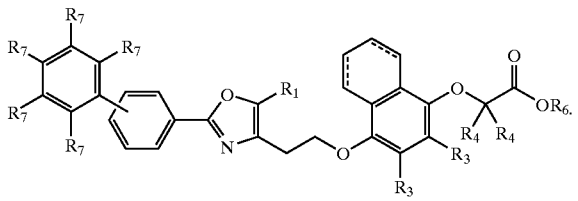

17. The pharmaceutical composition of claim 16, wherein the compound is selected from the group consisting of:
- 2-{4-[2-(2-biphenyl-4-yl-5-methyloxazol-4-yl)ethoxy] naphthalen-1-yloxy}-2-methyl propionic acid; and
- 2-{4-[2-(2-biphenyl-4-yl-5-methyloxazol-4-yl)-ethoxy]-5,6,7,8-tetrahydronaphthalen-1-yloxy}-2-methyl propionic acid;
- 2-{4-[2-(2-biphenyl-3-yl-5-methyloxazol-4-yl)-ethoxy]-5,6,7,8-tetrahydronaphthalen-1-yloxy}-2-methyl propionic acid; and
- 2-{4-[2-(2-biphenyl-3-yl-5-methyloxazol-4-yl)ethoxy] naphthalen-1-yloxy}-2-methyl propionic acid.

18. The pharmaceutical composition of claim 14, wherein the compound is represented by the following structural formula:

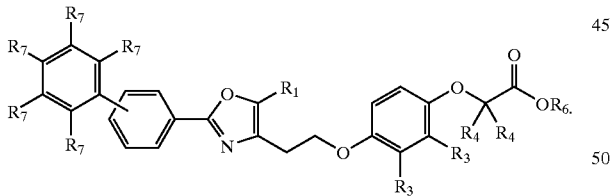

19. The pharmaceutical composition of claim 18, wherein $R_1$ and each $R_4$ are methyl.

20. The pharmaceutical composition of claim 19, wherein the compound is selected from the group consisting of:
- 2-{4-[2-(2-biphenyl-4-yl-5-methyloxazol-4-yl)ethoxy] phenoxy}-2-methylpropionic acid;
- 2-{4-[2-(2-biphenyl-4-yl-5-methyloxazol-4-yl)-ethyloxy]-2-propylphenoxy}-2-methyl-propionic acid;
- 2-{4-[2-(2-biphenyl-4-yl-5-methyloxazol-4-yl)-ethoxy]-2-methylphenoxy}-2-methylpropionic acid;
- 2-{4-[2-(2-biphenyl-4-yl-5-methyloxazol-4-yl)ethoxy]-3-butylphenoxy}-2-methylpropionic acid;
- 2-{4-[2-(2-biphenyl-4-yl-5-methyloxazol-4-yl)ethoxy]-3-propylphenoxy}-2-methylpropionic acid; and
- 2-{4-[2-(2-biphenyl-3-yl-5-methyloxazol-4-yl)ethoxy] phenoxy}-2-methylpropionic acid.

21. A pharmaceutical composition, comprising a pharmaceutically acceptable carrier and at least one compound selected from the group consisting of:
- 2-(4-{2-[2-(4'-fluorobiphenyl-4-yl)-5-methyloxazol-4-yl] ethoxy}phenoxy)-2-methylpropionic acid;
- 2-(4-{2-[2-(4'-formylbiphenyl-3-yl)-5-methyloxazol-4-yl]ethoxy}phenoxy)-2-methylpropionic acid;
- 3'-(4-{2-[3-(1-carboxy-1-methylethoxy)phenoxy]ethyl}-5-methyloxazol-2-yl)-biphenyl-4-carboxylic acid;
- 2-[4-(2-{2-[4'-(2-carboxyethyl)biphenyl-3-yl]-5-methyloxazol-4-yl}ethoxy)phenoxy]-2-methylpropionic acid;
- 2-(4-{2-[2-(3',5'-bis-trifluoromethylbiphenyl-4-yl)-5-methyloxazol-4-yl]ethoxy}-phenoxy)-2-methyl propionic acid;
- 2-(4-{2-[2-(2'-methoxy-biphenyl-4-yl)-5-methyloxazol-4-yl]-ethoxy}-phenoxy)-2-methylpropionic acid;
- 2-methyl-2-(4-{2-[5-methyl-2-(2'-methyl-biphenyl-4-yl) oxazol-4-yl]-ethox}-phenoxy)propionic acid;
- 2-methyl-2-(4-{2-[5-methyl-2-(2'-trifluoromethyl-biphenyl-4-yl)-oxazol-4-yl]-ethoxy}-phenoxy) propionic acid;
- 2-(4-{2-[2-(2'-fluorobiphenyl-4-yl)-5-methyloxazol-4-yl]-ethoxy}-phenoxy)-2-methylpropionic acid;
- 2-(4-{2-[2-(2',6'-difluorobiphenyl-4-yl)-5-methyloxazol-4-yl]-ethoxy}-phenoxy)-2-methylpropionic acid;
- 2-(4-{2-[2-(2',6'-dichloro-biphenyl-4-yl)-5-methyloxazol-4-yl]-ethoxy}-phenoxy)-2-methylpropionic acid;
- 2-(4-{2-[2-(4'-tert-butylcarbamoyl)biphenyl-3-yl)-5-methyloxazol-4-yl]ethoxy}phenoxy)-2-methyl propionic acid;
- 2-[4(2-{2-[4-(3,5-dimethyl-isoxazol-4-yl)-phenyl]-5-methyloxazol-4-yl}-ethoxy)-phenoxy]-2-methylpropionic acid;
- 2-methyl-2-[4-(2-{5-methyl-2-[4-(1H-pyrrol-2-yl)-phenyl]-oxazol-4-yl}-ethoxy)-phenoxy]propionic acid;
- 2-methyl-2-(4-{2-[5-methyl-2-(4-pyrimidin-2-yl-phenyl)-oxazol-4-yl]-ethoxy}-phenoxy)-propionic acid;
- 2-methyl-2-(4-{2-[5-methyl-2-(4-pyrimidin-5-yl-phenyl)-oxazol-4-yl]-ethoxy}-phenoxy)-propionic acid;
- 2-{3-[2-(2-biphenyl-4-yl-5-methyloxazol-4-yl)-ethoxy] phenoxy}-2-methylpropionic acid;
- 2-{3-[2-(2-biphenyl-3-yl-5-methyloxazol-4-yl)-ethoxy] phenoxy}-2-methylpropionic acid;
- 2-{4-[2-(2-biphenyl-4-yl-5-methyloxazol-4-yl)-ethoxy]-2-methylphenoxy}-2-methylpropionic acid;
- 2-{4-[2-(2-biphenyl-4-yl-5-methyloxazol-4-yl)-ethoxy]-2-cyclohexylmethylphenoxy}-2-methyl-propionic acid;

2-(4-{2-[2-(4-thiophen-2-yl-phenyl)-5-methyloxazol-4-yl]ethoxy}phenoxy)-2-methylpropionic acid;

2-{4-[2-(2-biphenyl-4-yl-5-methyloxazol-4-yl)-ethoxy]-2-phenethylphenoxy}-2-methylpropionic acid;

2-{4-[2-(2-biphenyl-3-yl-5-methyloxazol-4-yl)-ethoxy]-2-phenethylphenoxy}-2-methylpropionic acid;

2-{4-[2-(2-biphenyl-3-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-phenethylphenoxy}-2-methylpropionic acid;

2-{4-[2-(2-biphenyl-4-yl-5-methyloxazol-4yl)ethoxy]-3-cyclohexylmethylphenoxy}-2-methylpropionic acid;

2-{2-benzyl-4-[2-(2-biphenyl-3-yl-5-methyloxazol-4-yl)-ethoxy]-phenoxy}-2 -methyl-propionic acid;

2-{2-benzyl-4-[2-(2-biphenyl-4-yl-5-methyloxazol-4-yl)-ethoxy]-phenoxy}-2-methyl-propionic acid;

2-(4-{2-[2-(4-benzofur-2-yl-phenyl)-5-methyloxazol-4-yl]ethoxy}phenoxy)-2-methylpropionic acid;

2-{5-[2-(2-biphenyl-4-yl-5-methyloxazol-4-yl)-ethoxy]-biphenyl-2-yloxy}-2-methyl-propionic acid;

2-(4-{2-[2-(4'-trifluoromethylbiphenyl-4-yl)-5-methyloxazol-4-yl]ethoxy}phenoxy)-2-methylpropionic acid;

2-{3-[2-(2-biphenyl-4-yl-5-methyloxazol-4-yl)ethoxy]-4-butylphenoxy}-2-methylpropionic acid;

2-{5-[2-(2-biphenyl-4-yl-5-methyloxazol-4-yl)ethoxy]-2-butylphenoxy}-2-methylpropionic acid;

2-{5-[2-(2-biphenyl-3-yl-5-methyloxazol-4-yl)ethoxy]-2-butylphenoxy}-2-methylpropionic acid;

2-{5-[2-(2-biphenyl-4yl-5-methyloxazol-4-yl)ethoxy]-2-propylphenoxy}-2-methylpropionic acid;

2-{5-[2-(2-biphenyl-3-yl-5-methyloxazol-4-yl)ethoxy]-2-propylphenoxy}-2-methylpropionic acid;

2-{4-[2-(2-biphenyl-4-yl-5-methyl-thiazol-4-yl)ethoxy]-phenoxy}-2-methylpropionic acid;

2-{4-[2-(2-biphenyl-3-yl-5-methyl-thiazol-4yl)-ethoxy]-phenoxy}-2-methylpropionic acid;

2-{4-[2-(2-biphenyl-4-yl-5-methyloxazol-4-yl)-ethylsulfanyl]-phenoxy}-2-methyl-propionic acid;

2-{4-[2-(2-biphenyl-4-yl-5-methyloxazol-4-yl)ethoxy]naphthalen-1-yloxy}-2-methyl propionic acid;

2-{4-[2-(2-biphenyl-3-yl-5-methyloxazol-4-yl)ethoxy]naphthalen-1-yloxy}-2-methyl propionic acid;

2-{4-[2-(2-biphenyl-4-yl-5-propyl-oxazol-4-yl)-ethoxy]-phenoxy}-2-methyl-propionic acid;

2-{4-[2-(2-biphenyl-4-yl-5-phenyl-oxazol-4-yl)-ethoxy]-phenoxy}-2-methylpropionic acid;

2-{4-[2-(2-biphenyl-4-yl-5-trifluoromethyloxazol-4-yl)-ethoxy]-phenoxy}-2-methyl-propionic acid;

2-(4-{2-[2-(4'-methoxybiphenyl-4-yl)-5-methyloxazol-4-yl]ethoxy}phenoxy)-2-methylpropionic acid;

2-(4-{2-[2-(4-{5'-methylthiophen-2-y)}-phenyl)-5-methyloxazol-4yl]ethoxy}phenoxy)-2-methylpropionic acid;

2-(4-{2-[2-(4-pyrid-3-yl-phenyl)-5-methyloxazol-4-yl]ethoxy}phenoxy)-2-methylpropionic acid;

2-(4-{2-[2-(4-pyrid-4-phenyl)-5-methyloxazol-4-yl]ethoxy}phenoxy)-2-methylpropionic acid;

2-{4-[2-(2-biphenyl-4-yl-5-methyloxazol-4-yl)-ethylsulfanyl dioxide]-phenoxy}-2-methyl-propionic acid;

2-{4-[2-(2-biphenyl-4yl-5-methyloxazol-4-yl)-ethyloxy]-2-propylphenoxy}-2-methyl-propionic acid;

2-{4-[2-(2-biphenyl-4-yl-5-methyloxazol-4-yl)-ethyloxy]-3-propylphenoxy}-ethanoic acid; and 2-{4-[2-(2-biphenyl-4-yl-5-methyloxazol-4-yl)-ethyloxy]-propylphenoxy}-ethanoic acid.

22. A method of modulating a peroxisome proliferator activated receptor, comprising the step of contacting the receptor with at least one compound represented by the following structural formula:

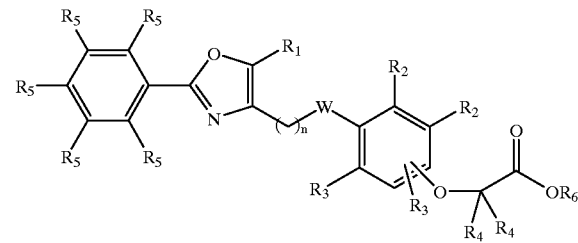

and pharmaceutically acceptable salts, solvates and hydrates thereof, wherein:

n is 2, 3, or 4;

W is O, S, or $SO_2$;

$R_1$ is H, a C1–C4 alkyl, phenyl or trifluoromethyl;

$R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, an aryl-C1–C6 alkyl, a cycloalkyl-C1–C4 alkyl, an aryl, or a cycloalkyl;

$R_4$ are each, independently, H, a C1–C4 alkyl, an aryl, or benzyl;

$R_5$ are each, independently, H or a substituted or unsubstituted aryl, provided that at least one $R_5$ is a substituted or unsubstituted aryl; and $R_6$ is H, a C1–C4 alkyl, or an aminoalkyl.

23. The method of claim 22, wherein the compound is represented by the following structural formula:

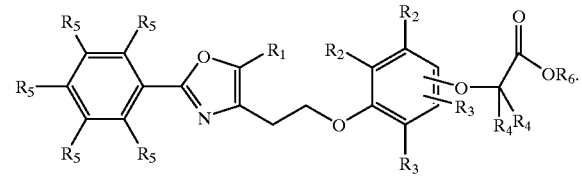

24. The method of claim 23, wherein the compound is represented by the following structural formula:

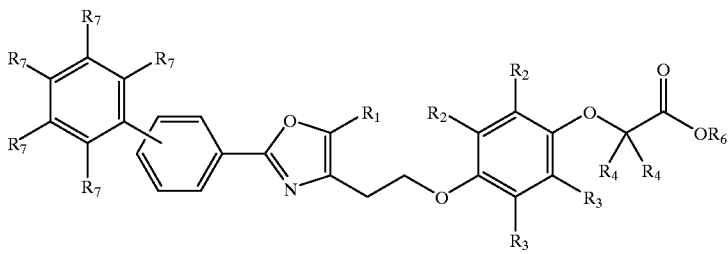

wherein, $R_7$ are each, independently, H, halo, a C1–C6 alkyl, trifluoromethyl, a C1–C6 alkoxy, C(O)OH, C(O)NHC(CH$_3$)$_3$, (CH$_2$)$_2$C(O)OH, or CHO.

25. The method of claim 24, wherein the compound is selected from the group consisting of:

2-{4-[2-(2-biphenyl-4-yl-5-methyloxazol-4-yl)ethoxy]phenoxy}-2-methylpropionic acid;

2-{4-[2-(2-biphenyl-4-yl-5-methyloxazol-4-yl)-ethyloxy]-2-propylphenoxy}-2-methyl-propionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-propylphenoxy}-2-methylpropionic acid; and 2-{4-[2-(2-biphenyl-3-yl-5-methyloxazol-4-yl)ethoxy]phenoxy}-2-methylpropionic acid.

26. The method of claim 24, wherein the compound is represented by the following structural formula:

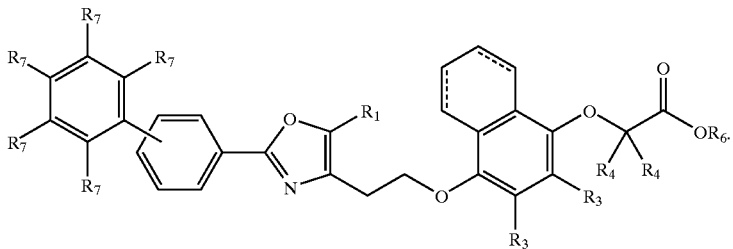

27. The method of claim 26, wherein the compound is selected from the group consisting of:

2-{4-[2-(2-biphenyl-4-yl-5-methyloxazol-4-yl)ethoxy]naphthalen-1-yloxy}-2-methyl propionic acid; and 2-{4-[2-(2-biphenyl-4-yl-5-methyloxazol-4-yl)-ethoxy]-5,6,7,8-tetrahydronaphthalen-1-yloxy}-2-methyl propionic acid;

2-{4-[2-(2-biphenyl-3-yl-5-methyloxazol-4-yl)-ethoxy]-5,6,7,8-tetrahydronaphthalen-1-yloxy}-2-methyl propionic acid; and 2-{4-[2-(2-biphenyl-3-yl-5-methyloxazol-4-yl)ethoxy]naphthalen-1-yloxy}-2-methyl propionic acid.

28. The method of claim 22, wherein the peroxisome proliferator activated receptor is an α receptor.

29. The method of claim 22, wherein the peroxisome proliferator activated receptor is an γ receptor.

30. A method of treating or preventing diabetes mellitus in a patient, comprising the step of administering to the mammal a therapeutically effective amount of at least one compound represented by the following structural formula:

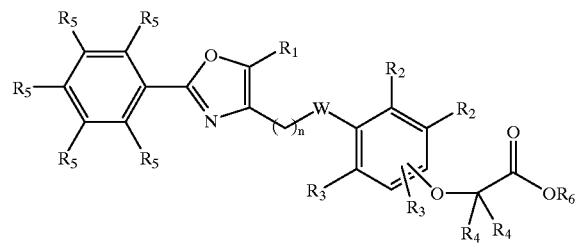

and pharmaceutically acceptable salts, solvates and hydrates thereof, wherein:

n is 2, 3, or 4;

W is O, S, or SO$_2$;

$R_1$ is H, a C1–C4 alkyl, phenyl or trifluoromethyl;

$R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H s a C1–C6 alkyl an aryl-C1–C6 alkyl , a cycloalkyl-C1–C4 alkyl aryl, or a cycloalkyl;

$R_4$ are each, independently, H, a C1–C4 alkyl, an aryl, or benzyl;

$R_5$ are each, independently, H or a substituted or unsubstituted aryl, provided that at least one $R_5$ is a substituted or unsubstituted aryl; and $R_6$ is H, a C1–C4 alkyl, or an aminoalkyl.

31. The method of claim 30, wherein the compound is represented by the following structural formula:

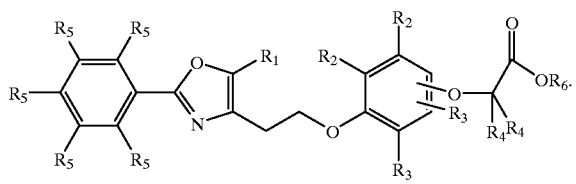

32. The method of claim 31, wherein the compound is represented by the following structural formula:

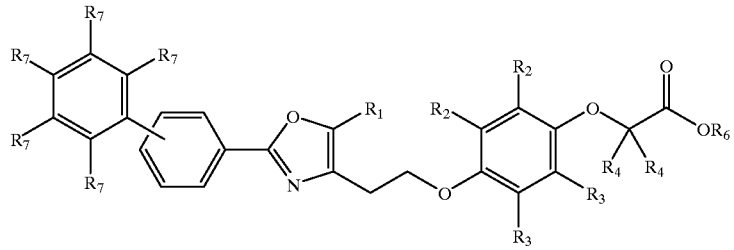

wherein, $R_7$ are each, independently, H, halo a C1–C6 alkyl, trifluoromethyl, a C1–C6 alkoxy, C(O)OH, C(O)NHC(CH$_3$)$_3$, (CH$_2$)$_2$C(O)OH, or CHO.

33. The method of claim 32, wherein the compound is selected from the group consisting of:

2-{4-[2-(2-biphenyl-4-yl-5-methyloxazol-4-yl)ethoxy]phenoxy}-2-methylpropionic acid;

2-{4-[2-(2-biphenyl-4-yl-5-methyloxazol-4-yl)-ethyloxy]-2-propylphenoxy}-2-methyl-propionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-propylphenoxy}-2-methylpropionic acid; and 2-{4-[2-(2-biphenyl-3-yl-5-methyloxazol-4-yl)ethoxy]phenoxy}-2-methylpropionic acid.

34. The method of claim 32, wherein the compound is represented by the following structural formula:

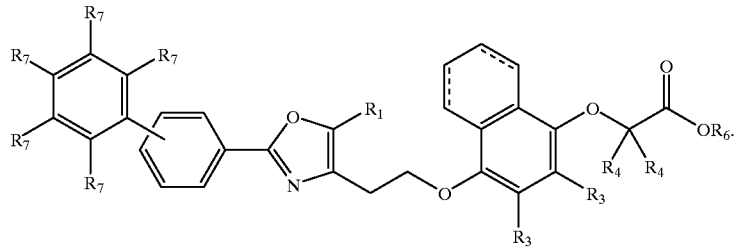

35. The method of claim 34, wherein the compound is selected from the group consisting of:

2-{4-[2-(2-biphenyl-4-yl-5-methyloxazol-4-yl)ethoxy]naphthalen-1-yloxy}-2-methyl propionic acid; and 2-{4-[2-(2-biphenyl-4-yl-5-methyloxazol-4-yl)-ethoxy]-5,6,7,8-tetrahydronaphthalen-1-yloxy}-2-methyl propionic acid;

2-{4-[2-(2-biphenyl-3-yl-5-methyloxazol-4-yl)-ethoxy]-5,6,7,8-tetrahydronaphthalen-1-yloxy}-2-methyl propionic acid; and 2-{4-[2-(2-biphenyl-3-yl-5-methyloxazol-4-yl)ethoxy]naphthalen-1-yloxy}-2-methyl propionic acid.

36. The method of claim 30, wherein the compound lowers blood glucose levels.

37. A method of treating or preventing cardiovascular disease in a patient, comprising the step of administering to the mammal a therapeutically effective amount of at least one compound represented by the following structural formula:

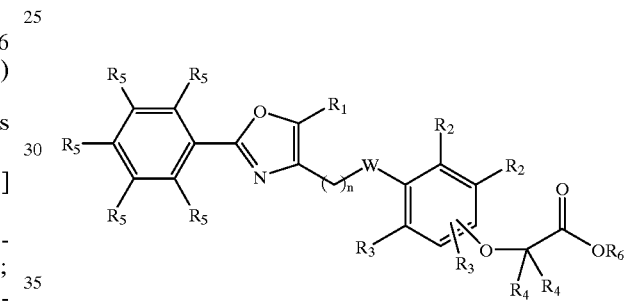

and pharmaceutically acceptable salts, solvates and hydrates thereof, wherein:

n is 2, 3, or 4;

W is O, S, or SO$_2$;

$R_1$ is H, a C1–C4 alkyl, phenyl or trifluoromethyl;

$R_2$ are each, independently, H, a C1–C6 alkyl, an aryl-C1–C6 alkyl, a cycloalkyl-C1 14 C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, an aryl-C1–C6 alkyl, a cycloalkyl-C1–C4 alkyl, an aryl, or a cycloalkyl;

$R_4$ are each, independently, H, a C1–C4 alkyl, an aryl, or benzyl;

R5 are each, independently, H or a substituted or unsubstituted aryl, provided that at least one R5 is a substituted or unsubstituted aryl; and R6 is H, a C1–C4 alkyl, or an aminoalkyl.

38. The method of claim 37, wherein the compound is represented by the following structural formula:

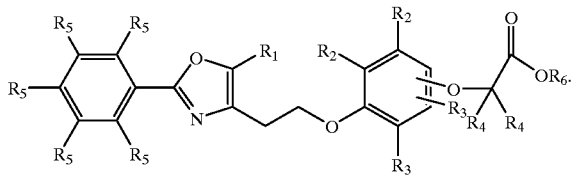

39. The method of claim 38, wherein the compound is represented by the following structural formula:

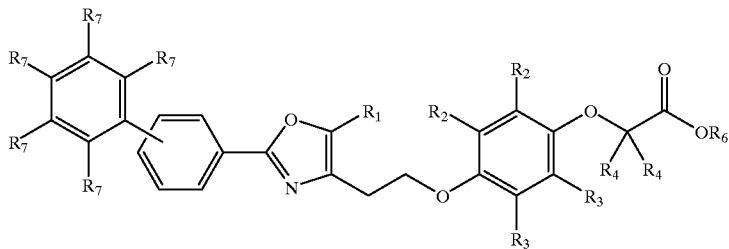

wherein, R7 are each, independently, H halo, a C1–C6 alkyl, trifluoromethyl, a C1–C6 alkoxy, C(O)OH, C(O)NHC(CH3)3, (CH2)2C(O)OH, or CHO.

40. the method of claim 39, wherein the compound is selected from the group consisting of;

2-{4-[2-(2-biphenyl-4-yl-5-methyloxazol-4-yl)ethoxy]phenoxy}-2-methylpropionic acid;

2-{4-[2-(2-biphenyl-4-yl-5-methyloxazol-4-yl)-ethyloxy]-2-propylphenoxy}-2methyl-propionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-propylphenoxy}-2-methylpropionic acid; and 2-{4-[2-(2-biphenyl-3-yl-5-methyloxazol-4-yl)ethoxy]phenoxy}-2-methylpropionic acid.

41. The method of claim 39, wherein the compound is represented by the following structural formula:

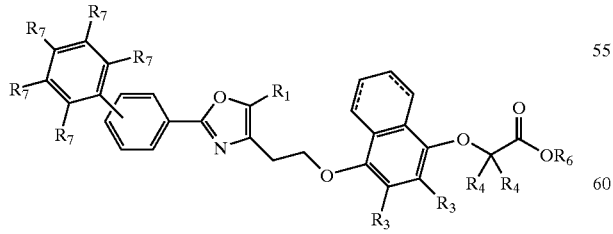

42. The method of claim 41, wherein the compound is selected from the group consisting of:

2-{4-[2-(2-biphenyl-4-yl-5-methyloxazol-4-yl)ethoxy]naphthalen-1-yloxy}-2-methyl propionic acid; and 2-{4-[2-(2-biphenyl-4-yl-5-methyloxazol-4-yl)-ethoxy]-5,6,7,8-tetrahydronaphthalen-1-yloxy}-2-methyl propionic acid;

2-{4-[2-(2-biphenyl-3-yl-5-methyloxazol-4-yl)-ethoxy]-5,6,7,8-tetrahydronaphthalen-1-yloxy}-2-methyl propionic acid; and 2-{4-[2-(2-biphenyl-3-yl-5-methyloxazol-4-yl)ethoxy]naphthalen-1-yloxy}-2-methyl propionic acid.

43. the method of claim 37, wherein the compound lowers triglycerides in the patient.

44. The method of claim 37, wherein the compound increases high density lipoproteins in a patient.

45. A method of treating or preventing Syndrome X in a patient, comprising the step of administering to the mammal a therapeutically effective amount of at least one compound represented by the following structural formula:

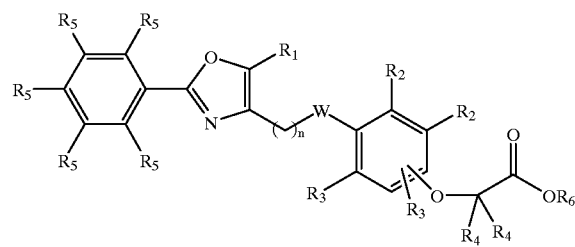

and pharmaceutically acceptable salts, solvates and hydrates thereof, wherein:

n is 2, 3, or 4;

W is O, S, or $SO_2$;

$R_1$ is H, a C1–C4 alkyl, phenyl or trifluoromethyl;

$R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, an aryl-C1–C6 alkyl, a cycloalkyl-C1–C4 alkyl, an aryl, or a cycloalkyl;

$R_4$ are each, independently, H, a C1–C4 alkyl, an aryl, or benzyl;

$R_5$ are each, independently, H or a substituted or unsubstituted aryl, provided that at least one $R_5$ is a substituted or unsubstituted aryl; and $R_6$ is H, a C1–C4 alkyl, or an aminoalkyl.

46. The method of claim 45, wherein the compound is represented by the following structural formula:

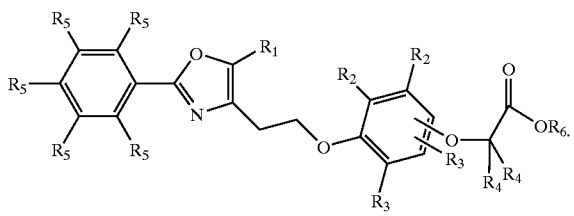

47. The method of claim 46, wherein the compound is represented by the following structural formula:

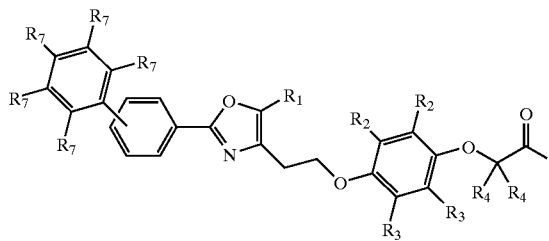

wherein, $R_7$ are each, independently, H, halo, a C1–C6 alkyl, trifluoromethyl, a C1–C6 alkoxy, C(O)OH, C(O)NHC(CH$_3$)$_3$, (CH$_2$)$_2$C(O)OH, or CHO.

48. The method of claim 47, wherein the compound is selected from the group consisting of:

2-{4-[2-(2-biphenyl-4-yl-5-methyloxazol-4-yl)ethoxy]phenoxy}-2-methylpropionic acid;

2-{4-[2-(2-biphenyl-4-yl-5-methyloxazol-4-yl)-ethyloxy]-2-propylphenoxy}-2-methyl-propionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-propylphenoxy}-2-methylpropionic acid; and 2-{4-[2-(2-biphenyl-3-yl-5-methyloxazol-4-yl)ethoxy]phenoxy}-2-methylpropionic acid.

49. The method of claim 47, wherein the compound is represented by the following structural formula:

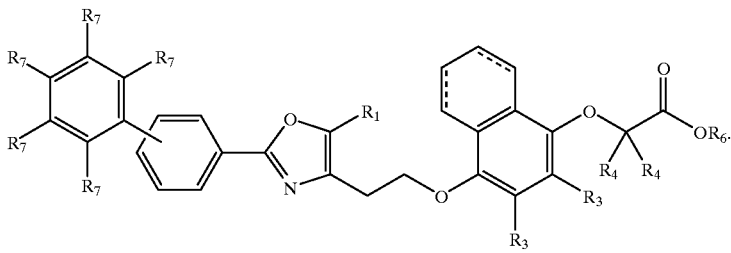

50. The method of claim 49, wherein the compound is selected from the group consisting of:

2-{4-[2-(2-biphenyl-4-yl-5-methyloxazol-4-yl)ethoxy]naphthalen-1-yloxy}-2-methyl propionic acid; and 2-{4-[2-(2-biphenyl-4-yl-5-methyloxazol-4-yl)-ethoxy]-5,6,7,8-tetrahydronaphthalen-1-yloxy}-2-methyl propionic acid;

2-{4-[2-(2-biphenyl-3-yl-5-methyloxazol-4-yl)-ethoxy]-5,6,7,8-tetrahydronaphthalen-1-yloxy}-2-methyl propionic acid; and 2-{4-[2-(2-biphenyl-3-yl-5-methyloxazol-4-yl)ethoxy]naphthalen-1-yloxy}-2-methyl propionic acid.

51. The method of claim 45, wherein the compound lowers blood glucose levels.

52. The method of claim 45, wherein the compound lowers serum concentration of triglycerides in the mammal.

53. The method of claim 45, wherein the compound increases serum concentration of high density lipoproteins in a mammal.

54. A compound for use in therapy for a disorder modulated by a peroxisome proliferator activated receptor, wherein the compound is represented by the following structural formula:

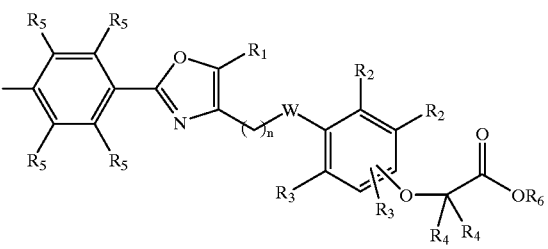

and pharmaceutically acceptable salts, solvates and hydrates thereof, wherein:

n is 2, 3, or 4;

W is O, S, or SO$_2$;

$R_1$ is H, a C1–C4 alkyl, phenyl or trifluoromethyl;

$R_2$ are each, independently, H, a C1–C6 alkyl, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, an aryl-C1-C6 alkyl, a cycloalkyl-C1–C4 alkyl, an aryl, or a cycloalkyl;

$R_4$ are each, independently, H, a C1–C4 alkyl, an aryl, or benzyl;

$R_5$ are each, independently, H or a substituted or unsubstituted aryl, provided that at least one $R_5$ is a substituted or unsubstituted aryl; and $R_6$ is H, a C1–C4 alkyl, or an aminoalkyl.

55. A compound selected from the group consisting of:

2-(4-{2-[2-(4'-fluorobiphenyl-4-yl)-5-methyloxazol-4-yl]ethoxy}phenoxy)-2-methylpropionic acid;

2-(4-{2-[2-(4'-formylbiphenyl-3-yl)-5-methyloxazol-4-yl]ethoxy}phenoxy)-2-methylpropionic acid;

3'-(4-{2-[3-(1-carboxy-1-methylethoxy)phenoxy]ethyl}-5-methyloxazol-2-yl)-biphenyl-4carboxylic acid;

2-[4-(2-{2-[4'-(2-carboxyethyl)biphenyl-3-yl]-5-methyloxazol-4-yl}ethoxy)phenoxy]-2-methylpropionic acid;

2-(4-{2-[2-(3',5'-bis-trifluoromethylbiphenyl-4yl)-5-methyloxazol-4-yl]ethoxy}-phenoxy)-2-methyl propionic acid;

2-(4-{2-[2-(2'-methoxy-biphenyl-4-yl)-5-methyloxazol-4-yl]-ethoxy}-phenoxy)-2-methylpropionic acid;

2-methyl-2-(4-{2-[5-methyl-2-(2'-methyl-biphenyl-4-yl)-oxazol-4-yl]-ethoxy}-phenoxy)propionic acid;

2-methyl-2-(4-{2-[5-methyl-2-(2'-trifluoromethyl-biphenyl-4-yl)-oxazol-4-yl]-ethoxy}-phenoxy)propionic acid;

2-(4-{2-[2-(2'-fluorobiphenyl-4yl)-5-methyloxazol-4-yl]-ethoxy}-phenoxy)-2-methylpropionic acid;

2-(4-{2-[2-(2',6'-difluorobiphenyl-4-yl)-5-methyloxazol-4-yl]-ethoxy}-phenoxy)-2-methylpropionic acid;

2-(4-{2-[2-(2',6'-dichloro-biphenyl-4-yl)-5-methyloxazol-4-yl]-ethoxy}-phenoxy)-2-methylpropionic acid;

2-(4-{2-[2-(4'-tert-butylcarbamoylbiphenyl-3-yl)-5-methyloxazol-4-yl]ethoxy}phenoxy)-2-methyl propionic acid;

2-{3-[2-(2-biphenyl-4-yl-5-methyloxazol-4-yl)ethoxy]phenoxy}-2-methylpropionic acid;

2-{3-[2-(2-biphenyl-3-yl-5-methyloxazol-4-yl)ethoxy]phenoxy}-2-methylpropionic acid;

2-{4-[2-(2-biphenyl-4-yl-5-methyloxazol-4-yl)-ethoxy]-2-methylphenoxy}-2-methylpropionic acid;

2-{4-[2-(2-biphenyl-4-yl-5-methyloxazol-4yl)-ethoxy]-2-cyclohexylmethylphenoxy}-2-methyl-propionic acid;

2-{4-[2-(2-biphenyl-4-yl-5-methyloxazol-4-yl)ethoxy]-2-phenethylphenoxy}-2-methylpropionic acid;

2-{4-[2-(2-biphenyl-3-yl-5-methyloxazol-4-yl)ethoxy]-2-phenethylphenoxy}-2-methylpropionic acid;

2-{4-[2-(2-biphenyl-3-yl-5-methyloxazol-4-yl)ethoxy]-3-butylphenoxy}-2-methylpropionic acid;

2-{4-[2-(2-biphenyl-4-yl-5-methyloxazol-4-yl)ethoxy]-3-phenethylphenoxy}-2-methylpropionic acid;

2-{4-[2-(2-biphenyl-4-yl-5-methyloxazol-4-yl)ethoxy]-3-cyclohexylmethylphenoxy}-2-methylpropionic acid, 2-{2-benzyl-4-[2-(2-biphenyl-3-yl-5-methyloxazol-4-yl)-ethoxy]-phenoxy}-2-methyl-propionic acid;

2-{2-benzyl-4-[2-(2-biphenyl-4-yl-5-methyloxazol-4-yl)-ethoxy]-phenoxy}-2-methyl-propionic acid;

2-{5-[2-(2-biphenyl-4-yl-5-methyloxazol-4yl)-ethoxy]-biphenyl-2-yloxy}-2-methyl-propionic acid;

2-(4-{2-[2-(4'-trifluoromethylbiphenyl-4-yl)-5-methyloxazol-4-yl]ethoxy}phenoxy)-2-methylpropionic acid;

2-{3-[2-(2-biphenyl-4-yl-5-methyloxazol-4-yl)-ethoxy]-4butylphenoxy}-2-methylpropionic acid;

2-{5-[2-(2-biphenyl-4yl-5-methyloxazol-4-yl)ethoxy]-2-butylphenoxy}-2-methylpropionic acid;

2-{5-[2-(2-biphenyl-3-yl-5-methyloxazol-4-yl)ethoxy]-2-butylphenoxy}-2-methylpropionic acid;

2-{5-[2-(2-biphenyl-4-yl-5-methyloxazol-4-yl)ethoxy]-2-propylphenoxy}-2-methylpropionic acid;

2-{5-[2-(2-biphenyl-3-yl-5-methyloxazol-4-yl)ethoxy]-2-propylphenoxy}-2-methylpropionic acid;

2-{4-[2-(2-biphenyl-4-yl-5-methyloxazol-4-yl)-ethylsulfanyl]-phenoxy}-2-methyl-propionic acid;

2-{4-[2-(2-biphenyl-4yl-5-propyl-oxazol-4-yl)ethoxy]-phenoxy}-2-methylpropionic acid;

2-{4-[2-(2-biphenyl-4-yl-5-phenyl-oxazol-4-yl)-ethoxy]-phenoxy}-2-methyl-propionic acid;

2-{4-[2-(2-biphenyl-4-yl-5-trifluoromethyloxazol-4-yl)-ethoxy]-phenoxy}-2 -methyl-propionic acid;

2-(4-{2-[2-(4'-methoxybiphenyl-4yl)-5-methyloxazol-4-yl]ethoxy}phenoxy)-2-methylpropionic acid, 2-{4-[2-(2-biphenyl-4-yl-5-methyloxazol-4-yl)-ethylsulfanyldioxide]-phenoxy}-2-methyl-propionic acid;

2-{4-[2-(2-biphenyl-4-yl-5-methyloxazol-4-yl)-ethyloxy]-3-propylphenoxy}-ethanoic acid; and 2-{4-[2-(2-biphenyl-4-yl-5-methyloxazol-4-yl)-ethyloxy]-2-propylphenoxy}-ethanoic acid.

\* \* \* \* \*

UNITED STATES PATENT AND TRADEMARK OFFICE
CERTIFICATE OF CORRECTION

PATENT NO. : 6,417,212 B1 Page 1 of 1
DATED : July 9, 2002
INVENTOR(S) : Dawn A. Brooks et al.

It is certified that error appears in the above-identified patent and that said Letters Patent is hereby corrected as shown below:

<u>Column 136,</u>
Delete lines 43 through 54;

<u>Column 137,</u>
Delete lines 1-2;
Delete lines 20-21;
Delete lines 62-66;

<u>Column 138,</u>
Delete lines 1-2.

Signed and Sealed this

Twenty-sixth Day of November, 2002

Attest:

JAMES E. ROGAN
Attesting Officer    Director of the United States Patent and Trademark Office